United States Patent
Weng et al.

(10) Patent No.: US 11,531,393 B1
(45) Date of Patent: Dec. 20, 2022

(54) HUMAN-COMPUTER INTERFACE SYSTEMS AND METHODS

(71) Applicant: Sensoriai LLC, Dallas, TX (US)

(72) Inventors: Yaochung Weng, Dallas, TX (US); Puneeth Iyengar, Coppell, TX (US); Roya Norouzi Kandalan, Katy, TX (US)

(73) Assignee: Sensoriai LLC, Dallas, TX (US)

(*) Notice: Subject to any disclaimer, the term of this patent is extended or adjusted under 35 U.S.C. 154(b) by 114 days.

(21) Appl. No.: 16/912,948

(22) Filed: Jun. 26, 2020

Related U.S. Application Data

(60) Provisional application No. 62/868,775, filed on Jun. 28, 2019.

(51) Int. Cl.
| | | |
|---|---|---|
| *G06F 3/01* | (2006.01) | |
| *A61B 5/16* | (2006.01) | |
| *G06N 3/08* | (2006.01) | |
| *A61B 5/00* | (2006.01) | |
| *A61B 5/291* | (2021.01) | |

(52) U.S. Cl.
CPC .............. *G06F 3/015* (2013.01); *A61B 5/165* (2013.01); *A61B 5/291* (2021.01); *A61B 5/6814* (2013.01); *A61B 5/7203* (2013.01); *A61B 5/7264* (2013.01); *A61B 5/7275* (2013.01); *G06N 3/08* (2013.01)

(58) Field of Classification Search
CPC ......... G06F 3/015; G06V 40/15; A61B 5/291; A61B 5/165; G06N 3/08
See application file for complete search history.

(56) References Cited

U.S. PATENT DOCUMENTS

| | | | | |
|---|---|---|---|---|
| 2014/0082340 A1* | 3/2014 | Smith, II | ............ | G06F 11/1683 712/241 |
| 2015/0335288 A1* | 11/2015 | Toth | ..................... | A61B 5/6833 600/391 |
| 2020/0008725 A1* | 1/2020 | Bach | ..................... | A61B 5/6801 |

OTHER PUBLICATIONS

Duao et al. EEG Compression of Scalp Recordings based on Dipole Fitting (https://arxiv.org/pdf/1403.2001.pdf) (Year: 2014).*

* cited by examiner

*Primary Examiner* — Robert J Michaud
(74) *Attorney, Agent, or Firm* — Johnston IP Law, PLLC

(57) ABSTRACT

In one instance, a process for predicting and using emotions of a user in a virtual reality environment includes applying a plurality of physiological sensors to a user. The process further includes receiving physiological sensor signals from the physiological sensors and preparing the physiological sensor signals for further processing by removing at least some of the noise and artifacts and doing data augmentation. The process also includes producing an emotion-predictive signal by utilizing an emotion database. The emotion database has been developed based on empirical data from physiological sensors with known emotional states. The method also includes delivering the emotion-predictive signal to a virtual-reality system or other computer-implemented system. Other methods and systems are presented.

3 Claims, 114 Drawing Sheets

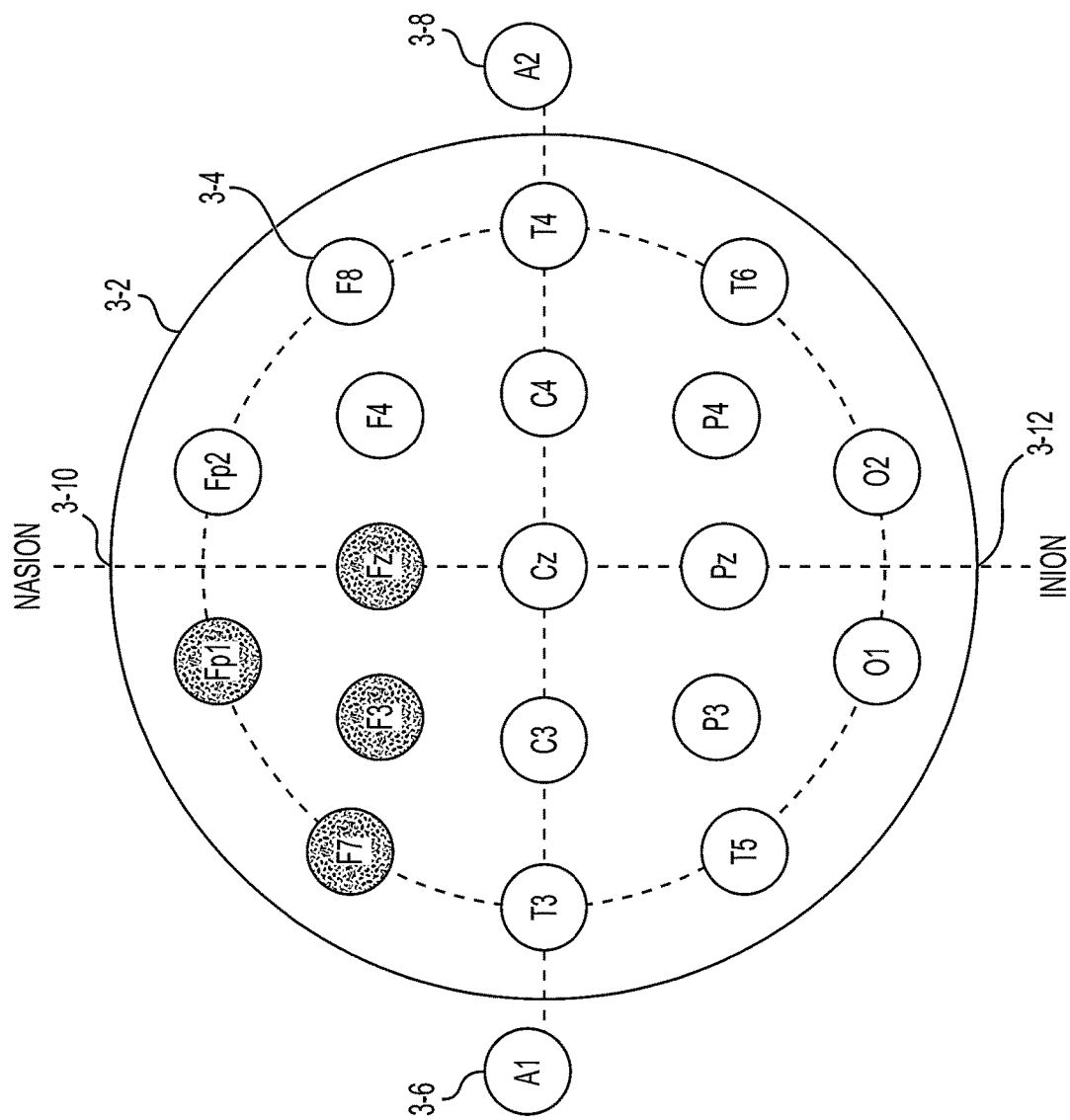
FIG. 3.1

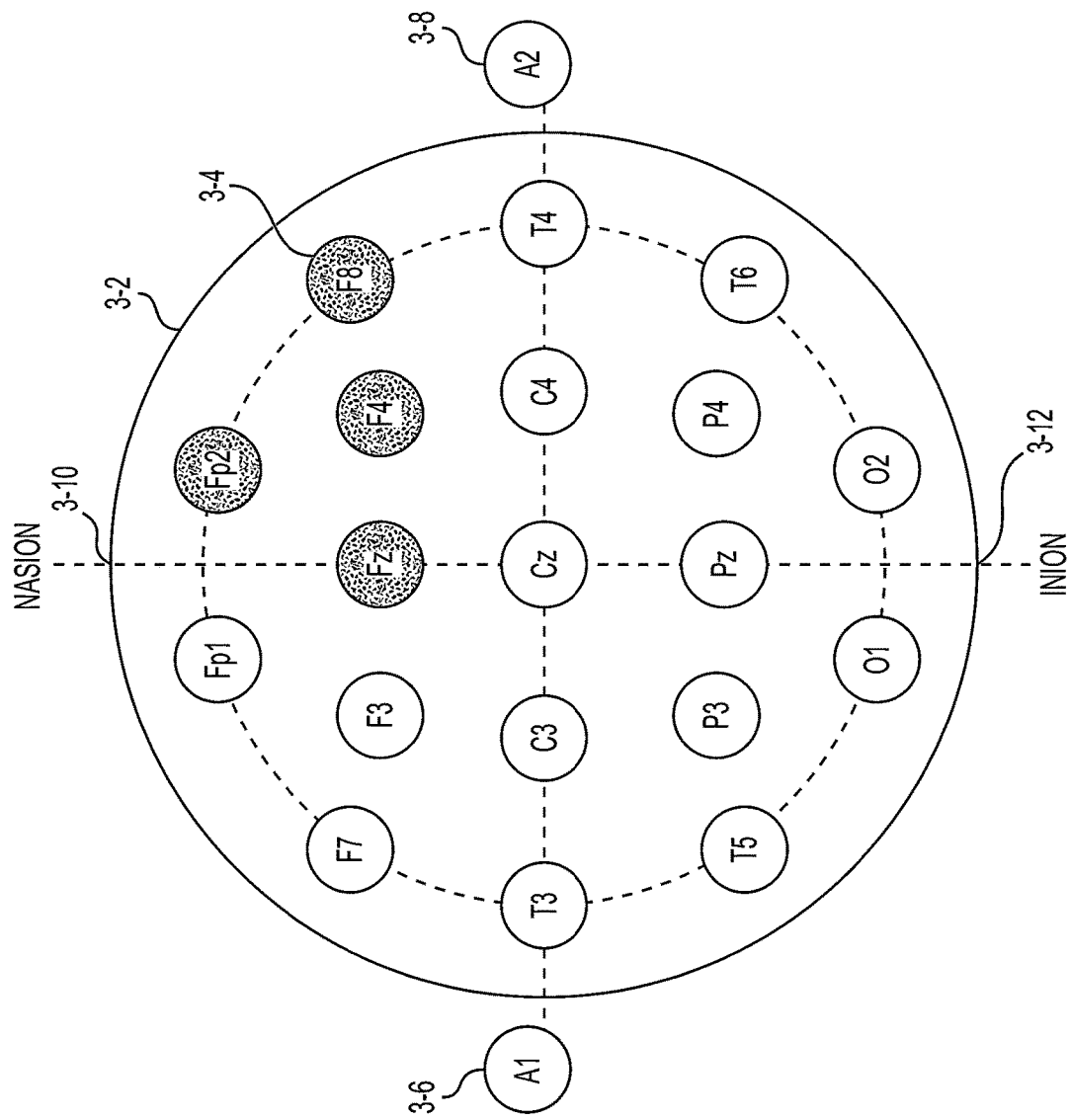
FIG. 3.2

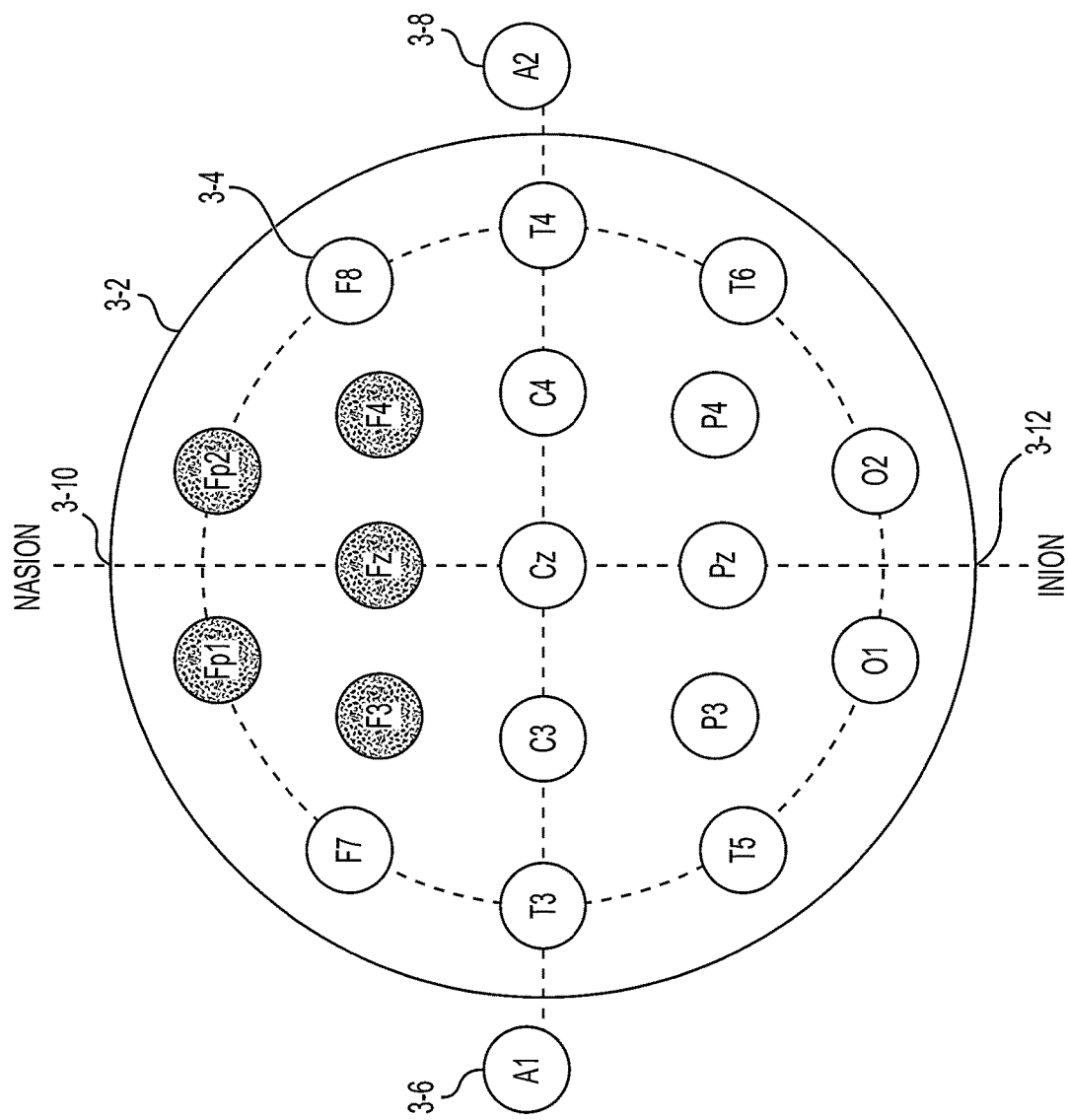
FIG. 3.3

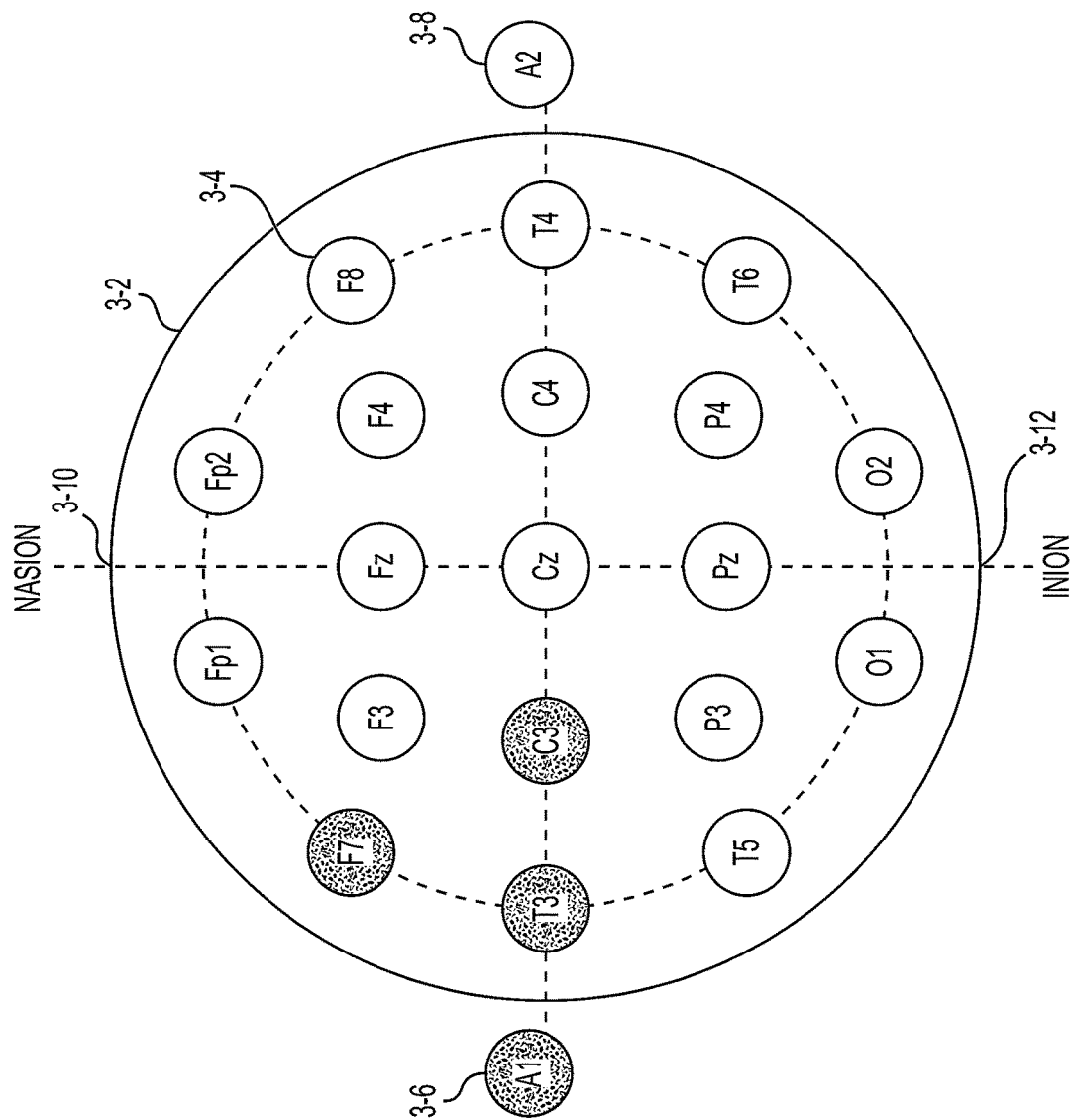
FIG. 3.4

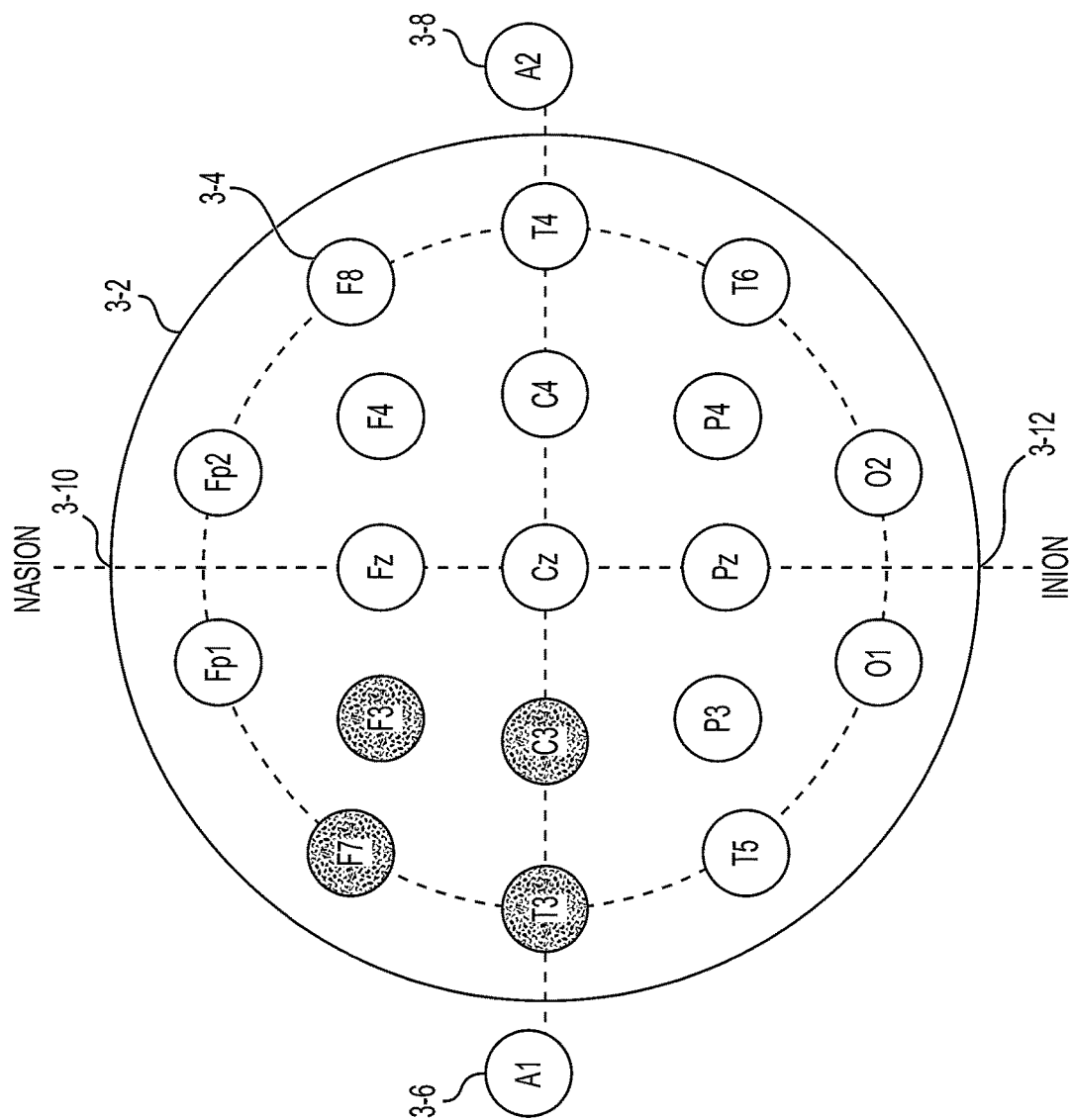
FIG. 3.5

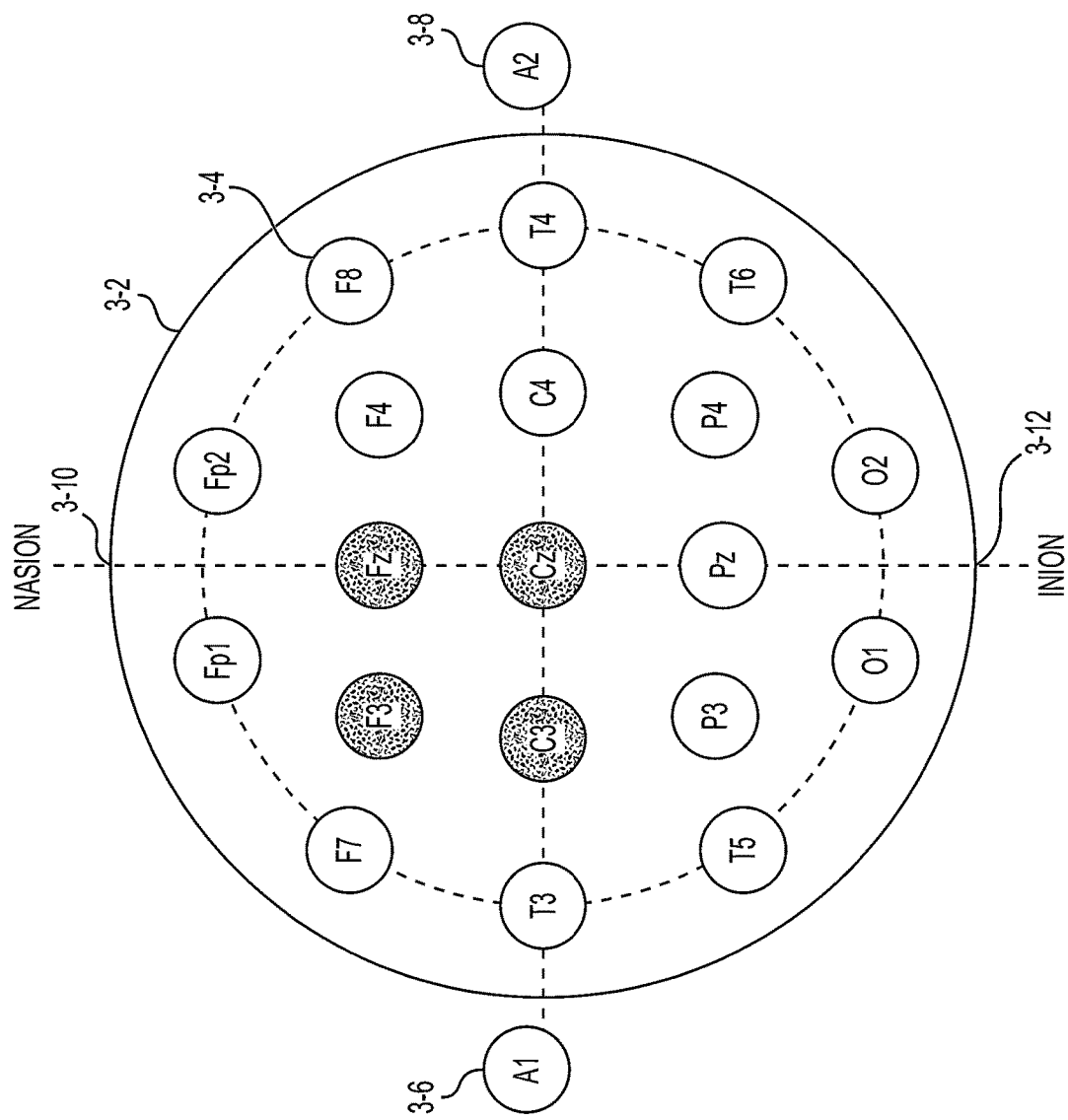
FIG. 3.6

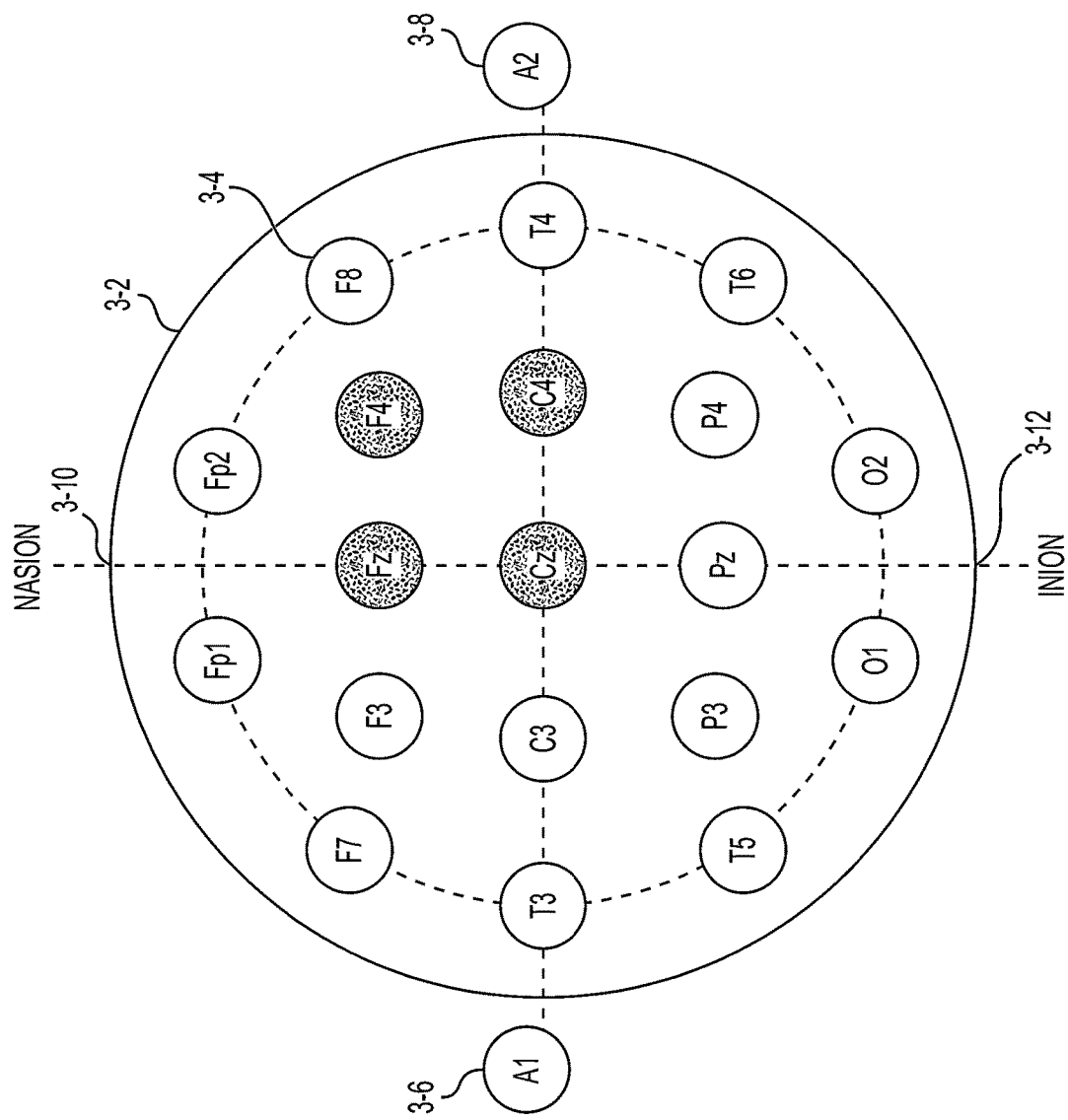
FIG. 3.7

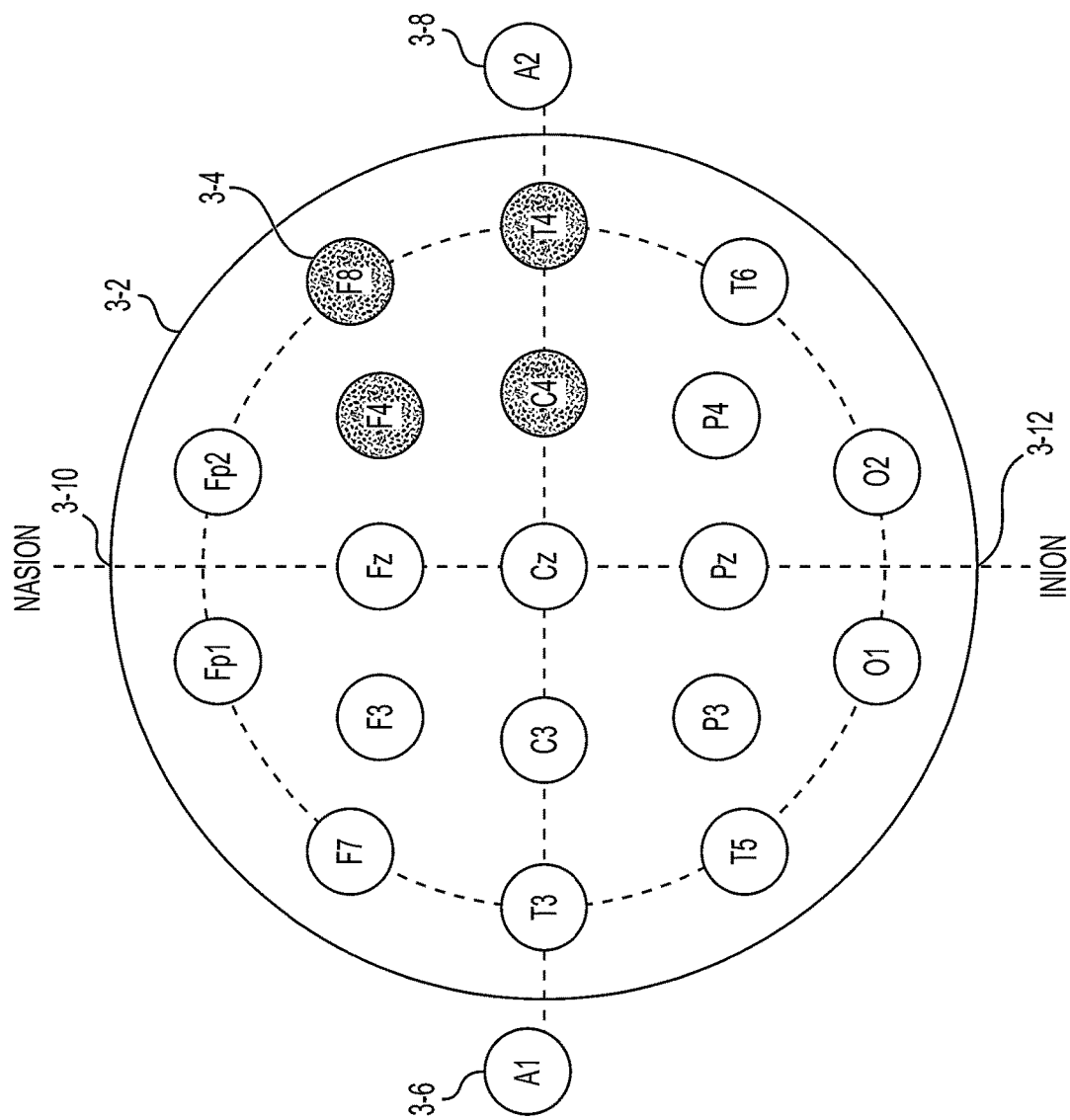
FIG. 3.8

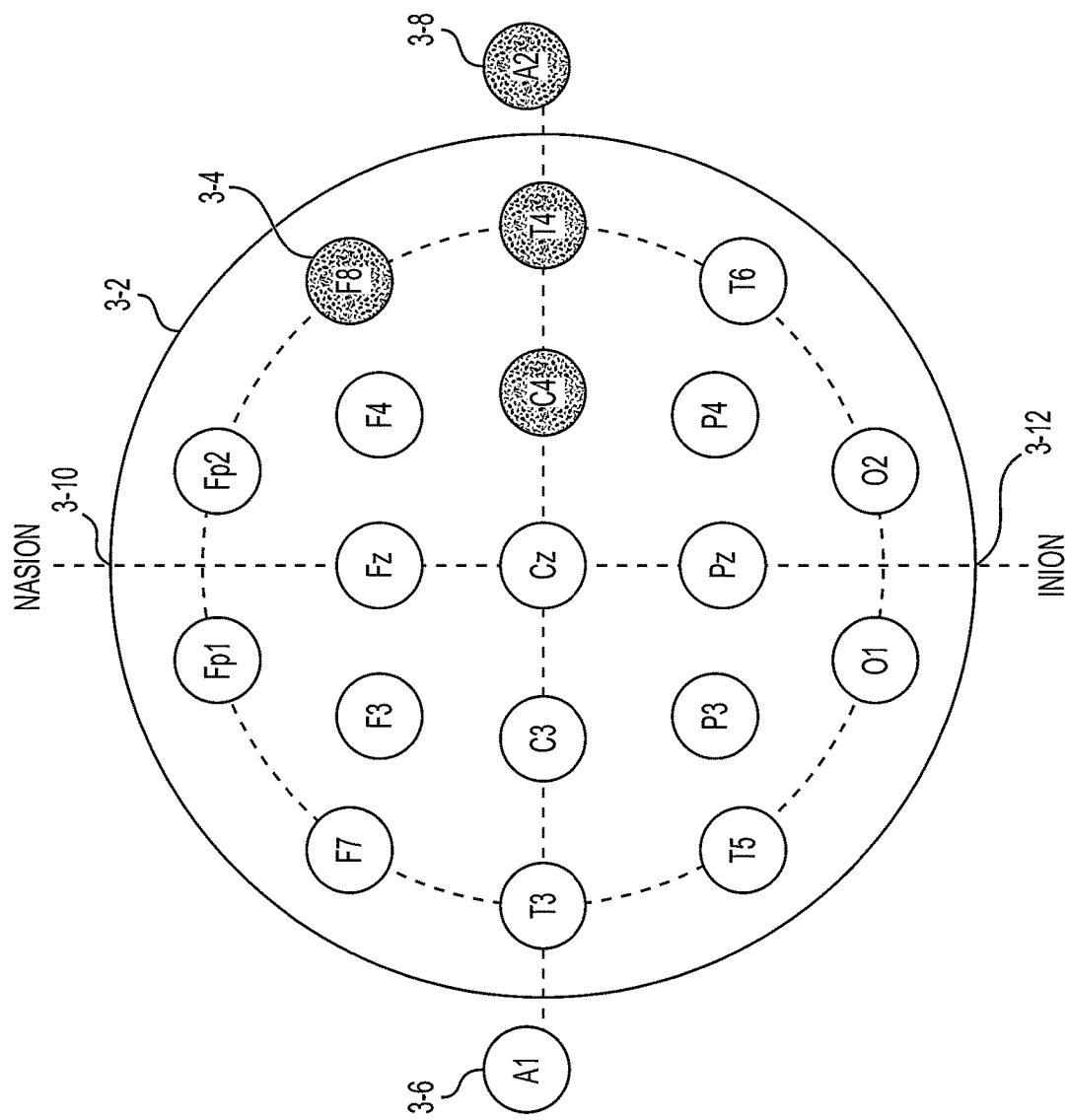
FIG. 3.9

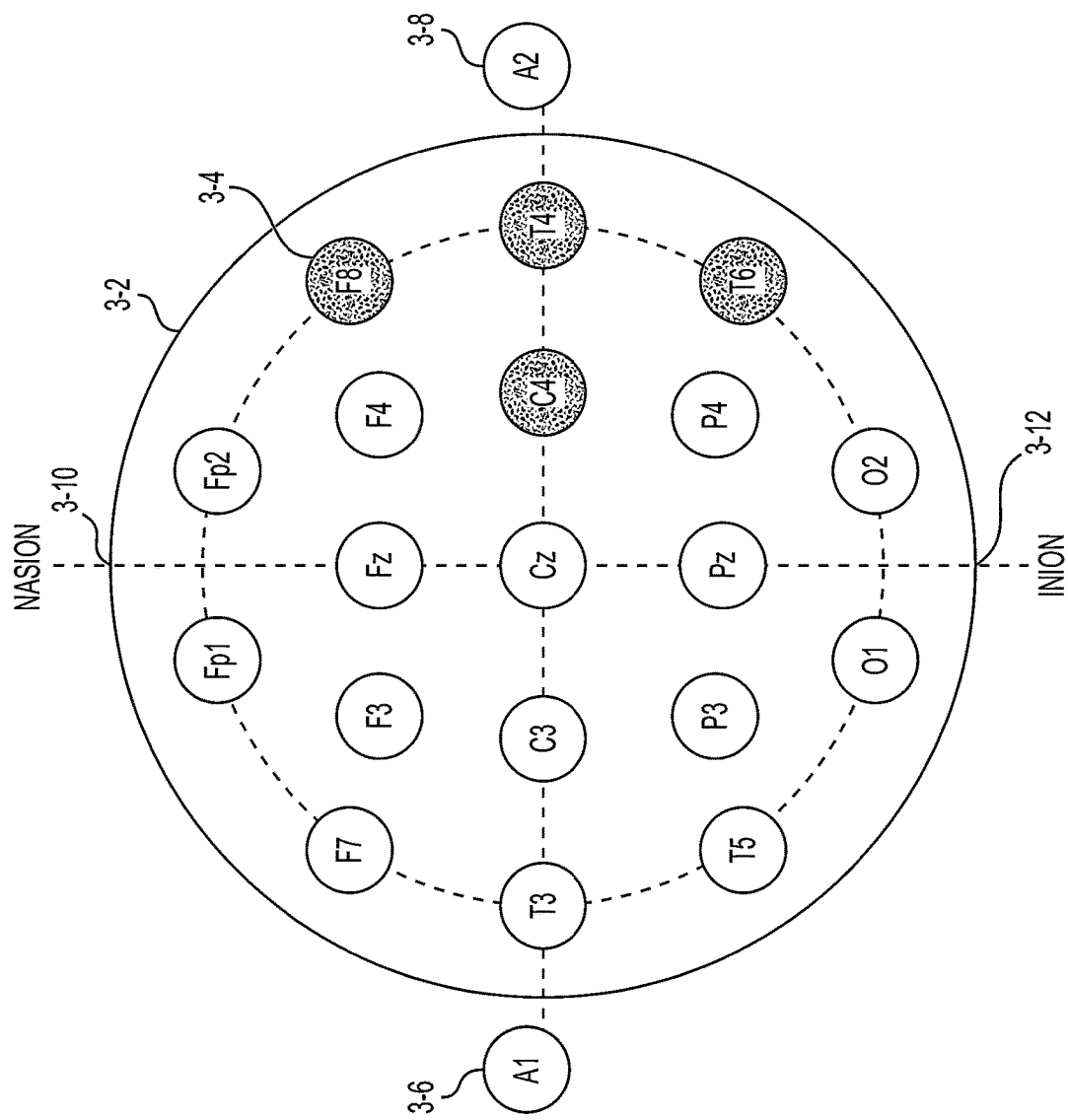
FIG. 3.10

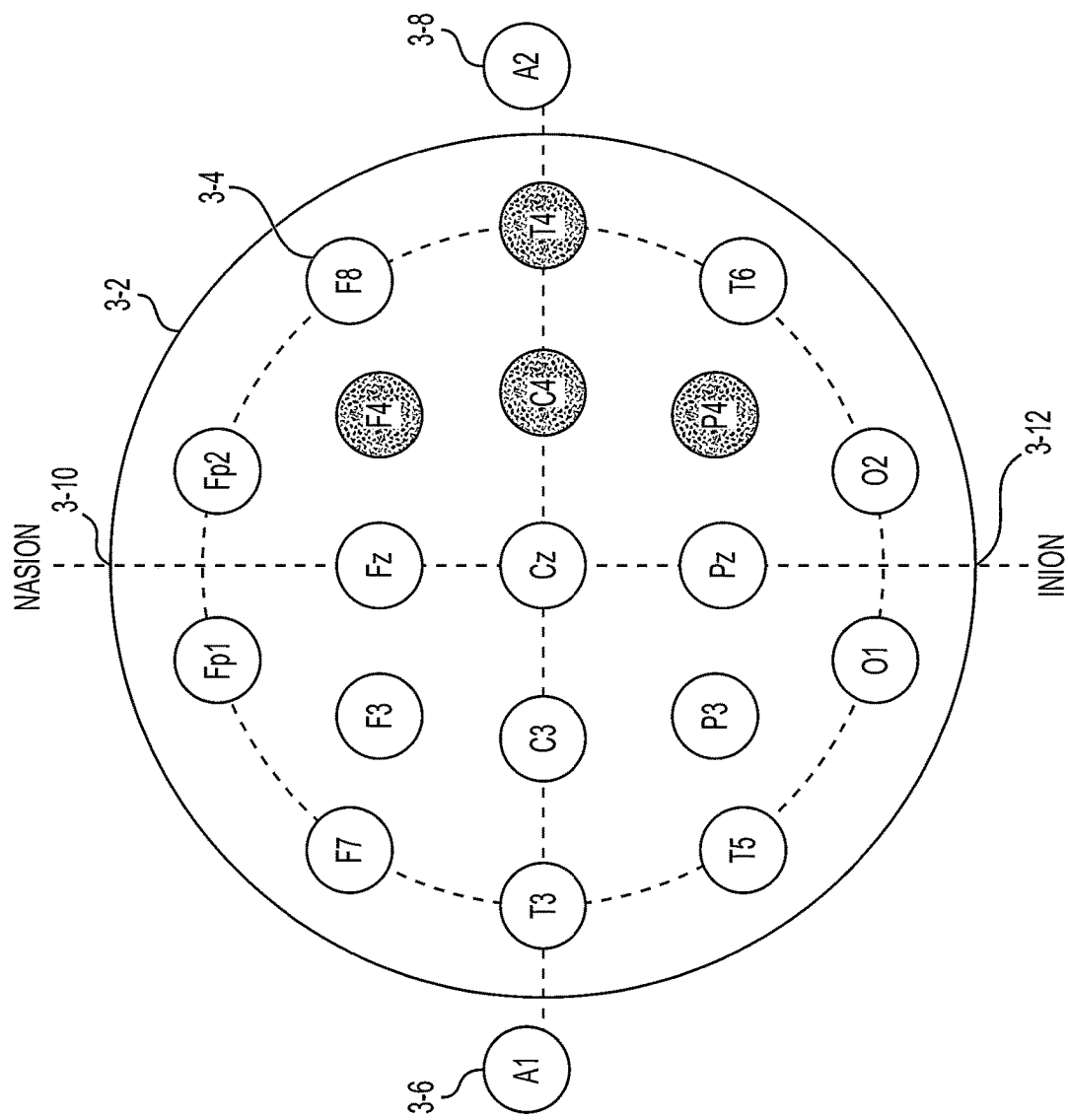
FIG. 3.11

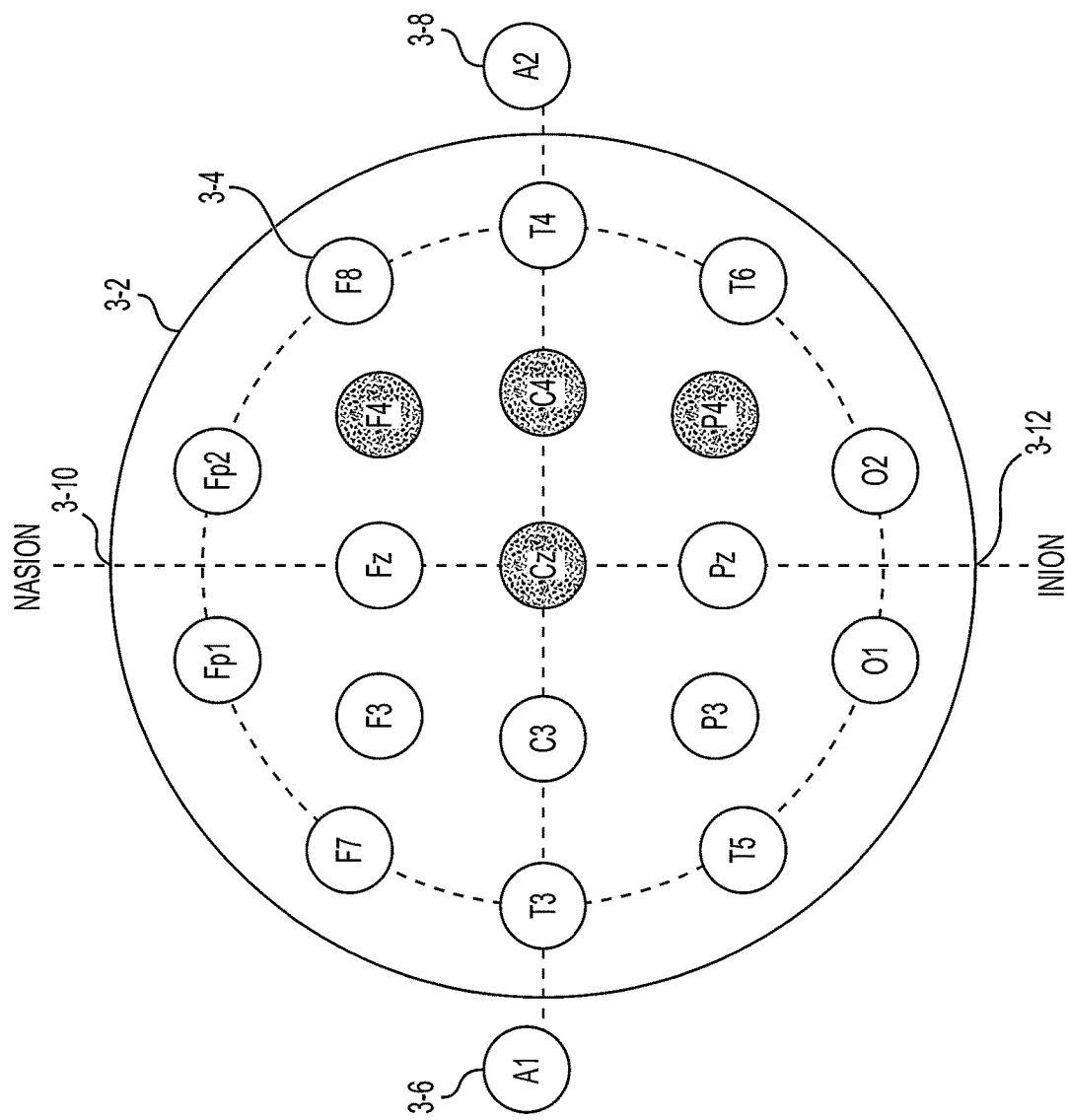
FIG. 3.12

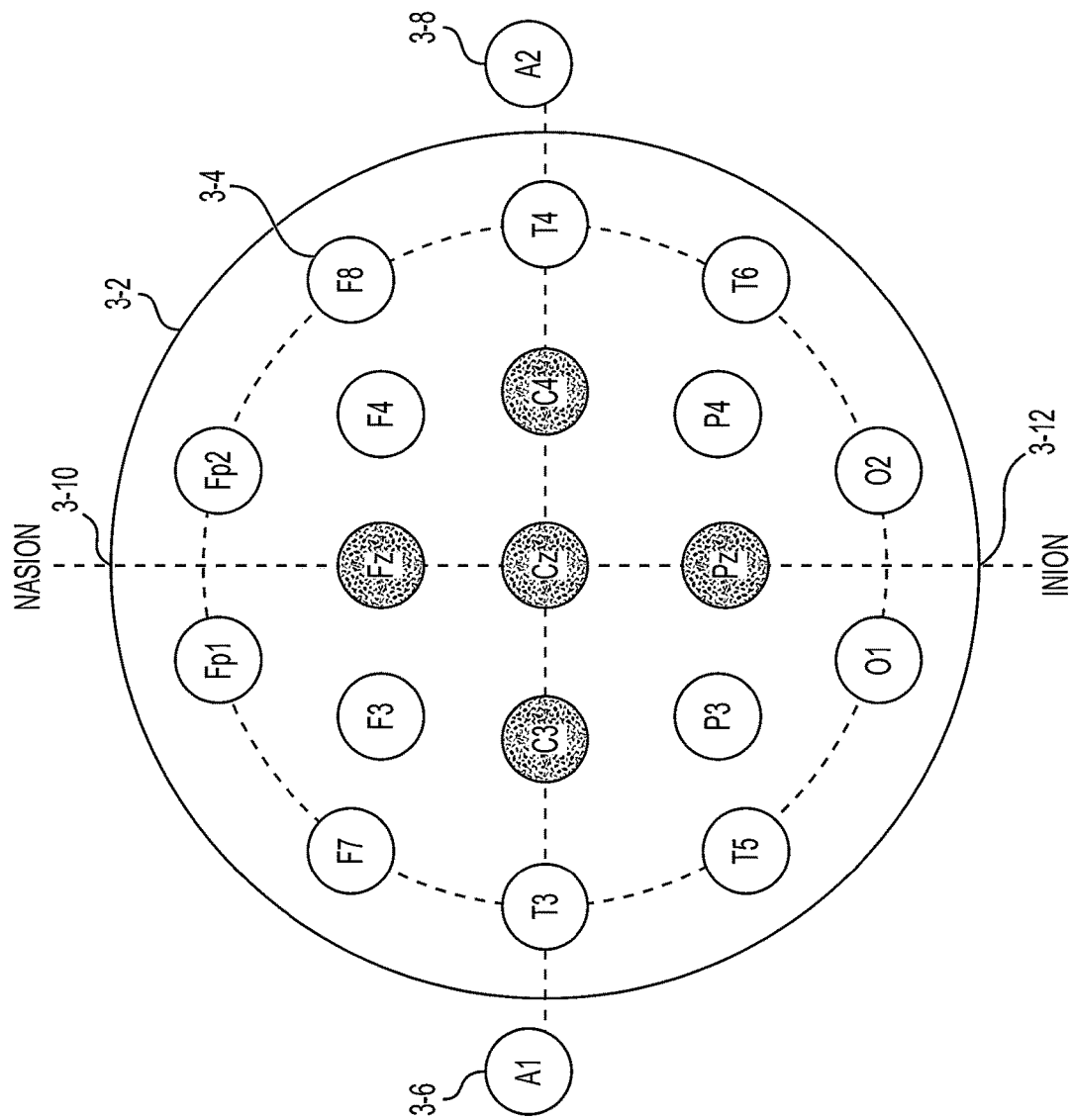
FIG. 3.13

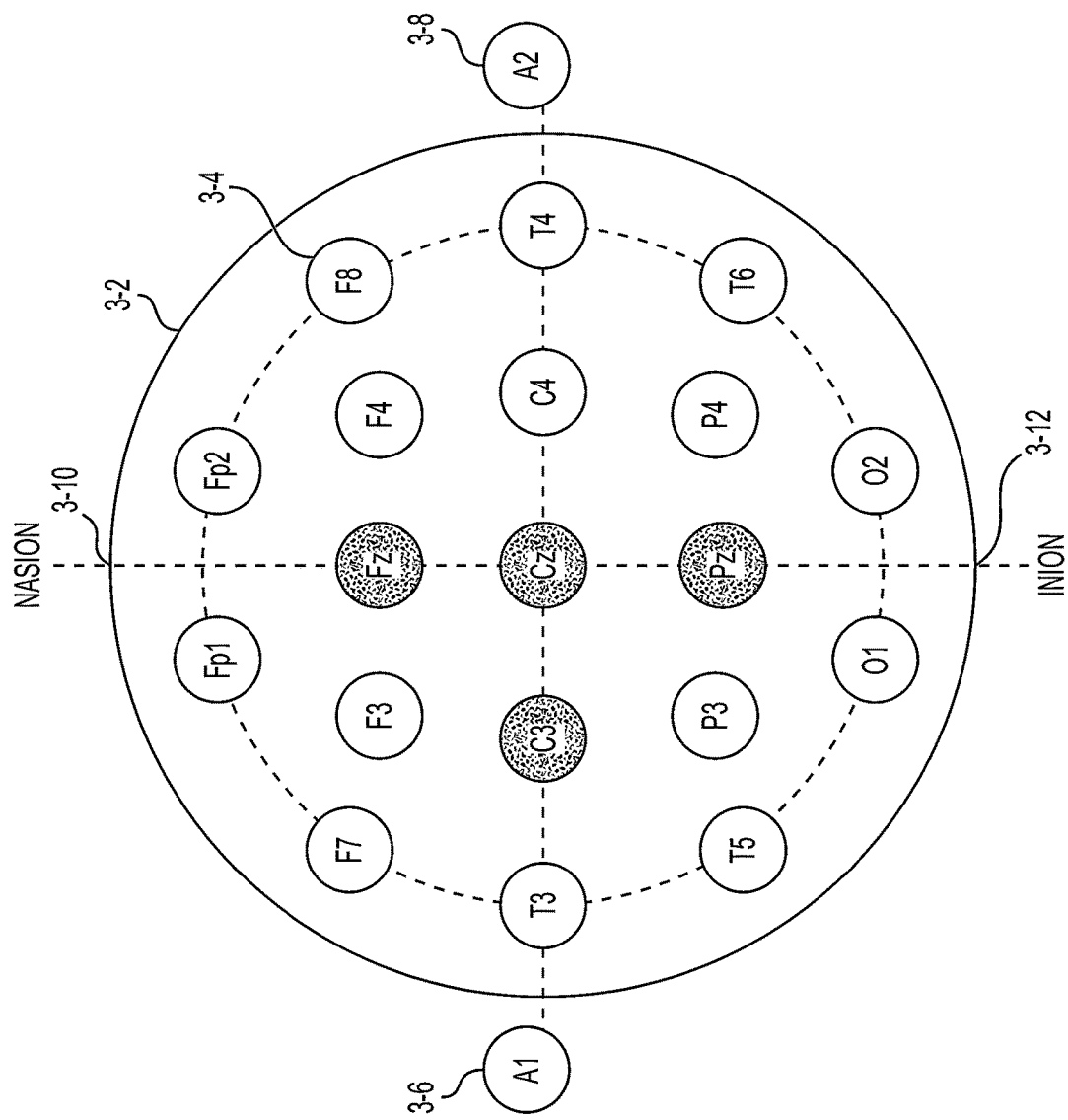
FIG. 3.14

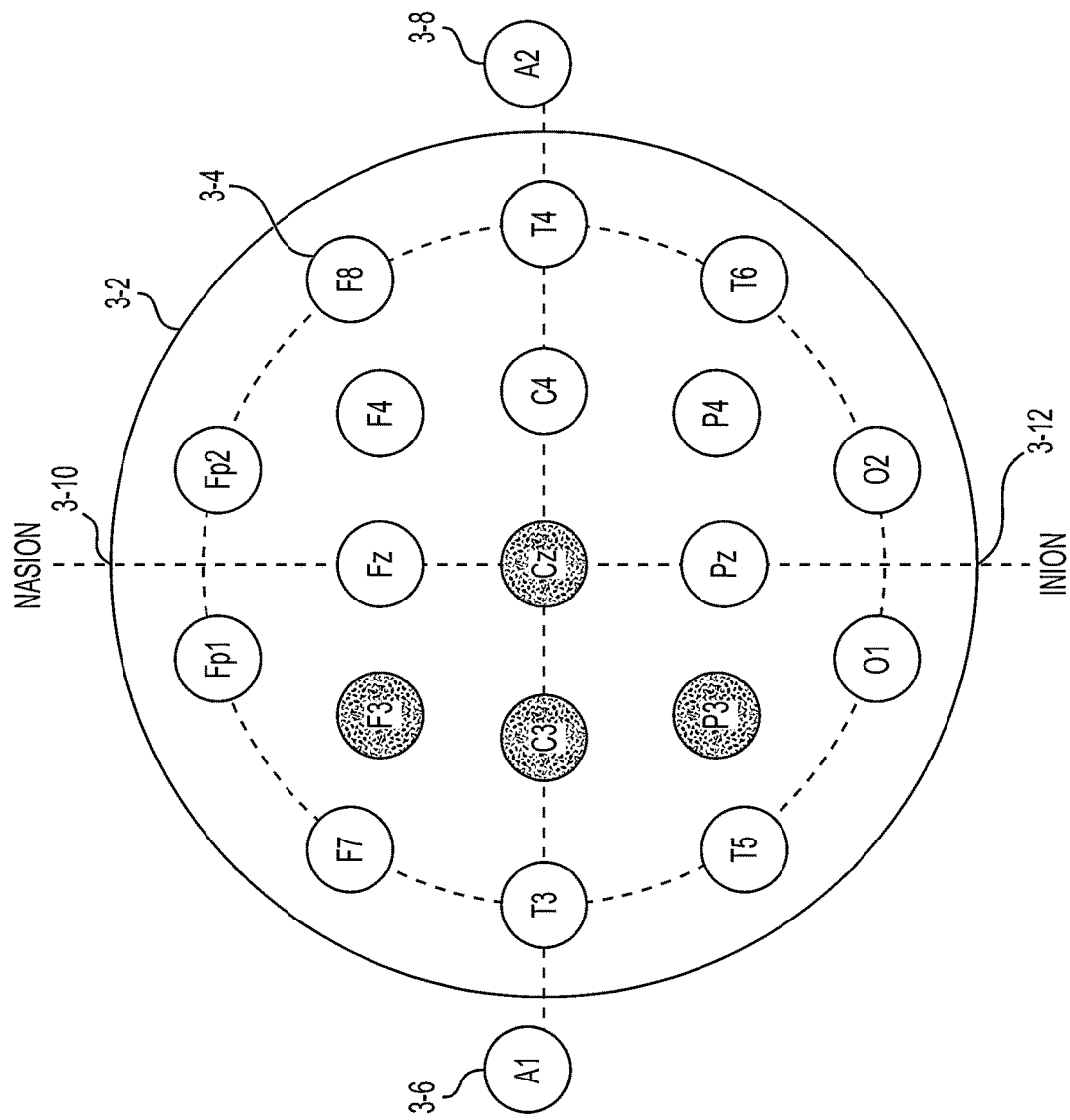
FIG. 3.15

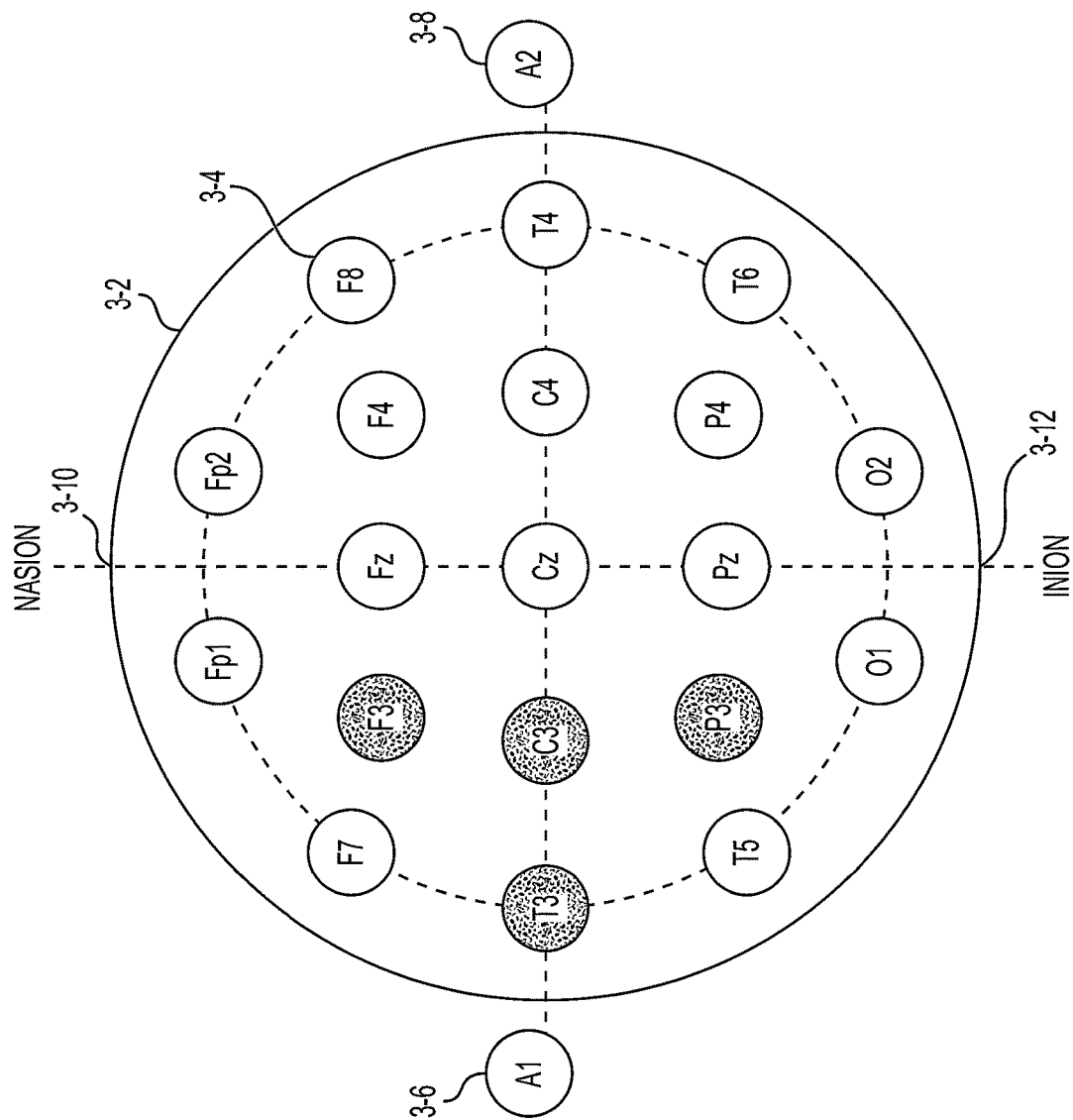
FIG. 3.16

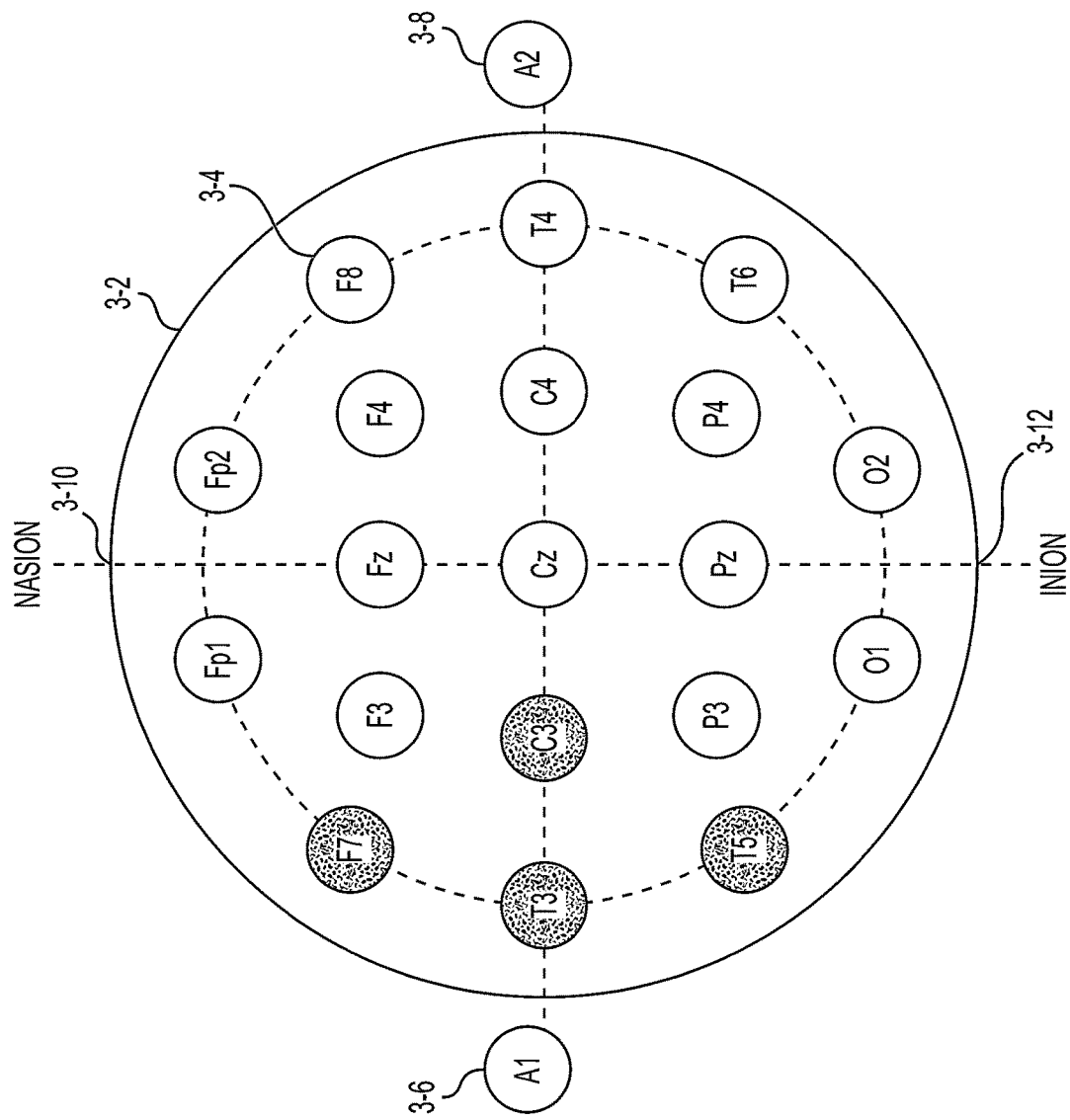
FIG. 3.17

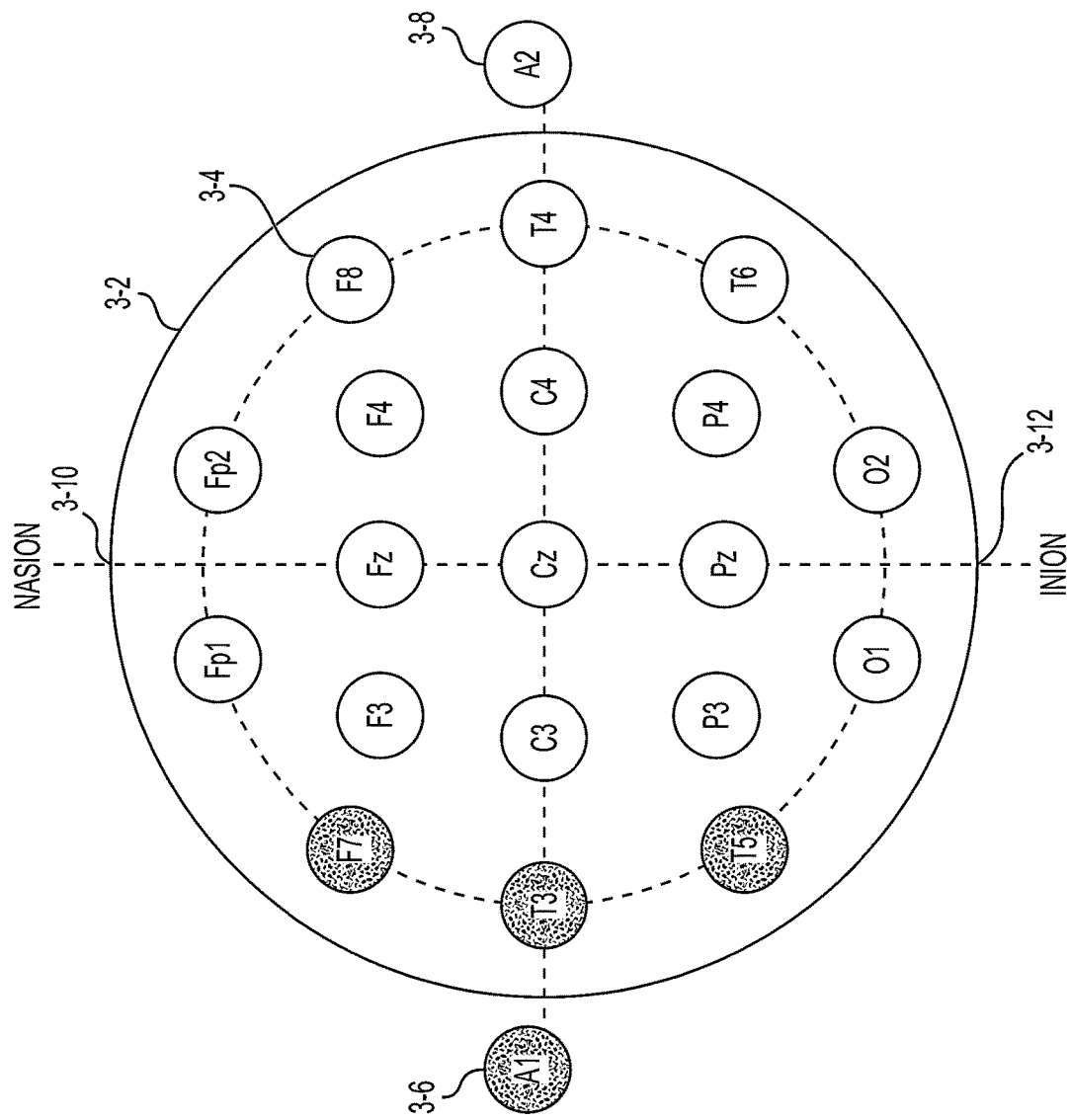
FIG. 3.18

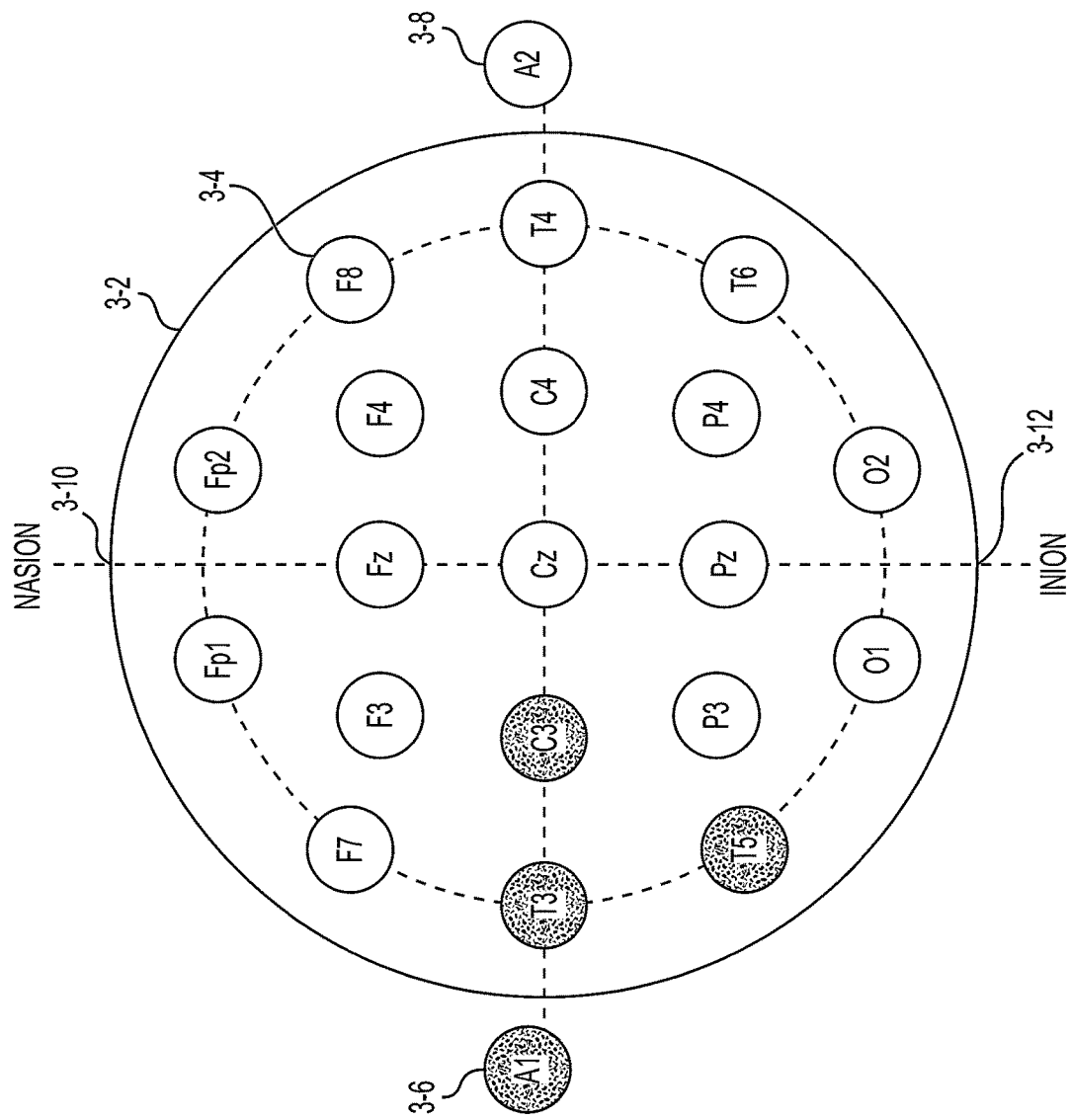
FIG. 3.19

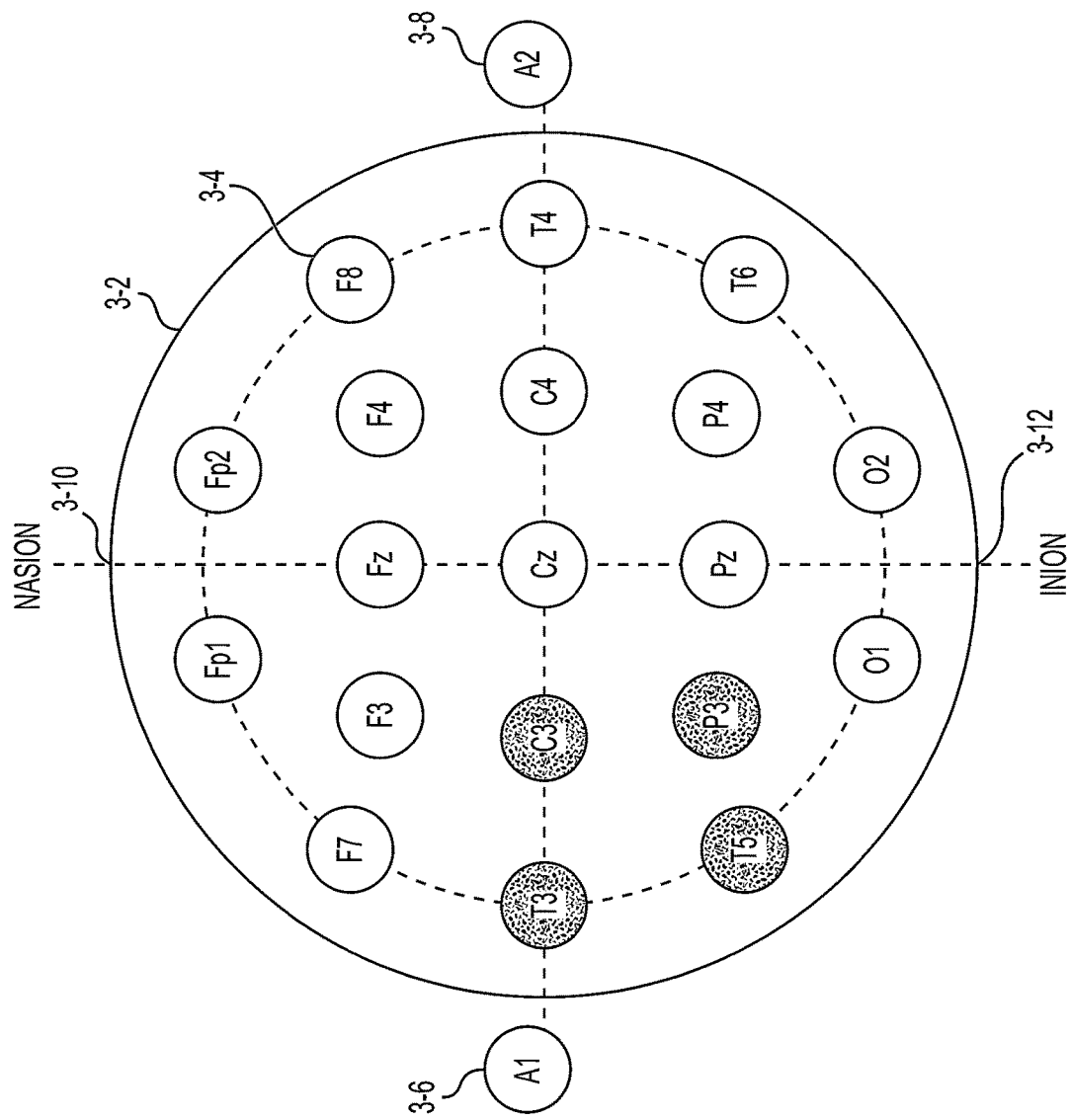
FIG. 3.20

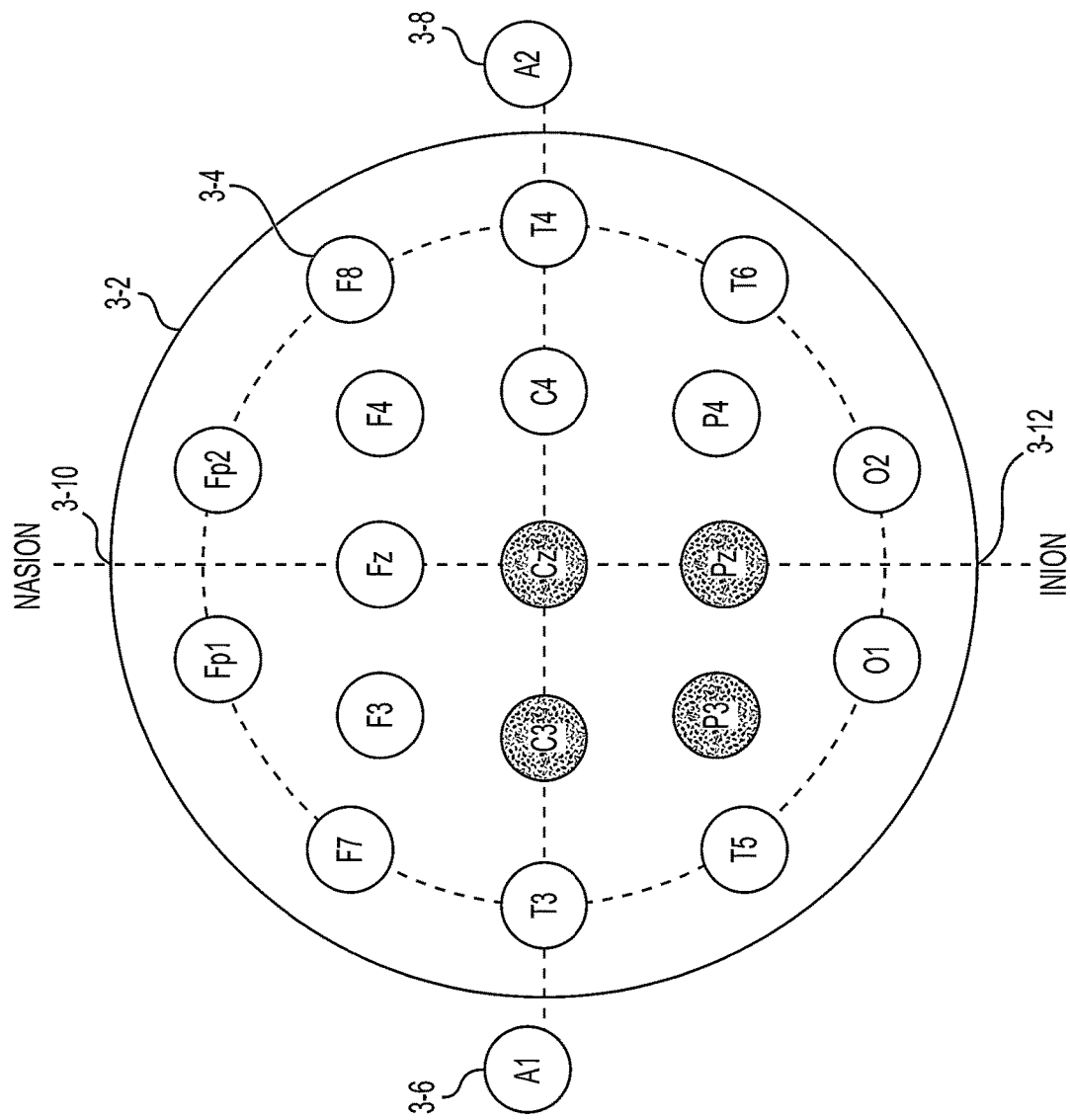
FIG. 3.21

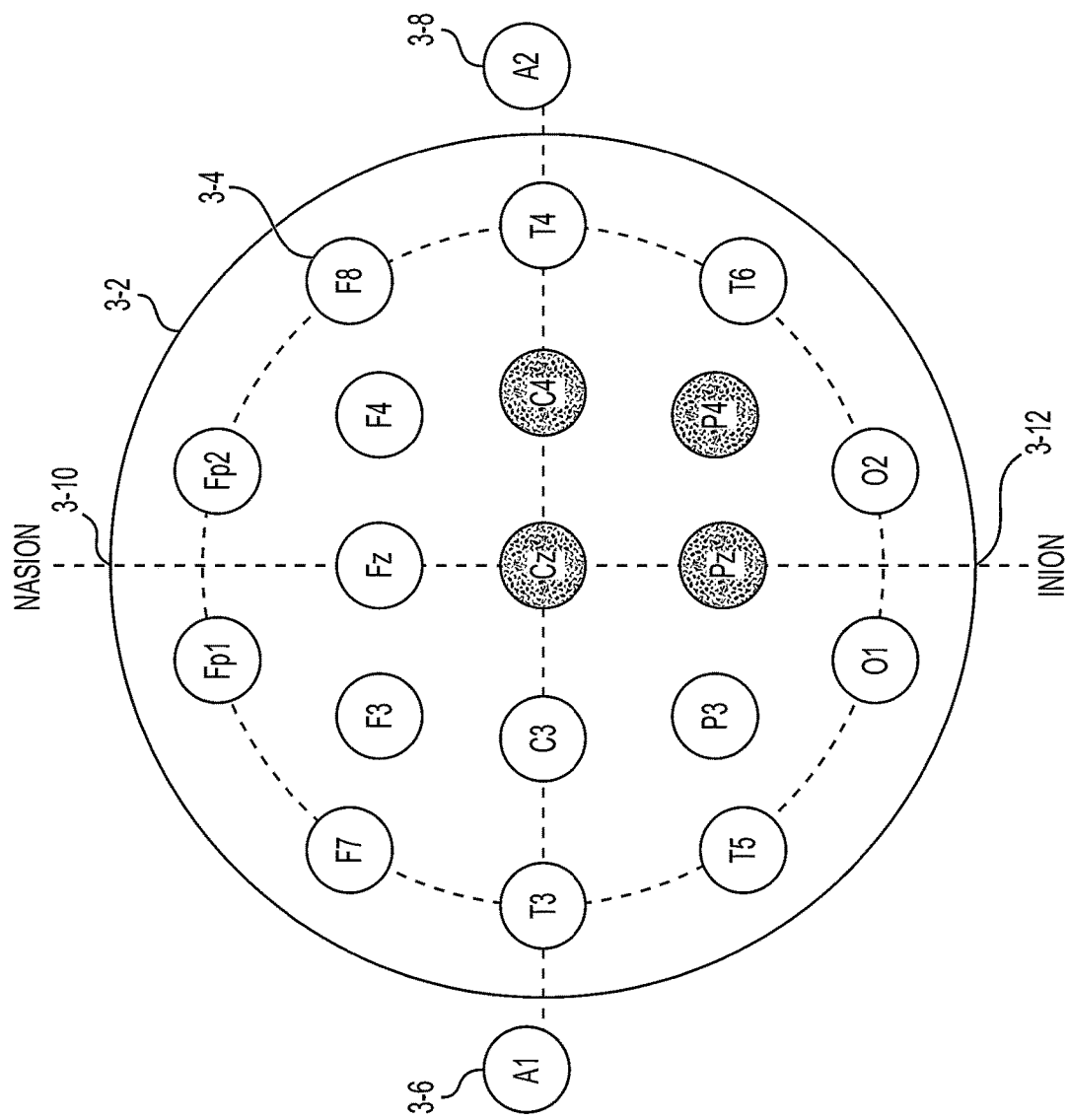
FIG. 3.22

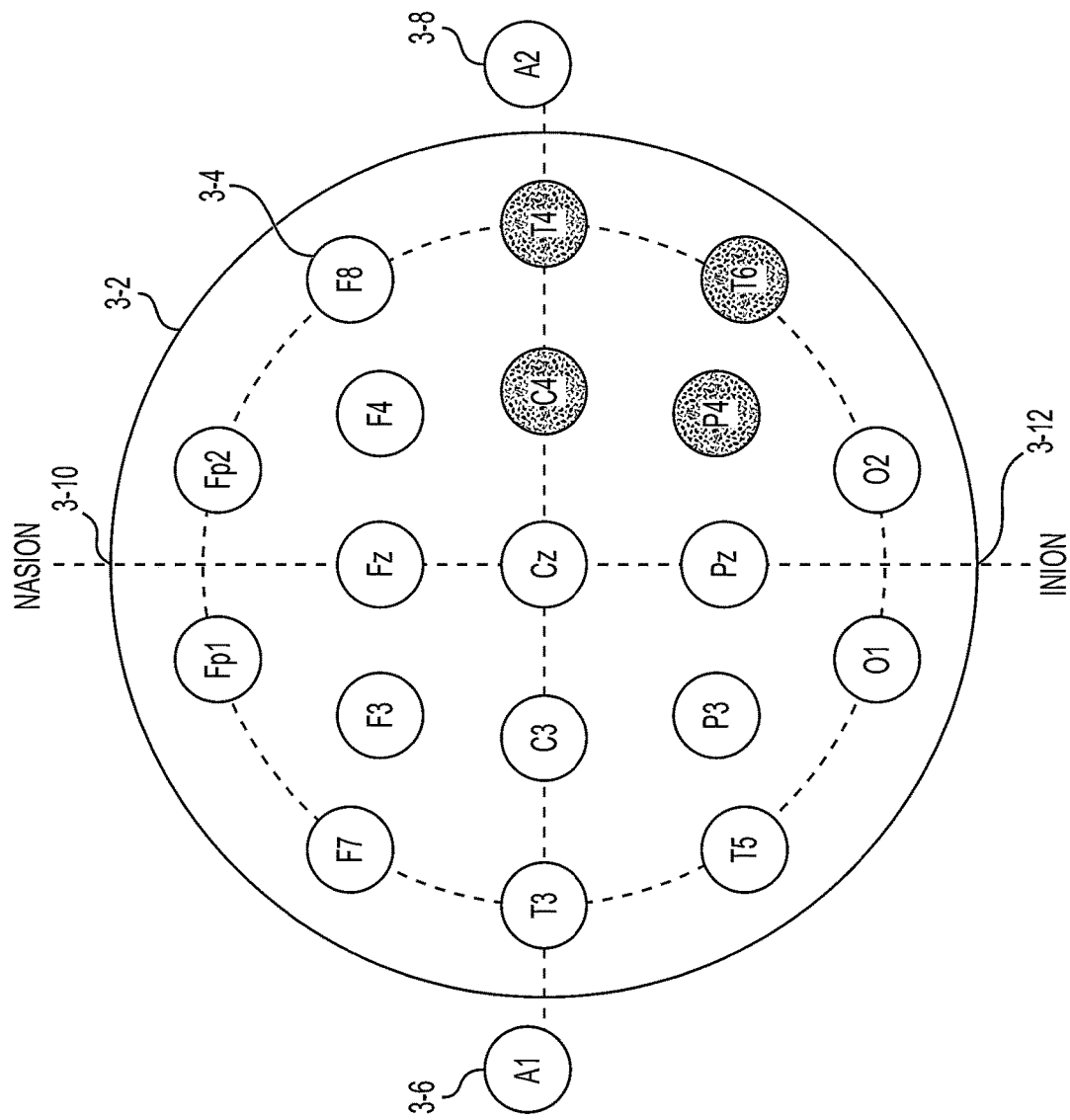
FIG. 3.23

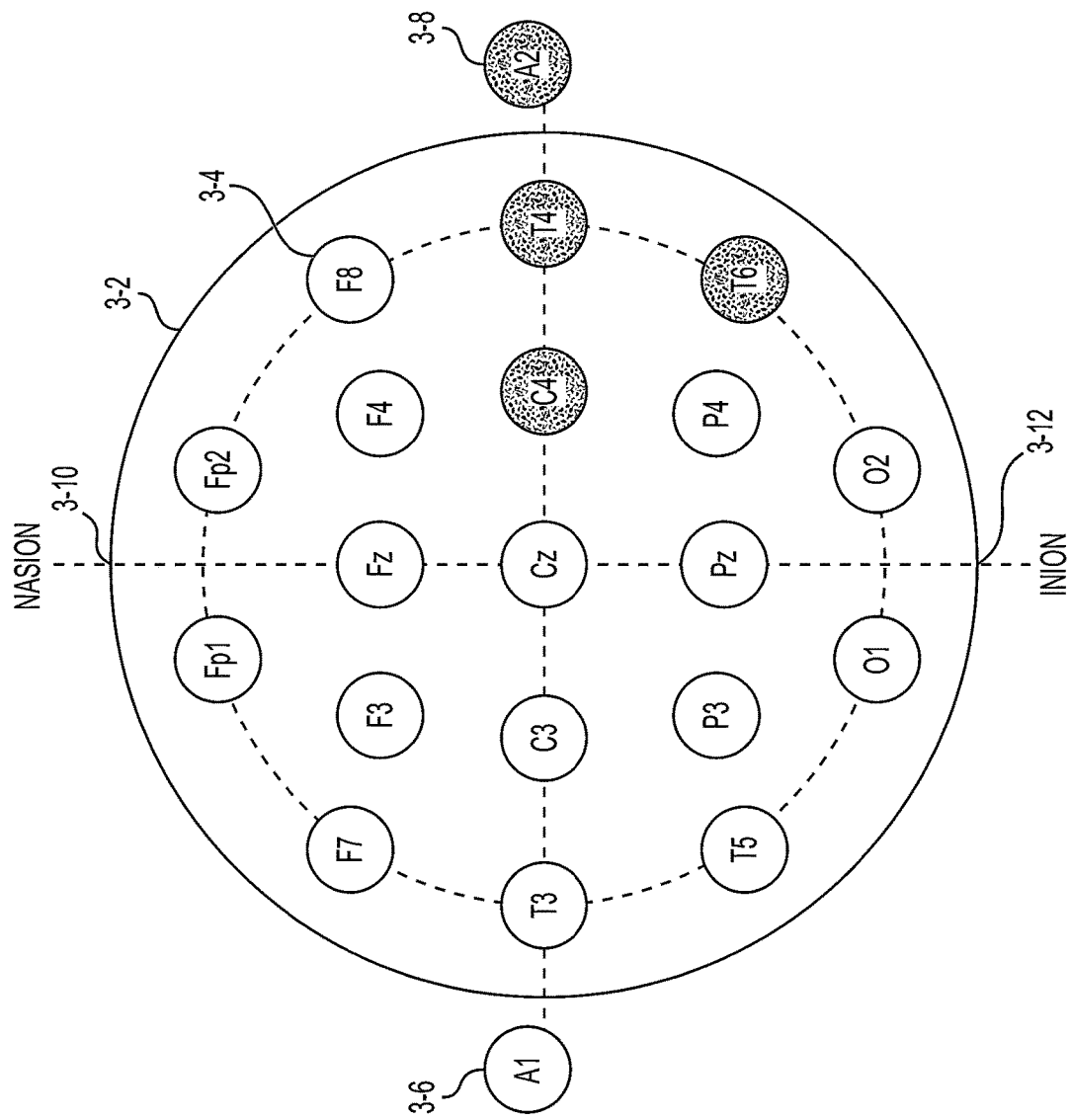
FIG. 3.24

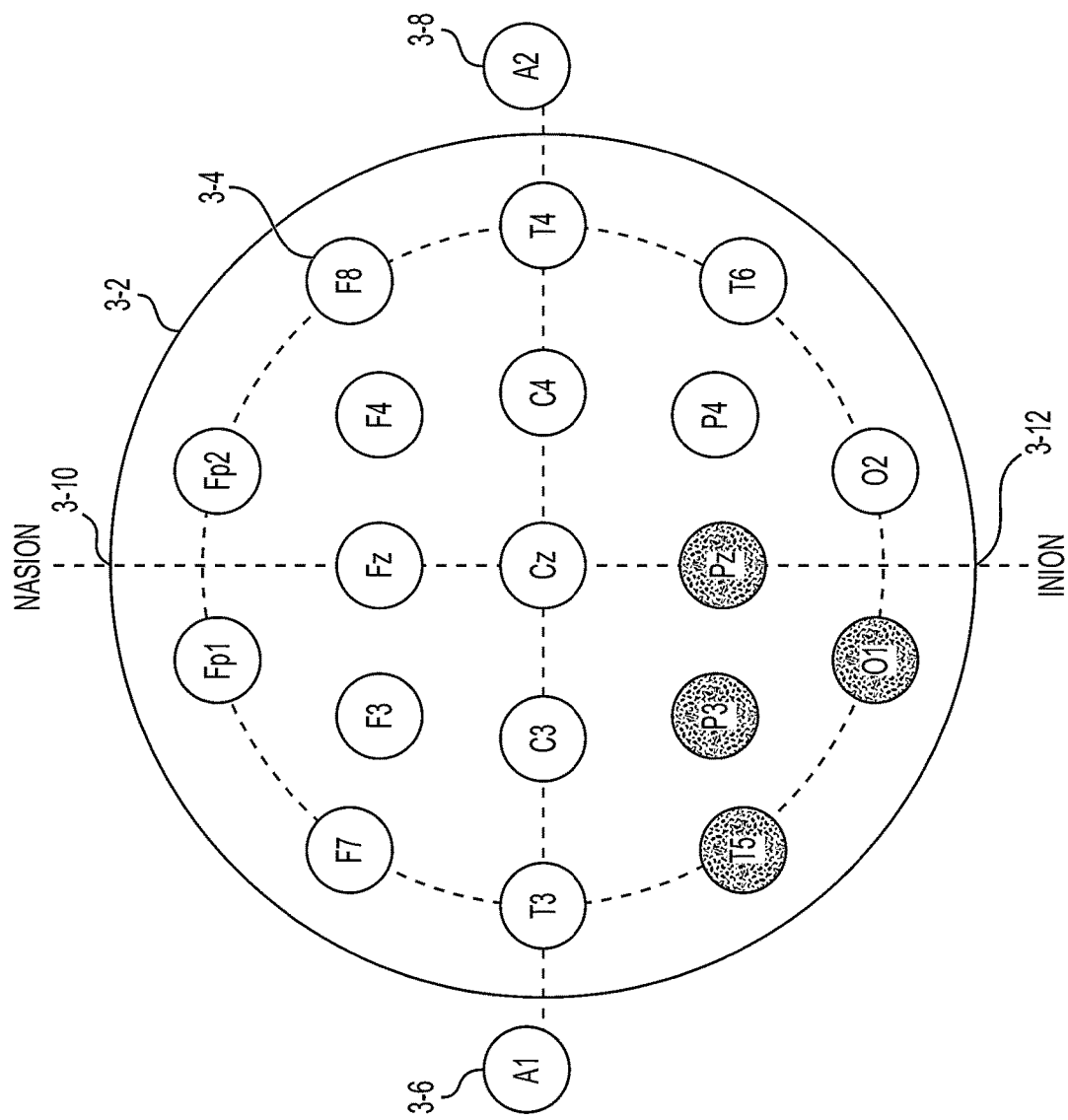
FIG. 3.25

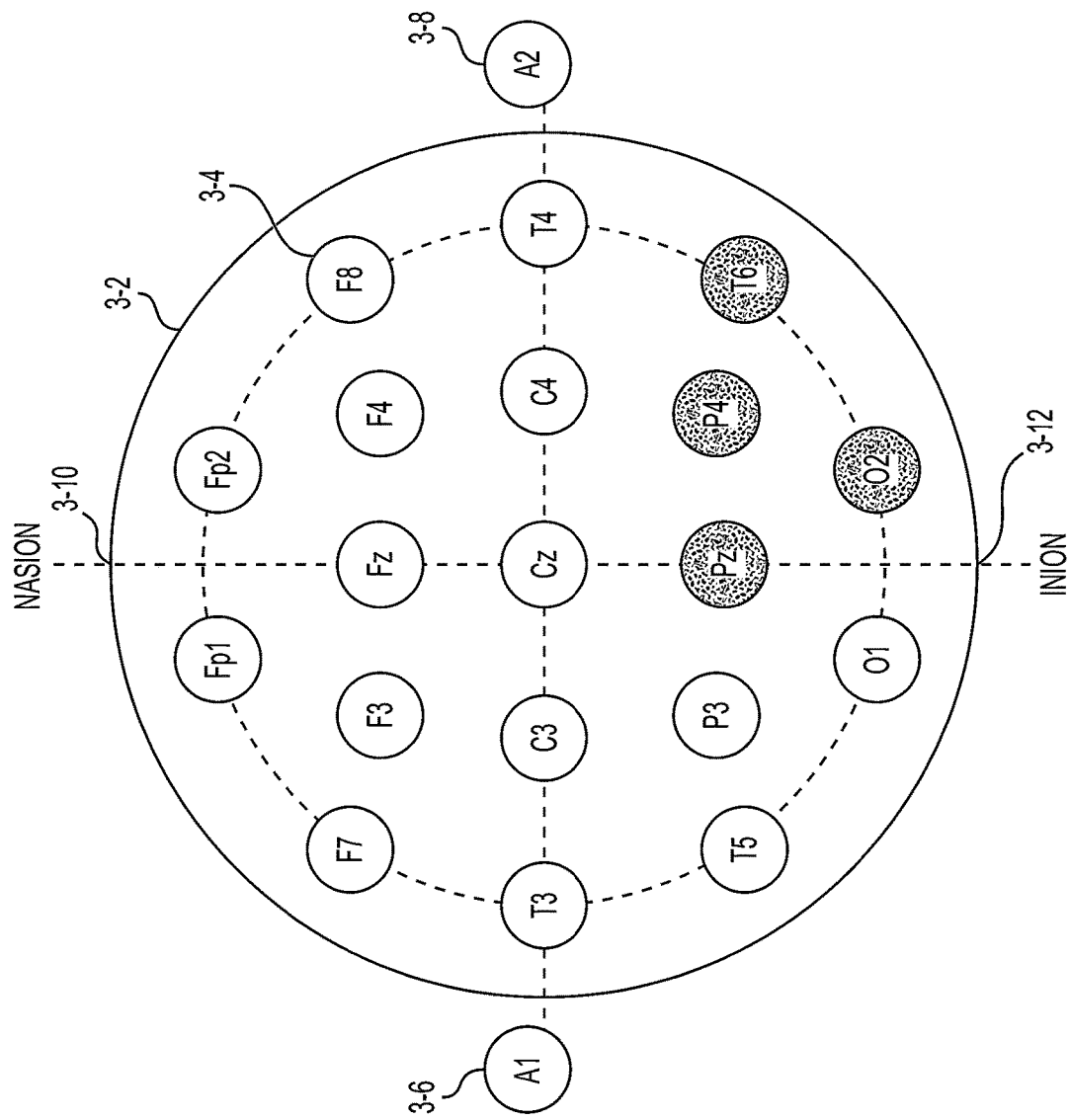
FIG. 3.26

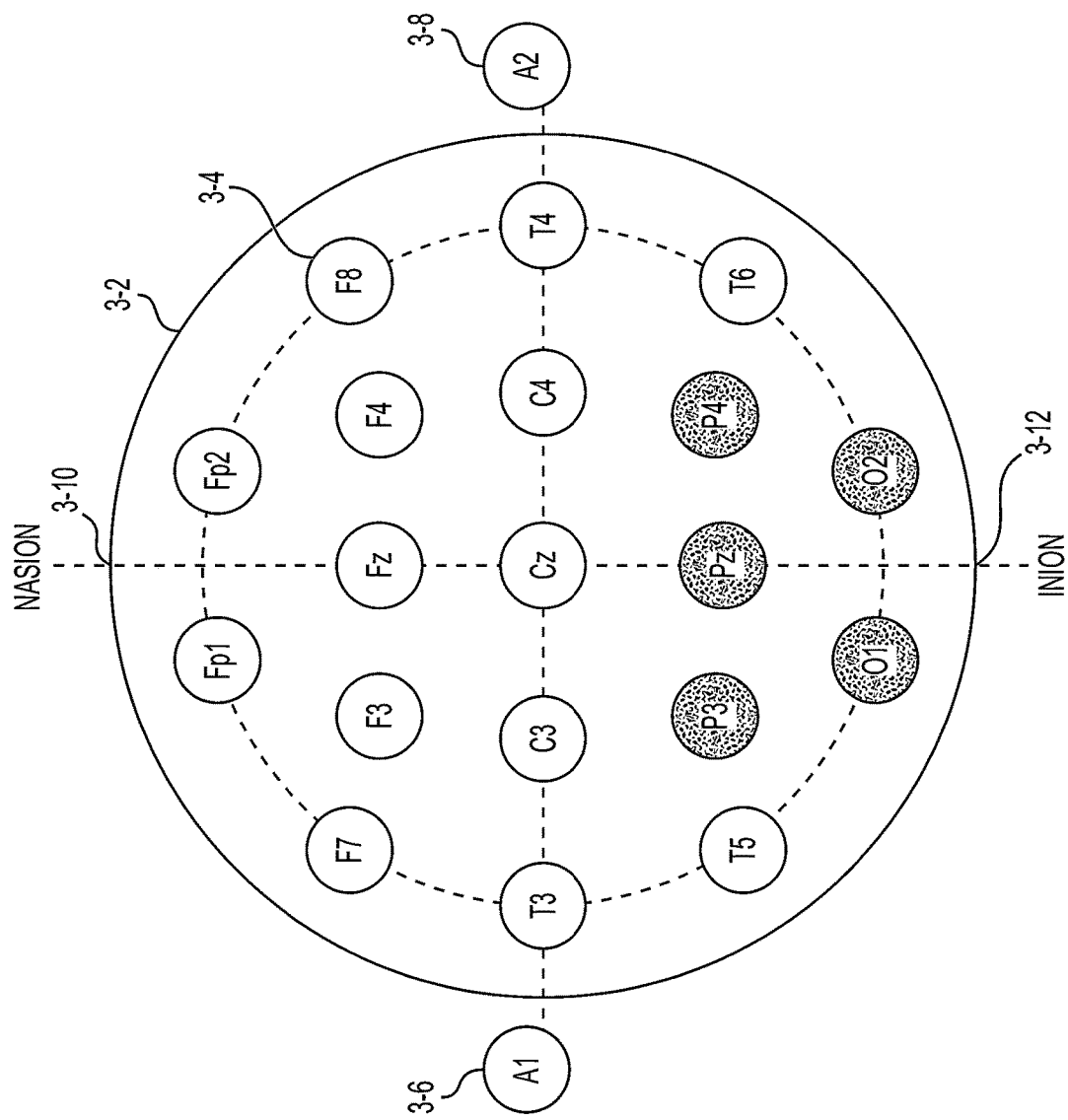
FIG. 3.27

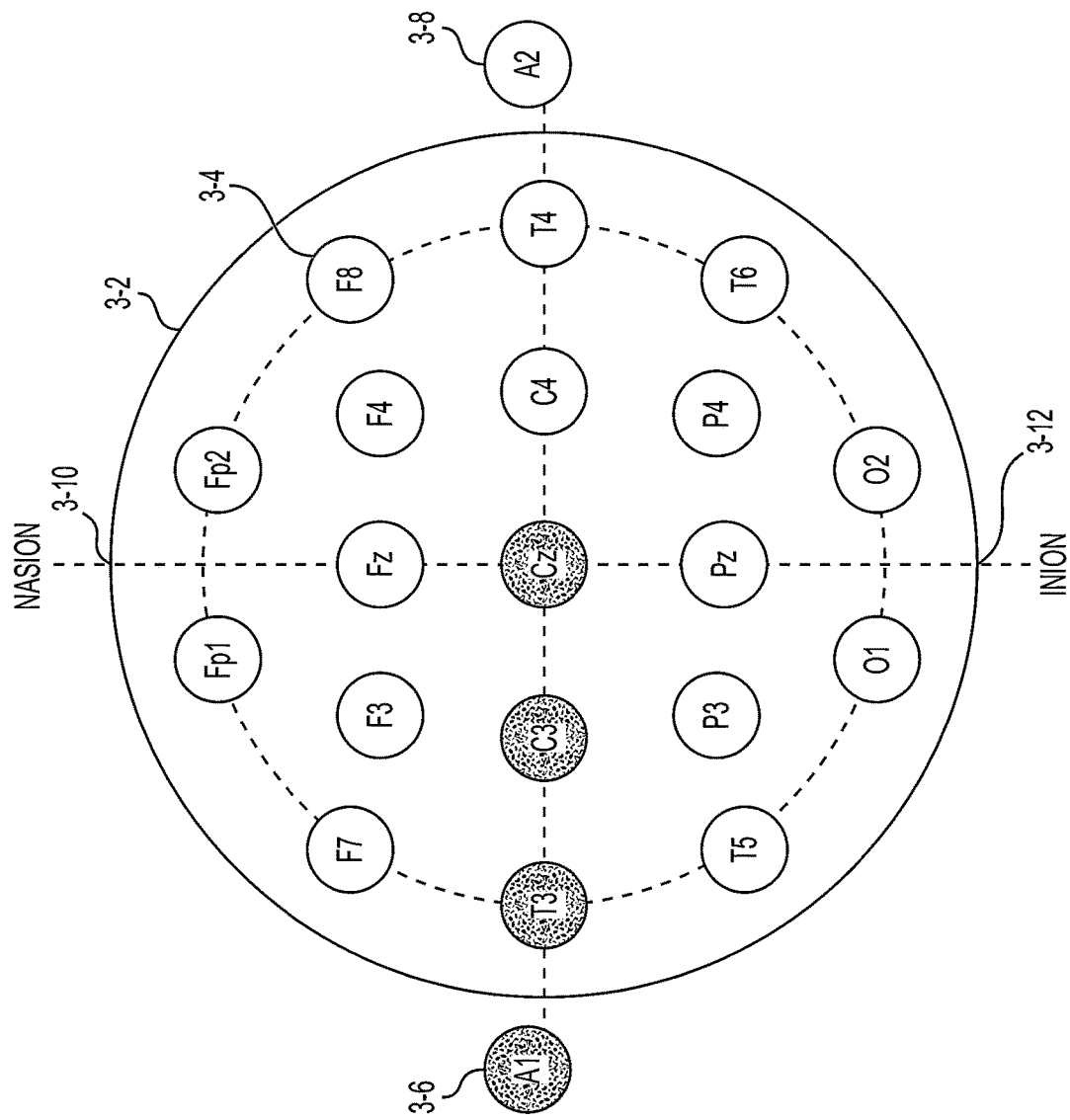
FIG. 3.28

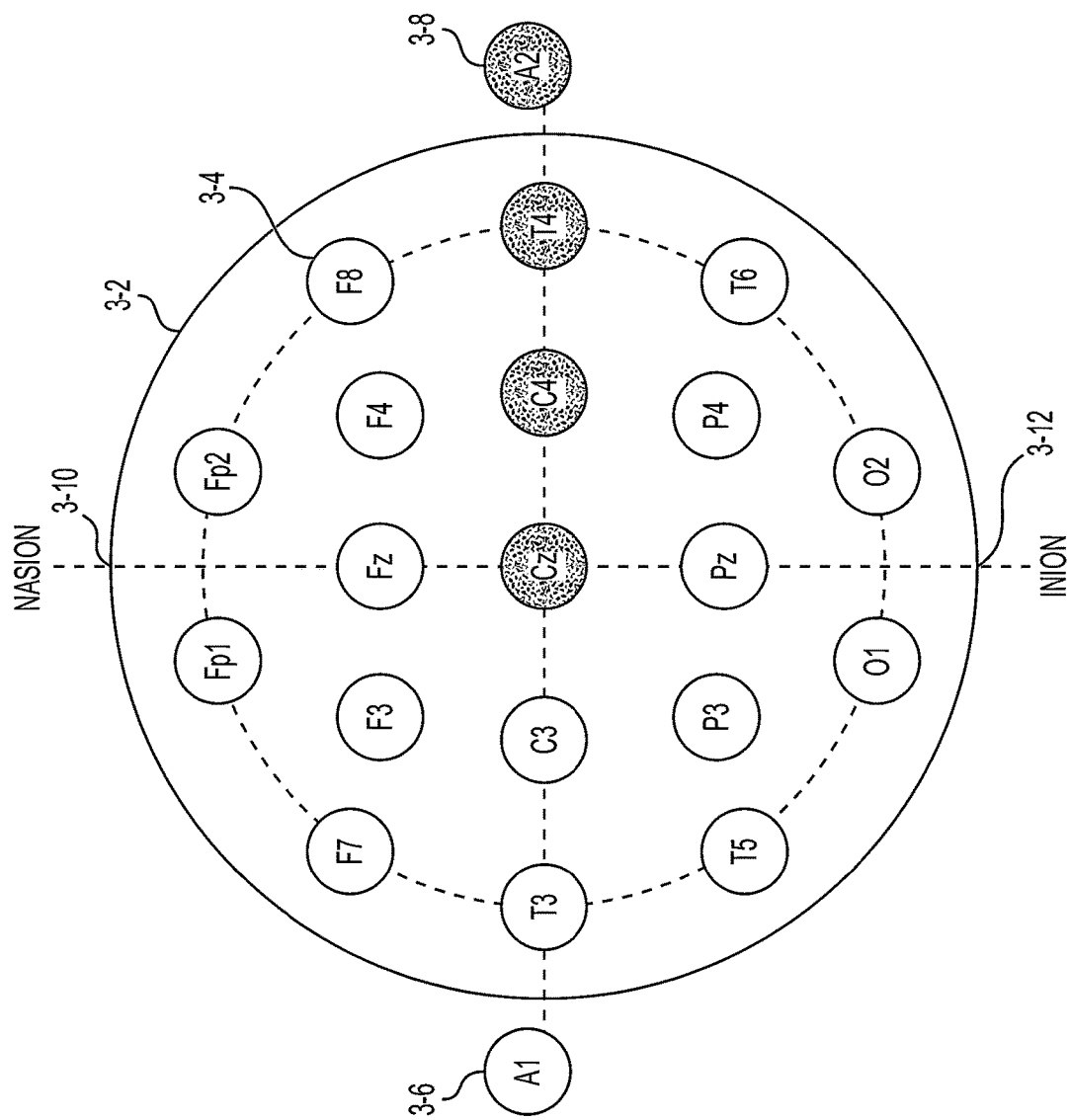
FIG. 3.29

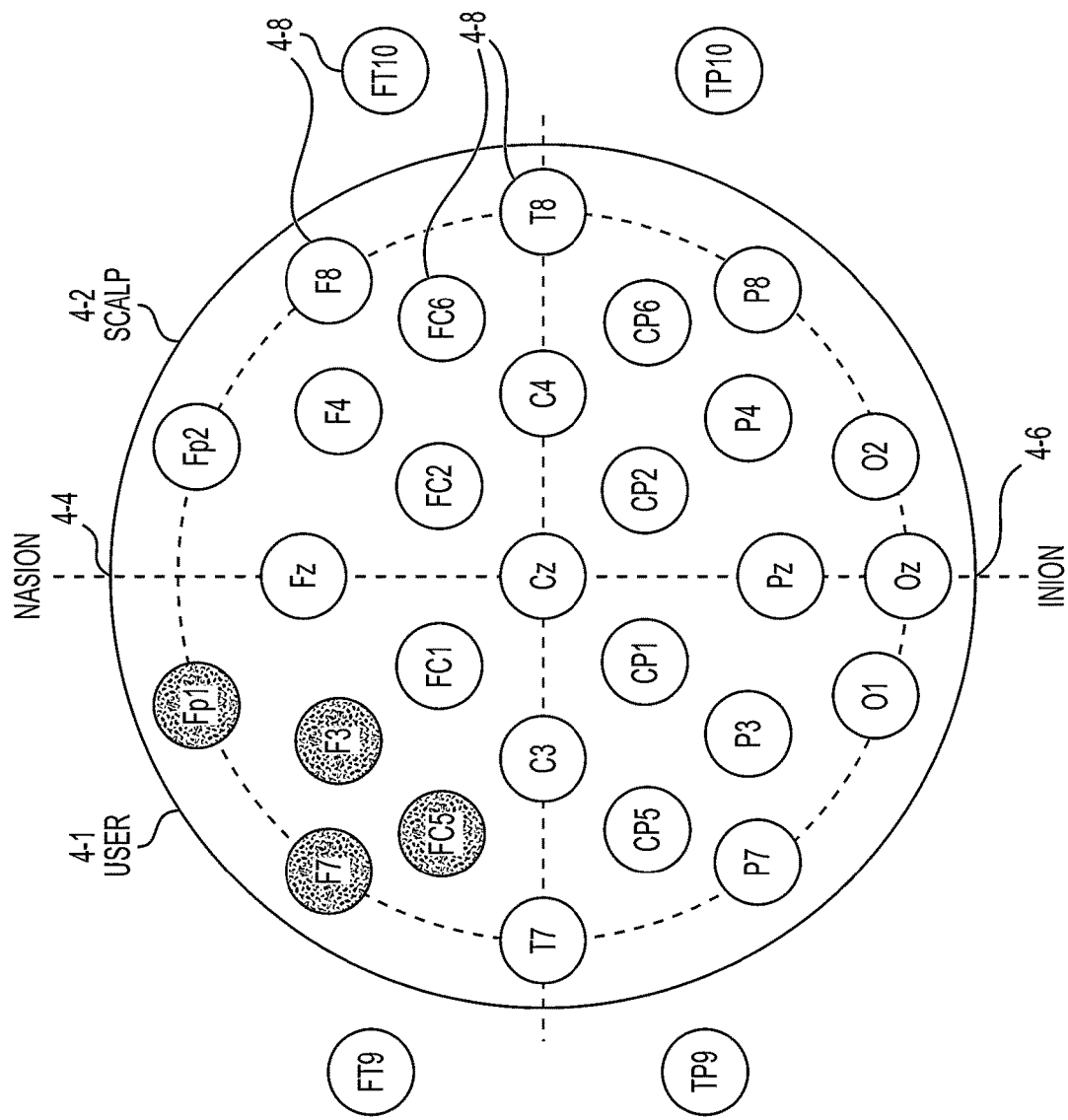
FIG. 4.1

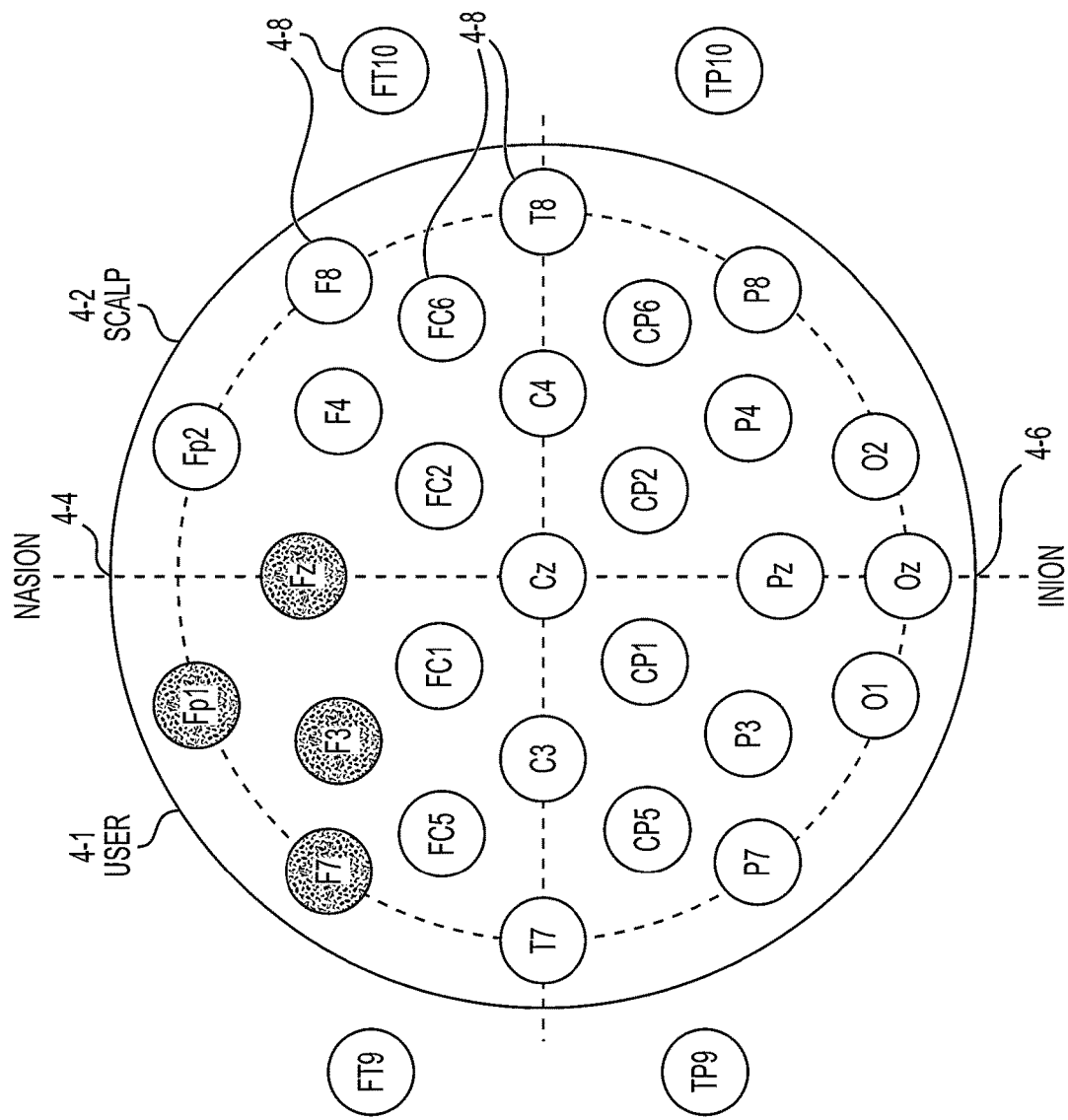
FIG. 4.2

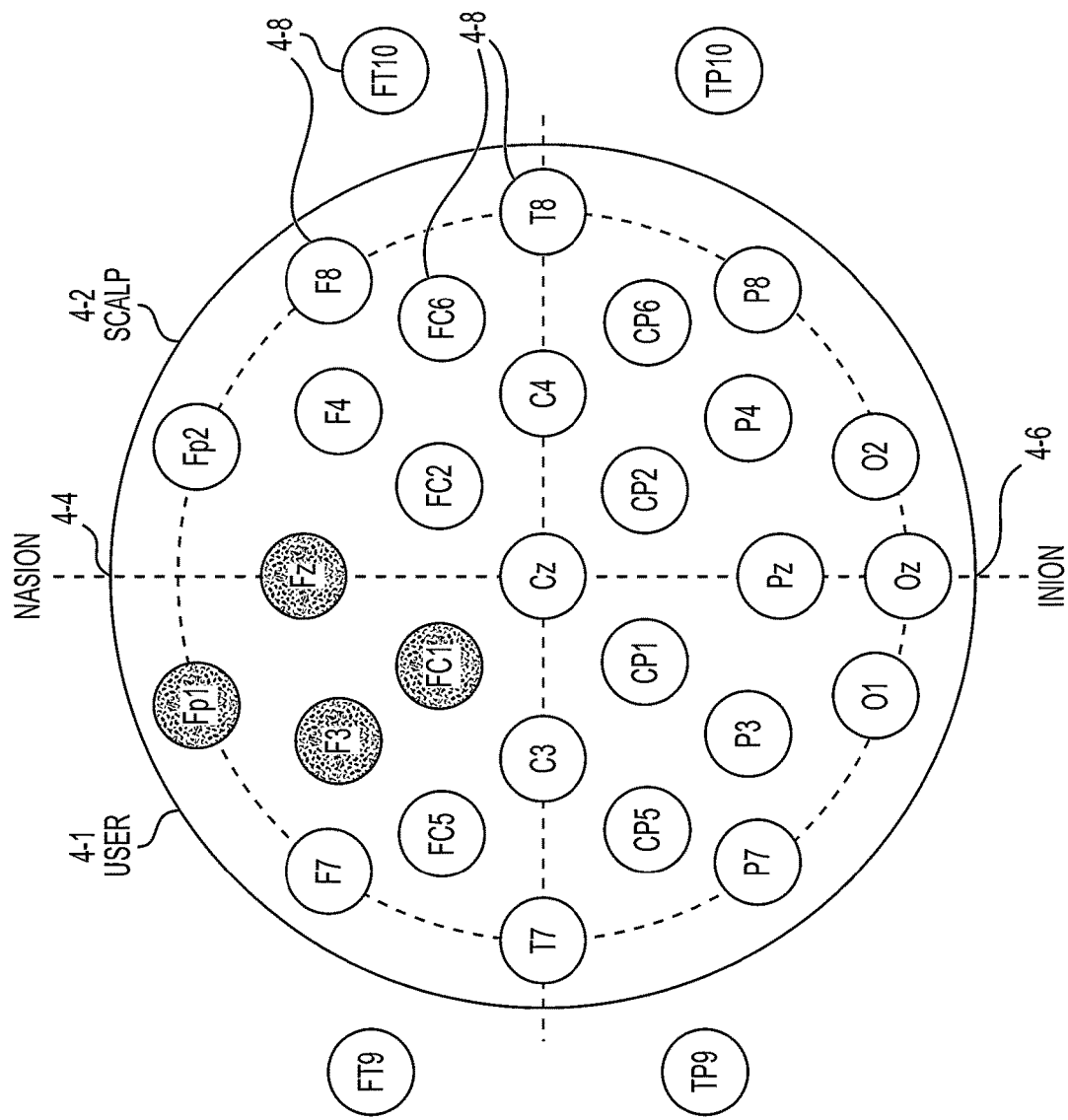
FIG. 4.3

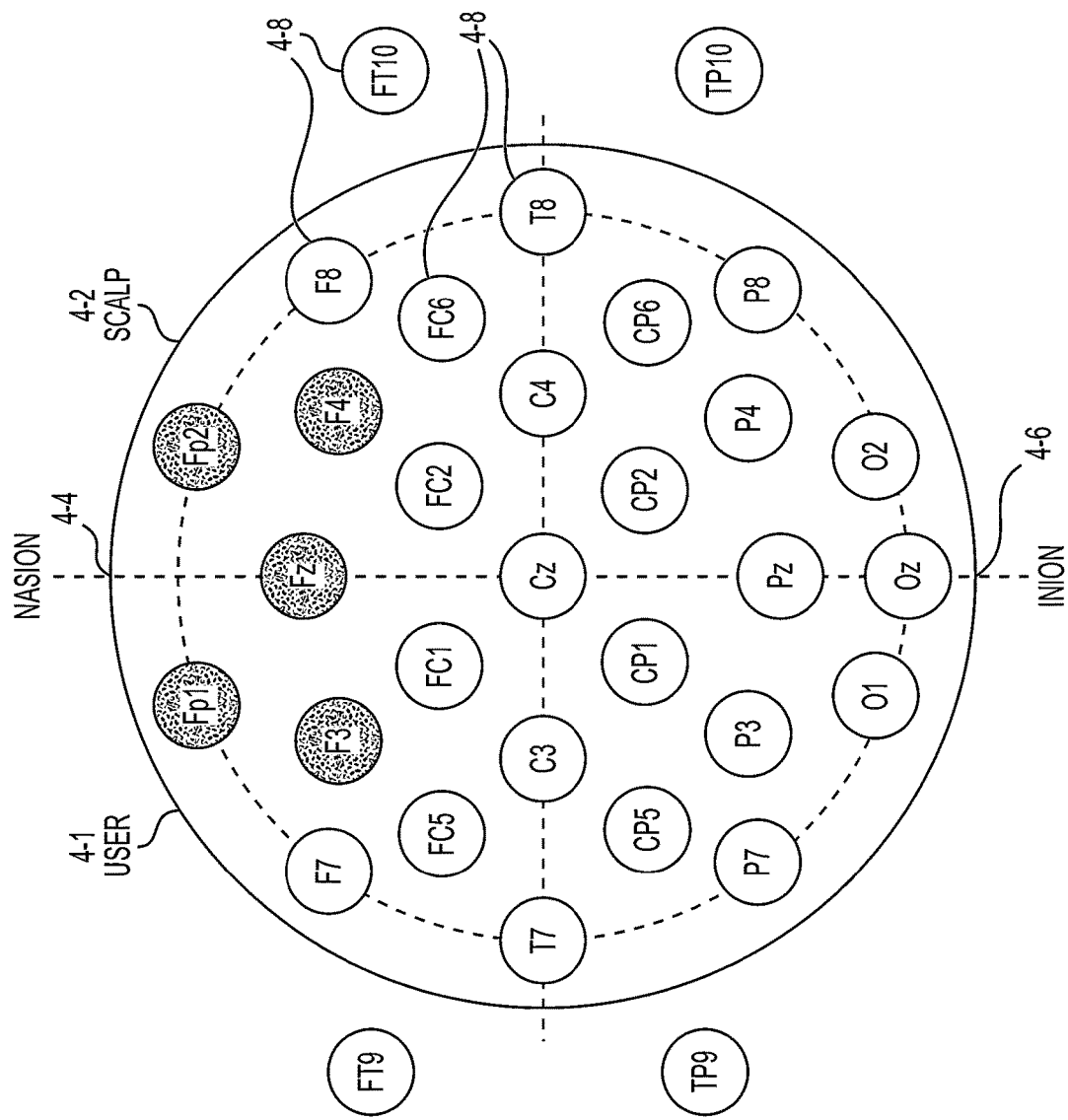
FIG. 4.4

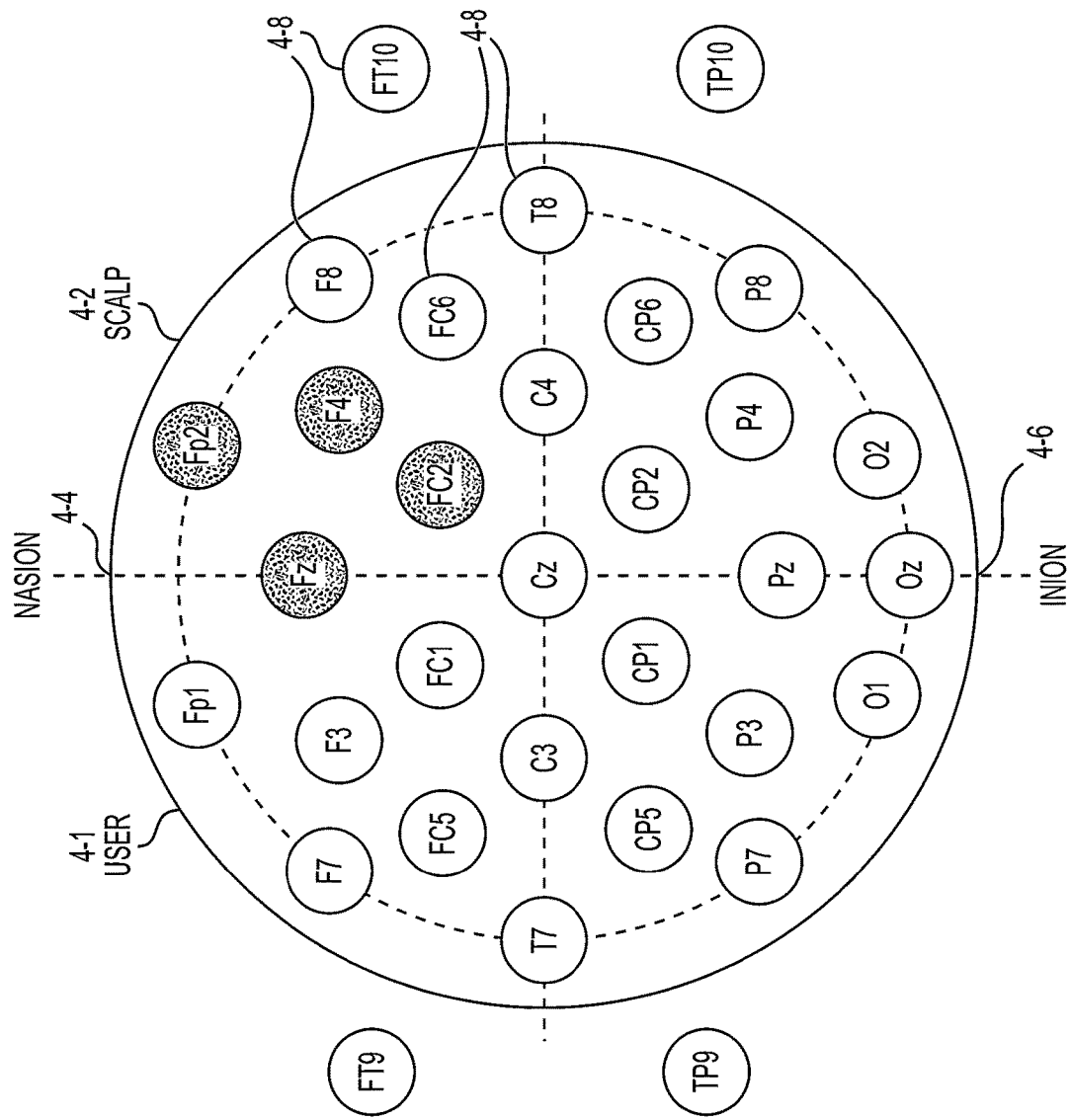
FIG. 4.5

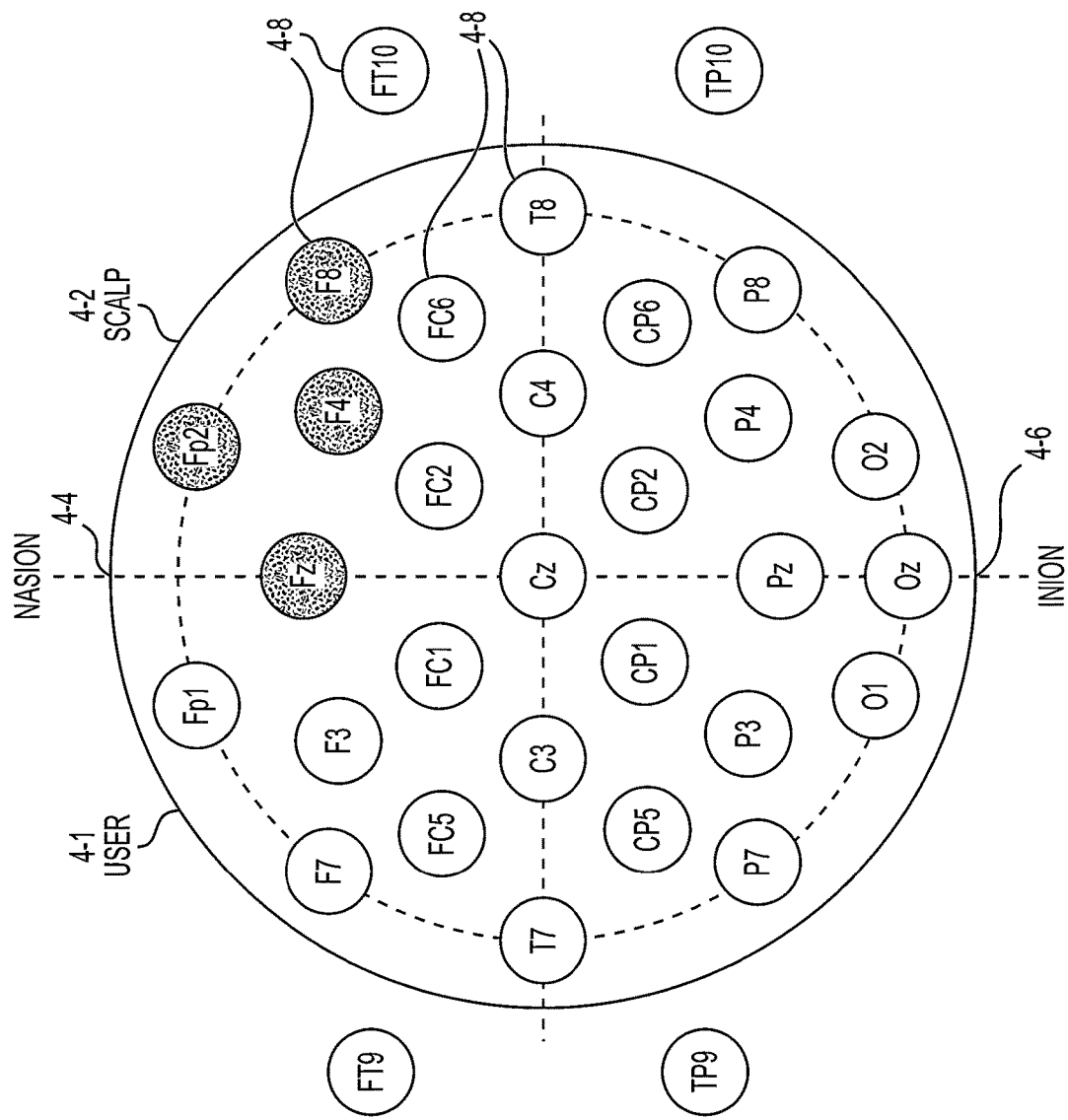
FIG. 4.6

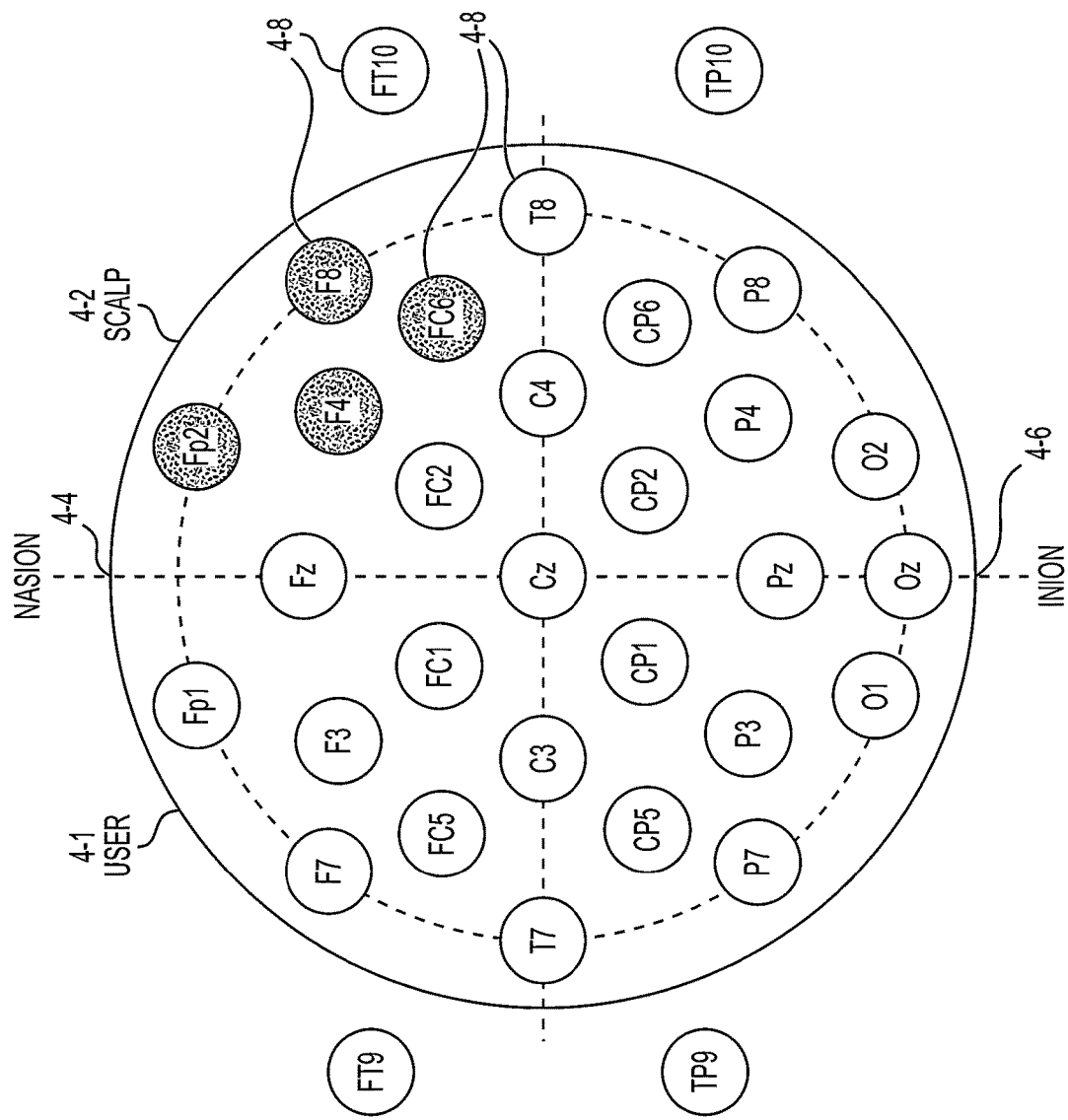
FIG. 4.7

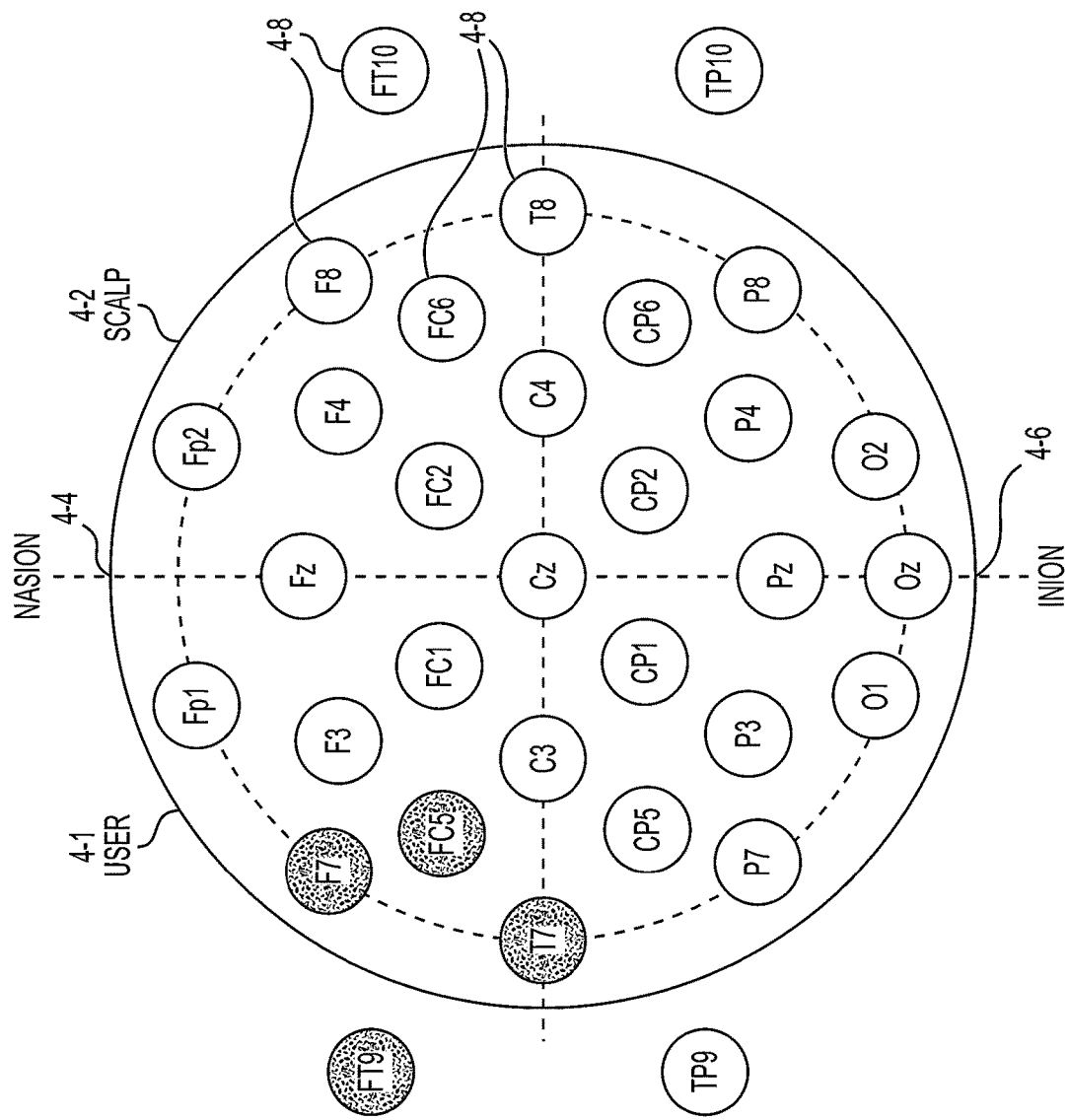
FIG. 4.8

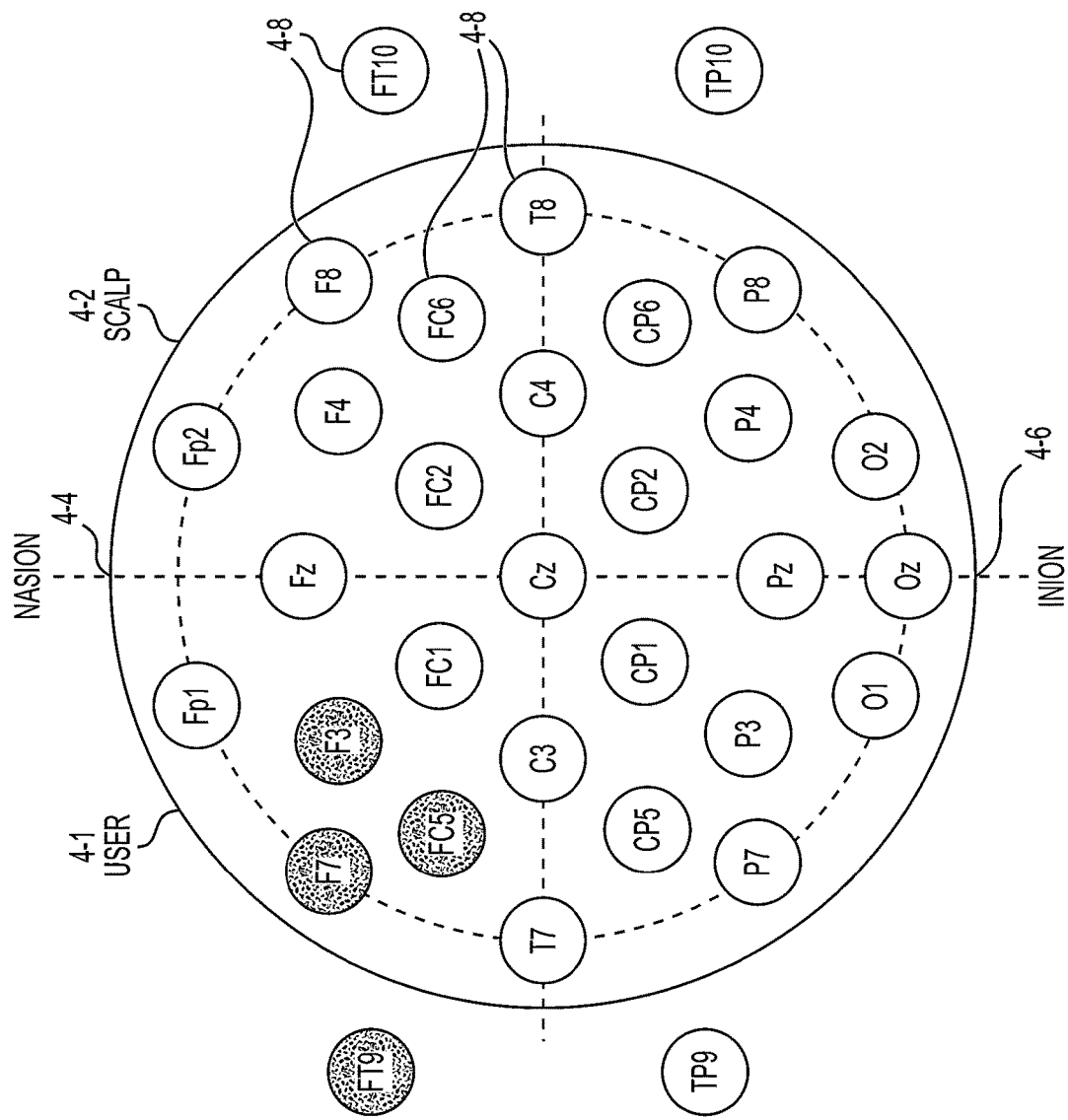
FIG. 4.9

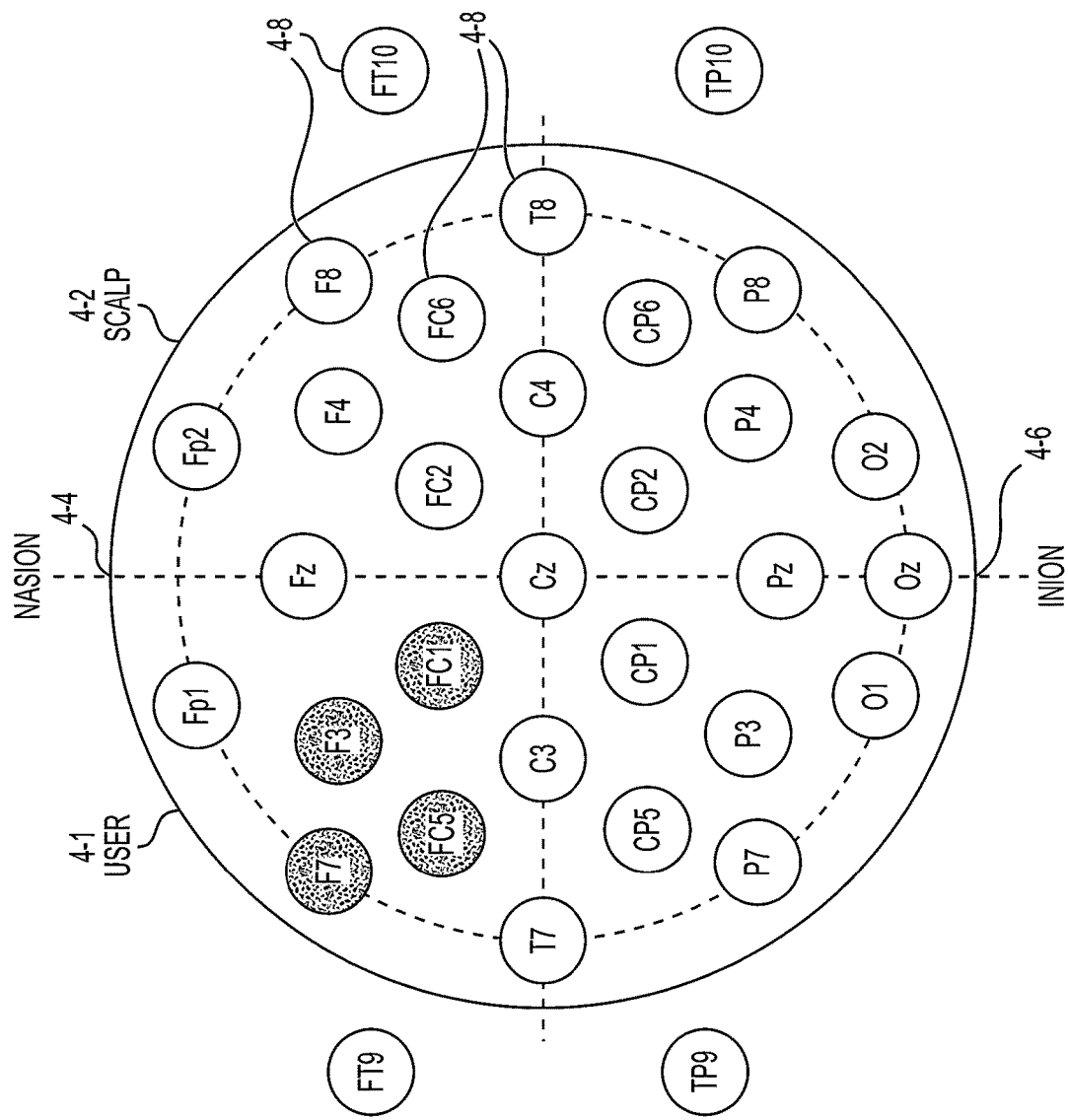
FIG. 4.10

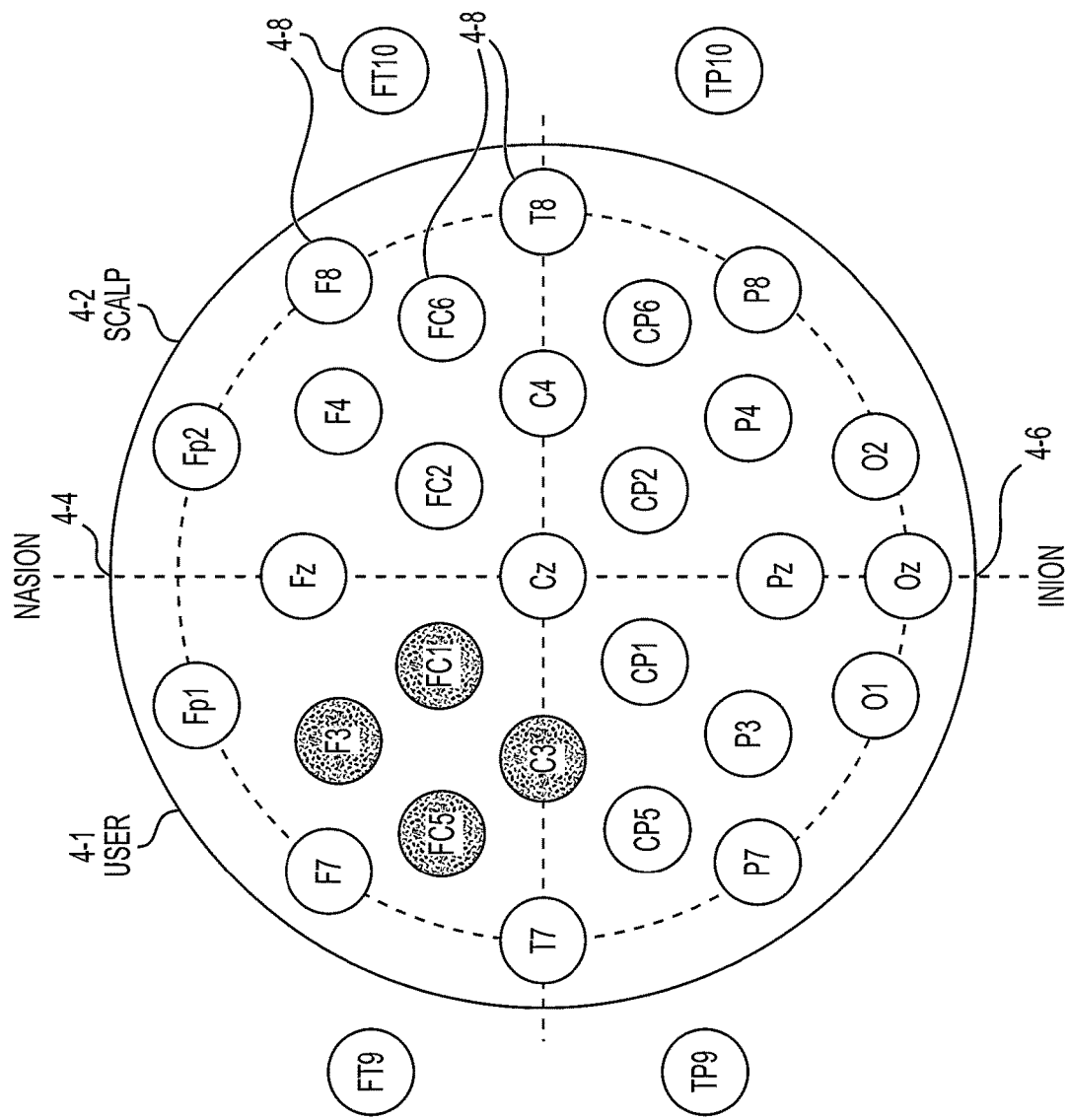
FIG. 4.11

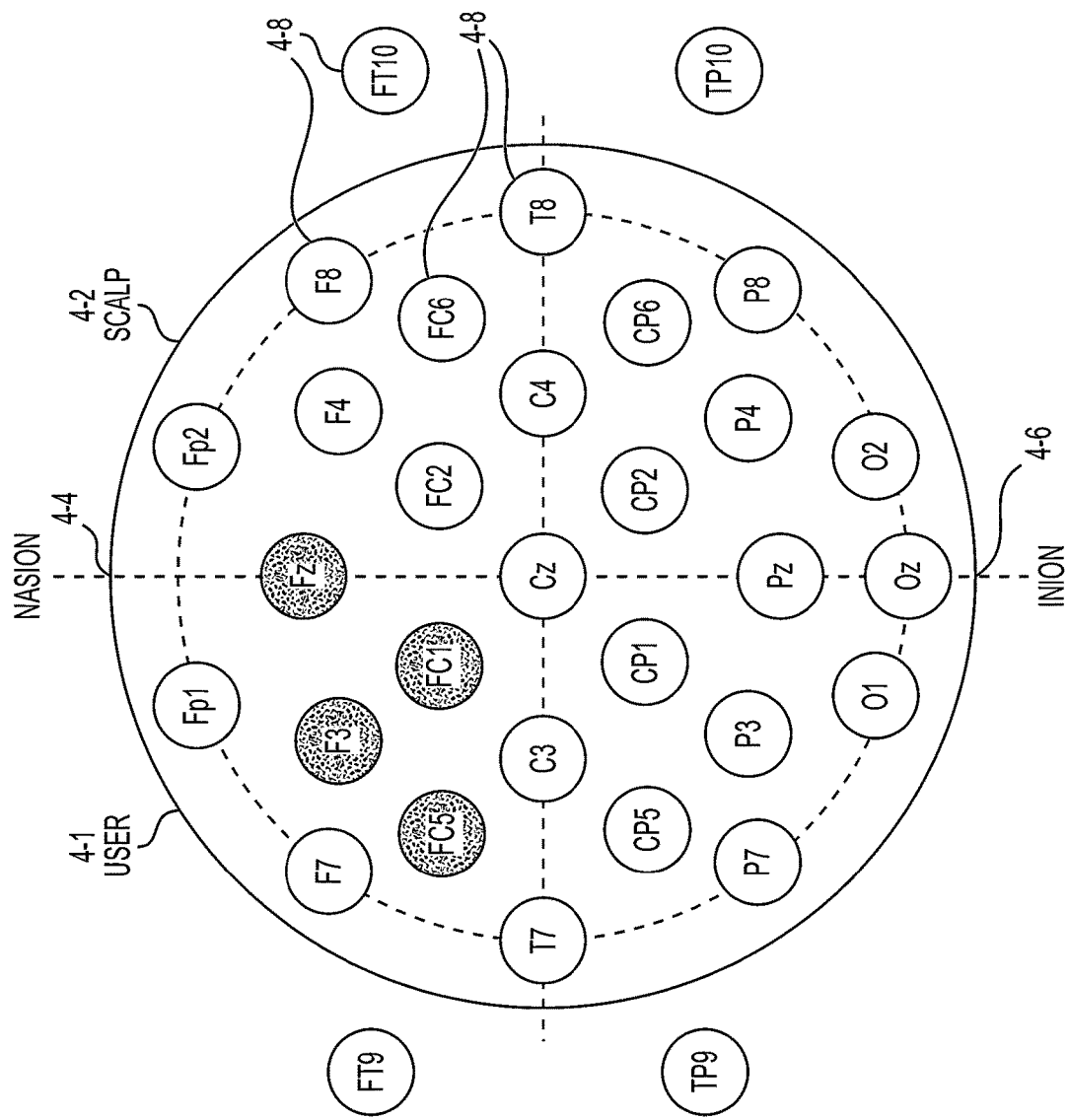
FIG. 4.12

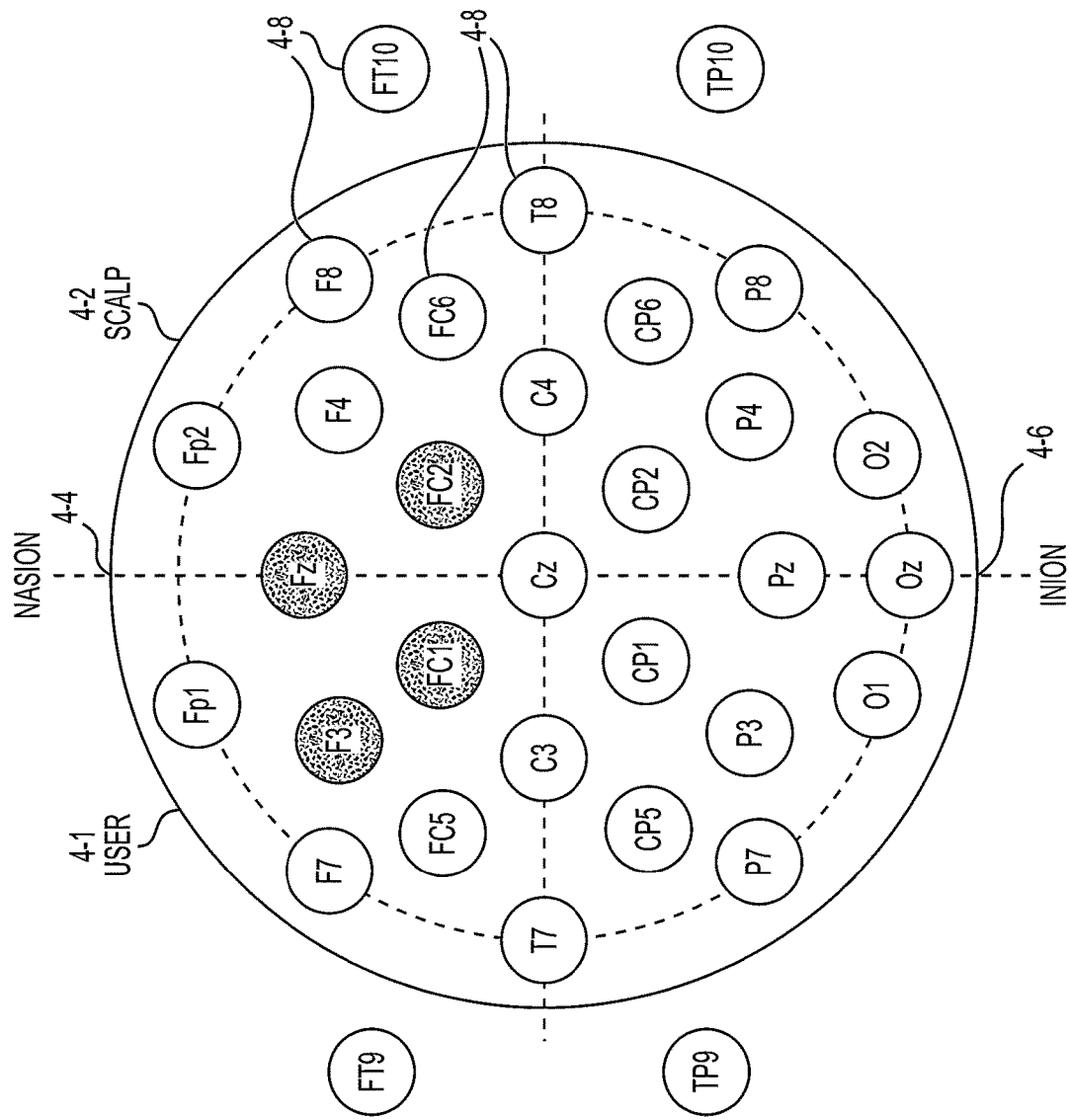
FIG. 4.13

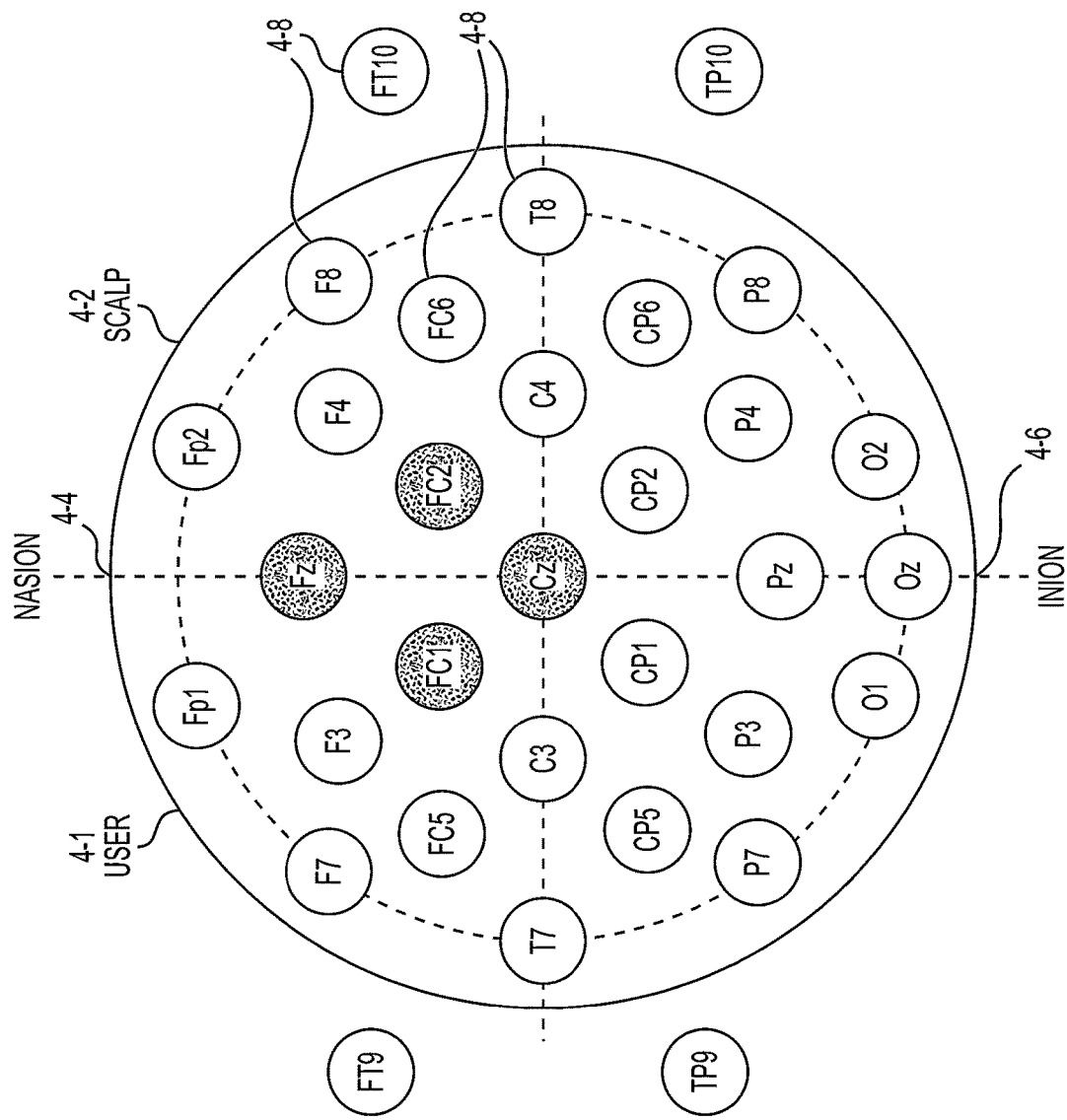
FIG. 4.14

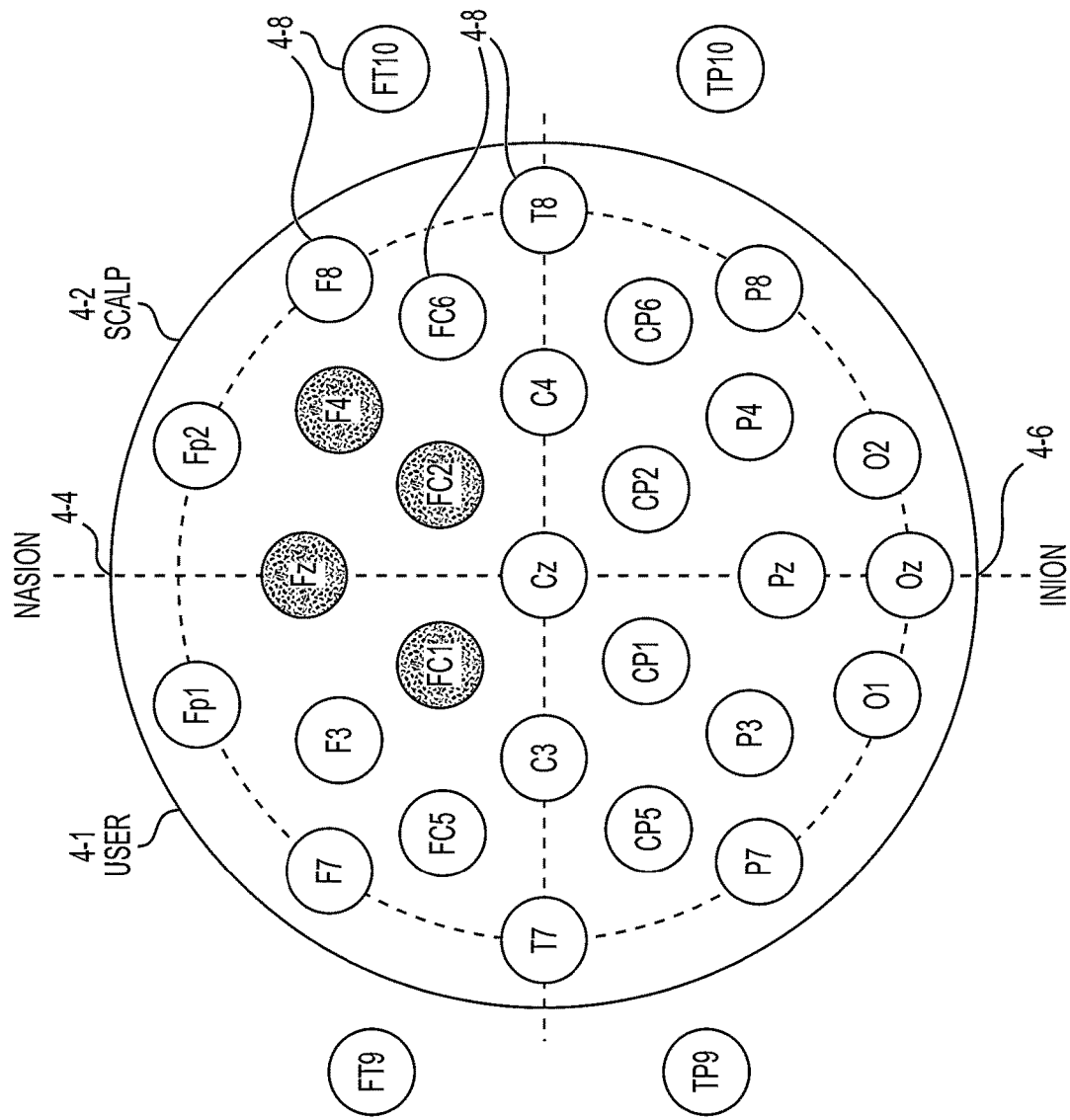
FIG. 4.15

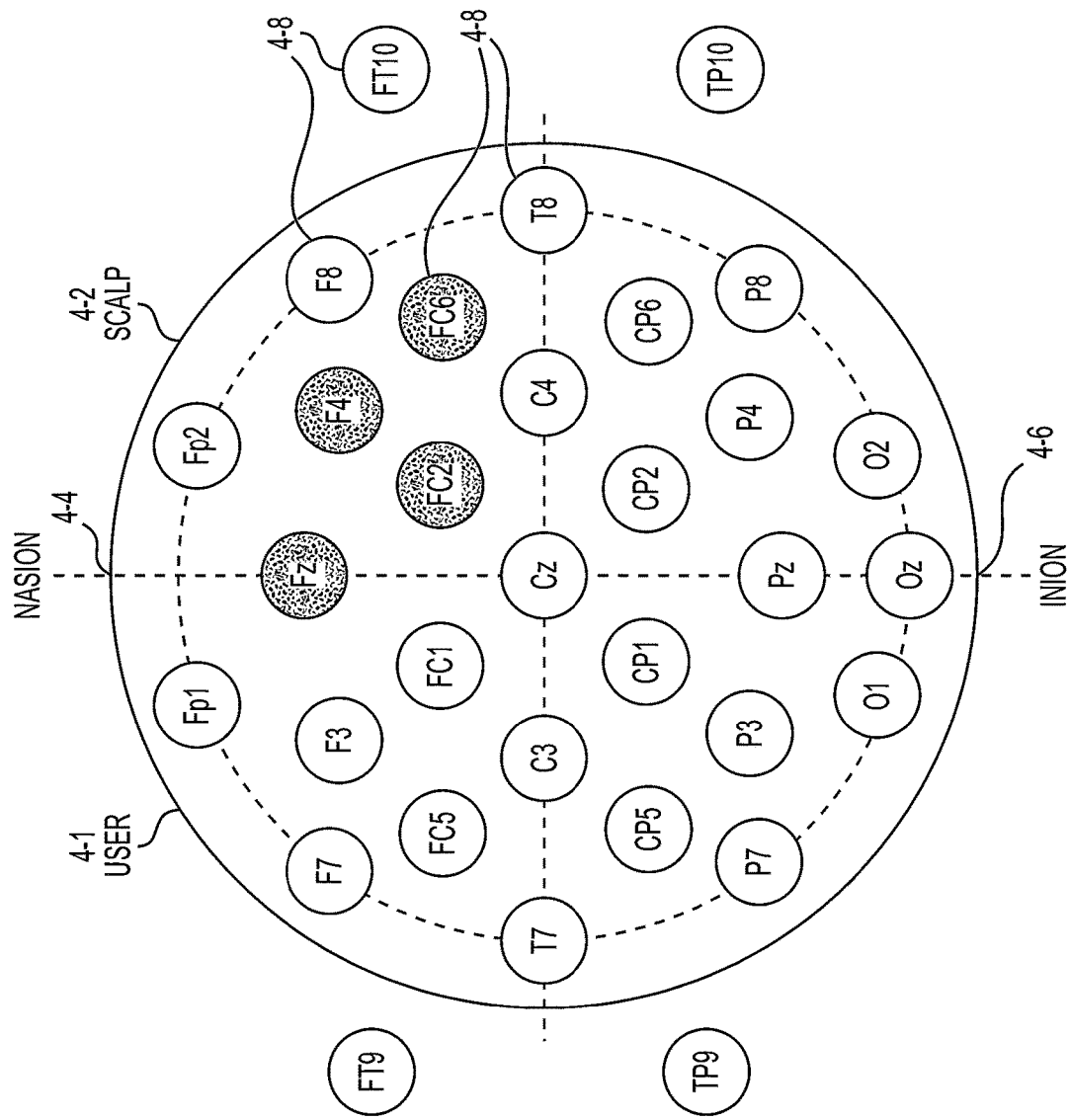
FIG. 4.16

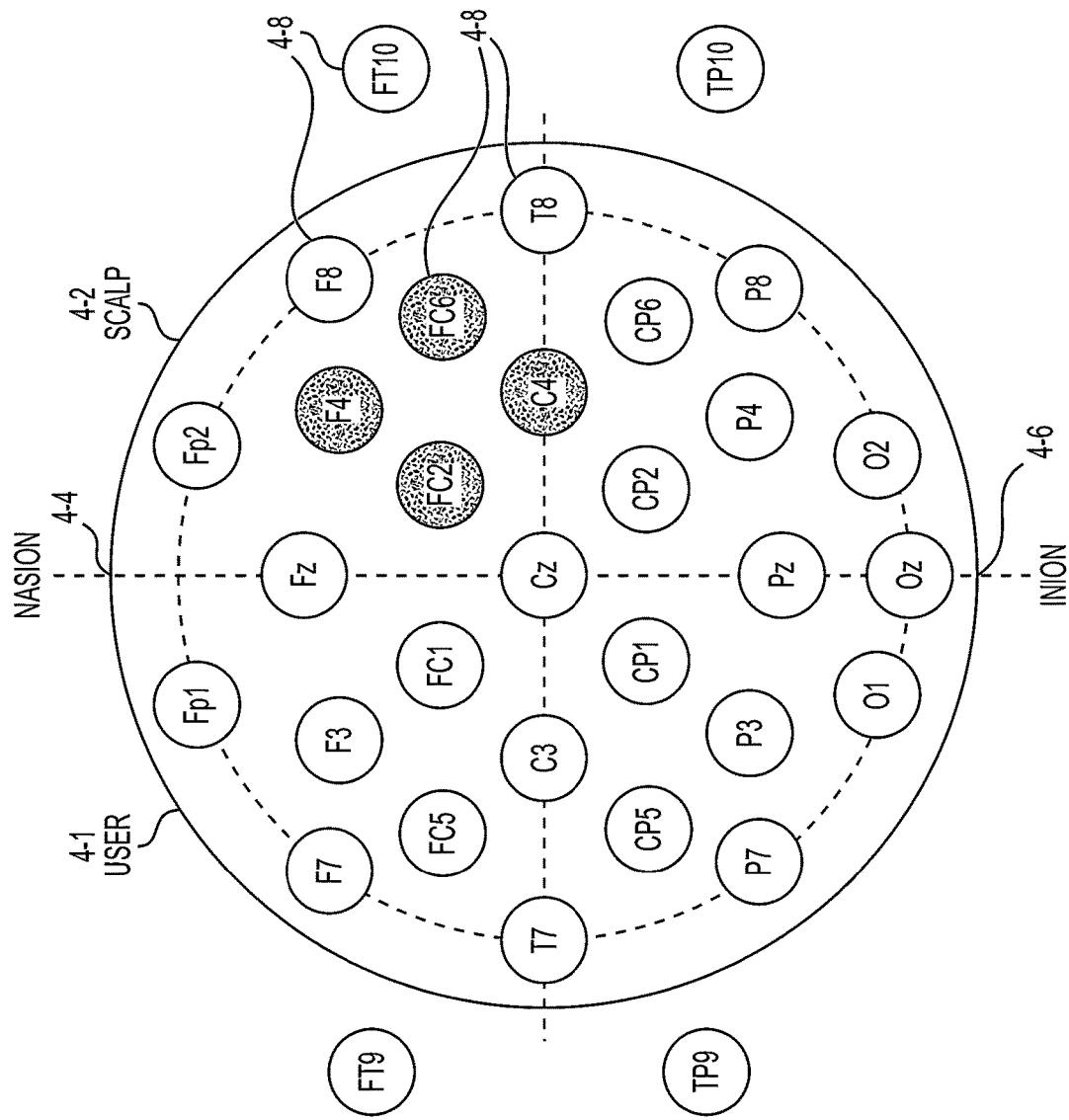
FIG. 4.17

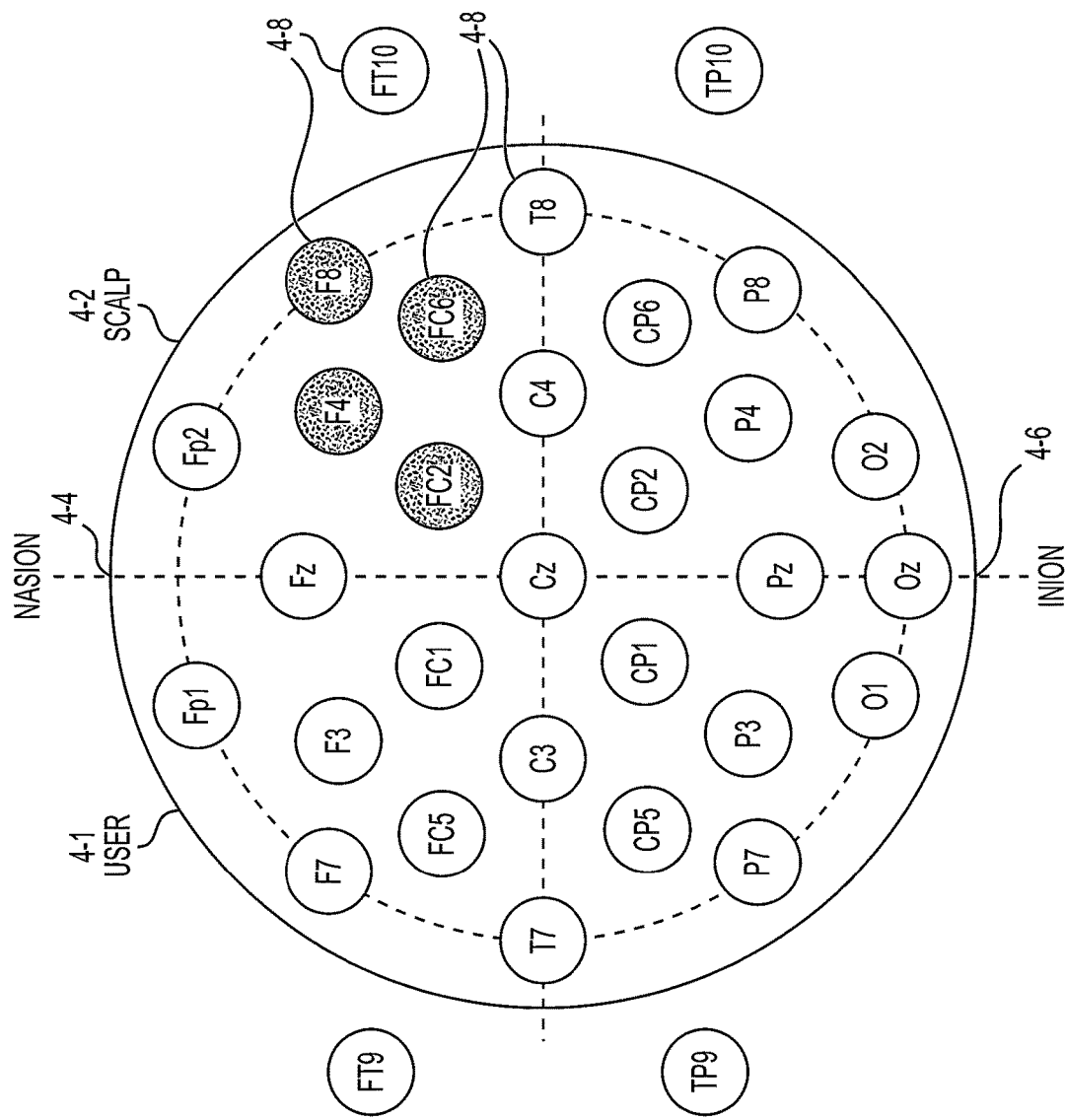
FIG. 4.18

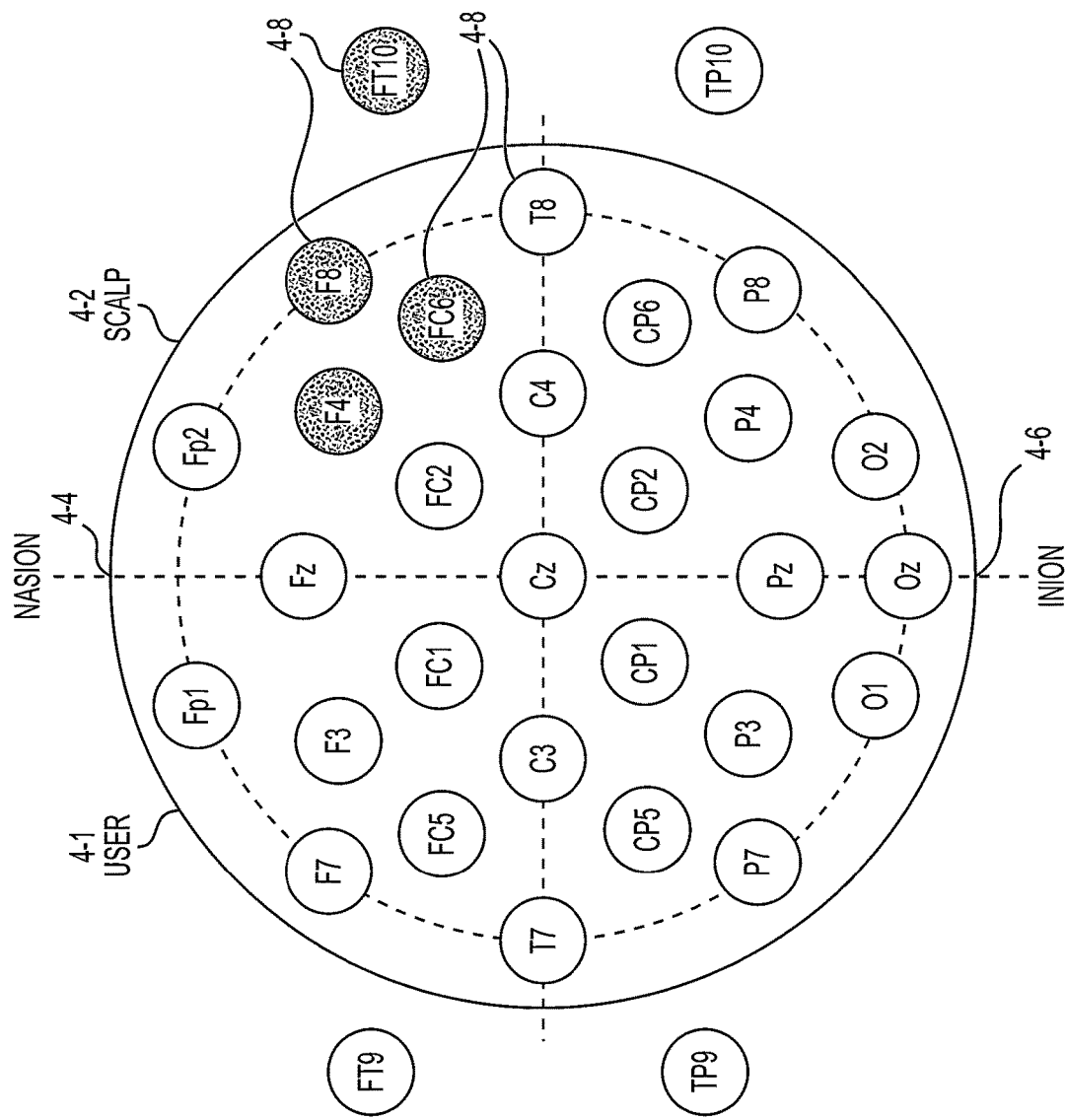
FIG. 4.19

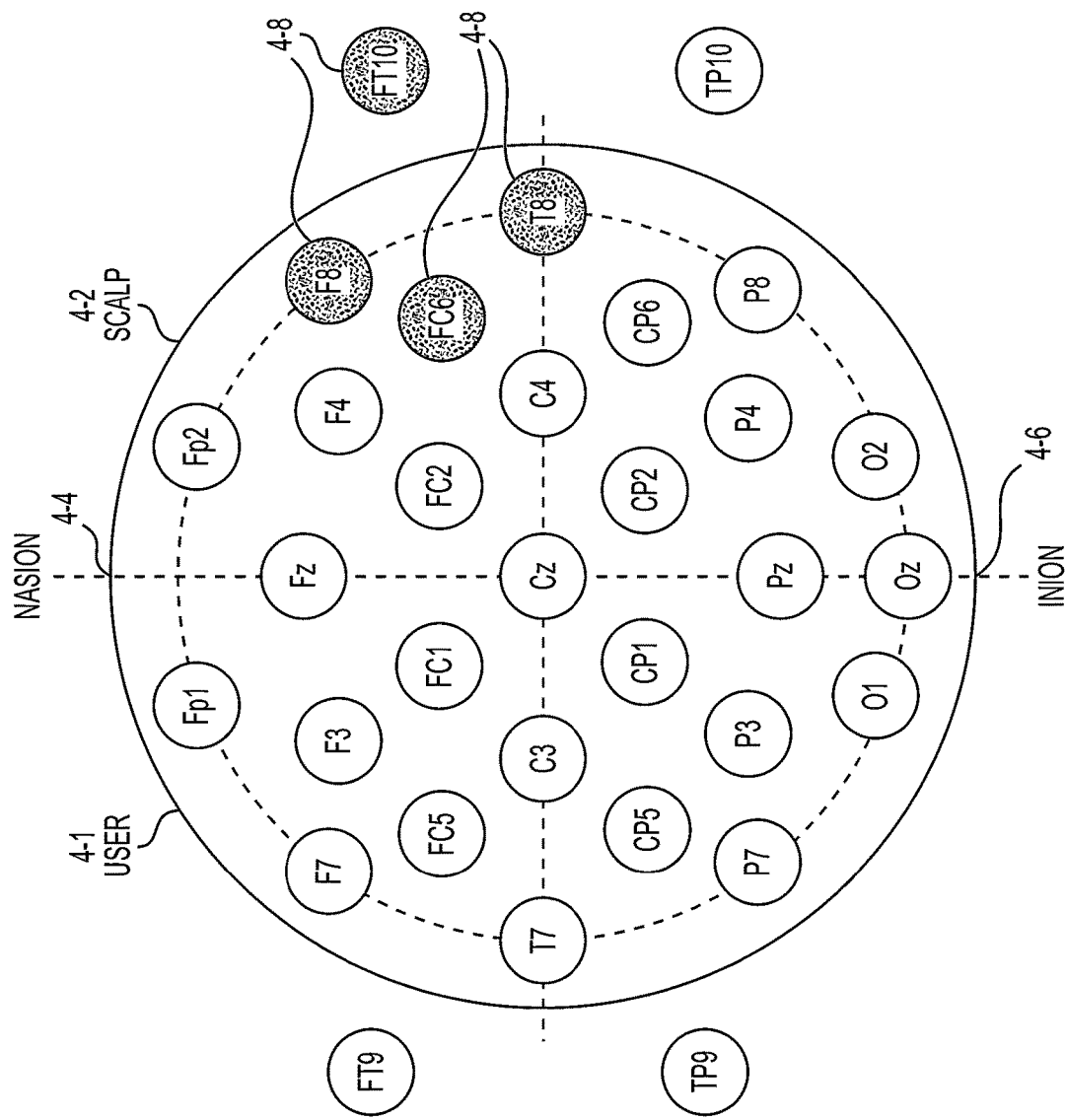
FIG. 4.20

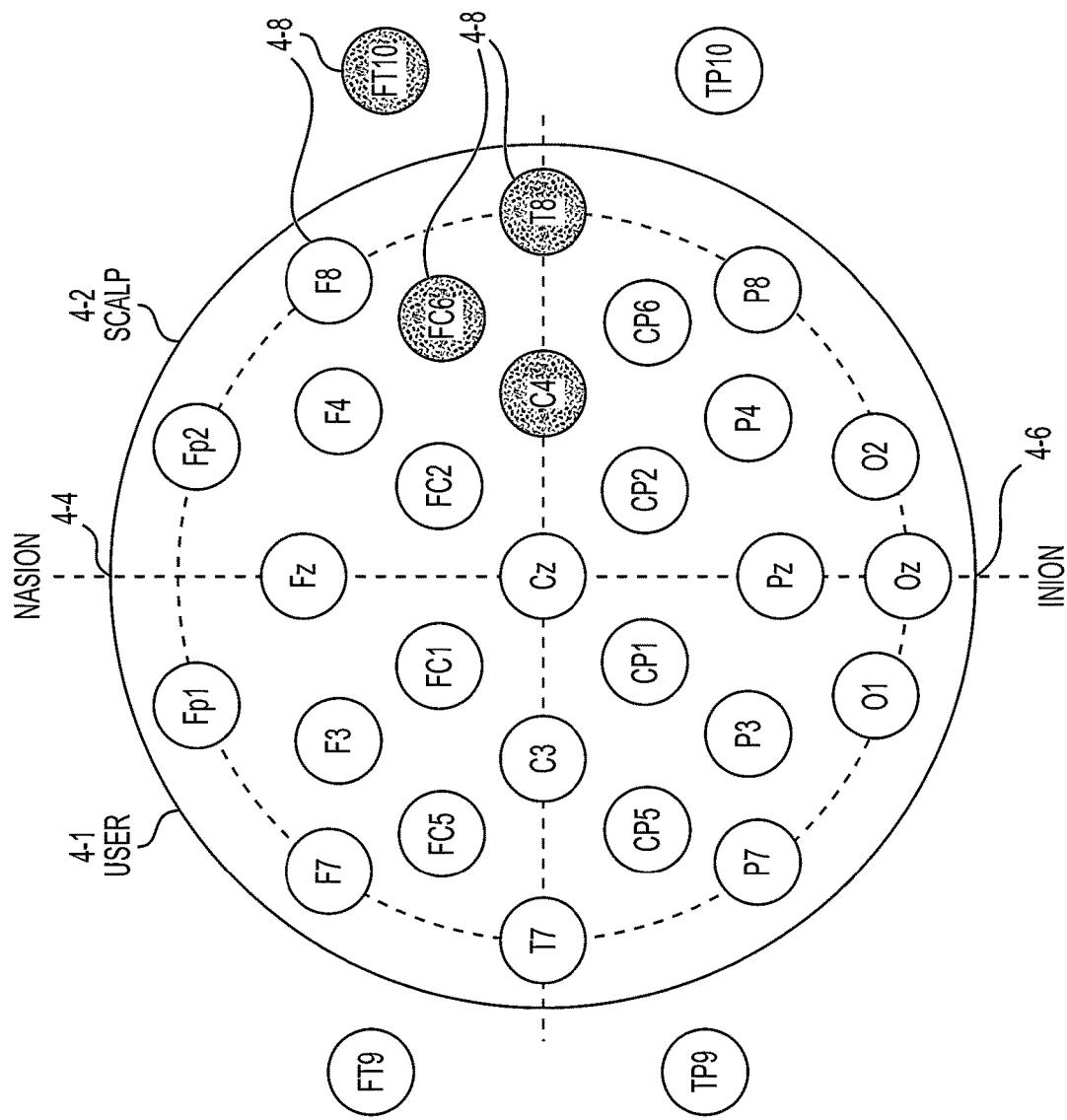
FIG. 4.21

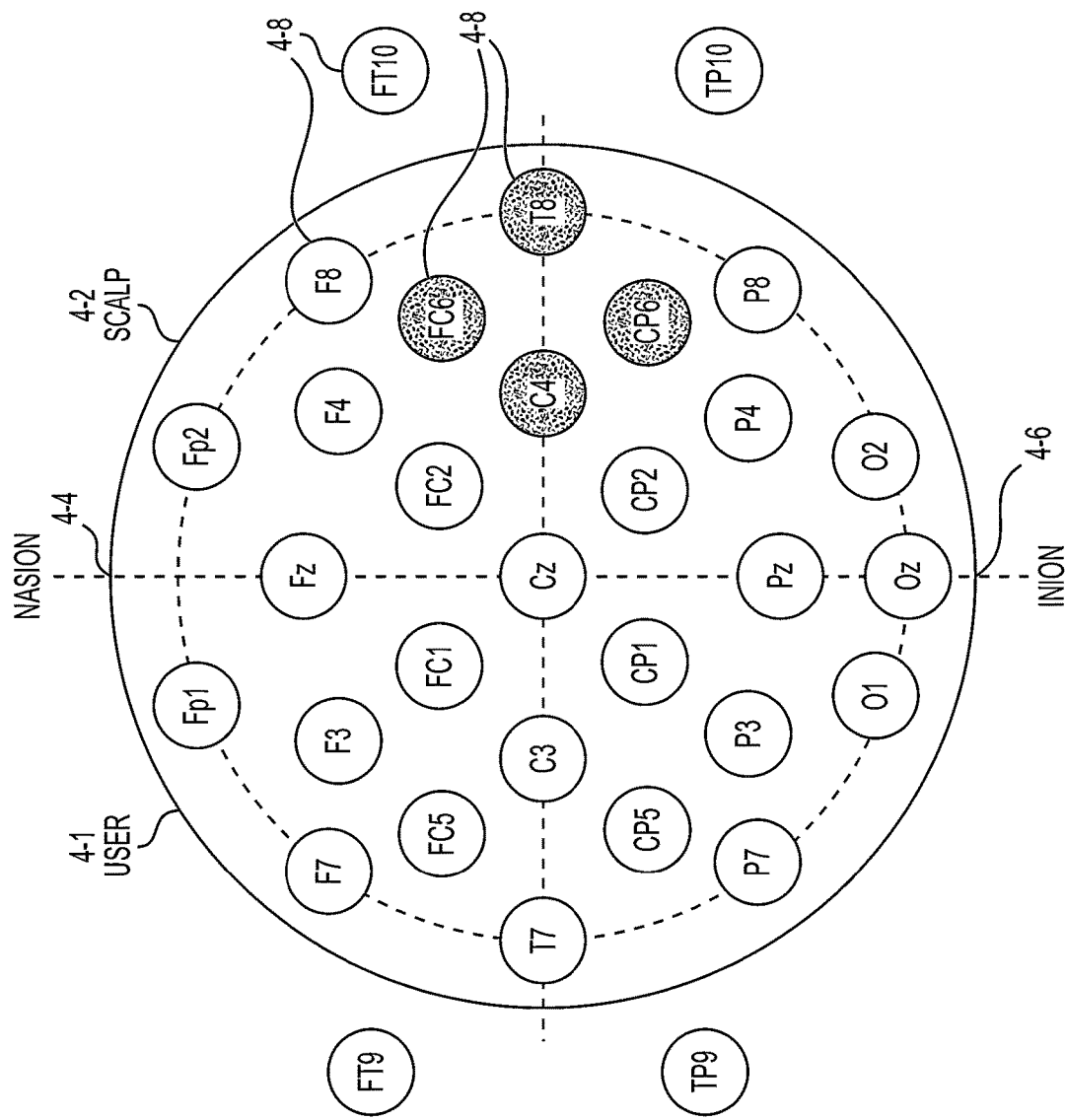
FIG. 4.22

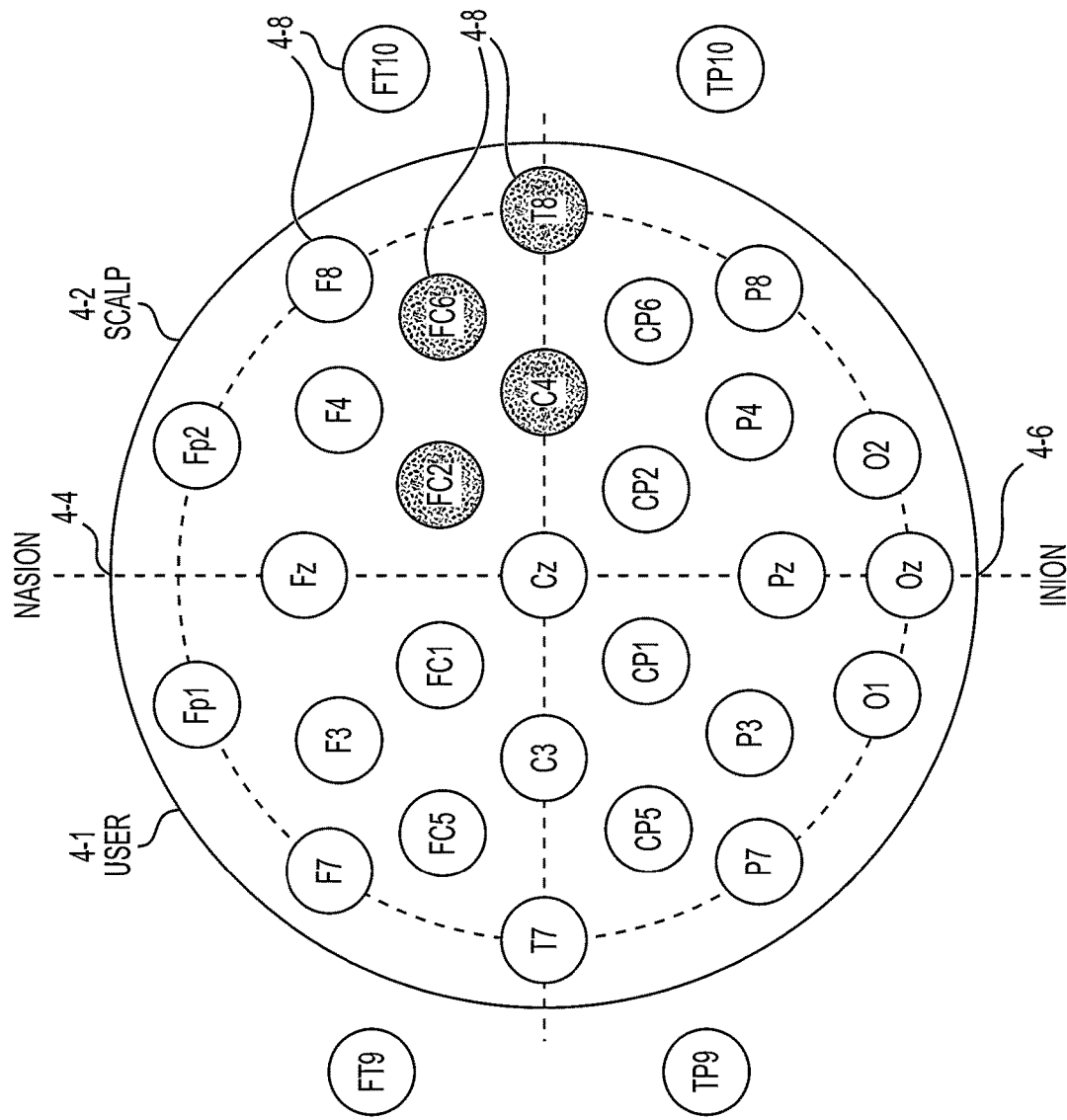
FIG. 4.23

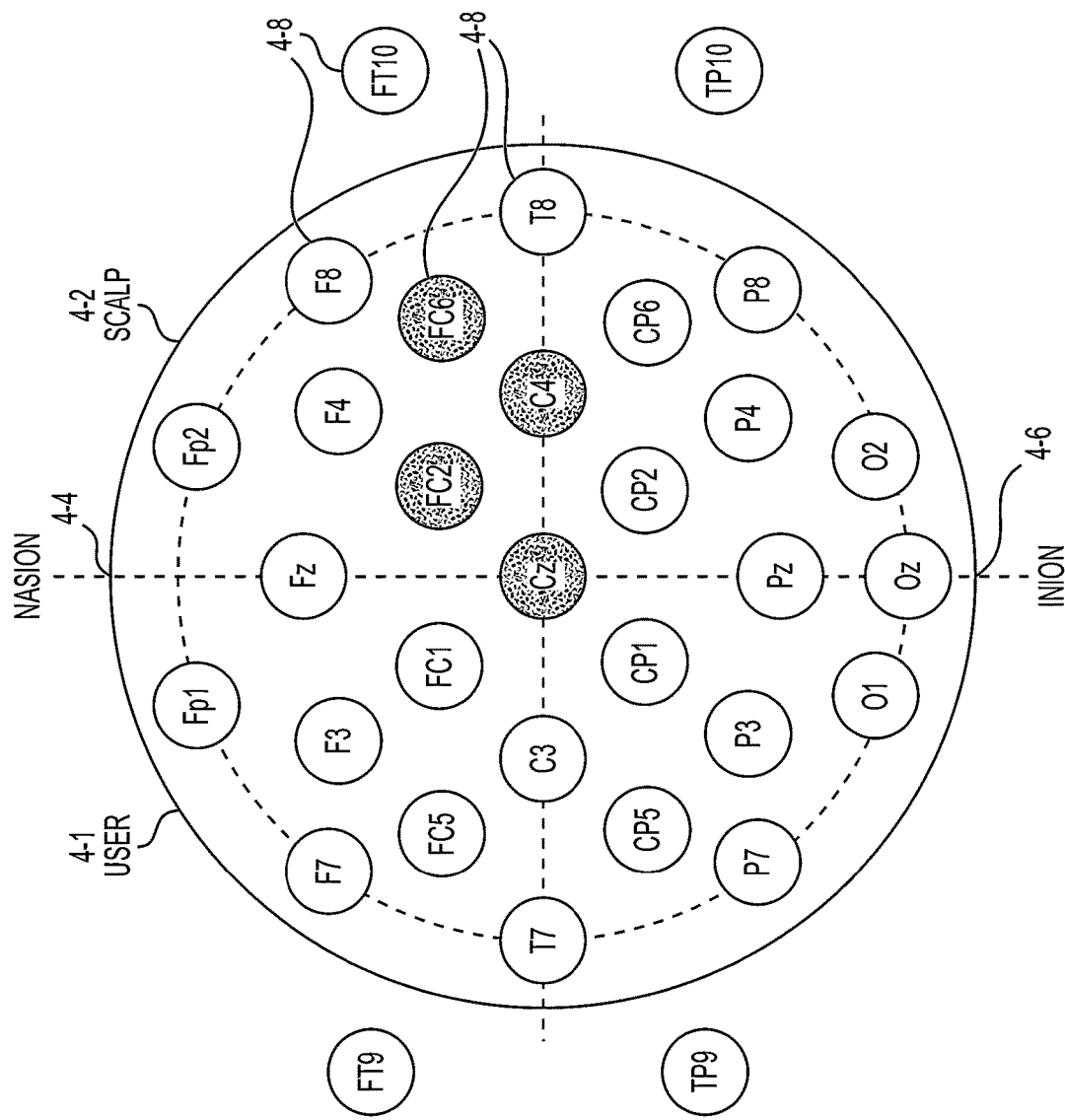
FIG. 4.24

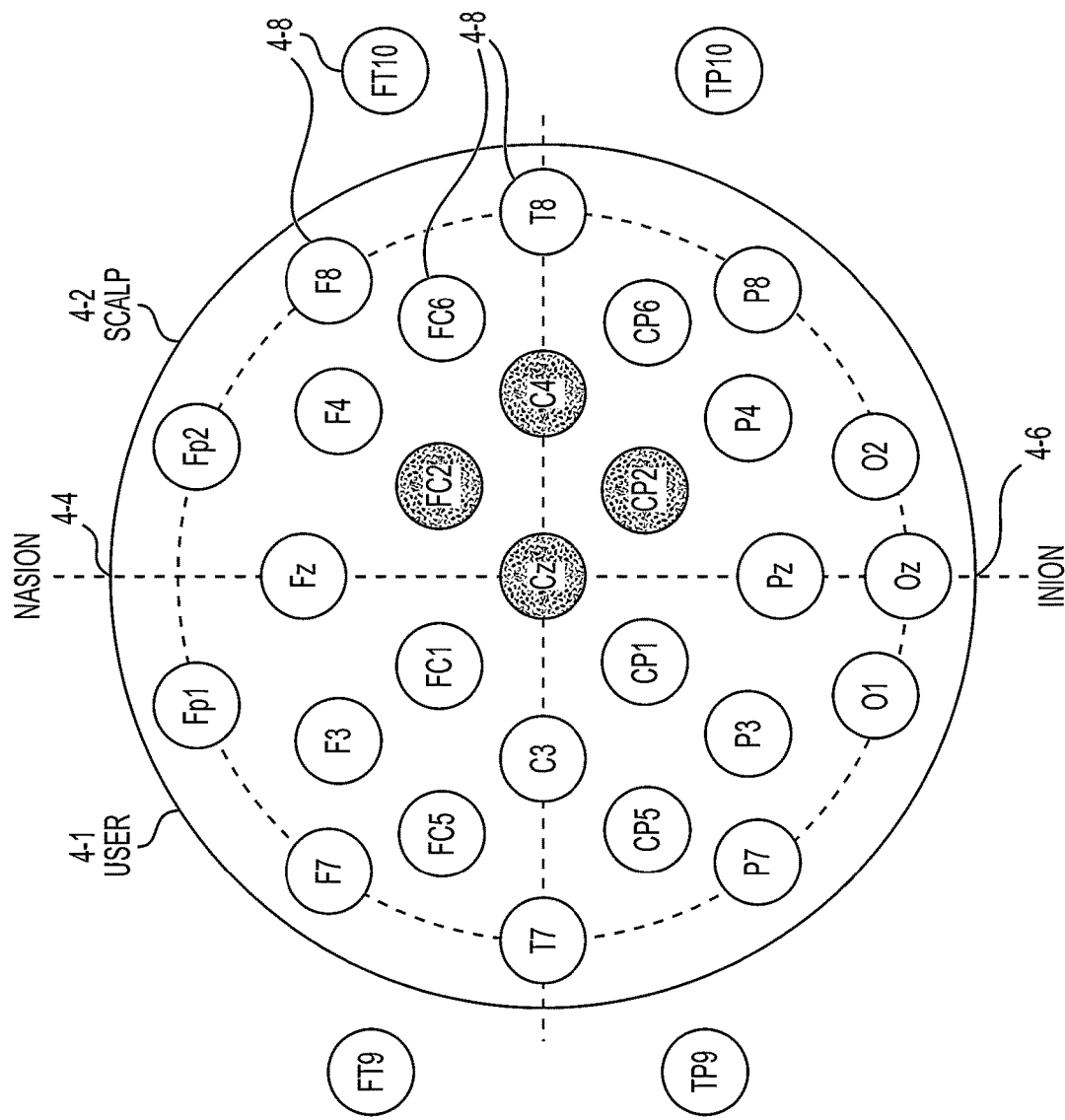
FIG. 4.25

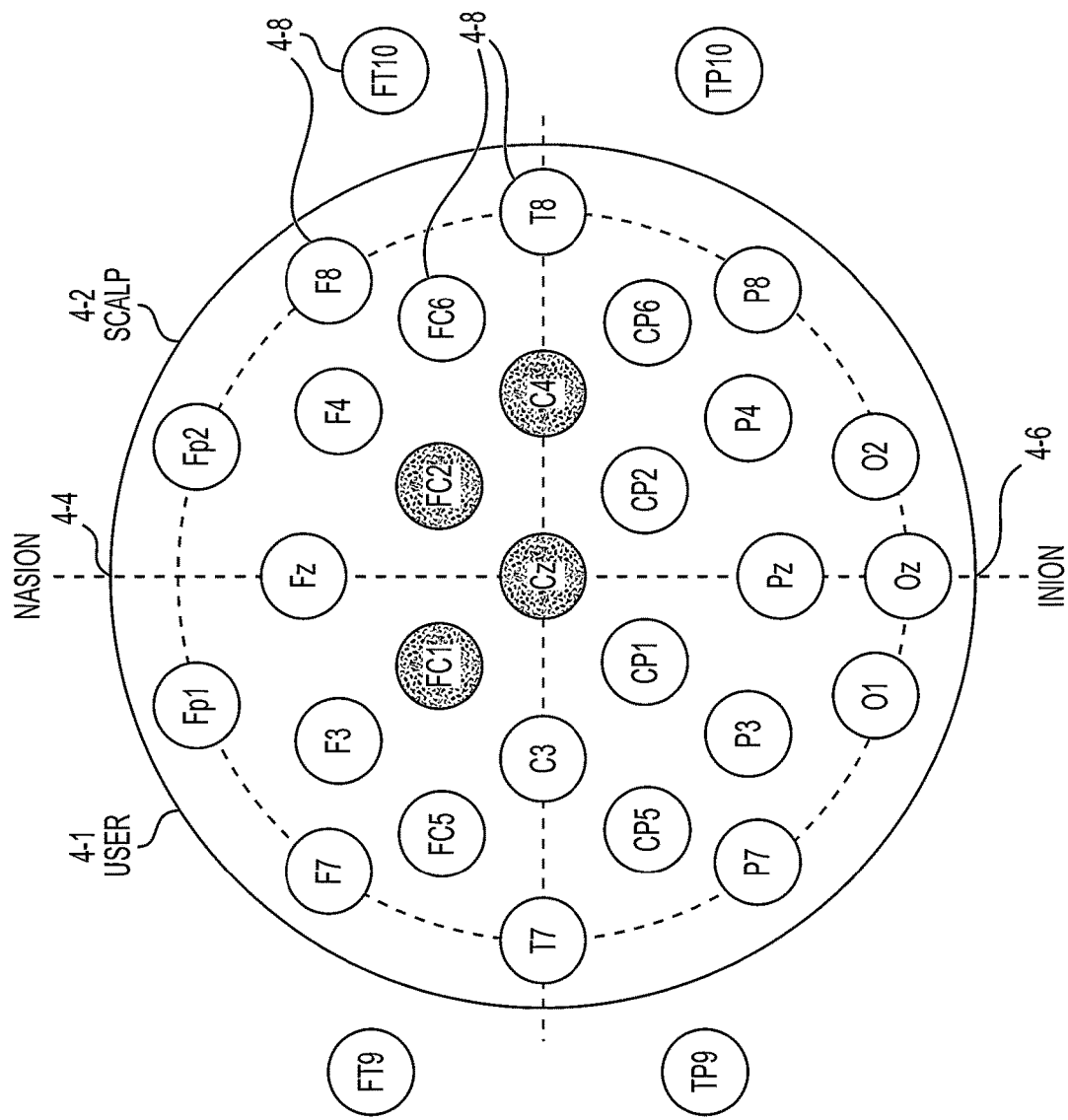
FIG. 4.26

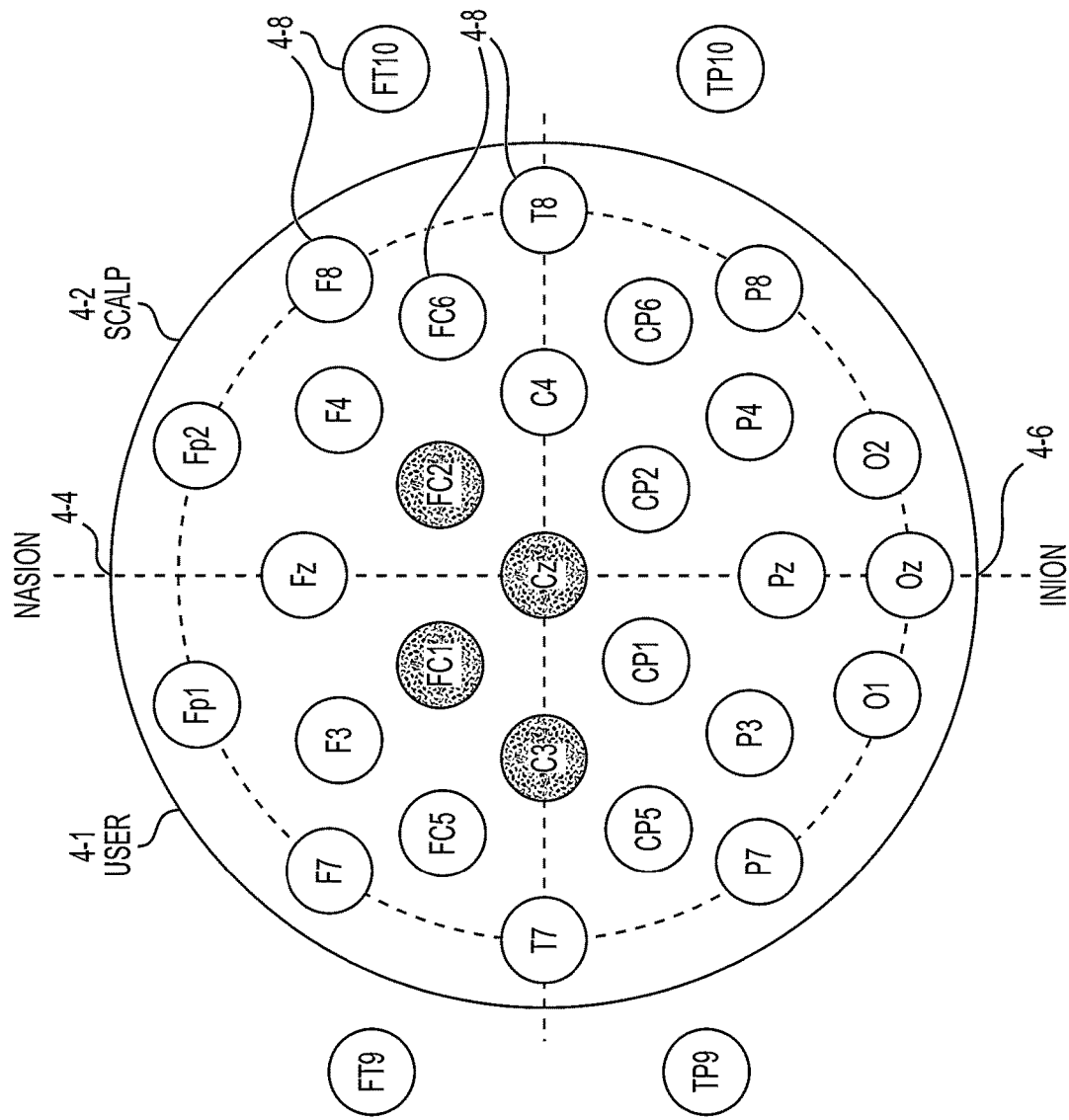
FIG. 4.27

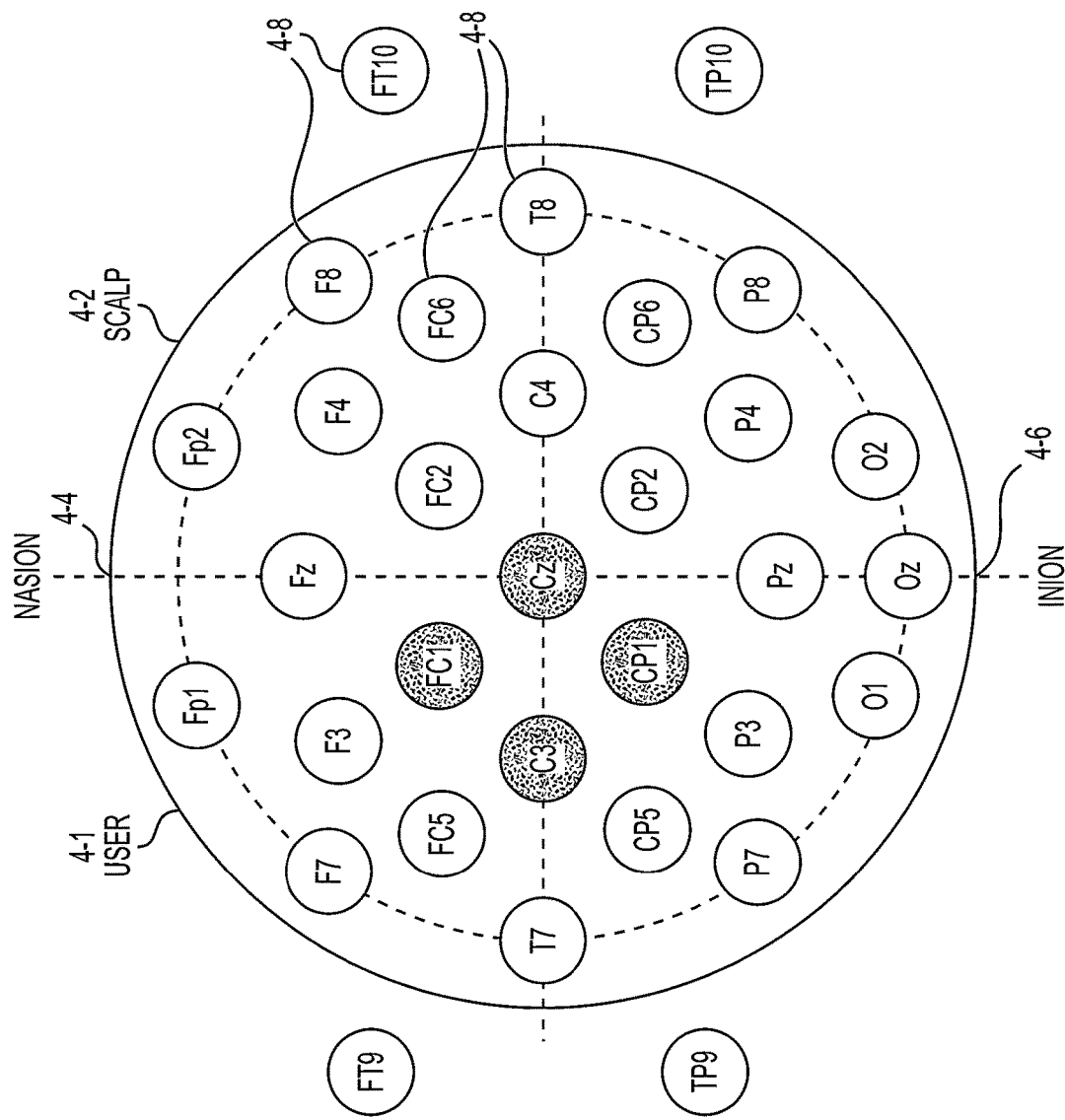
FIG. 4.28

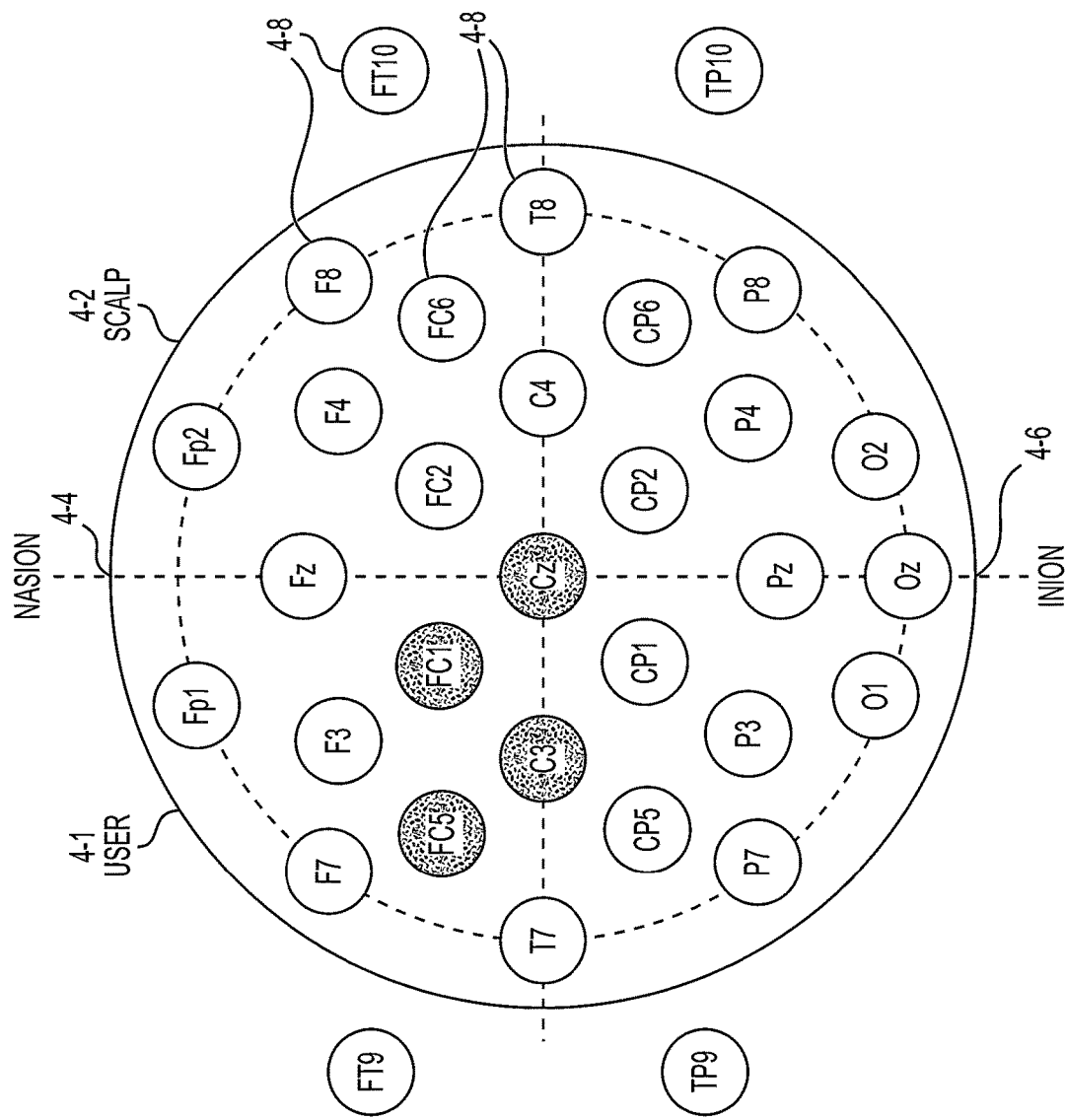
FIG. 4.29

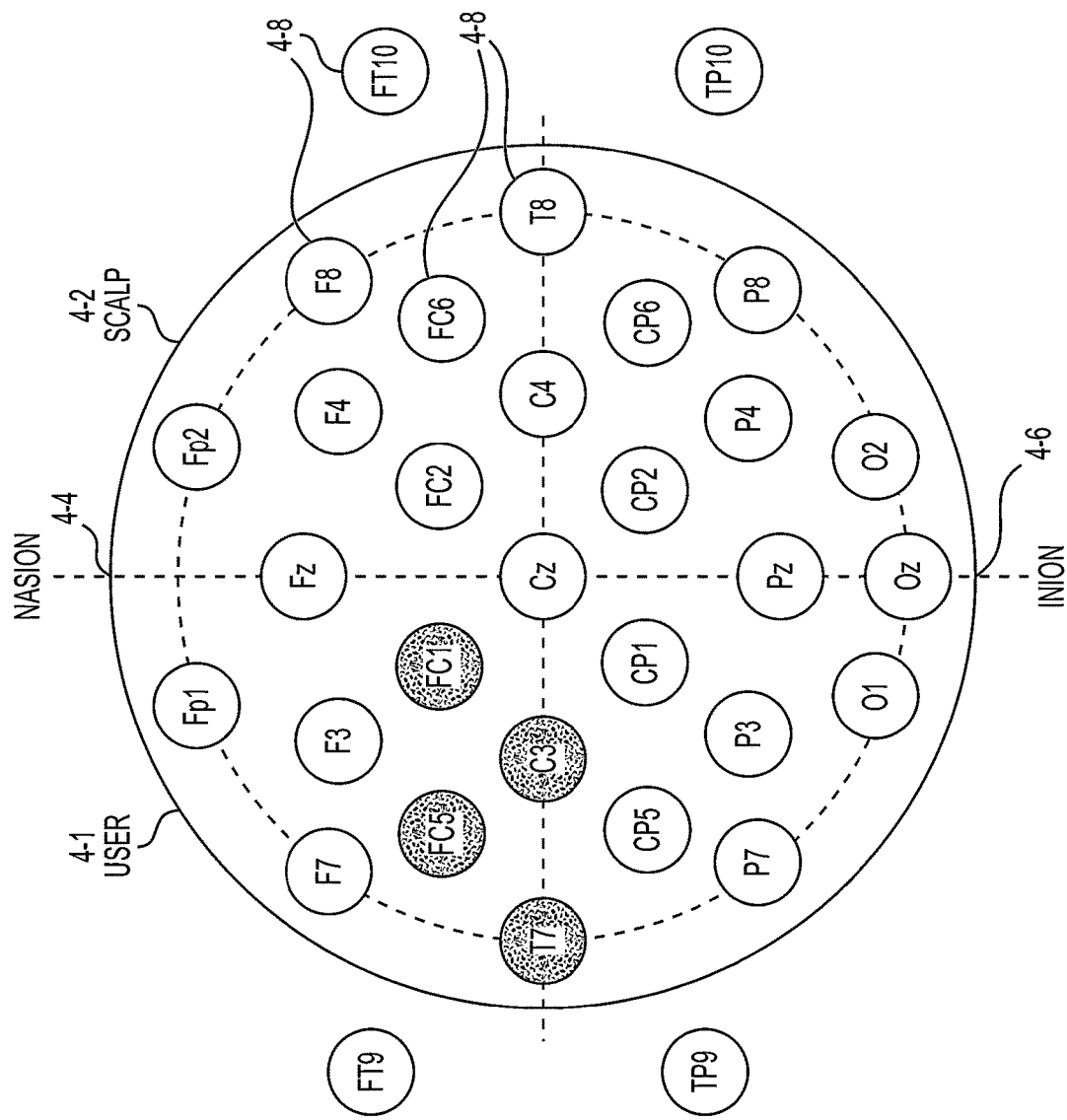
FIG. 4.30

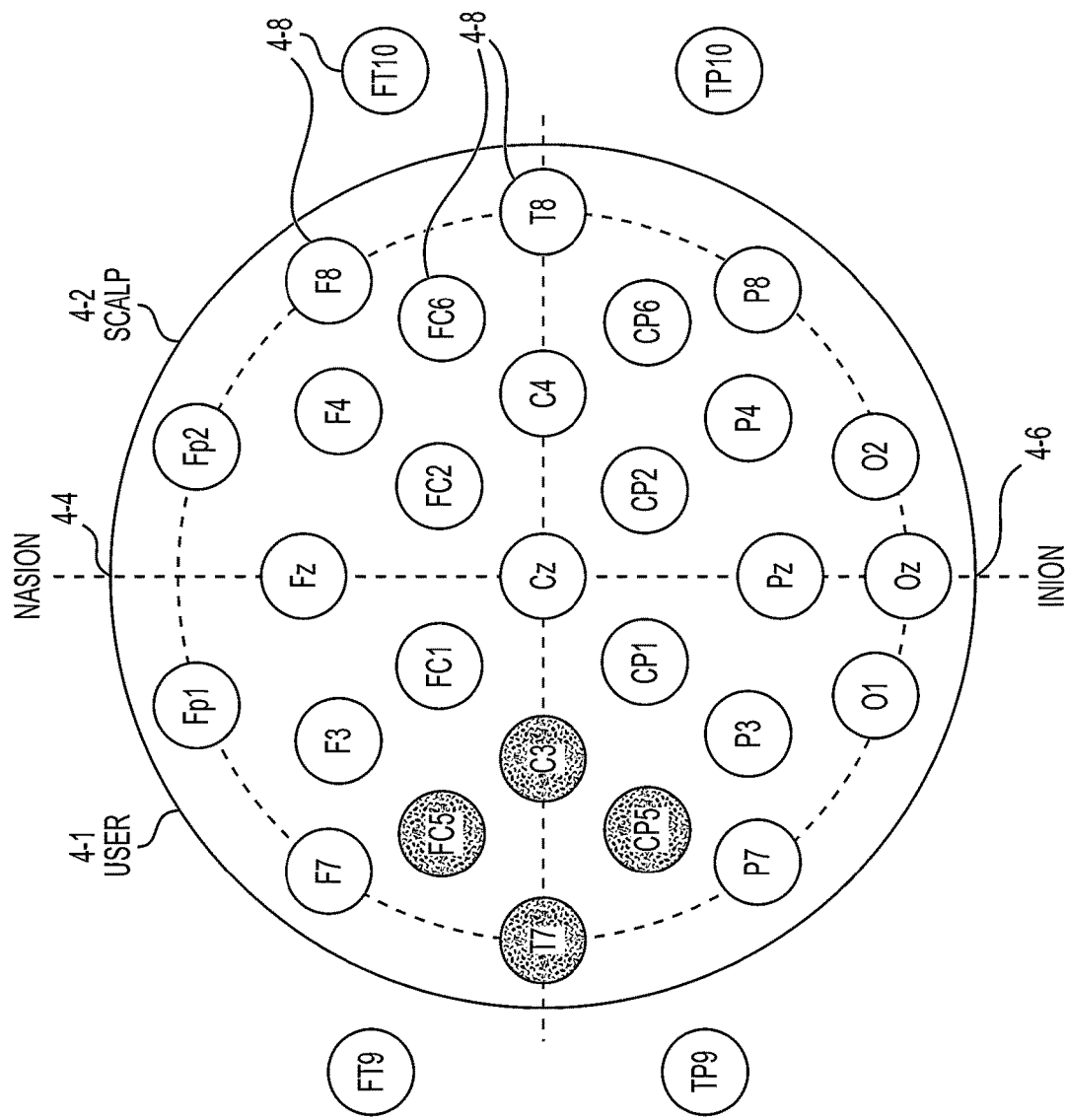
FIG. 4.31

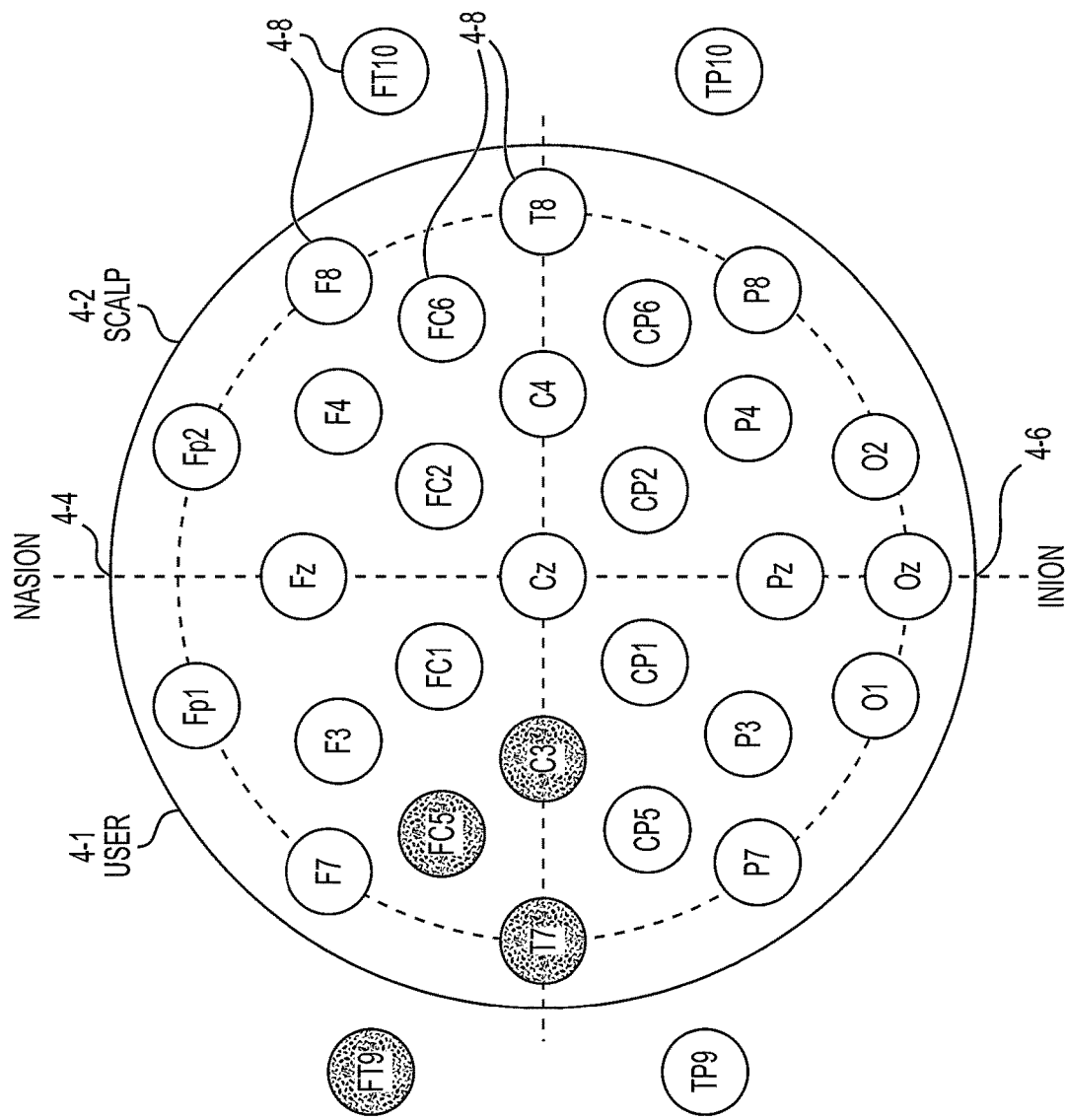
FIG. 4.32

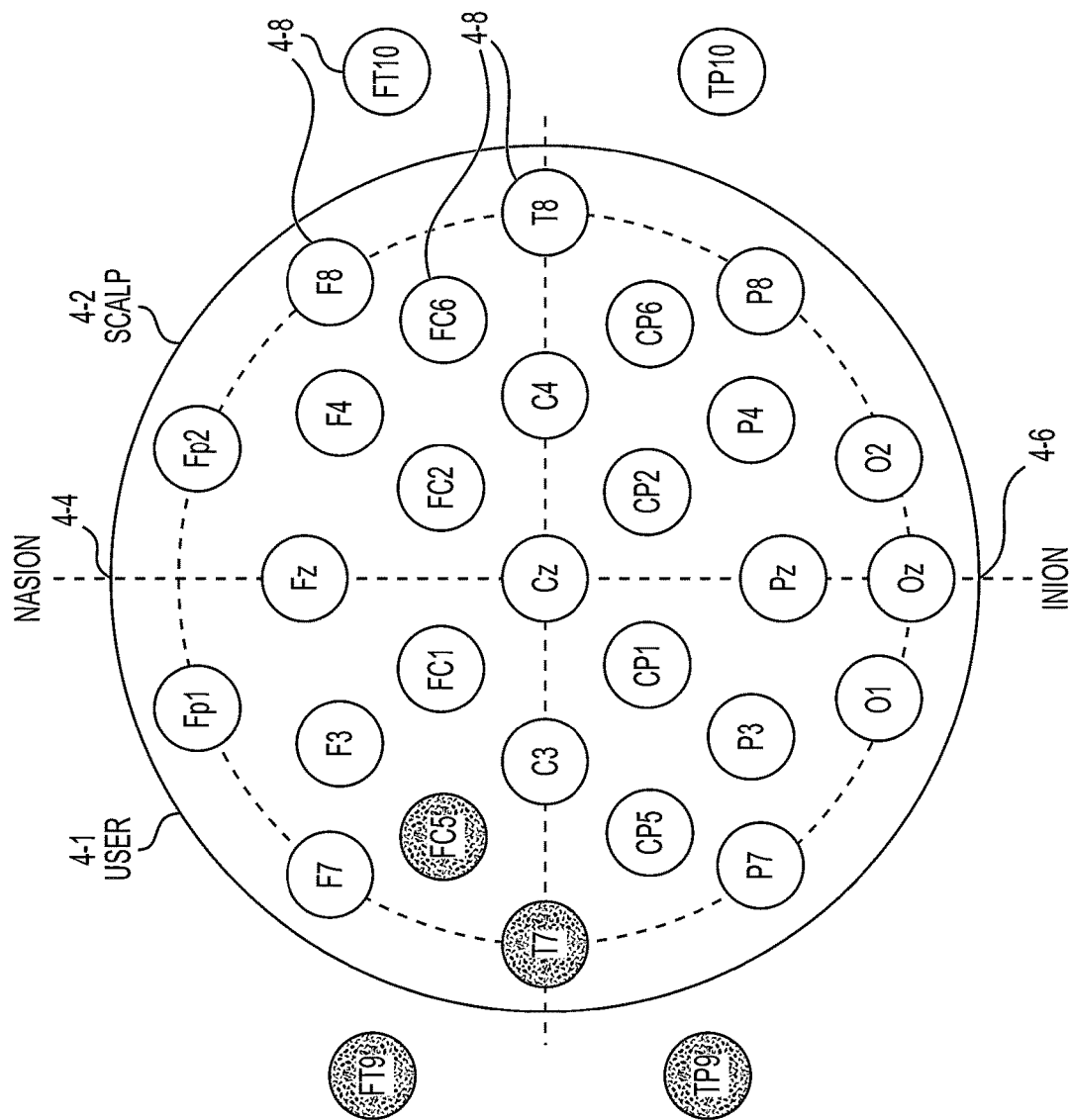
FIG. 4.33

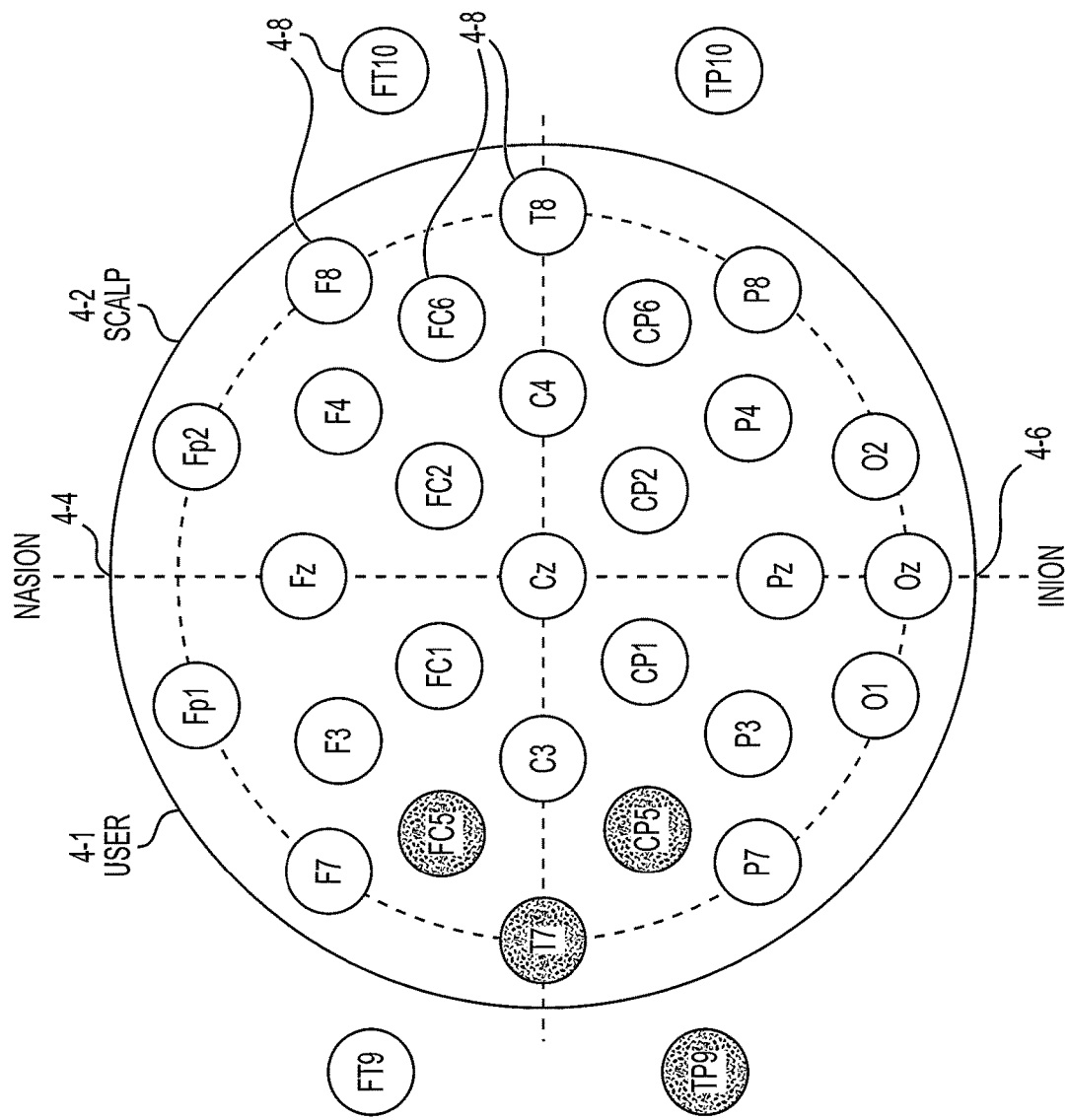
FIG. 4.34

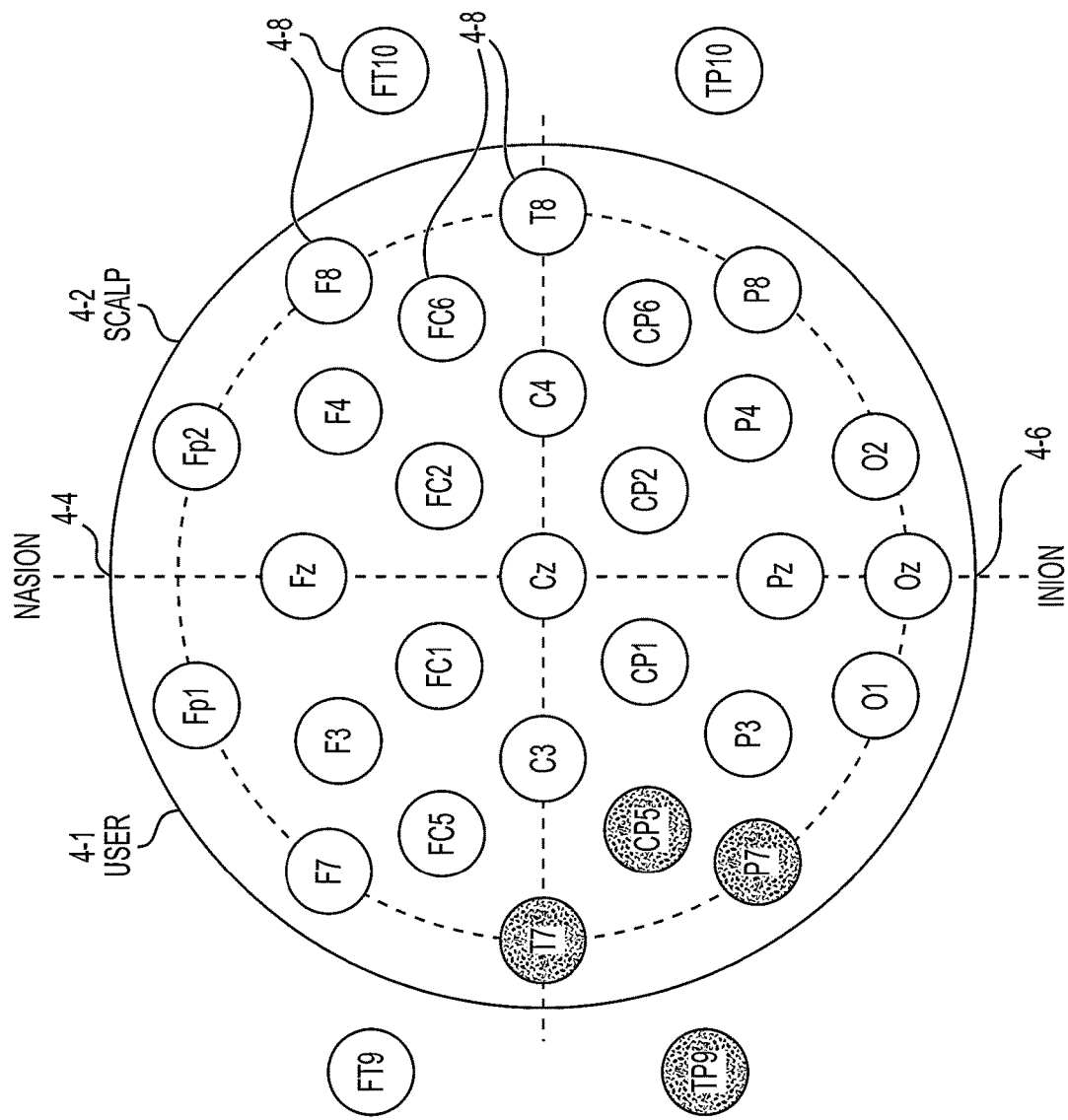
FIG. 4.35

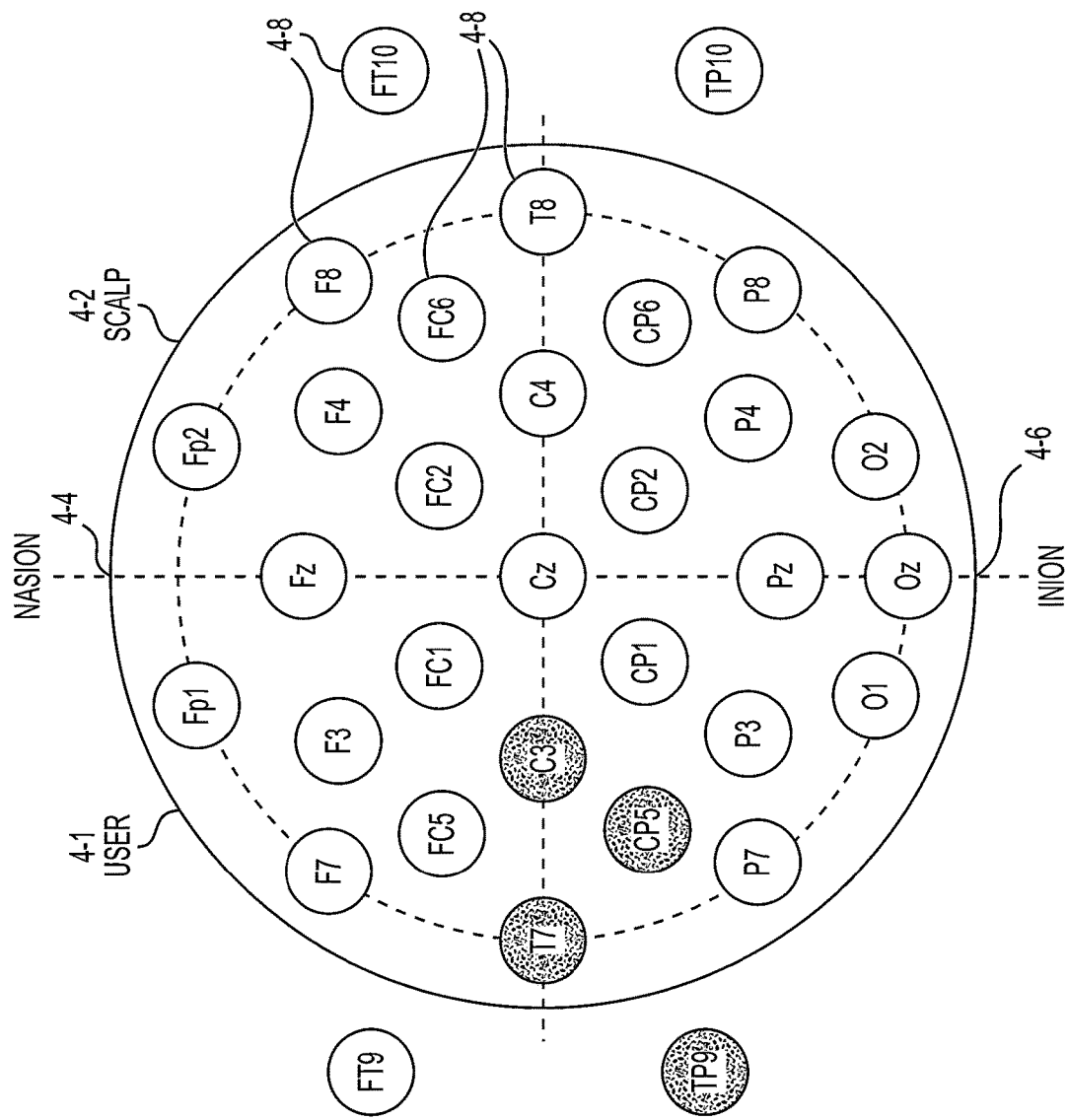
FIG. 4.36

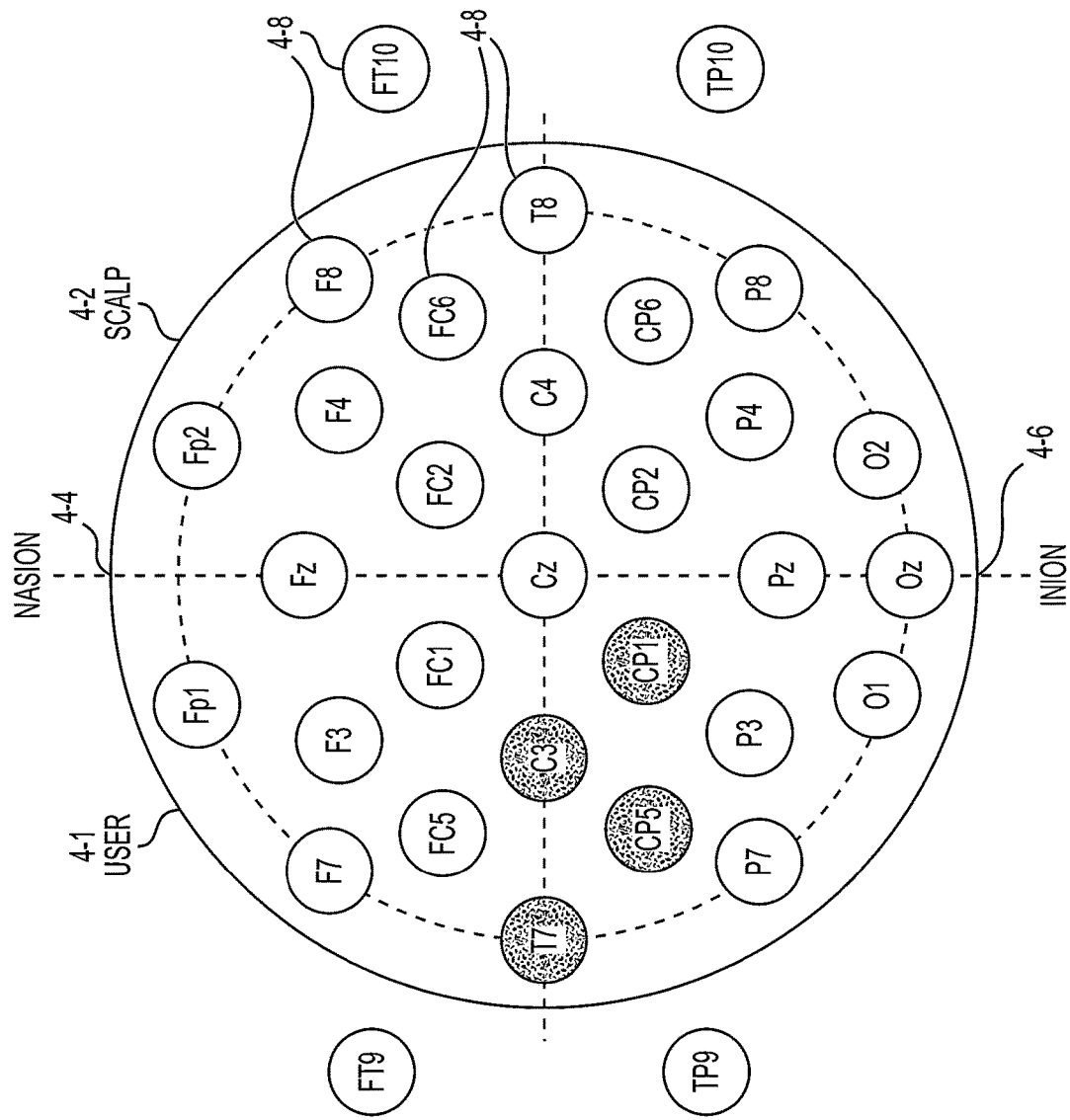
FIG. 4.37

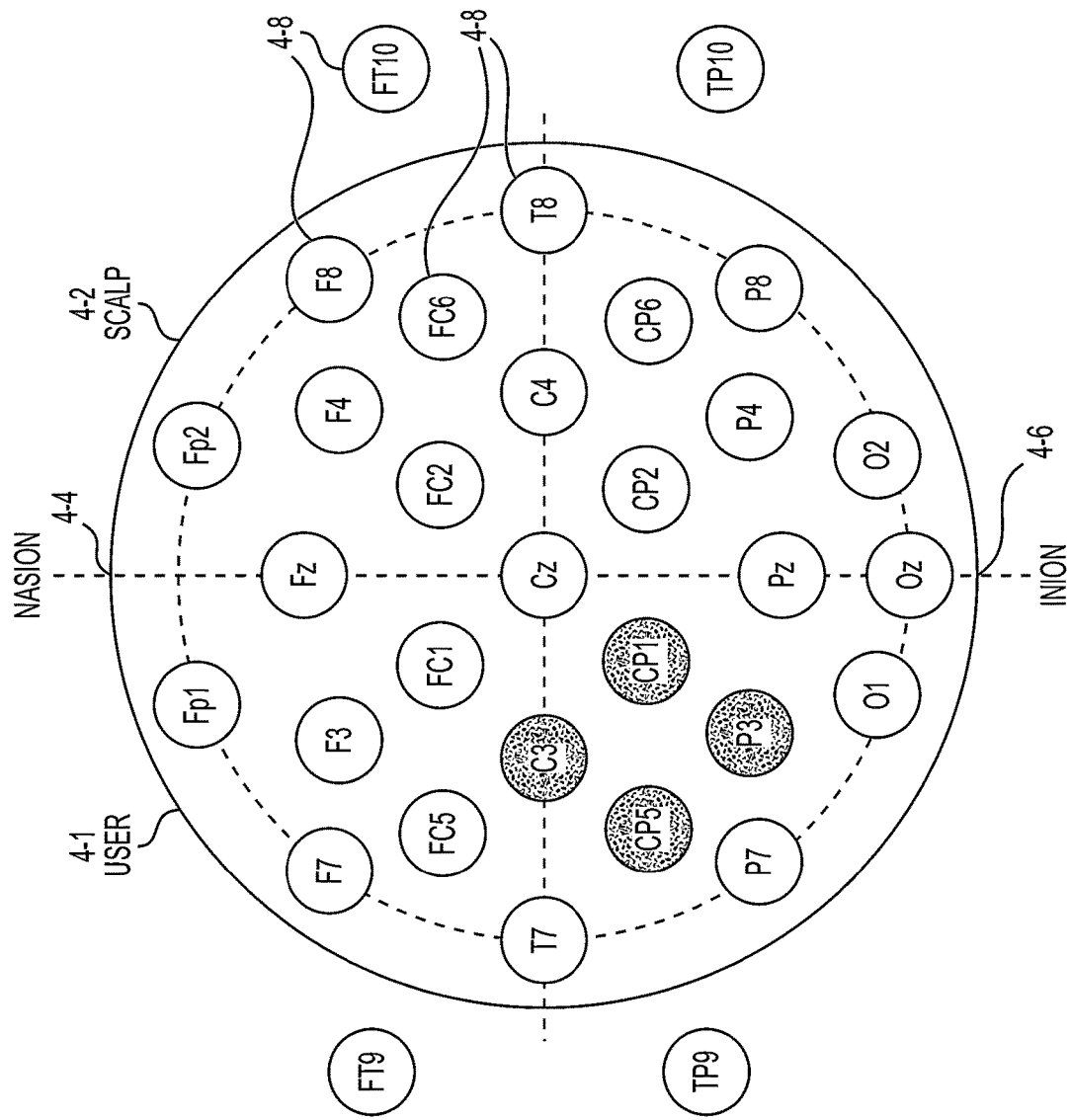
FIG. 4.38

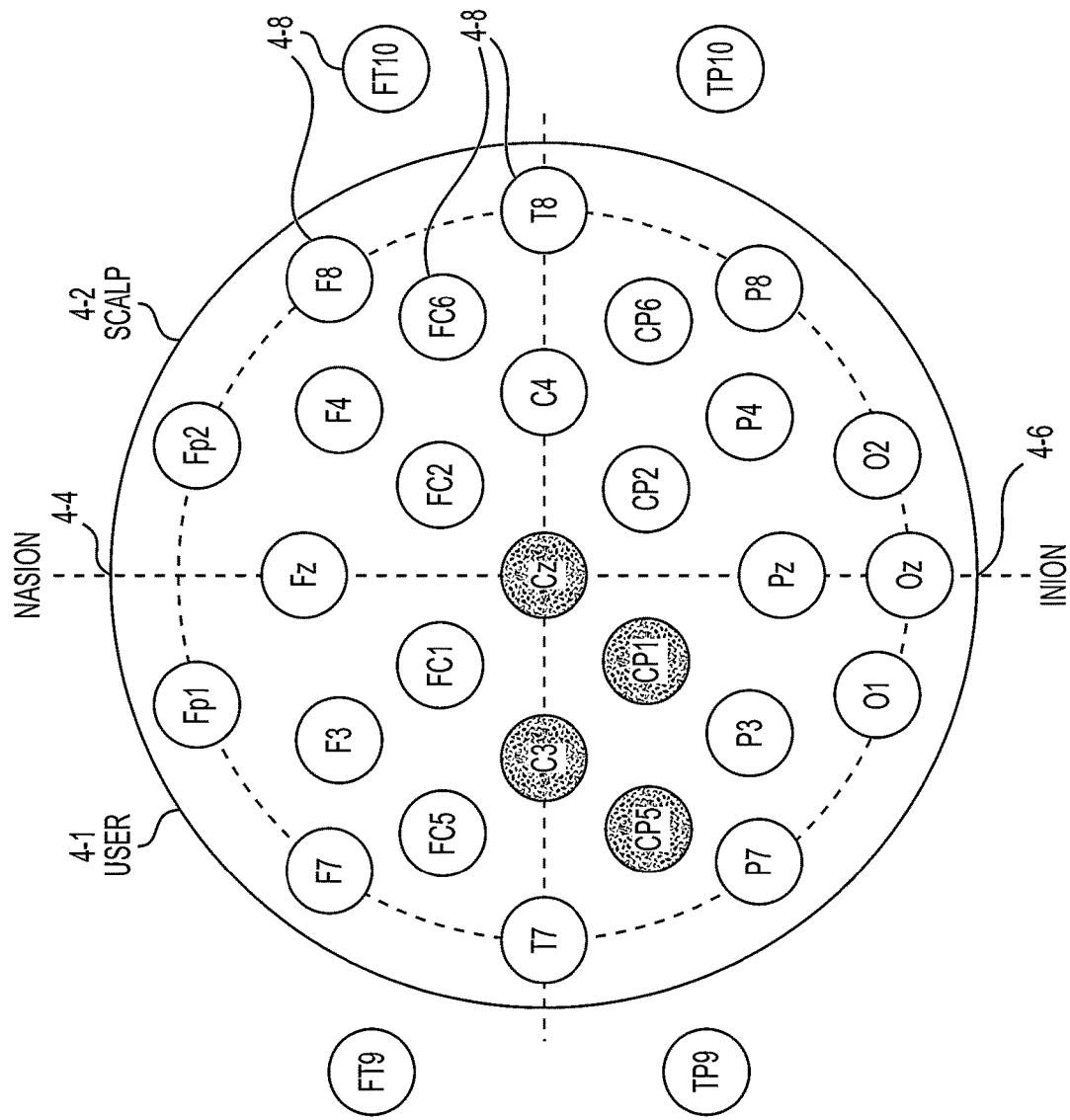
FIG. 4.39

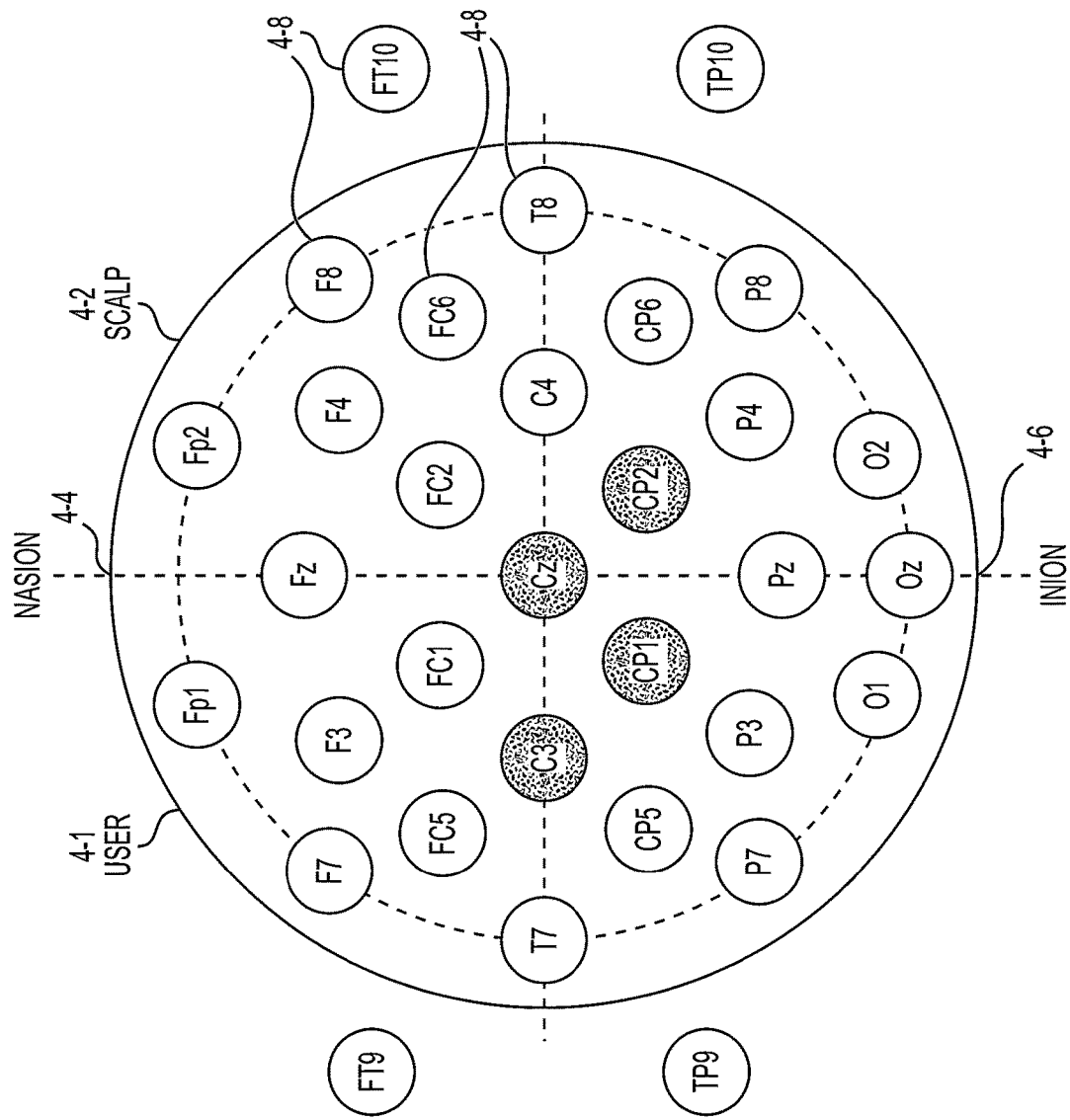
FIG. 4.40

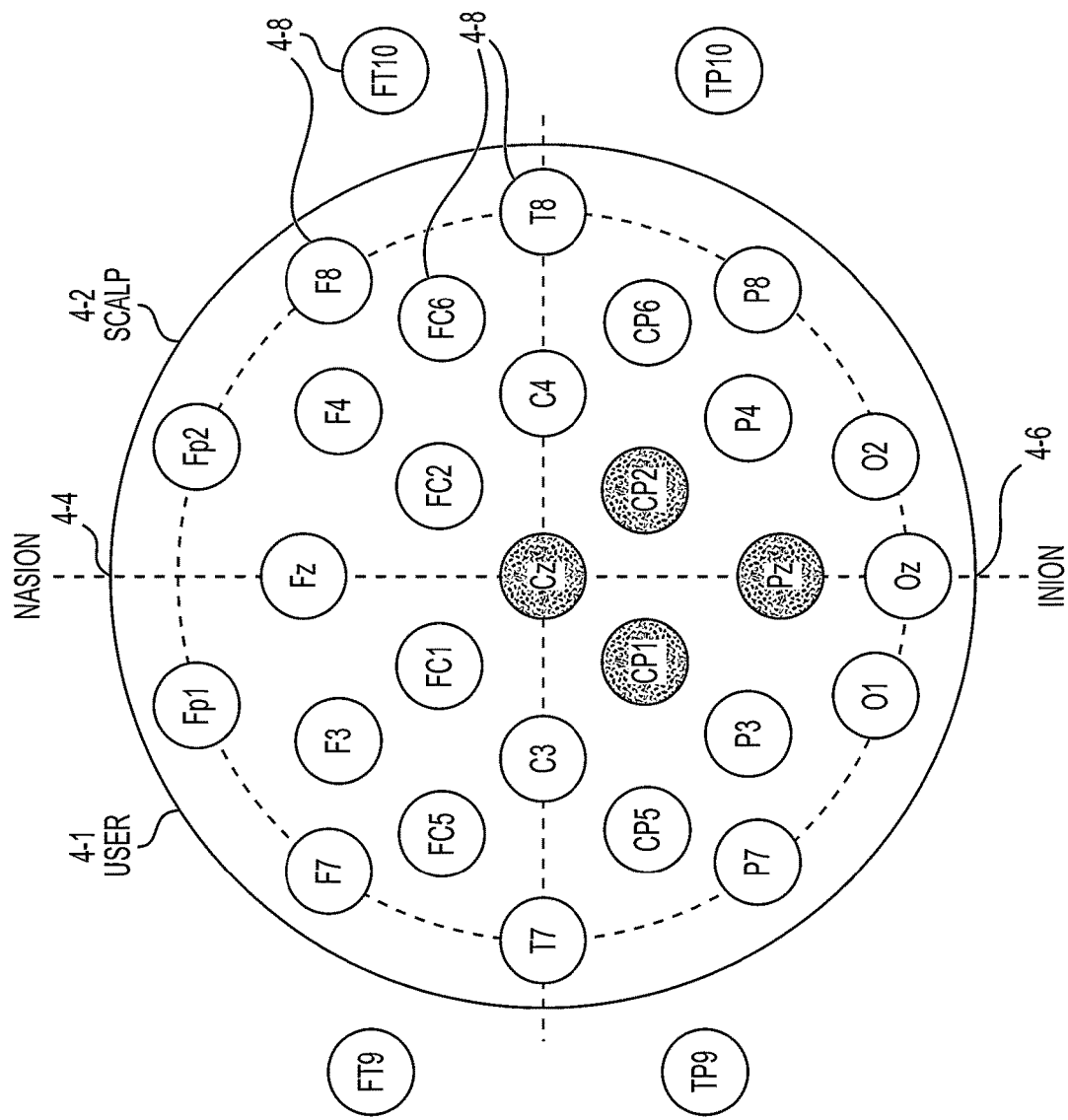
FIG. 4.41

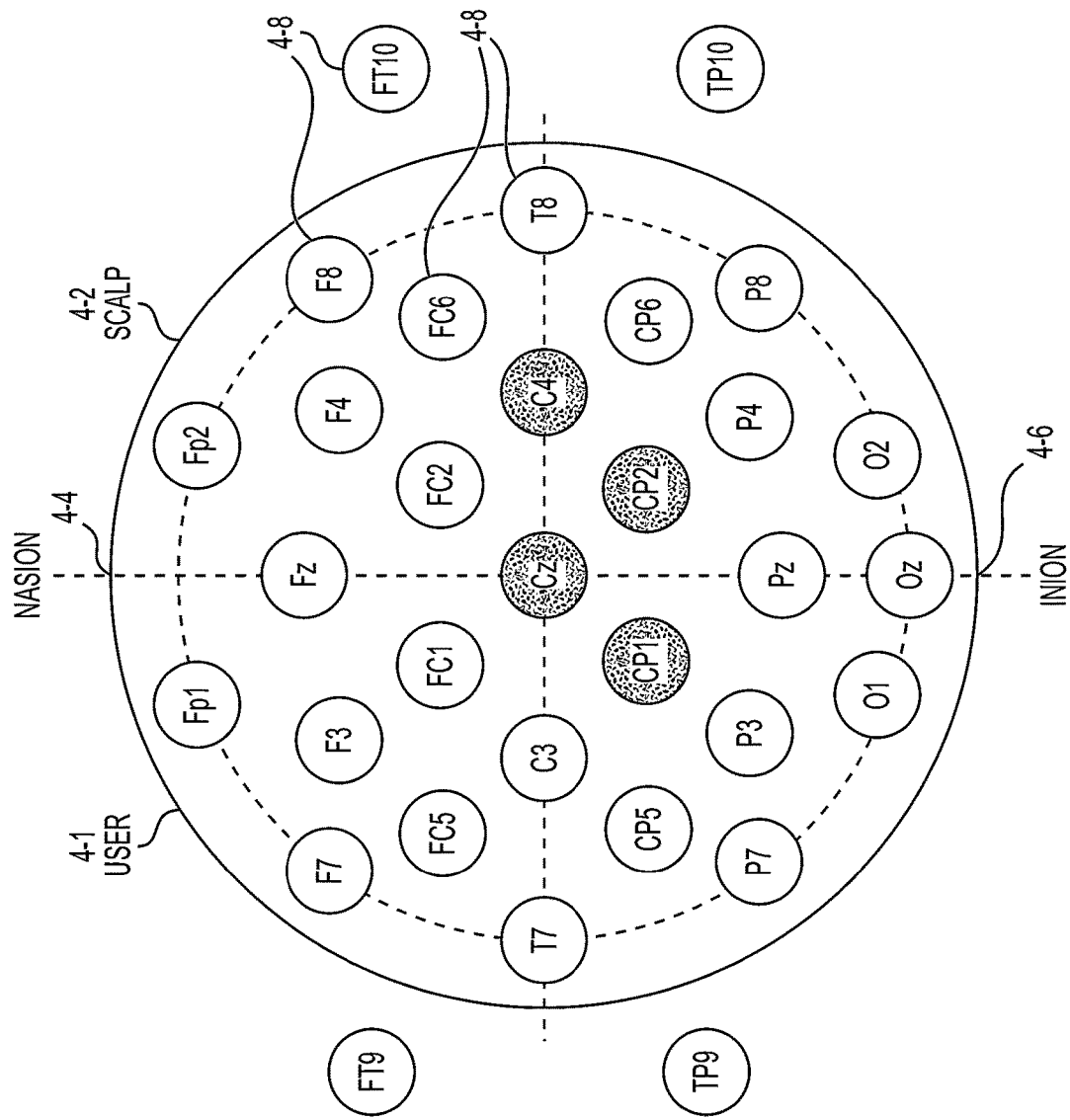
FIG. 4.42

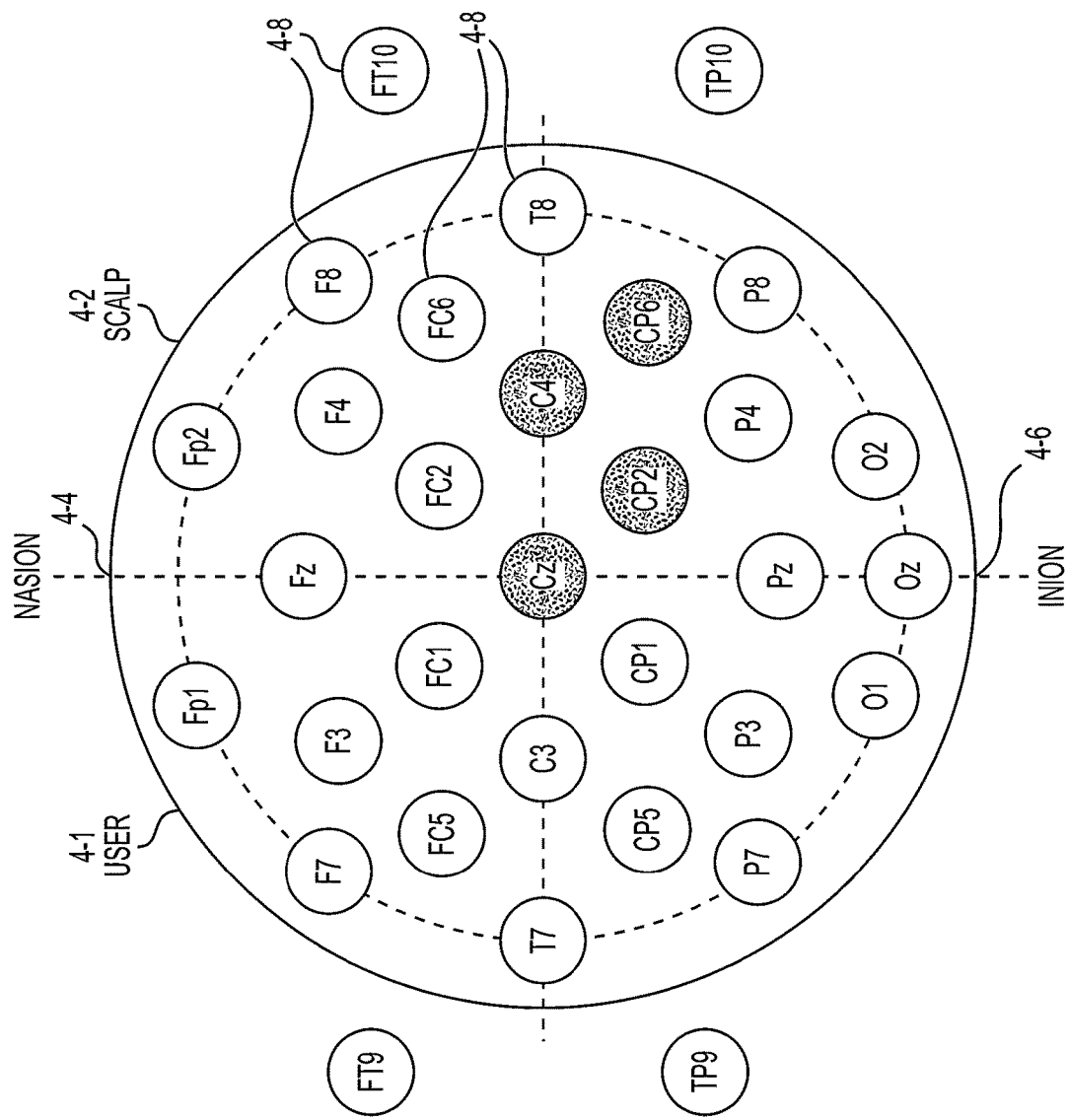
FIG. 4.43

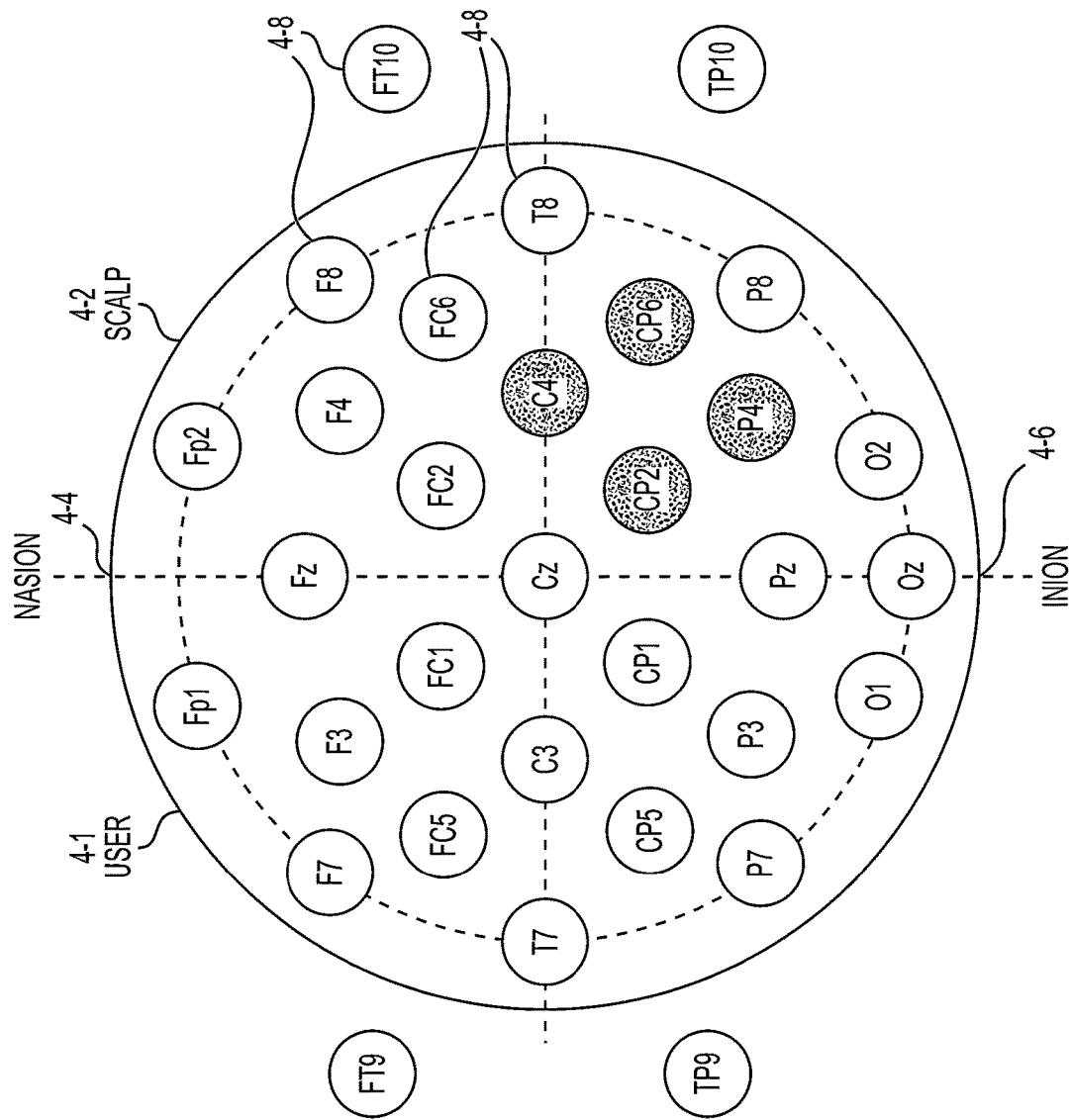
FIG. 4.44

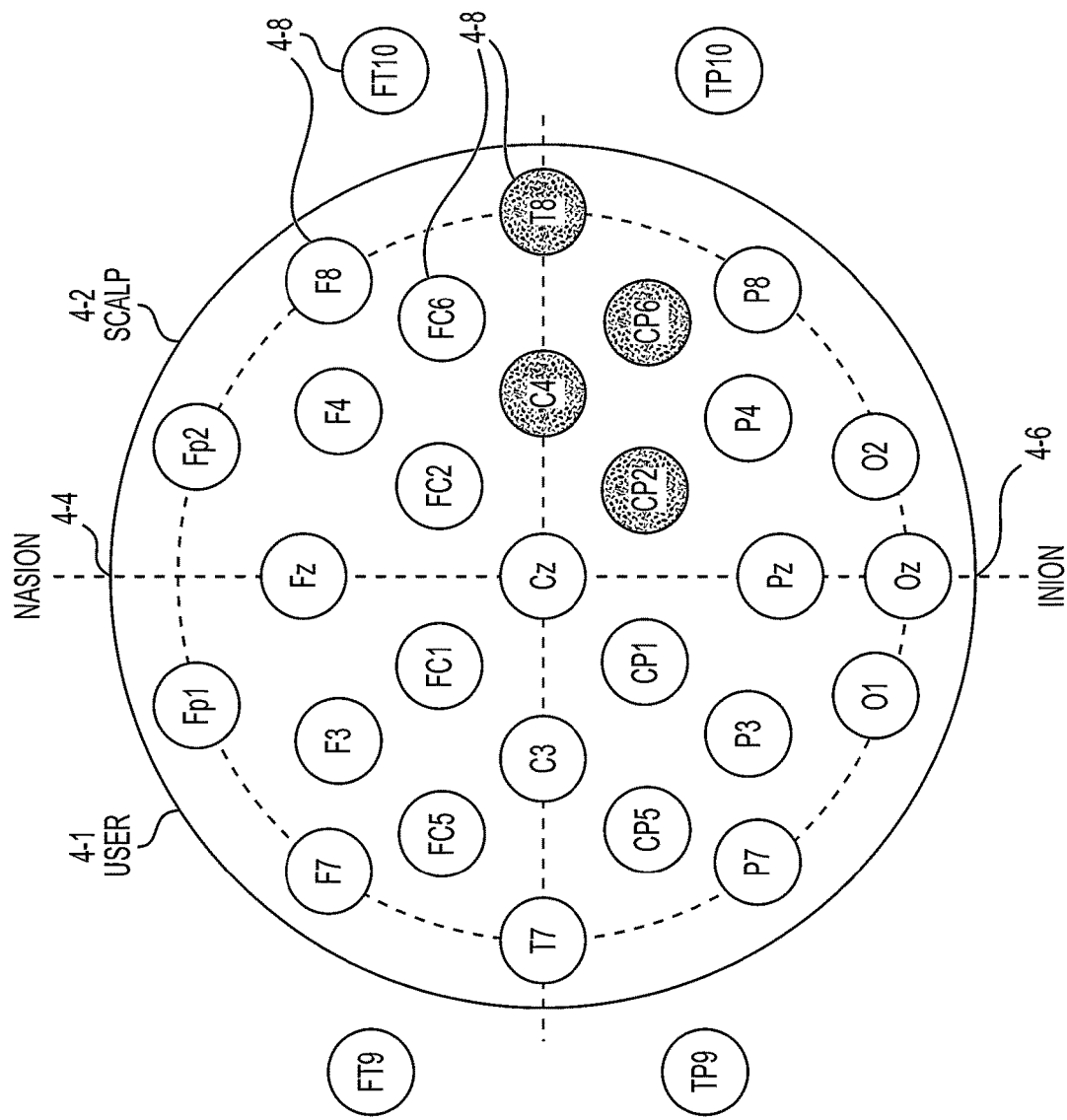
FIG. 4.45

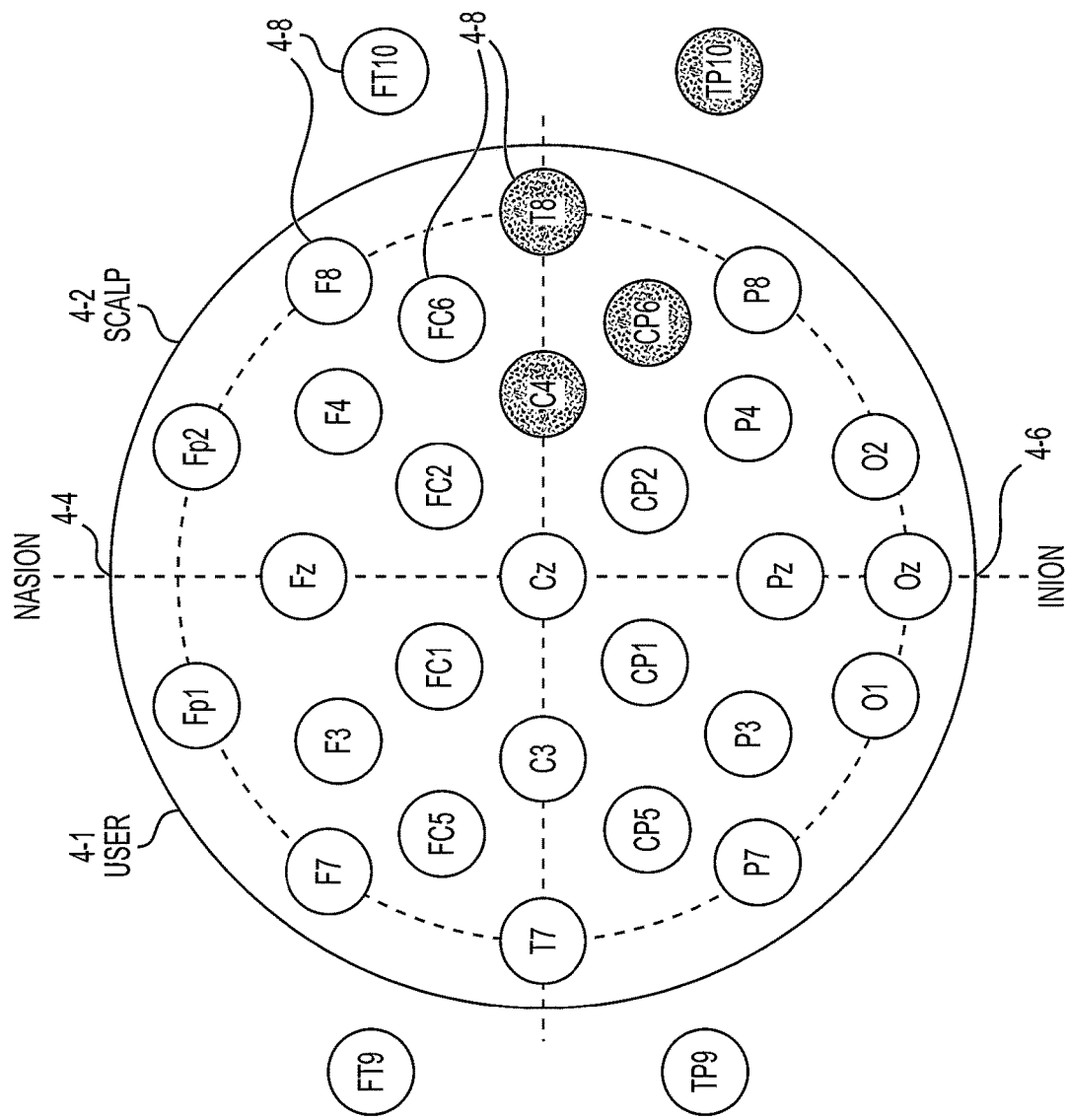
FIG. 4.46

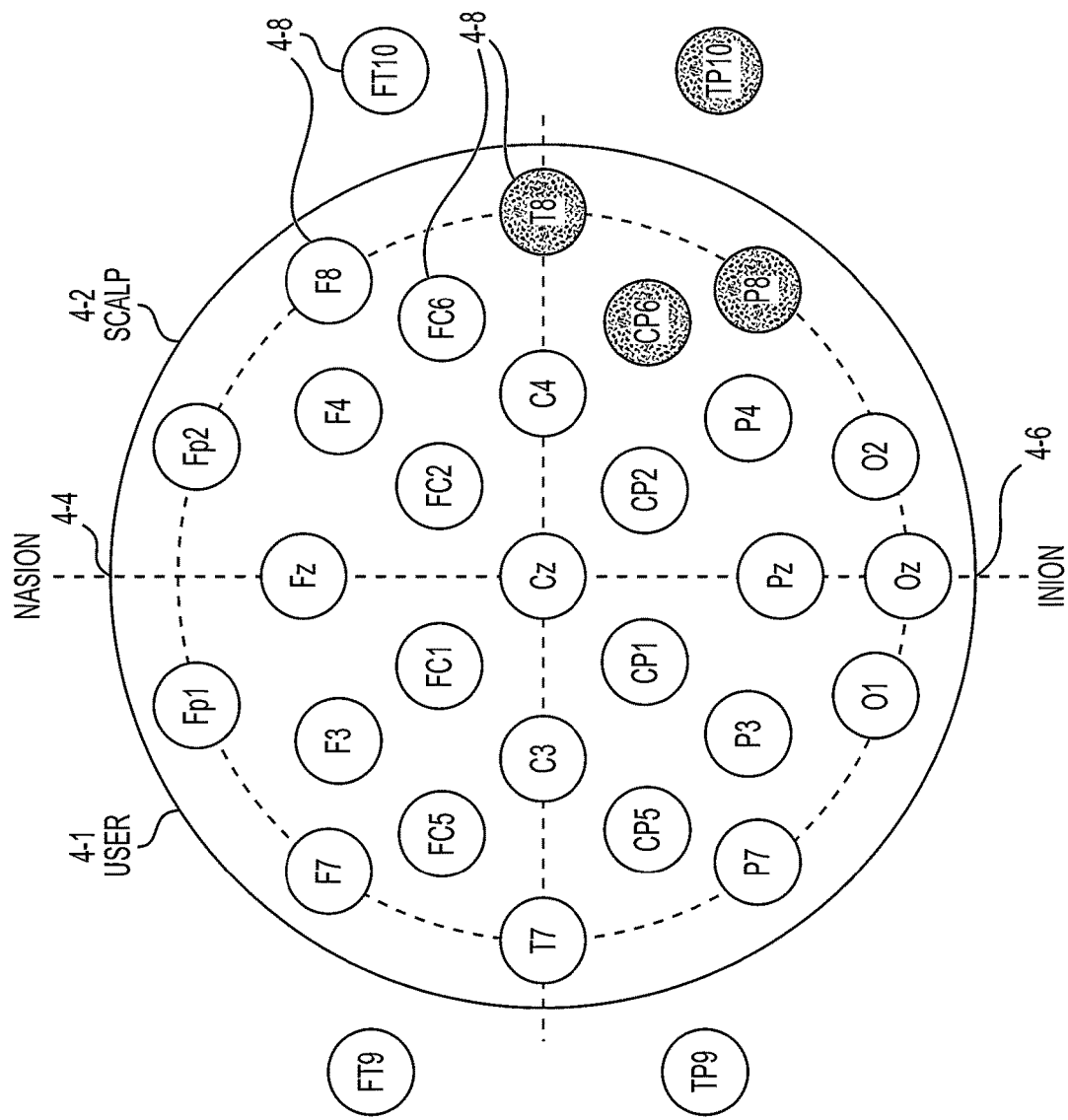

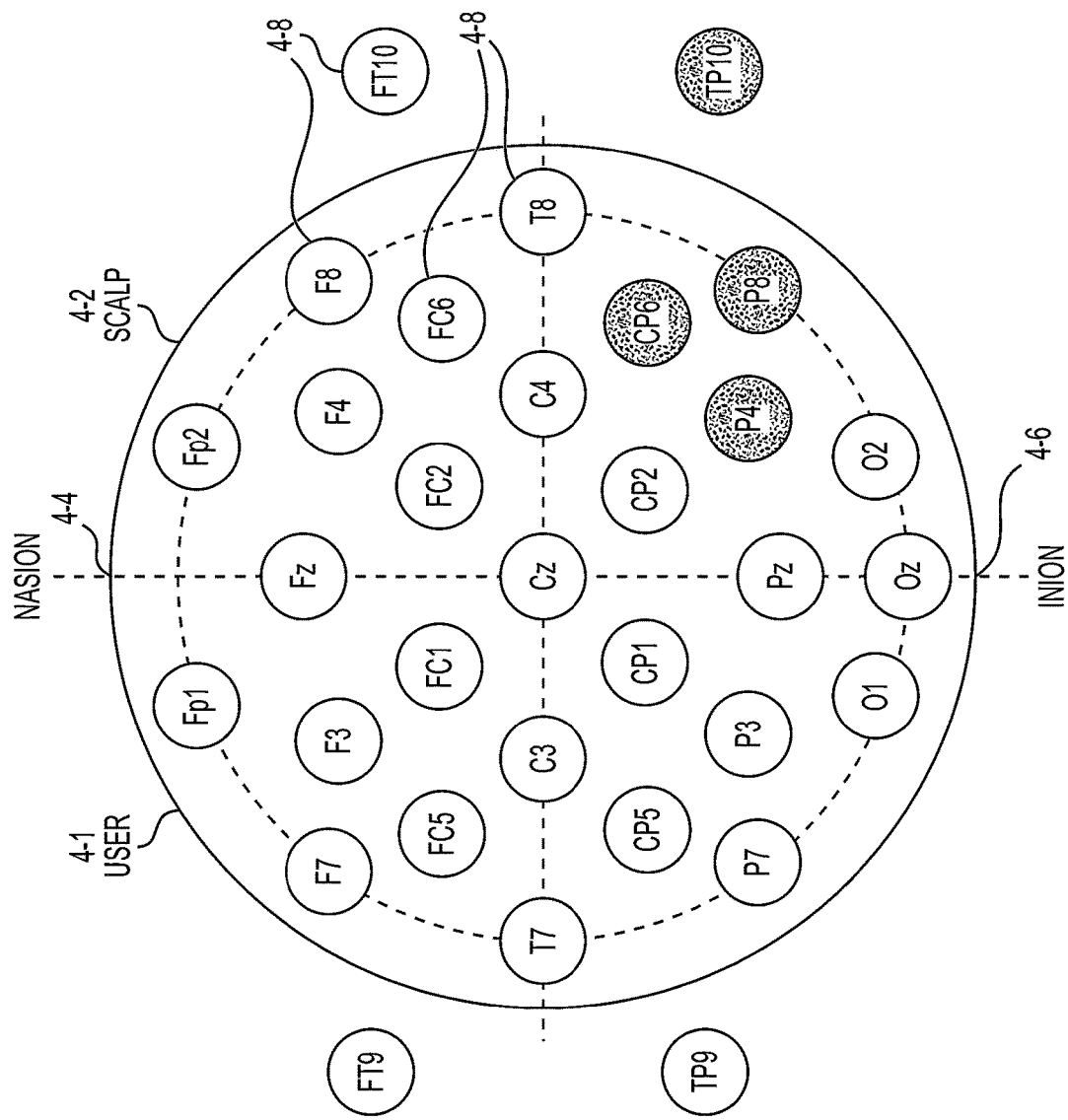
FIG. 4.48

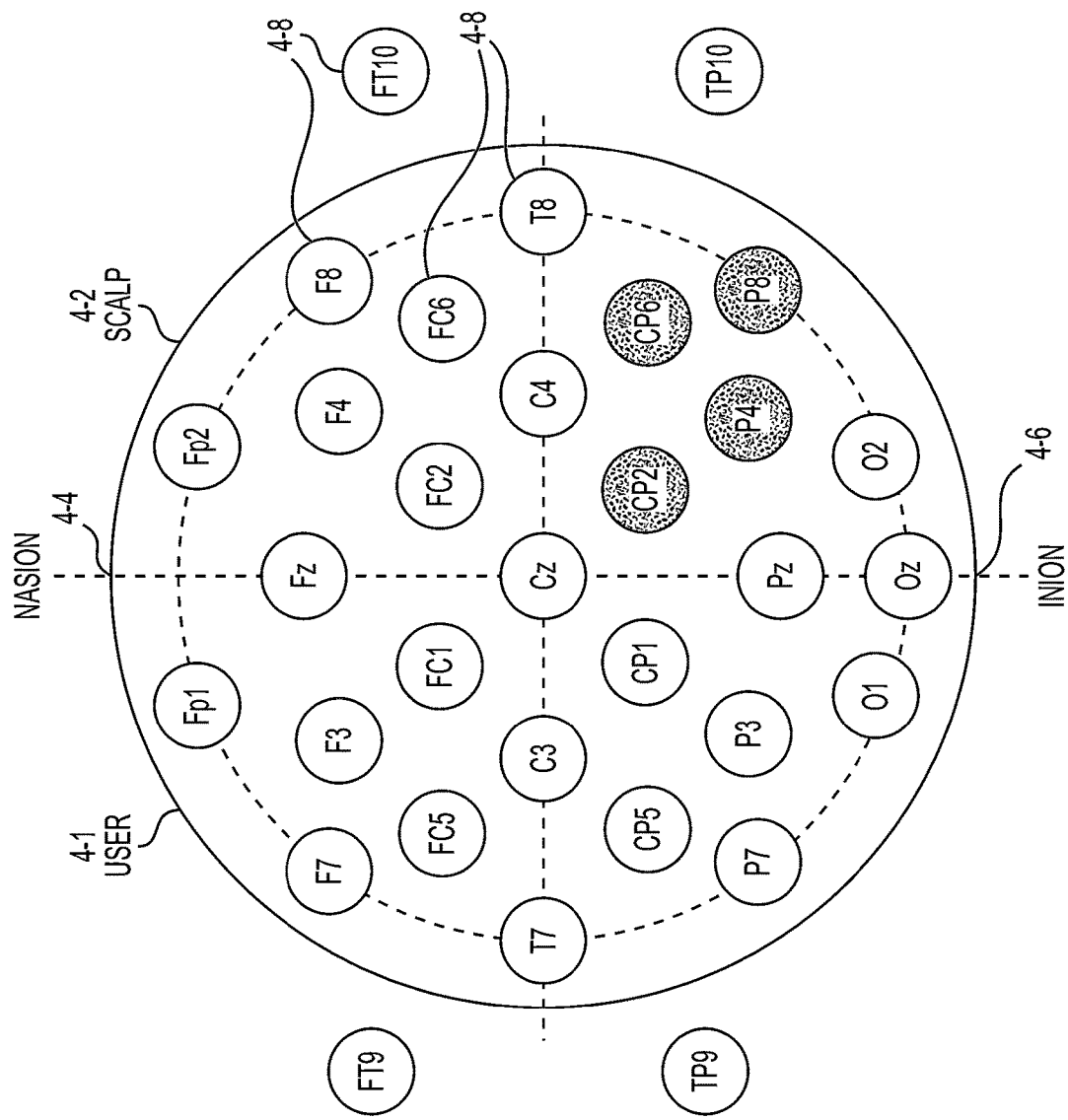
FIG. 4.49

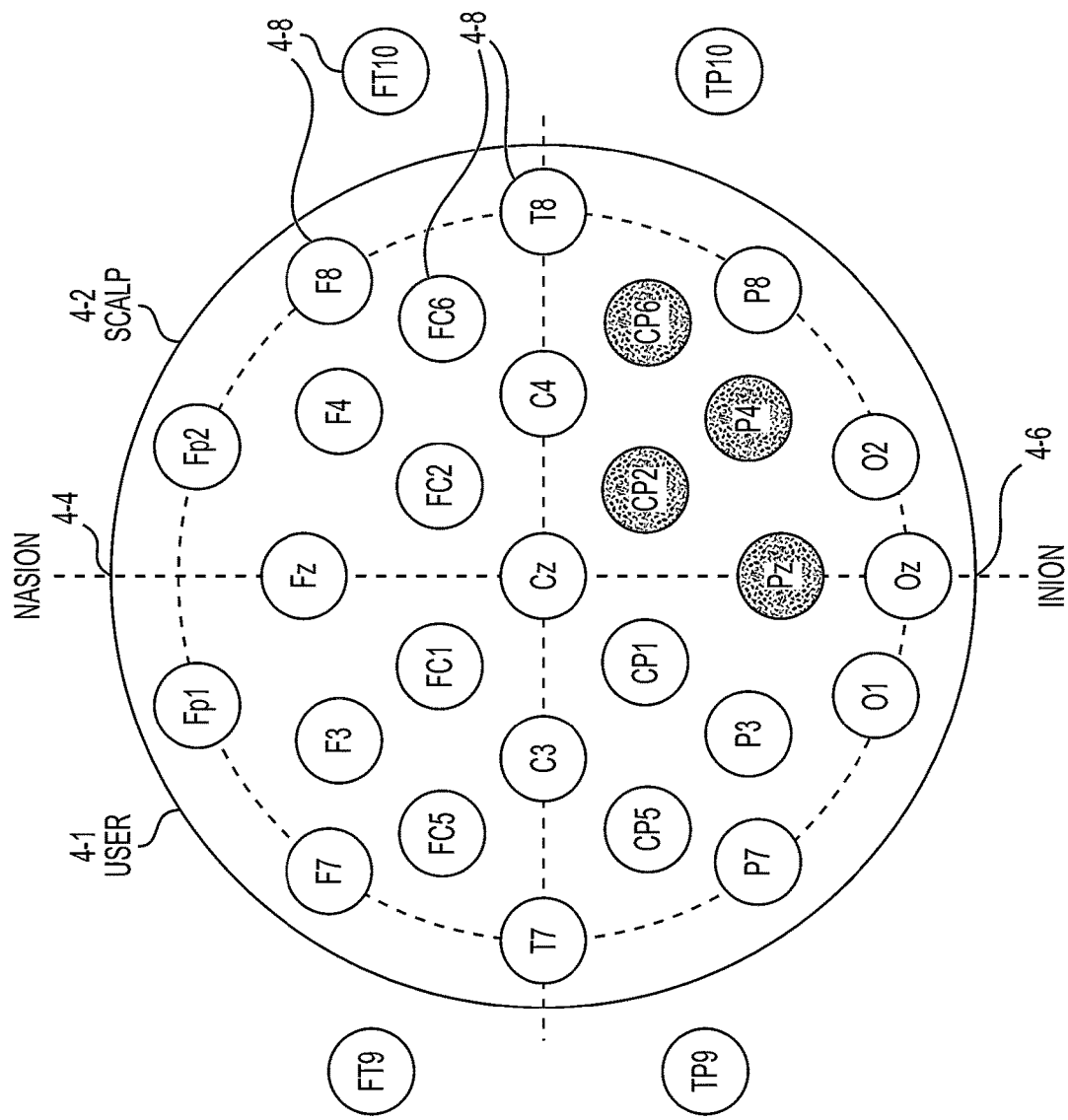
FIG. 4.50

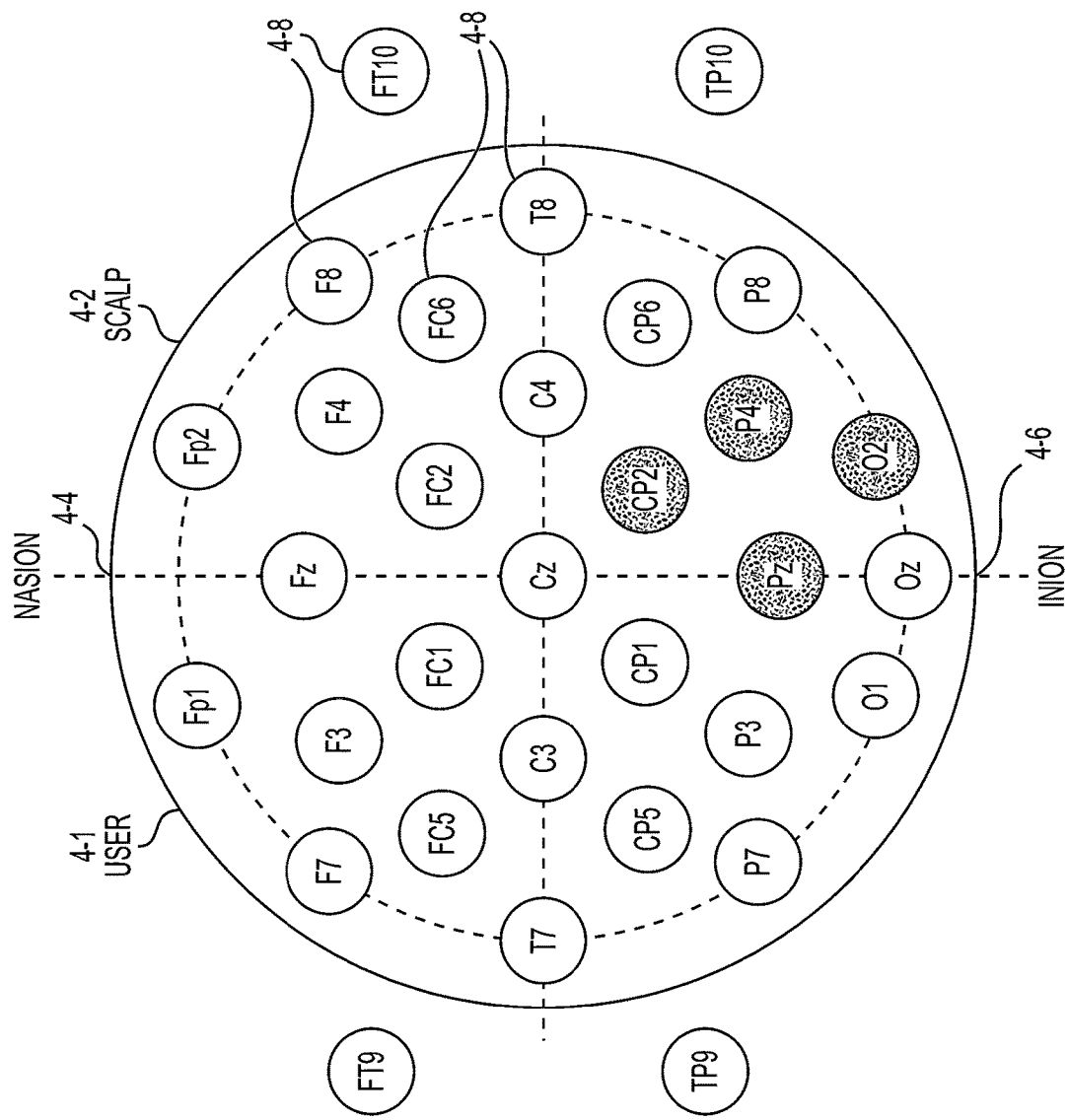
FIG. 4.51

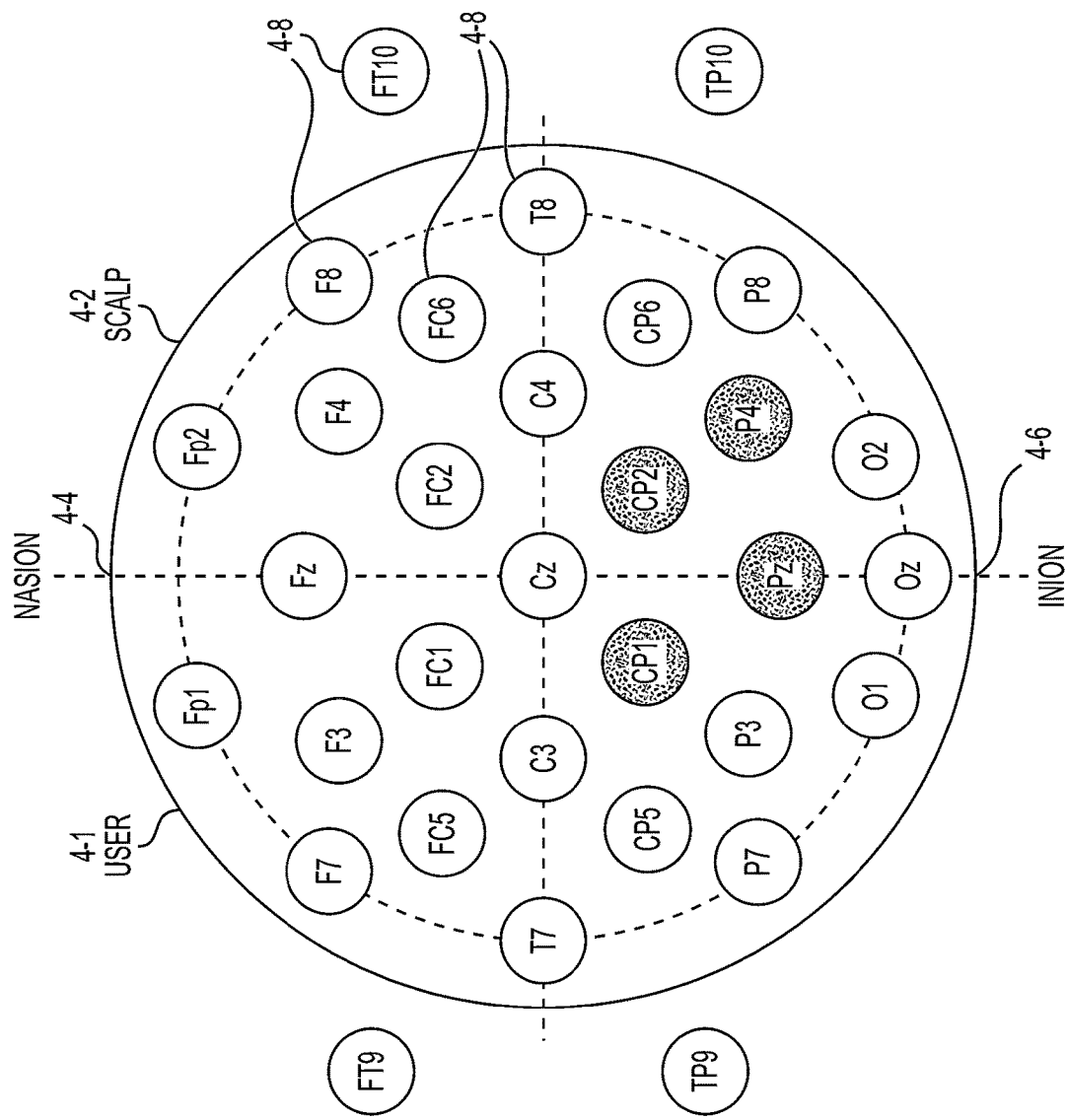
FIG. 4.52

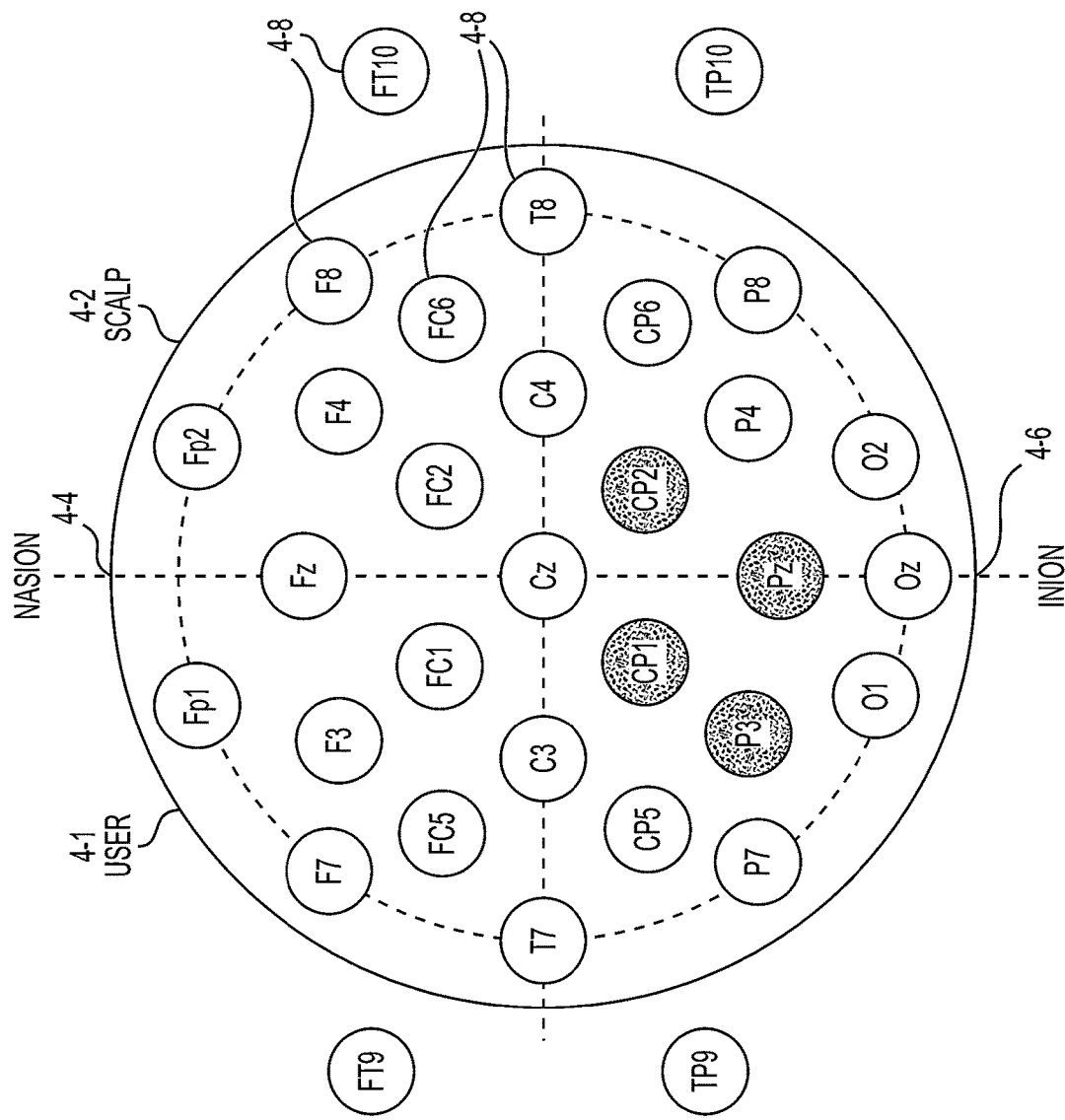
FIG. 4.53

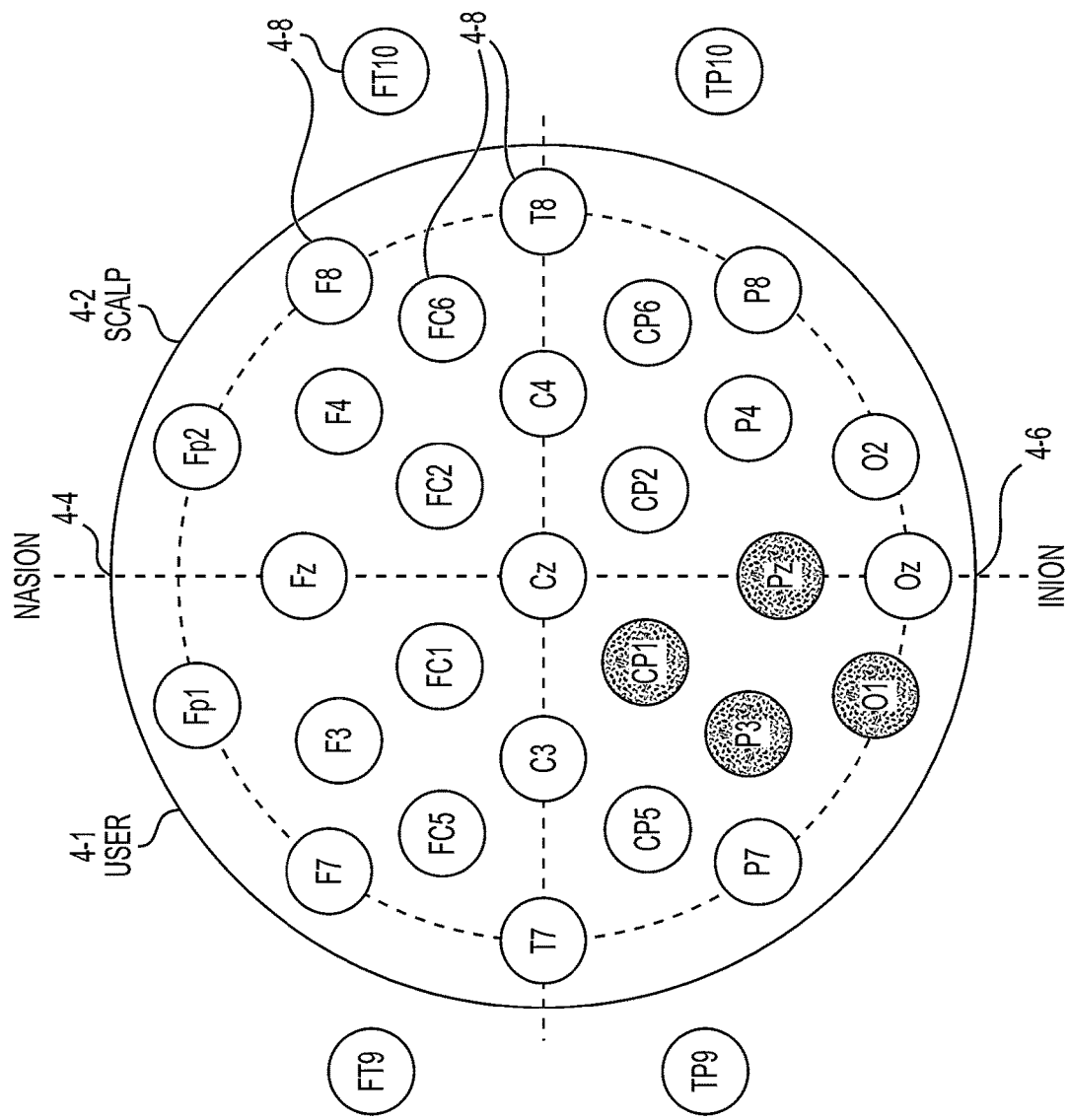
FIG. 4.54

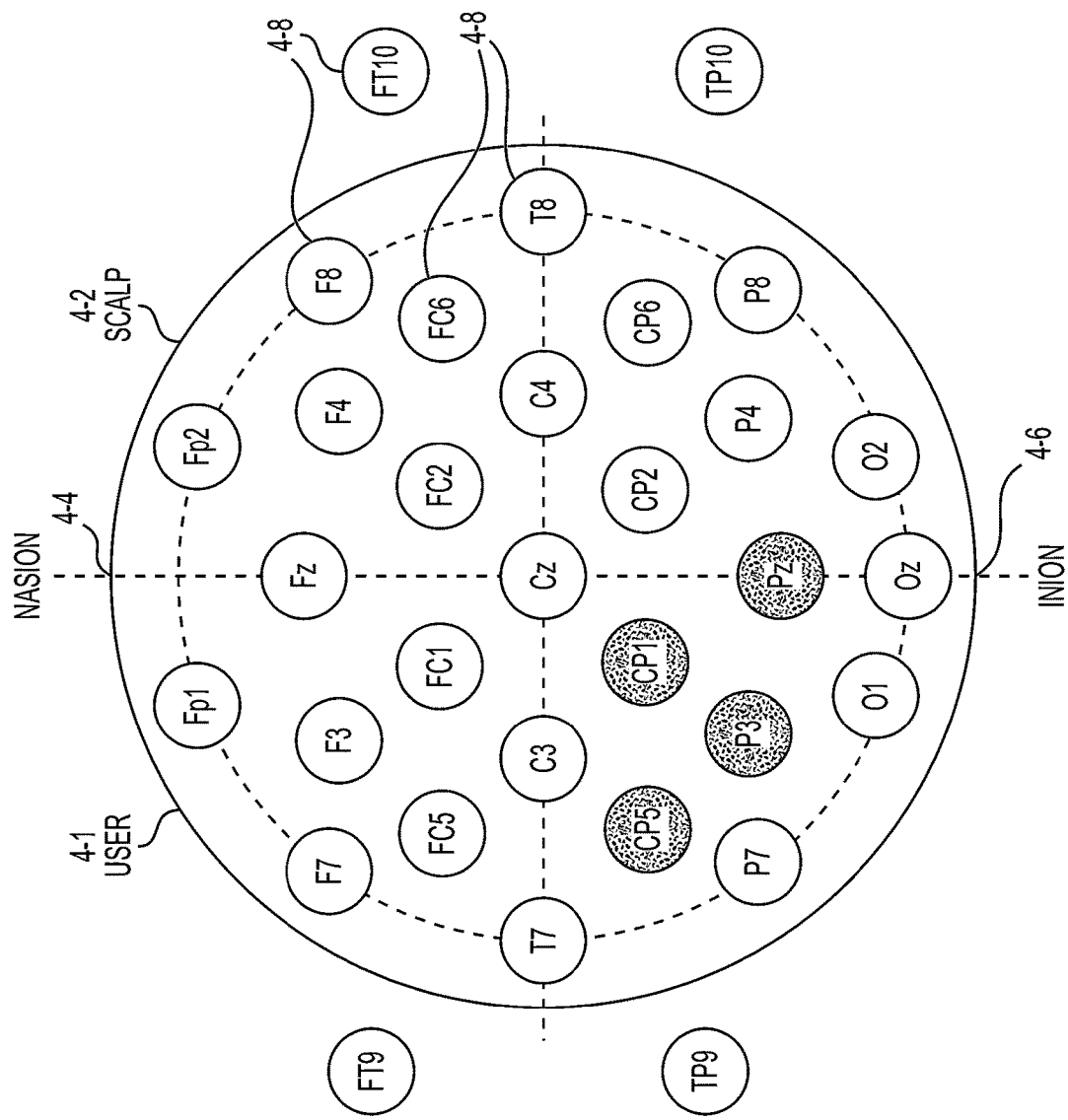
FIG. 4.55

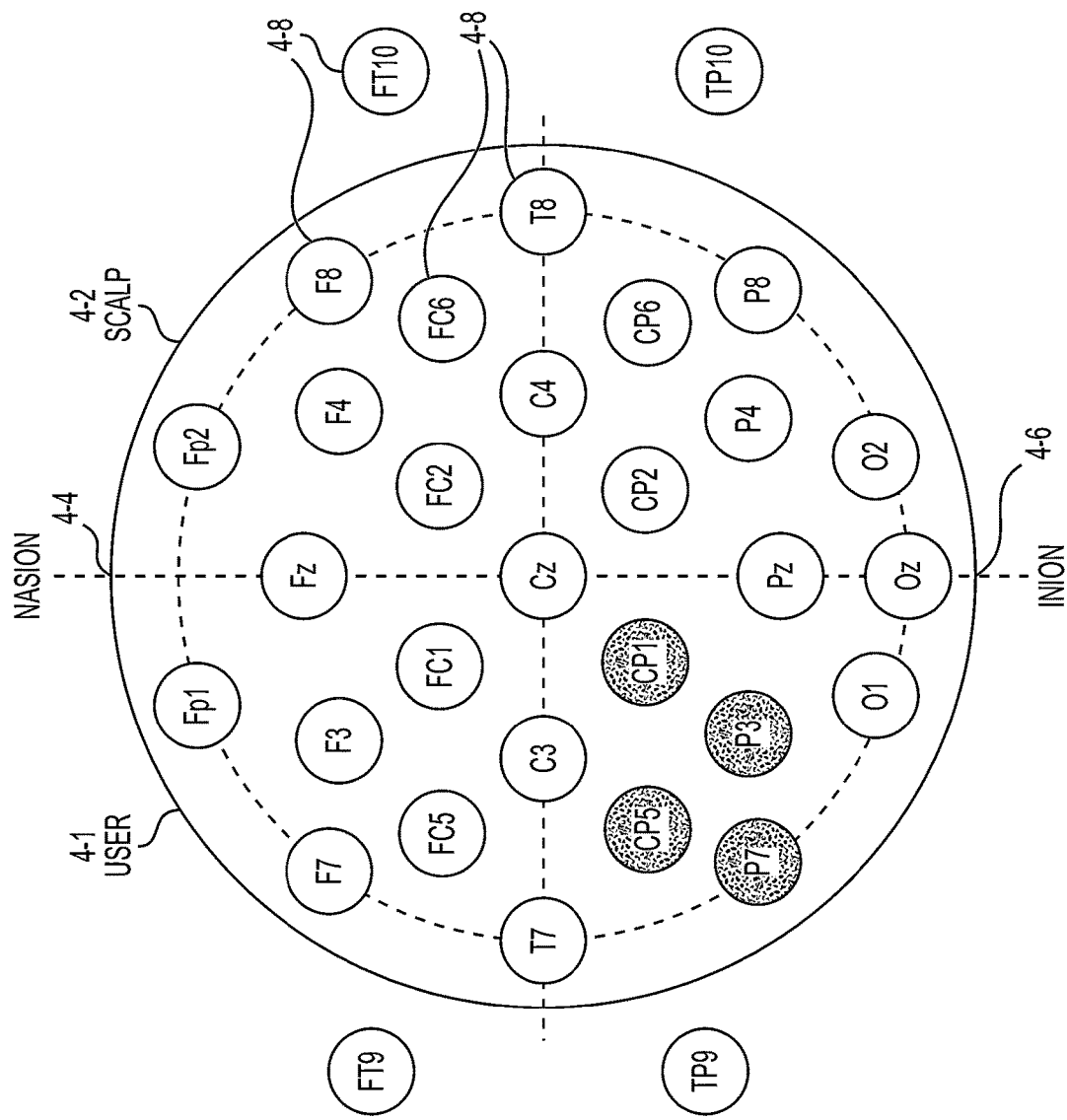
FIG. 4.56

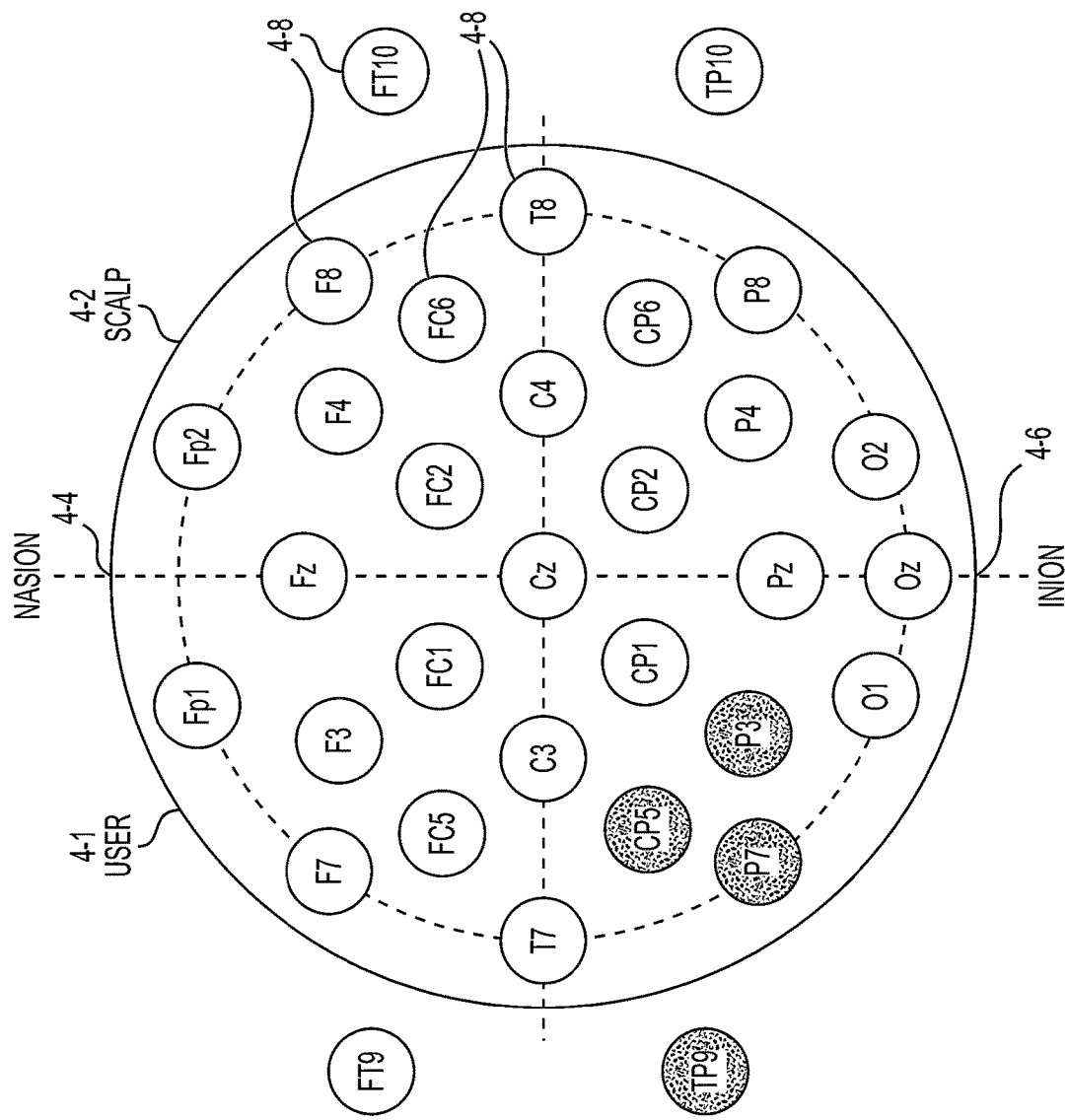
FIG. 4.57

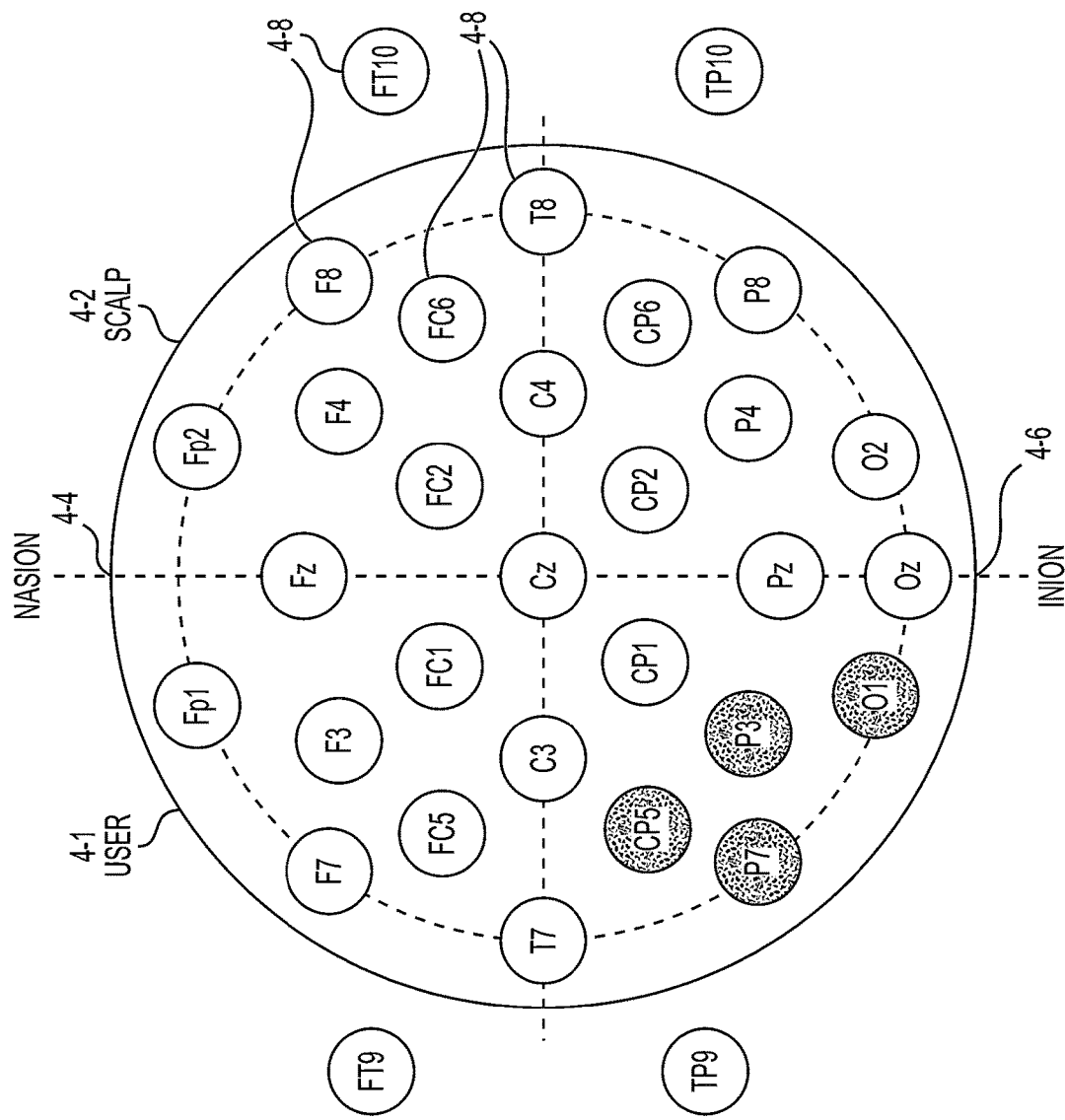
FIG. 4.58

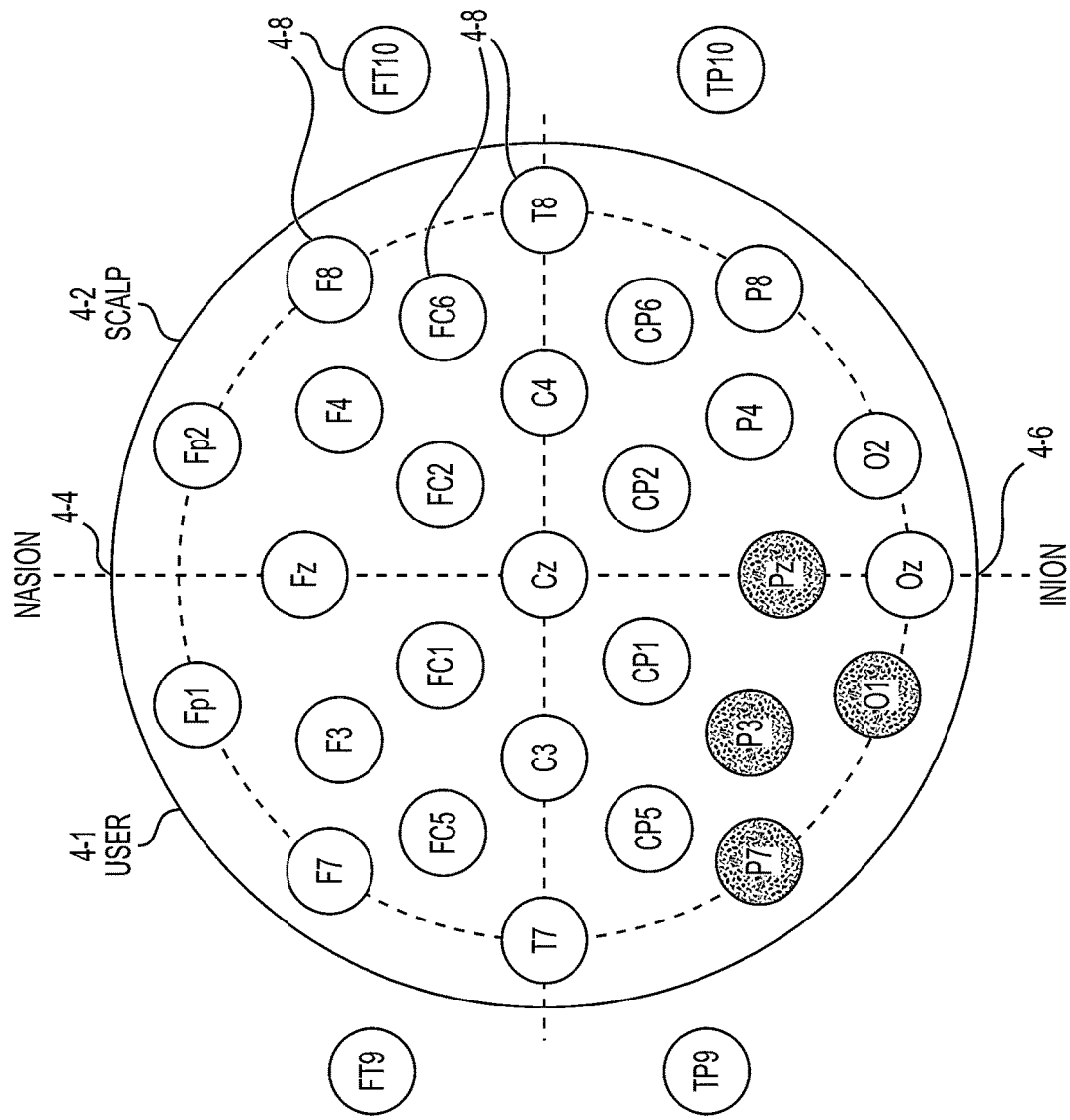
FIG. 4.59

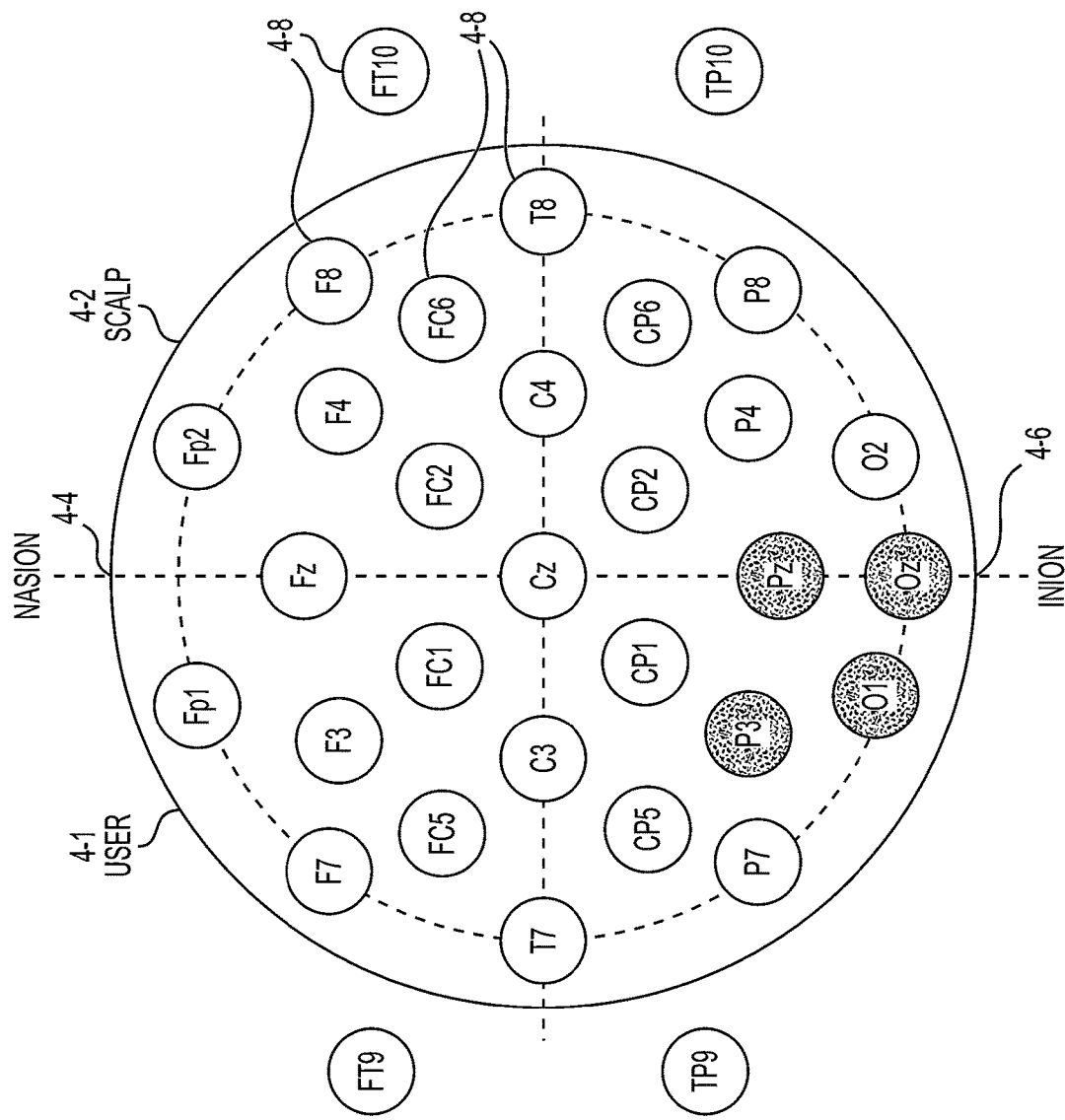
FIG. 4.60

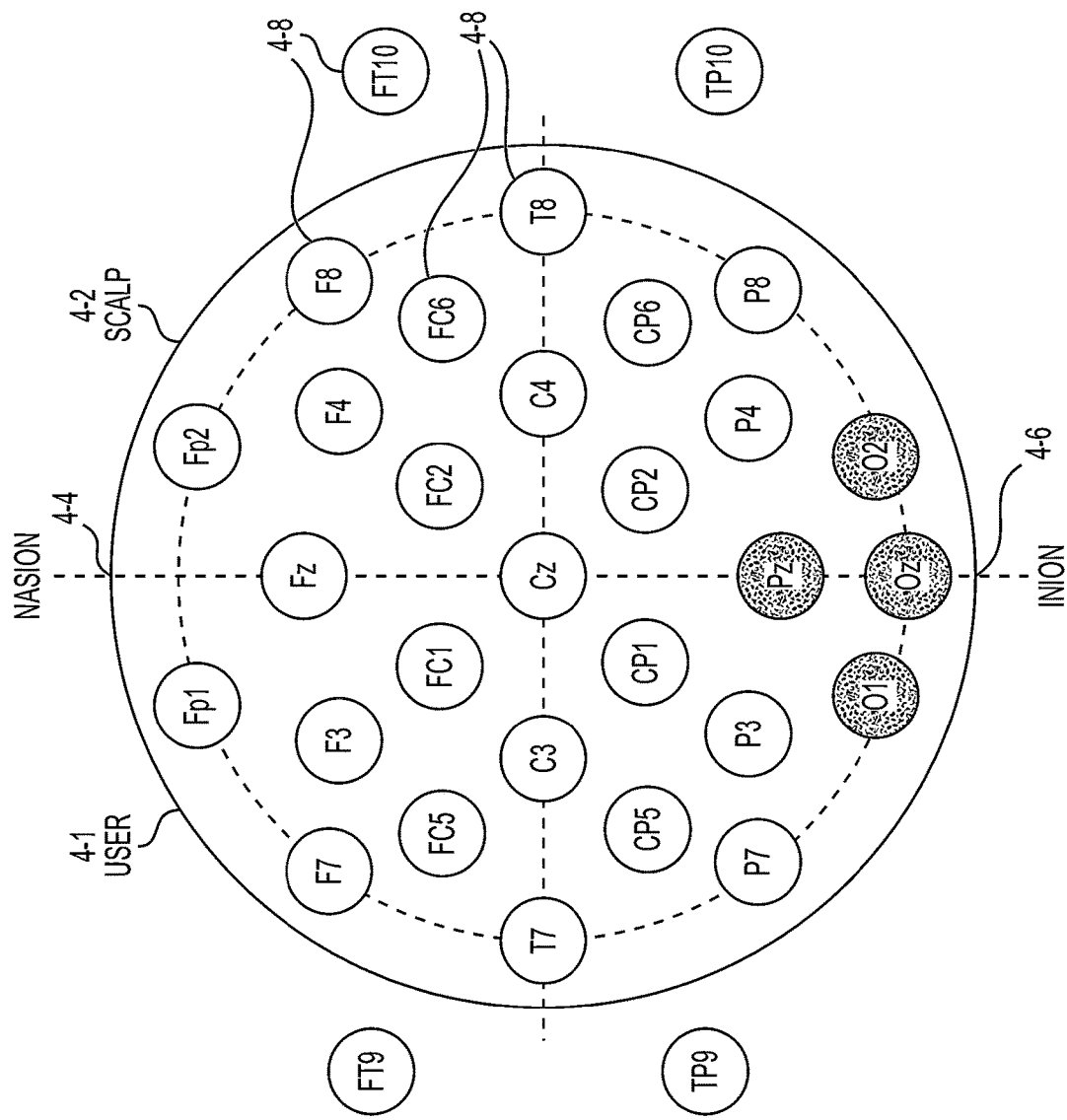
FIG. 4.61

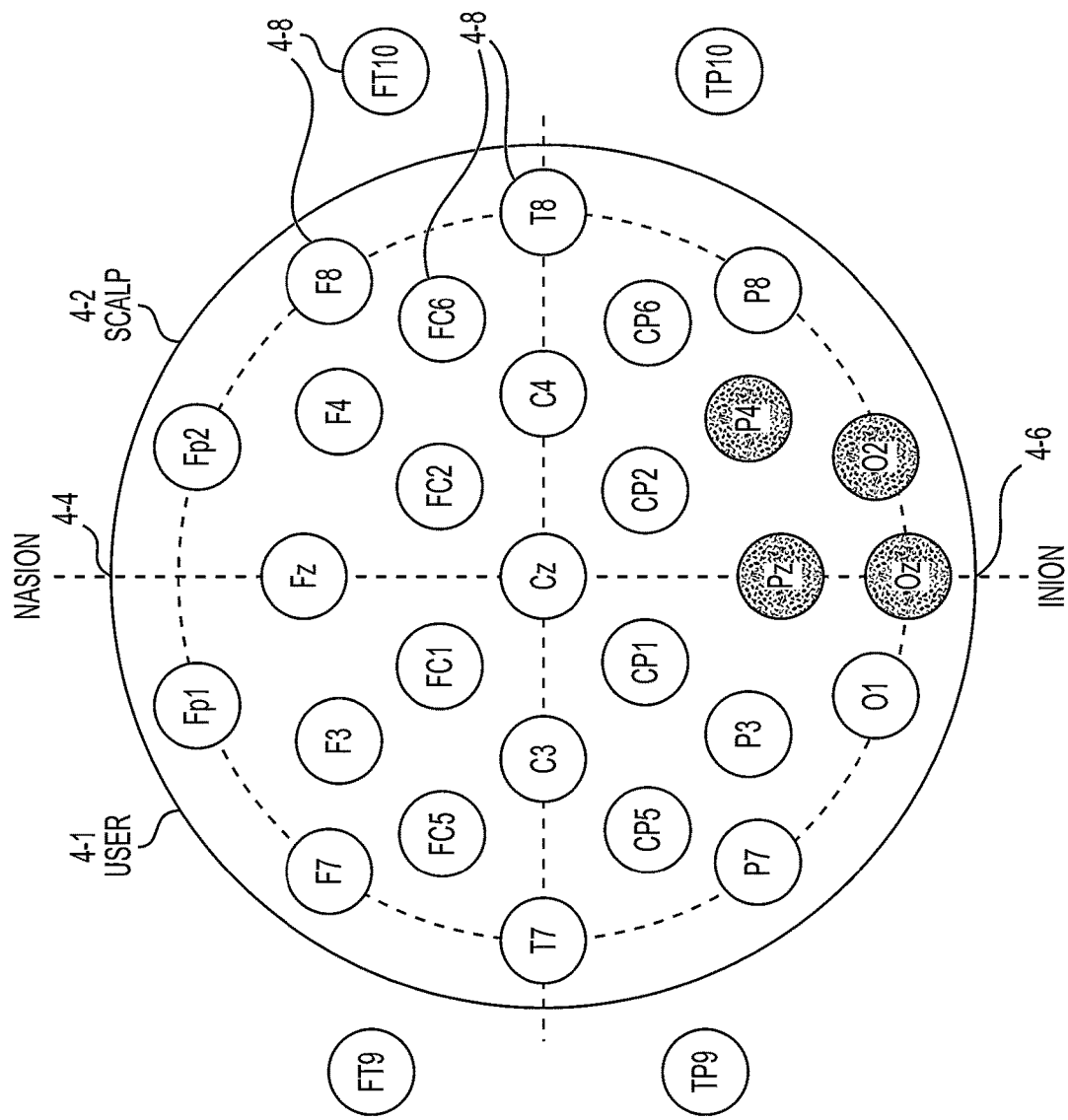
FIG. 4.62

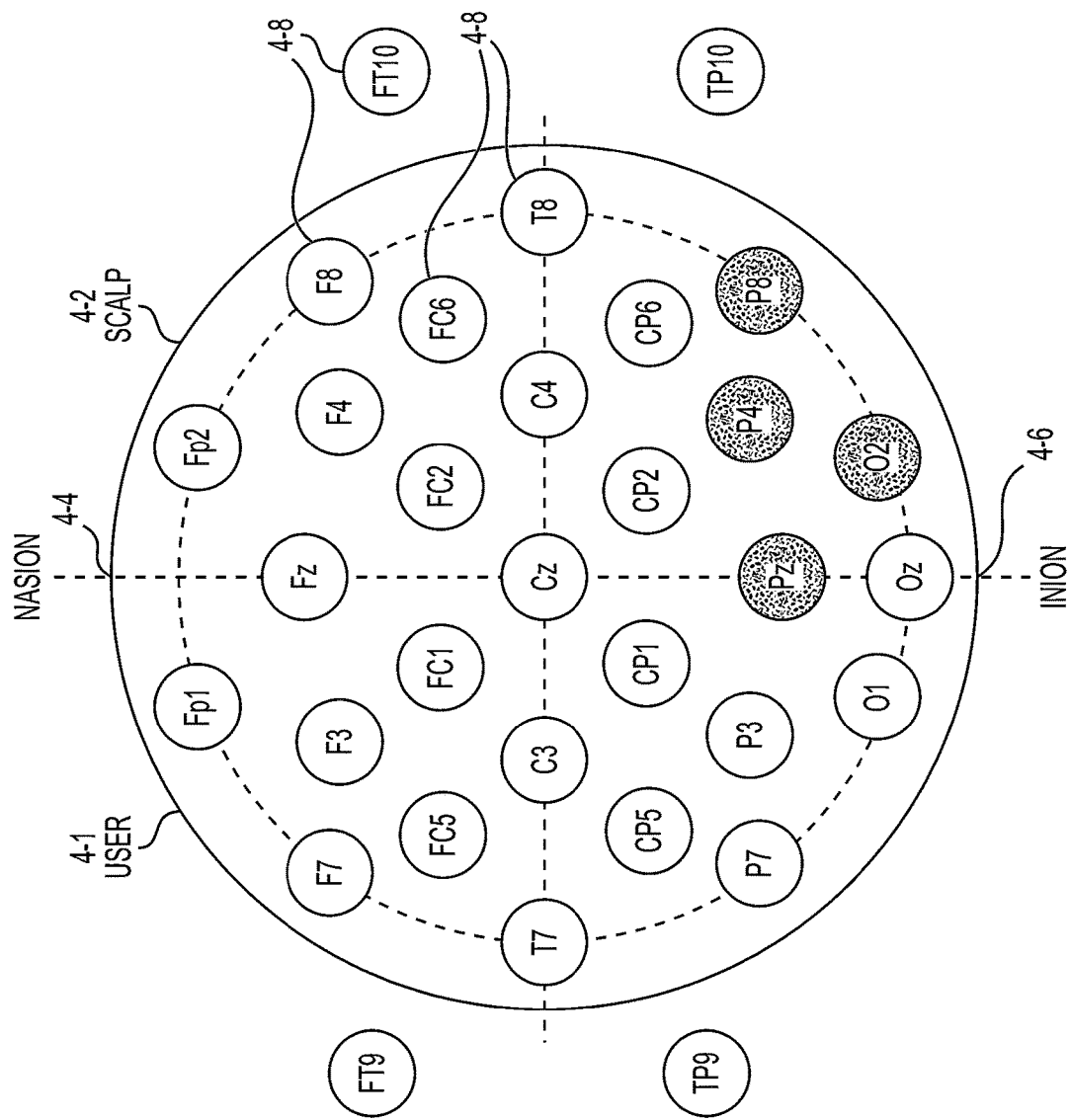
FIG. 4.63

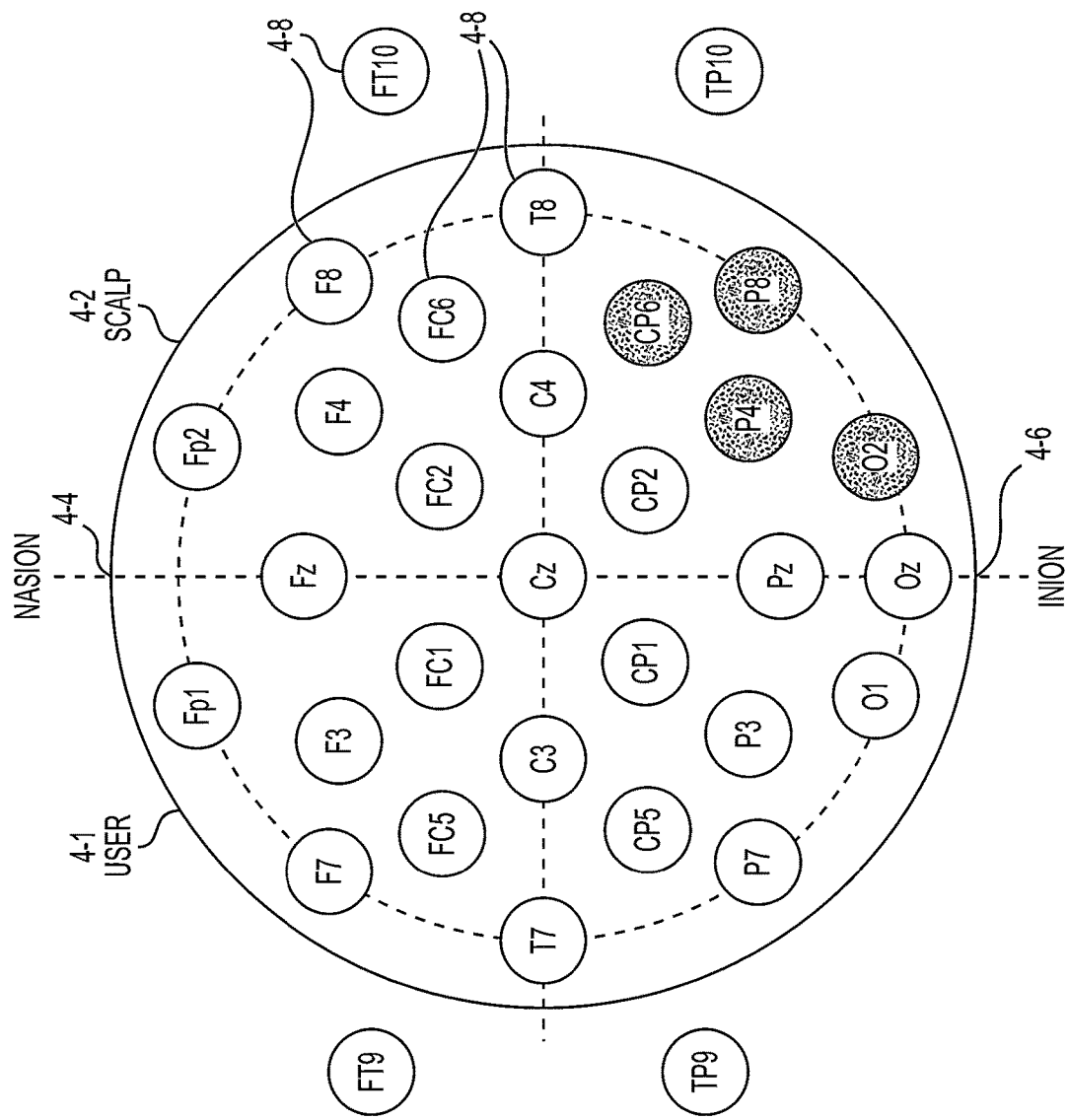
FIG. 4.64

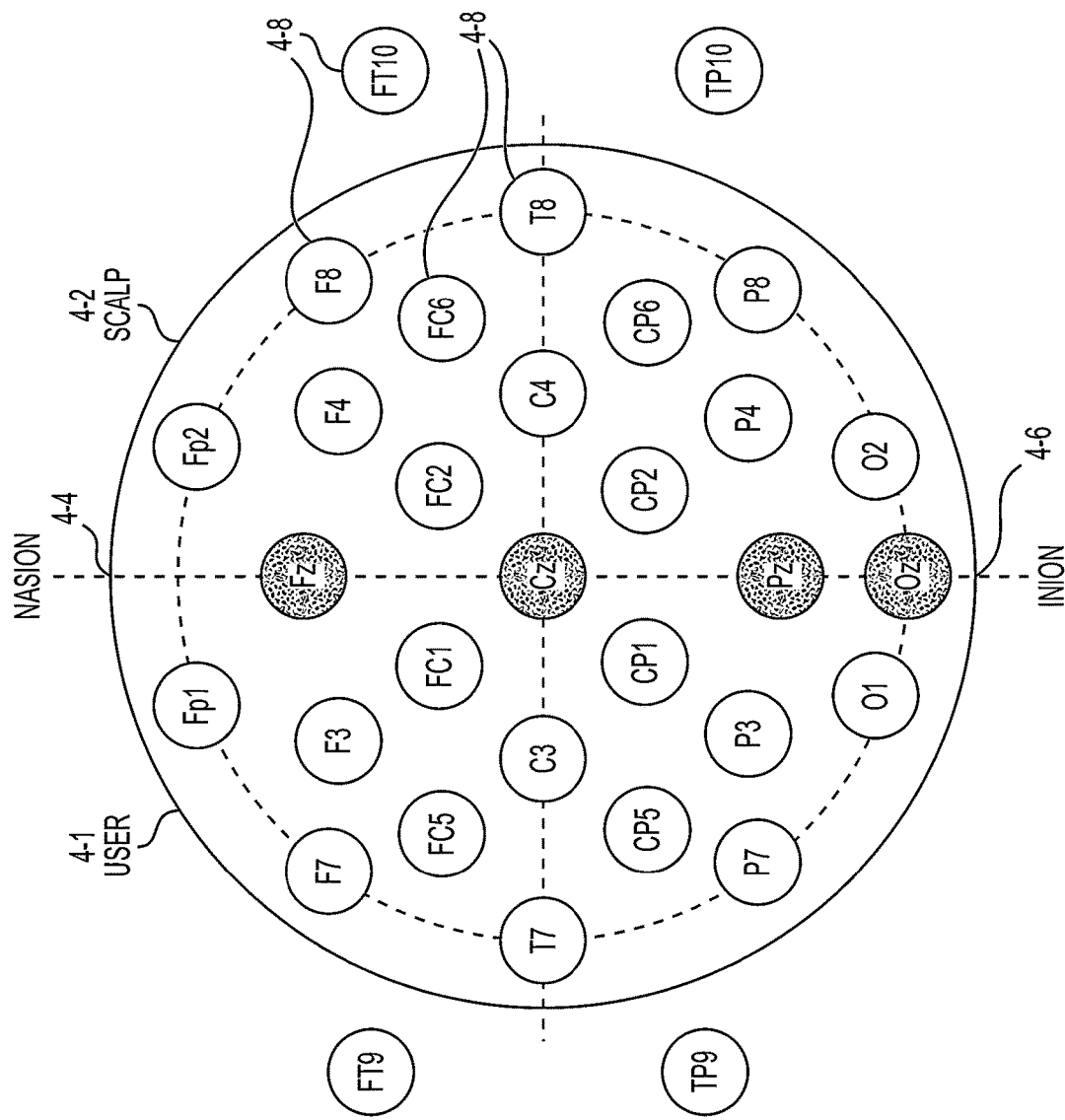
FIG. 4.65

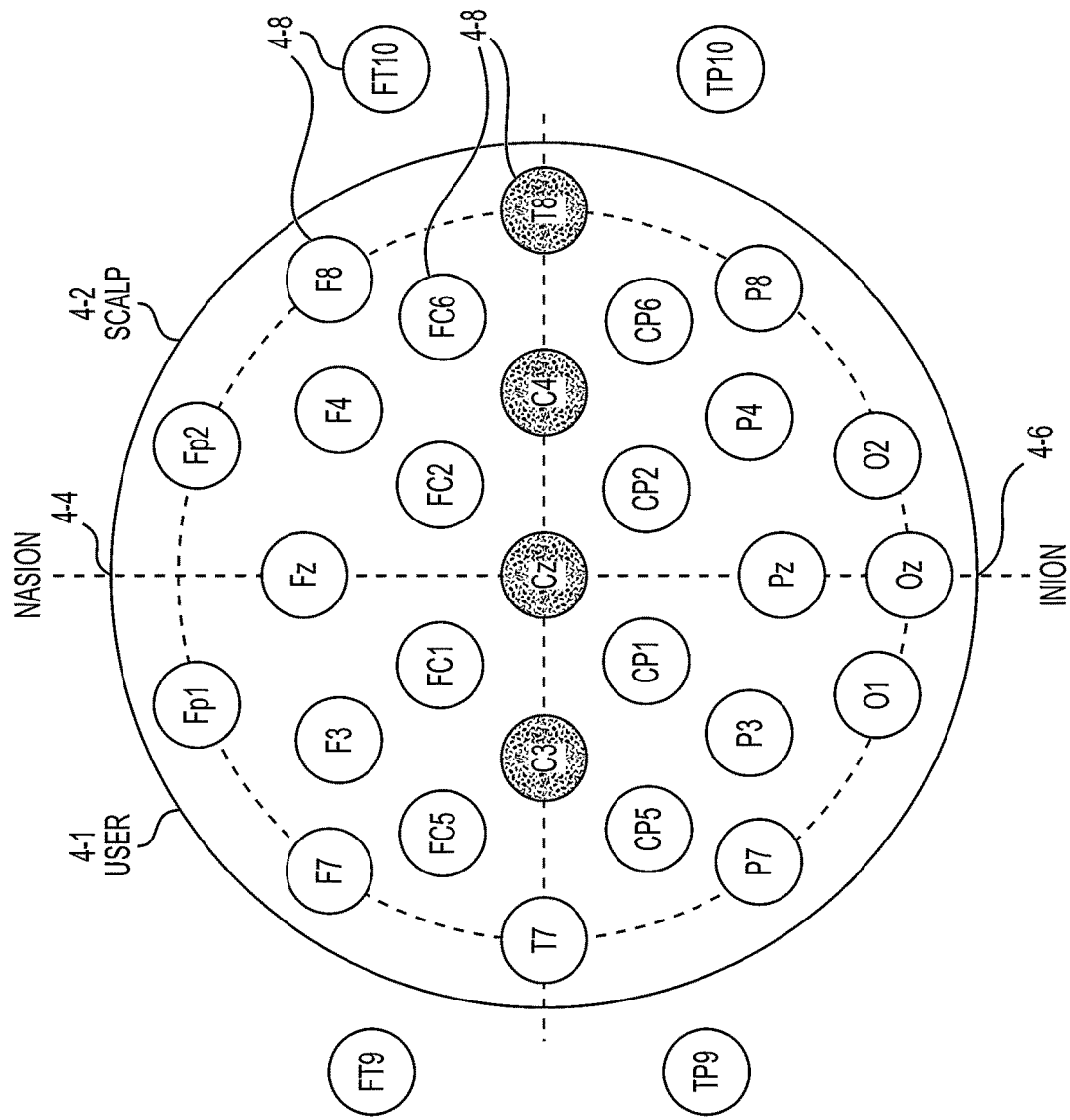
FIG. 4.66

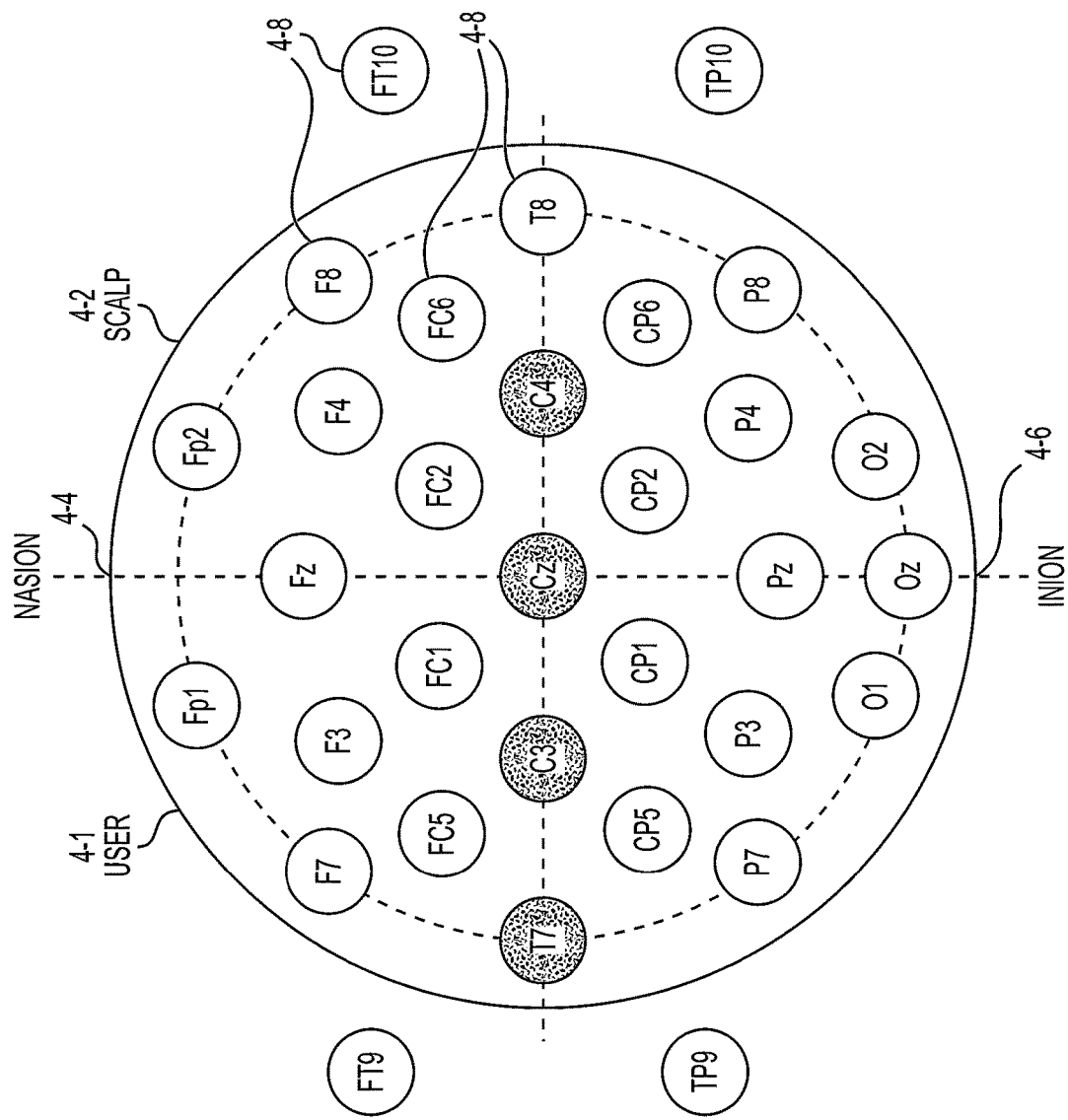
FIG. 4.67

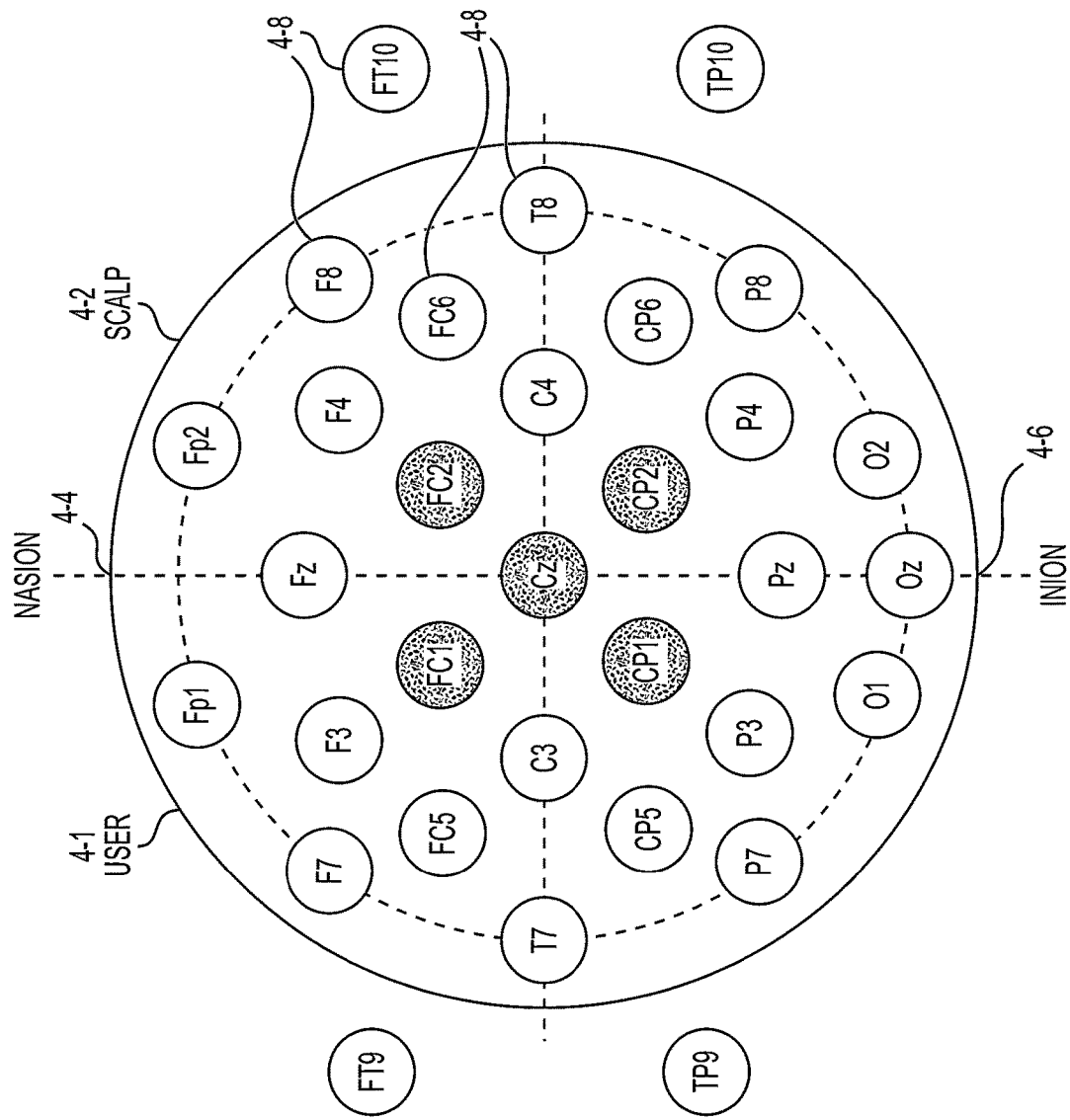
FIG. 4.68

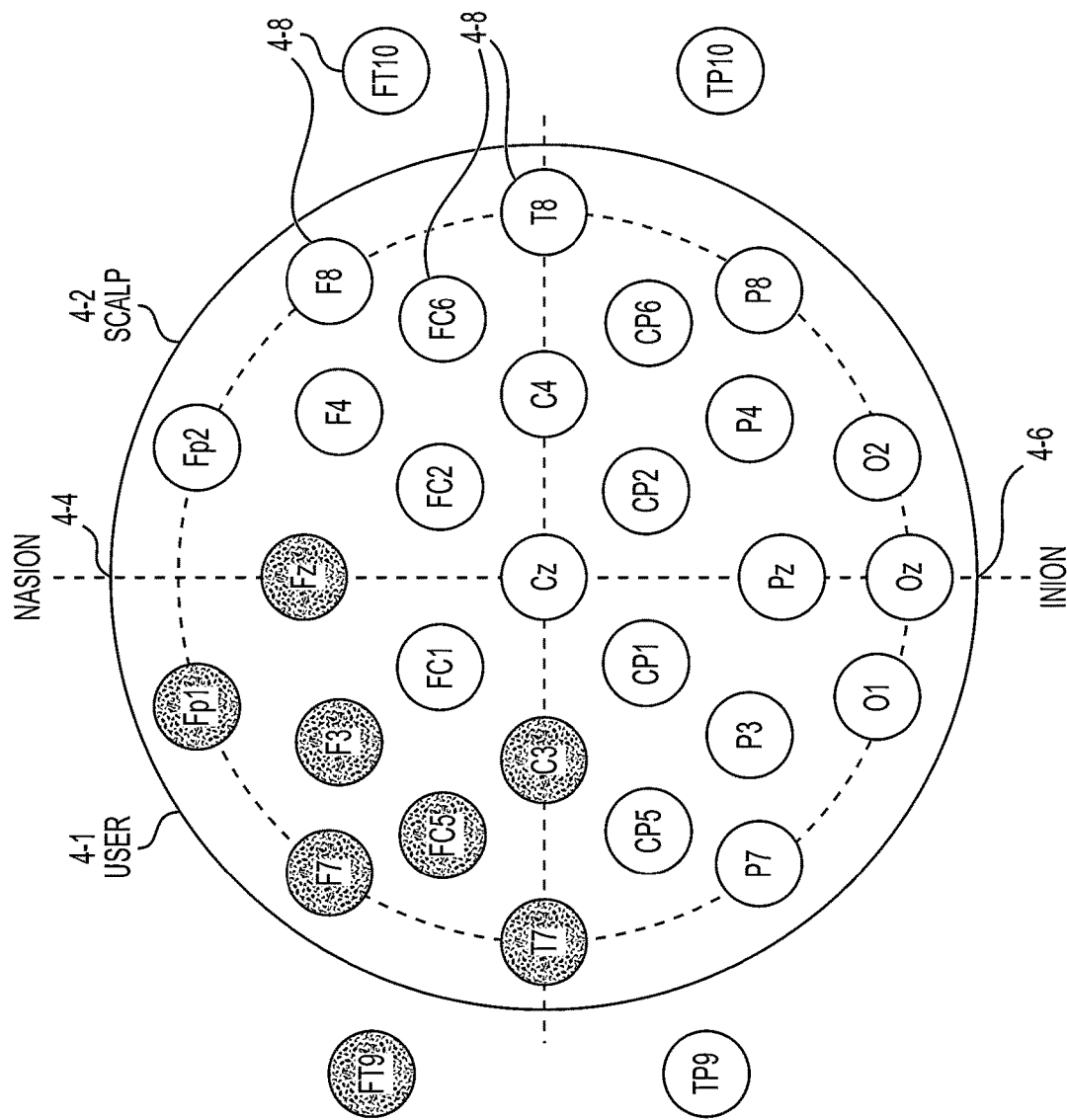
FIG. 4.69

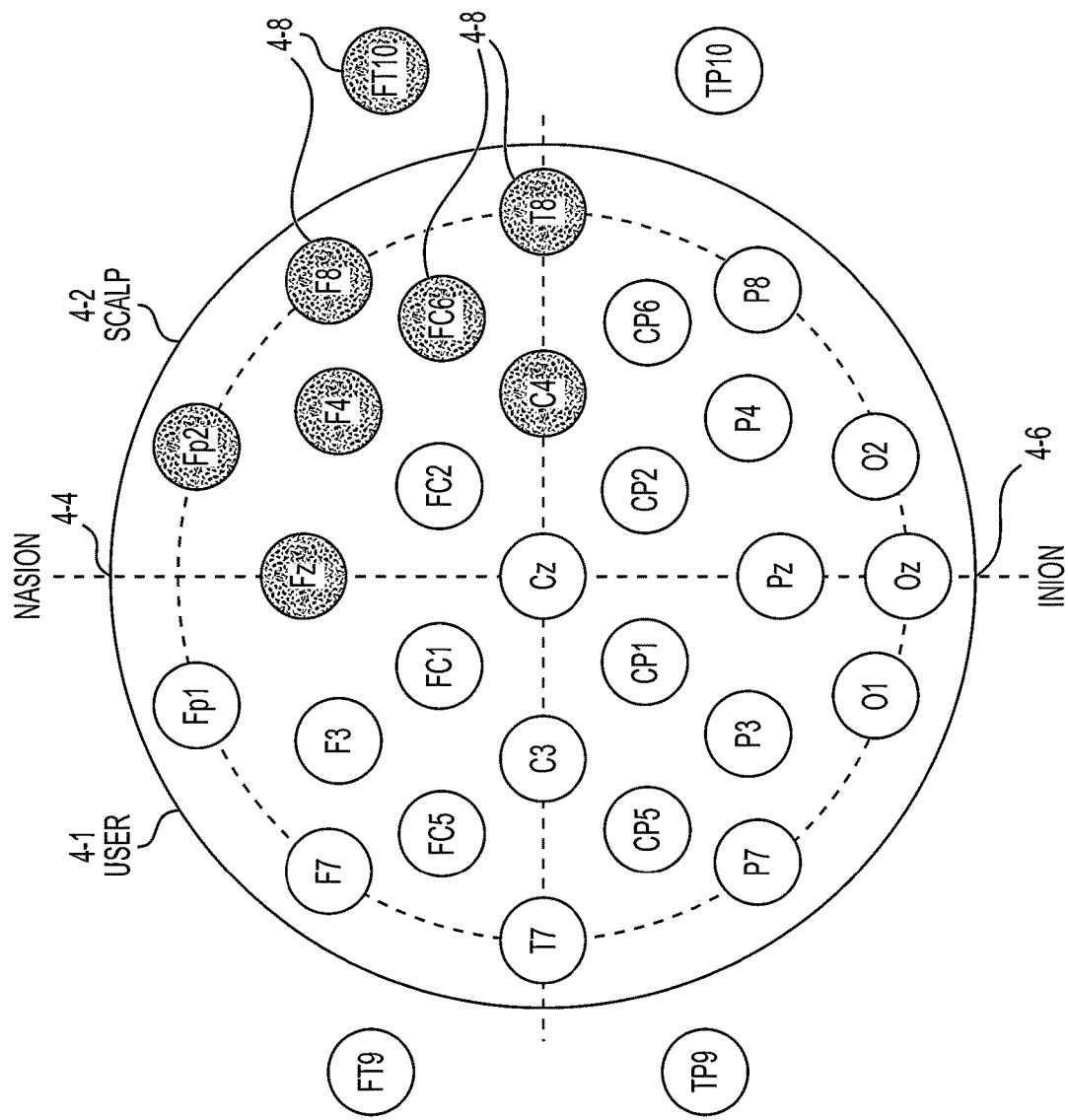
FIG. 4.70

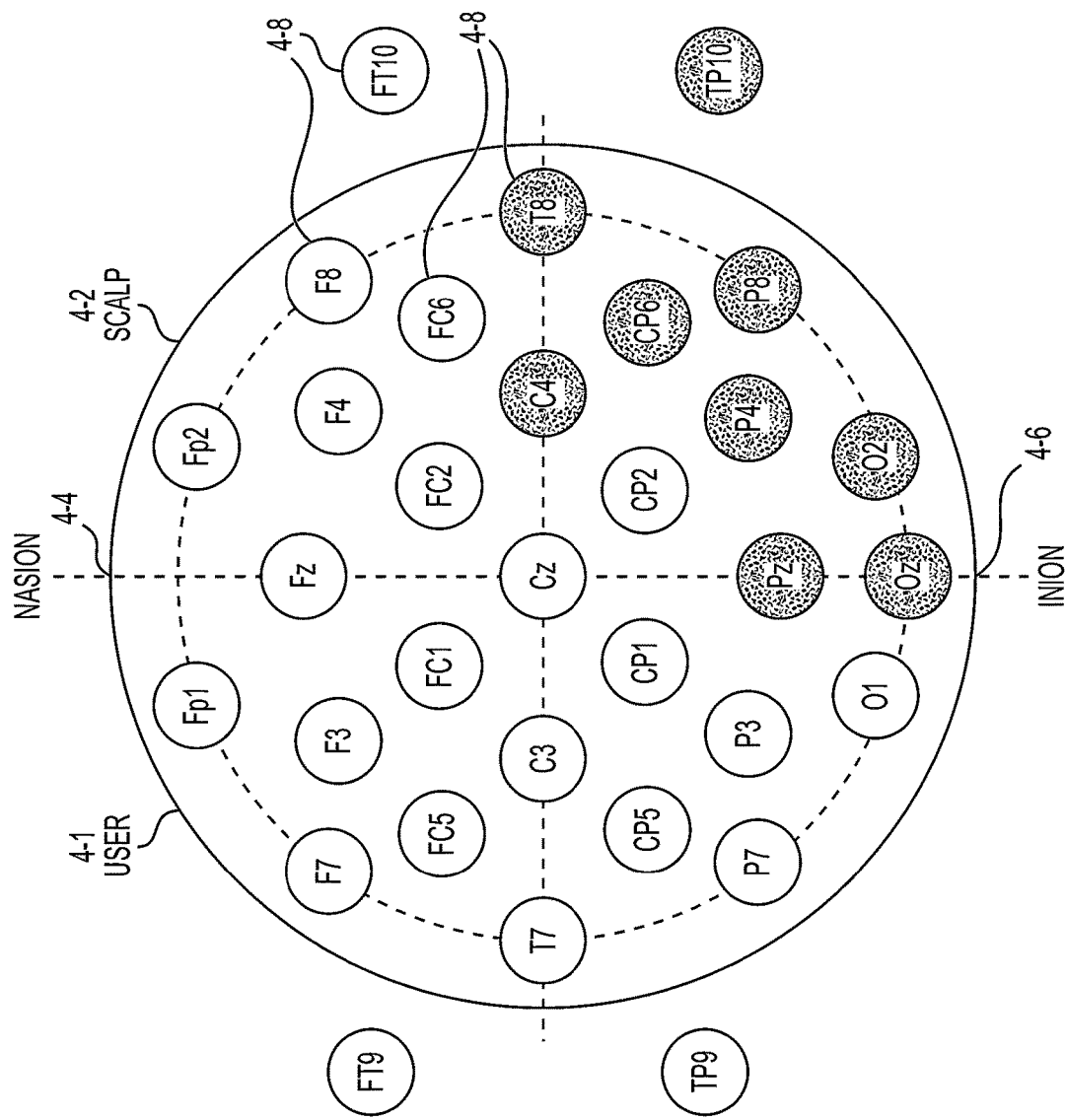
FIG. 4.71

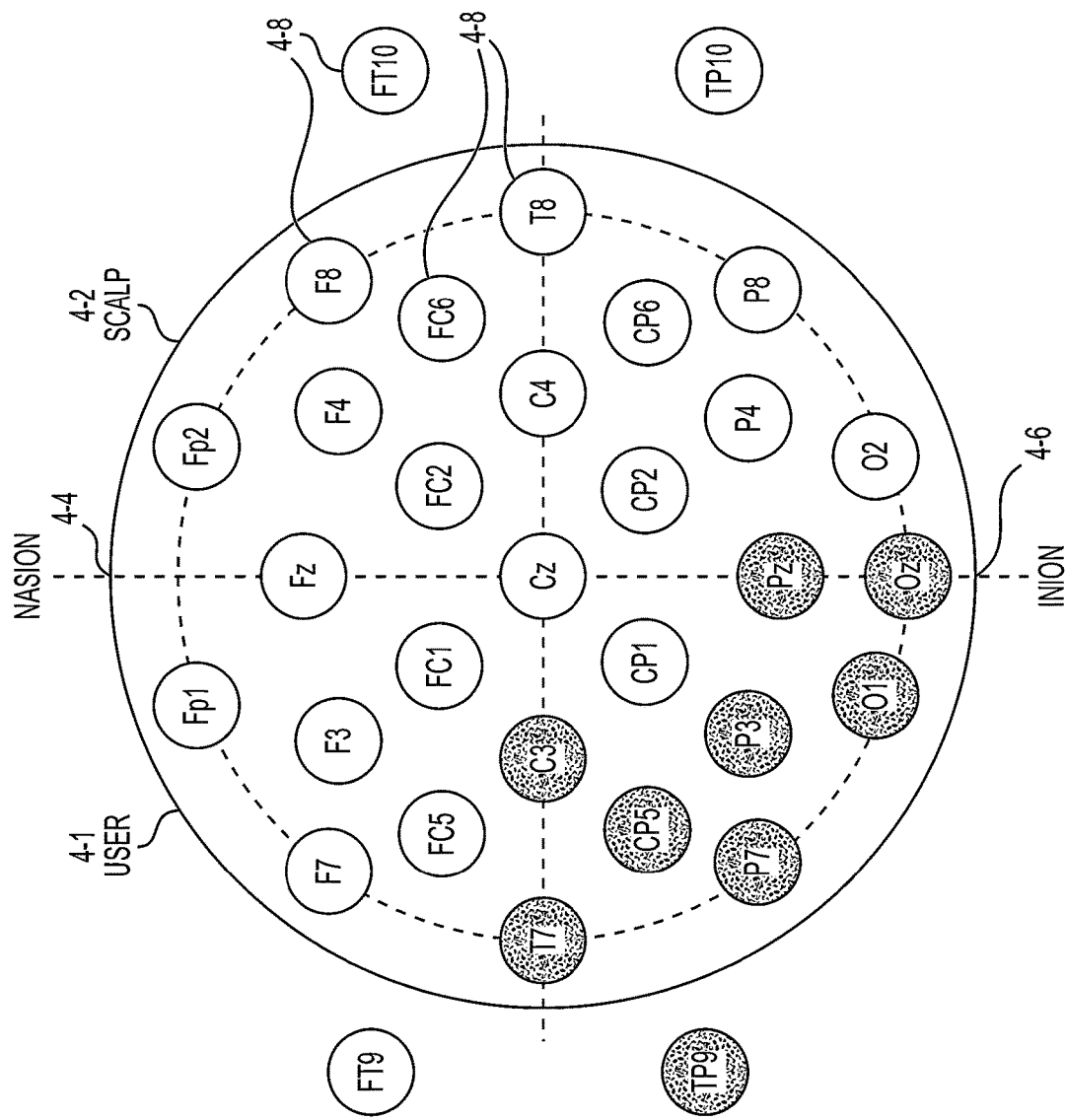
FIG. 4.72

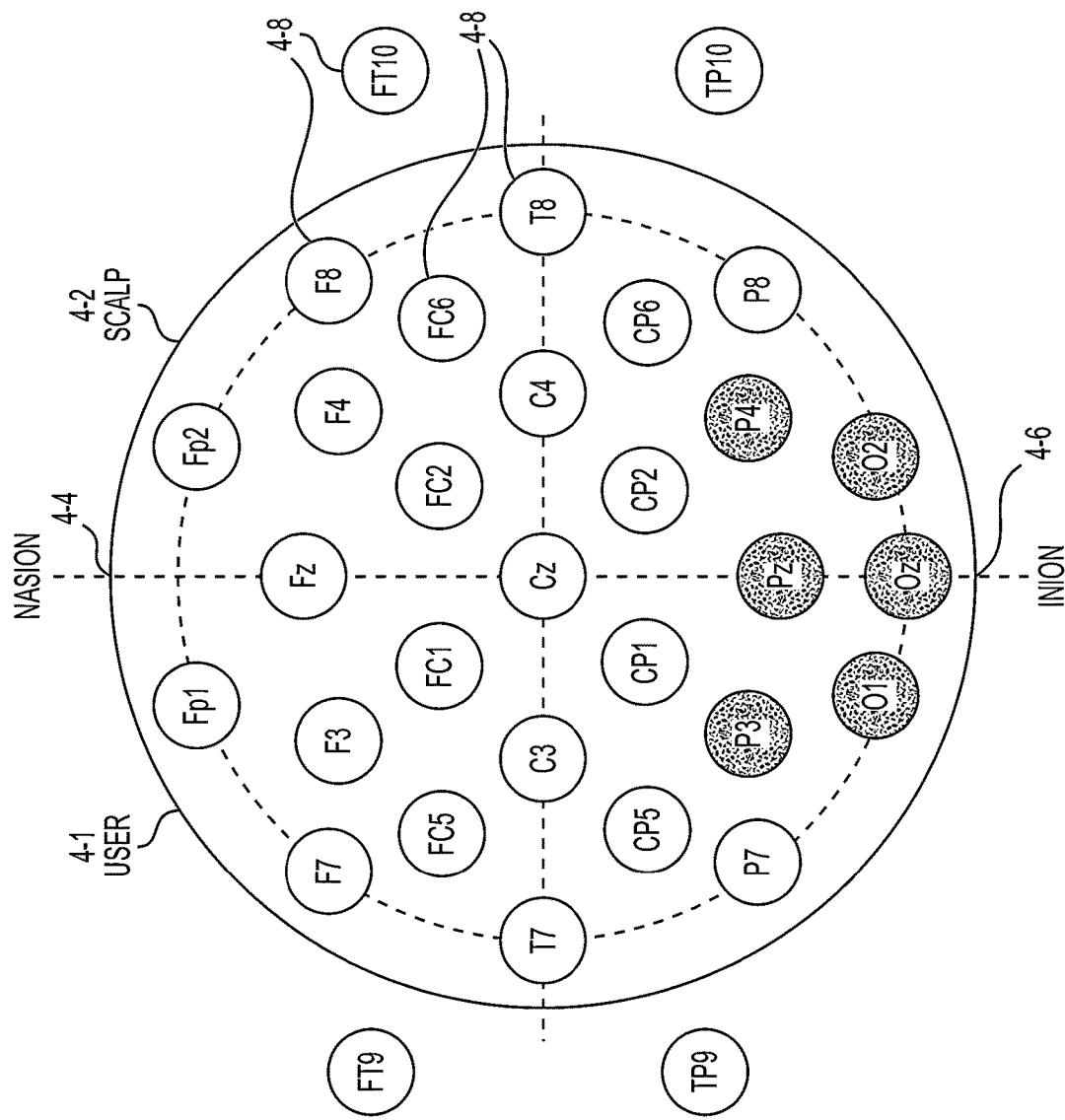
FIG. 4.73

HUMAN-COMPUTER INTERFACE SYSTEMS AND METHODS

CROSS-REFERENCE TO RELATED APPLICATION

This application claims the benefit of U.S. Provisional Application Ser. No. 62/868,775, filed on Jun. 28, 2019, entitled "Human-Computer Interface Systems and Methods," which is incorporated herein by reference in its entirety for all purposes.

COPYRIGHT NOTICE

A portion of the disclosure of this patent document contains material that is subject to copyright protection. The copyright owner has no objection, if issued, to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2019, 2020 Sensorial LLC. All Rights Reserved.

TECHNICAL FIELD

This application is directed, in general, to computer interfaces, and more specifically, to selective visual display systems, and more specifically still, to human-computer interface systems and methods involving sensor network integration and deep machine learning.

BACKGROUND

Currently, humans interact with machines via human interface devices (HID) such as mouse, keyboard, and joysticks. More recently, voice-activated devices and software allow humans to give commands via spoken language. In the seventh generation of video game consoles, the NINTENDO WII, SONY PLAYSTATION, and MICROSOFT X-BOX, have implemented technologies to track movements in the spatial dimension. These have enabled companies to make games that require human physical motion as an input such as tennis, boxing, baseball, and skiing. With the advent and advancement of virtual reality, new hardware interfaces are being developed to enhance realistic experiences for interactive games and meditation apps. These and others in development include wireless eeg headbands, fitbits, and sensors that detect sweat. Still, improved interfaces are desired. At times, brain sensors have been used, but there have been many issues created by inaccurate or variable locations of the sensors.

SUMMARY

According to an illustrative embodiment, a human-computer interface that integrates sensors and sensor networks to analyze human emotions and mental states is provided. In some embodiments, the systems and methods herein process signals from noisy sensors and sensor networks and apply deep learning to analyze the user's emotions. The systems or methods can supply any device or another human with the information of a person's emotion in real-time.

The ability to demonstrate and comprehend emotions is a hallmark of human interpersonal interactions. The interface between human and machine, however, has not yet evolved to this level of complexity. Typically, the human-machine interface involves a human giving commands to the machine through various inputs including keyboards, pointing devices, gamepads, remotes, and more recently, voice-activated systems. There does not exist a good, universal method by which emotional data from a human-device interface can be extracted, analyzed, and supplied to another entity whether living or nonliving. According to an illustrative embodiment, the systems, platforms, and methods comprise a software platform that enables the determination of the emotional and mental state of individuals for use in or with other computer-implemented systems. The methods and systems address the collection and processing of data from disparate physiological sensors and sensor networks through a hybrid algorithm or other techniques described that efficiently integrate sensors and sensor networks while allowing for fault tolerance.

In addition, in one illustrative embodiment, the systems and methods disclosed may improve robustness and operating range by reducing or minimizing noise and other confounding artifacts associated with certain conditions like user motion. The software platform employs deep learning to determine a mood index, or emotion-predictive signal, based on its prior experiences with human emotions and mental states. The systems and methods herein are brand insensitive and input agnostic as they can utilize an expandable set or subset of various physiologic sensors or sensor networks including electroencephalogram (EEG), electrocardiogram (ECG), pulse detection, respiratory rate monitoring, sweat monitoring, blood pressure monitoring, or other inputs. The systems and methods (are referred to as a "platform" in some places) are also output agnostic in that the platform can output a mood index or signal to any device, machine, or human that can appreciate real-time analyses of human emotion and mental state and then decide whether or not to effect change. The illustrative platform is versatile in that the platform can be employed in a multitude of daily applications and settings: the platform can be used when someone is listening to music or watching a movie; or when a gamer is playing a video game or undergoing virtual reality immersion; or when an audience is watching an advertisement or a presentation; or even in a situation to detect a driver who is unfit to operate a car. The platform distinguishes between different emotions and mental states so that devices or even another human who is receiving this information can provide feedback to the person and then elicit or optimize or take action for a certain response.

In one illustrative embodiment, a system and method are presented to address imprecision in EEG electrode placement on a user's scalp. The placement of the EEG electrode on a human scalp is often quite imprecise. It is difficult to reproduce the exact positions of the electrodes each time the EEG machine is set up on a user. When the EEG system is applied across different individuals, the uncertainty in electrode position on the scalp is compounded by the differences in anatomy, e.g., head sizes. At the same time, pattern recognition serves as the basis for emotion and mental state recognition, and the accuracy of detection is sensitive to differences in the mounting position of electrodes. In one illustrative embodiment, a unique solution that accounts for different head sizes, mitigates imprecisions in sensor positioning on the scalp, and improves sensor fault tolerance is presented. By accounting for all of these physical factors, the system enables the use of deep learning to accurately classify mental and emotional state of a user and that emotional-state data may be used by any of a number of devices or systems, e.g., a virtual reality device.

In one illustrative embodiment, the classification of emotions of a user is predicted by a system and the resultant signals may be used by any of a number of systems, e.g., a virtual reality system. Classifying emotion and mental state by deep learning may require heavy computation, typically done on a server with a substantial amount of computing power; for example, the computation may involve a deep learning cluster with multiple graphic process units (GPUs). A brain-computer interface that garners a readout of brain electrical activity (or brain waves) from an EEG should be able to process the data in real-time or near real-time and supply a computer/software with emotion and mental state information on the user. Typically the interfaces exist on local computing devices that do not have the computing power to perform deep learning. In one illustrative embodiment, the system is a brain-computer interface that leverages the pattern recognition capabilities processed on a deep learning cluster, to be embedded in a local device and supply a virtual reality software, game, or another non-virtual reality software with emotion and mental state information.

According to one illustrative process for predicting and using emotions of a user in a virtual reality environment, the process includes applying a plurality of physiological sensors to a user. The plurality of physiological sensors includes one or more brain sensors. The method further includes receiving physiological sensor signals from the physiological sensors and preparing the physiological sensor signals for further processing by removing at least some of the noise and artifacts. The process also includes producing an emotion-predictive signal by utilizing an emotion database, wherein the emotion database has been developed based on empirical data from physiological sensors with known emotional states; and delivering the emotion-predictive signal to a virtual-reality system. The physiological sensors signals may be manipulated to address fault tolerance. The emotion database may be developed using deep learning. Other embodiments are presented below.

DESCRIPTION OF THE DRAWINGS

Illustrative embodiments of the present disclosure are described in detail below with reference to the attached drawing figures, which are incorporated by reference herein and wherein:

FIGS. 3.1-3.29 are schematic diagrams representing use of the Brooks-Iyengar algorithm to detect the true signal in a region of the scalp for 20-lead EEG system;

FIGS. 4.1-4.73 are schematic diagrams representing the Brooks-Iyengar algorithm used to detect the true signal in a region of the scalp for 32-lead EEG system;

DETAILED DESCRIPTION

Figure 1A:
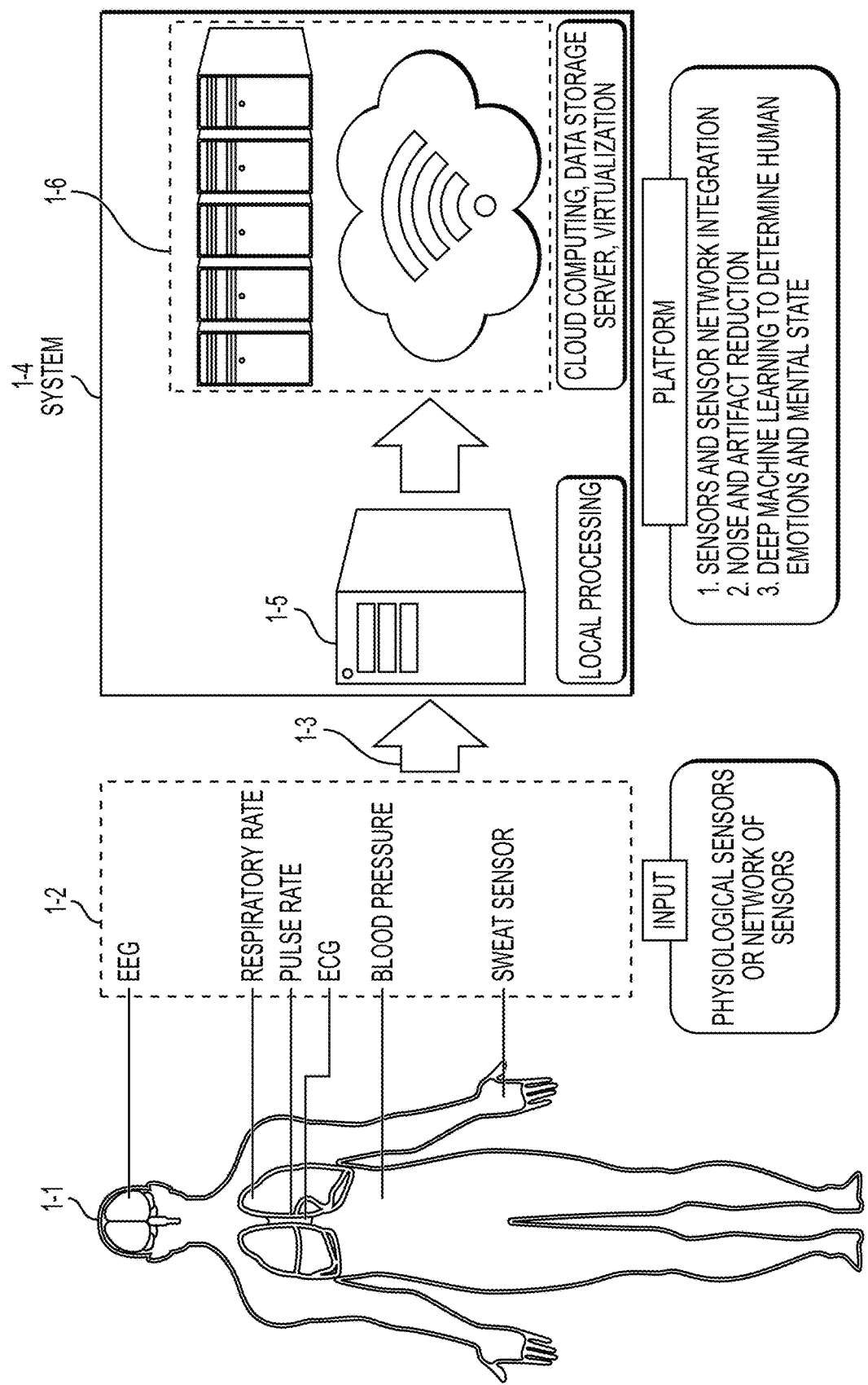
FIG. 1a is a schematic diagram showing inputs taken from physiological sensors on a human and introduced to an emotion-prediction module or platform.

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the claims.

Unless otherwise indicated, as used throughout this document, "or" does not require mutual exclusivity.

Humans interact with modern computers, machines, and electronic devices in a variety of ways. Human interface devices (HIDs) such as mouse, keyboards, and joysticks allow users to command the functionalities involved with a particular task. In addition, the popularization of smartphones and tablet computing have made touch screens ubiquitous and an essential aspect of day-to-day communication worldwide. The advent of the seventh-generation video game consoles, including the NINTENDO WII, the SONY PLAYSTATION 3, and the MICROSOFT XBOX 360, enabled the tracking of human movements in the spatial dimension which opened the avenue for physically interactive games. These technologies include, but are not limited to, accelerometers, motion sensors, and cameras. More recently, digital assistants enable voice recognition as well as human interaction with a machine by utilizing everyday spoken language. These interactions enable voluntary input of information at the interface between humans and devices.

The utilization of technologically-driven interfaces for the integration and deployment of emotional interactions with devices is still an area of current and developing research. Techniques from facial expression recognition, eye tracking, and EEGs to process, interpret, and act upon emotion have been attempted with limited success. There are many technical limitations and challenges in creating a practical and versatile implementation for the processing of human emotions, which would explain the current lack of widespread utilization of this technology. First, the complexity of the problem requires an efficient integration of hardware through software. Hardware forms the basis of the interface with humans. Multiple sensor types each measuring a different physiological parameter are required for improved resolution of an emotion. Information regarding emotion is buried within noisy sensor readouts which are subjected to multiple sources of interference and artifacts. Some of these sensors may be in a network of other redundant sensors that provide spatiotemporal information regarding how a certain emotion is expressed, e.g. brain mapping. Thus, a software system is required to integrate the hardware and should be able to decouple noise from the signals; it should be robust and support an appropriate level of fault tolerance. Second, the manifestation of identifiable traits for a certain emotion will vary from person to person; for example, key features detected as happy in one person may not be shared universally. Software is desired that is adaptive and intelligent; it should be able to learn, memorize, and recognize patterns based on current and all prior experiences with humans; it should be able to personalize the encounter specifically for the present user. Third, in pursuing software, large amounts of data must be typically processed simultaneously in real-time to support instantaneous computer feedback. Whether or not the human is fully aware of the ongoing interactions with the computer, the human is continuously, even involuntarily, providing valuable information on his or her current feelings and emotional state.

As a software platform, an illustrative system herein changes how the human emotion is detected, processed, analyzed, and distilled into meaningful conclusions that can then be integrated and optimized or addressed through deep learning. As used herein, "deep learning" includes a machine learning technique whereby complex multidimensional data are analyzed through multiple (3 or more) layers; each layer transforms or processes the data in such a fashion that nuances and subtle features, which may not obvious to the human, can be extracted. Applying this approach, deep learning requires a large quantity of examples to map a particular input to a particular output. It iteratively optimizes itself or improves itself to attain precision and accuracy while limiting consumption of computational resources and time.

As soon as data is collected from sensors and sensor networks, the illustrative software platform enables efficient and robust real-time data processing. The platform forms the basis of a feedback system whereby the source of physiological input is brand-insensitive and can be of any combination of sensors including EEG, EKG/pulse rate detection, sweat sensing, blood pressure monitoring, or other input. The platform utilizes physiological parameters (empirical data) and draws upon deep learning techniques to continuously build its database of human emotions and mental states. It leverages this extensive experience to make recommendations on whether a person is sad versus happy, angry or discontent versus satisfied, anxious versus serene, fearful versus relaxed, awake versus somnolent, agitated versus excited, distracted versus focused, or other emotional states. The output of the platform can be to any entity—living or nonliving—e.g. human, software, robot, or electronic device, which appreciates the deep learning's real-time analyses and recommendations on human emotion or mental state in order to achieve a specific goal or perform a specific function. Examples include, but are not limited to, altering a person's perceived reality (by virtual reality), actual experience (by affecting the tangible, physical reality), level of enjoyment (via entertainment or electronic devices), level of comfort (via software-controlled actuators), level of attention and concentration (via software directed guidance or electronic devices), and level of consciousness (by medical devices).

Referring now primarily to FIG. 1a, a user 1-1, e.g., a human, has a number of different physiological sensors on that are represented by those listed at 1-2 (EEG, respiratory rate, pulse rate, ECG, blood pressure, sweat sensor, etc.). Those sensors develop input signals, or physiological sensor signals, that are being inputted as shown at 1-3 into the system at 1-4, or the software platform or emotion-prediction module or system.

The emotion prediction system 1-4 is composed of both local processing or cloud processing and a server 1-6. Depending on the application, there may be more of the local processing done if there is a need for a more computational power or if one is using it, for example, on an app that requires additional processing. The latter may be a mobile phone or ipad and most of the processing is in the cloud and the server.

Figure 1B:
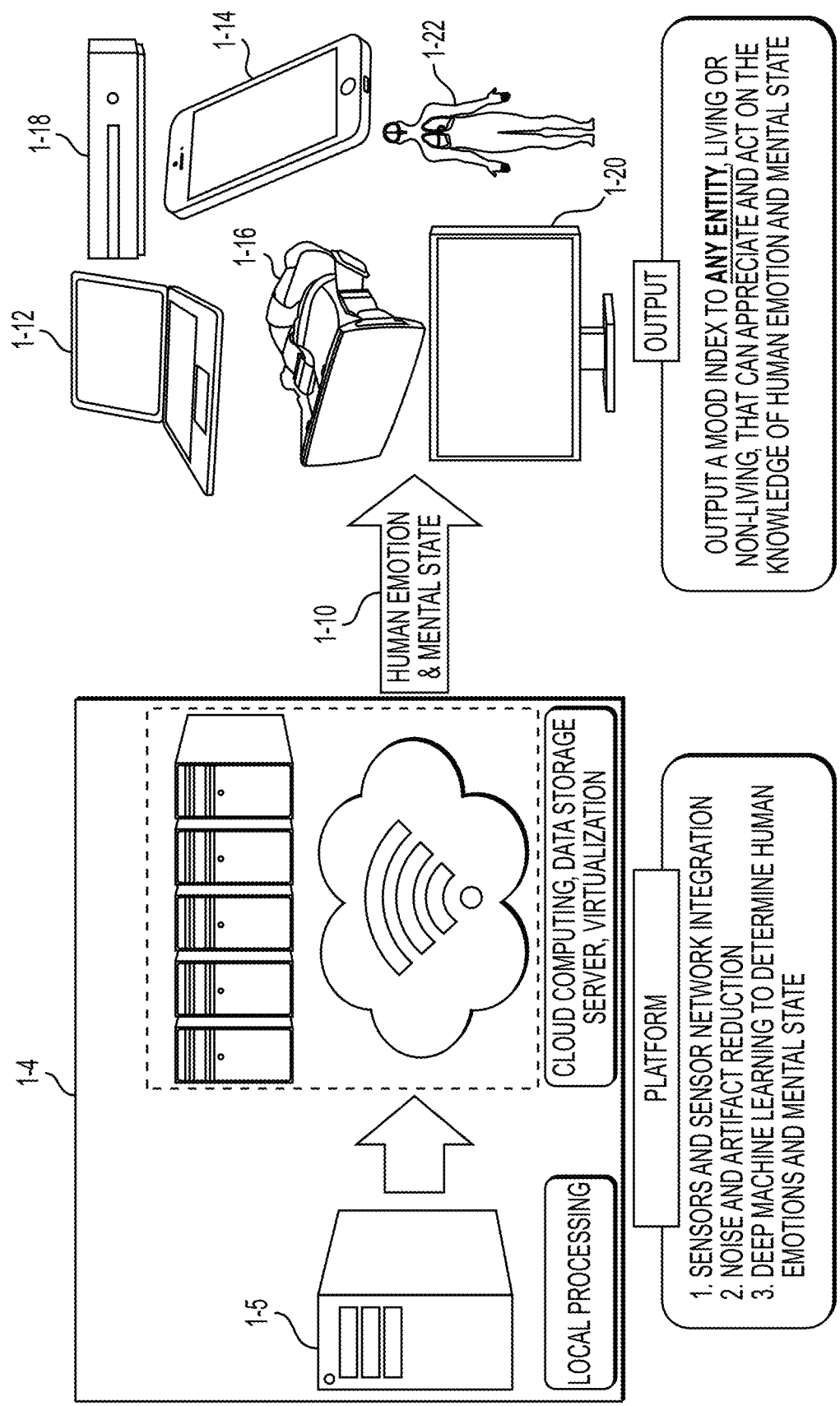
FIG. 1b is a schematic diagram showing outputs from the emotion-prediction module or platform.

Referring now primarily to FIG. 1b, the emotion prediction system or module 1-4 is shown producing an output of the emotion or mental state 1-10 or emotion predictive signal. The signal can be outputted to many different devices or users. For example, in some embodiments, the signal could go to a laptop 1-12 or a smart phone 1-14 or virtual-reality goggle 1-16, a gaming console 1-18 (e.g., XBOX or PLAY STATION 4/gaming console/AMAZON FIRE), a TV or a monitor 1-20, or to another user 1-22 through any medium.

In one particular embodiment, an EEG cap is has a plurality of spaced electrodes on the user's scalp. One skilled in the art will appreciate that various numbers and configurations of electrodes might be used and applied in numerous manners. The plurality of electrodes are communicatively (wired or wireless) coupled to an emotion prediction module. While not explicitly shown, the emotion prediction module may also receive input (physiological sensor signals) from devices on the user indicative of heart rate, breathing rate, perspiration (e.g., from palms), blood pressure, electrocardiogram (ECG), movement, eye movements, or other measurements.

The motion prediction module may be communicatively coupled to a network, by which updates or data may be accessed or provided. In this regard, the deep learning to develop an emotion database may be done with heavy computing on servers and then be delivered to a local database for processing the signals in real time.

The user is also wearing a virtual reality headset. As used herein, "virtual reality" refers to a computing environment that is wholly or partially included in a virtual space (e.g., a perceived space that is not embodied by physical components). A virtual reality environment is implemented by any suitable combination of hardware or software, including (without limitation) cameras, projectors (e.g., simulated display projected onto eyewear), accelerometers, pressure switches, sensors worn by the user (e.g., head position sensors), emitters worn by the user (e.g., gloves with light-emitting diodes), or any other suitable device or module. In some cases, a VR environment includes non-virtual components. For example, a computing environment that includes both physical components (e.g., a keyboard and display) and virtual components (e.g., additional projected displays and a cursor enabled by eye-tracking) is considered as a VR environment herein, unless otherwise indicated. It should be understood that while VR environments are discussed as an aspect of this disclosure, the emotion predictive signals produced may be used by many different types of computer-controlled or computer-implemented devices.

The virtual reality headset is communicatively coupled (wireless or wired) to a virtual reality module. The virtual reality module may provide signals to the virtual reality headset to provide images and experiences therein. In addition, the virtual reality module may receive manual or explicit input from the user.

One illustrative embodiment presents an illustrative process for predicting and using emotions of a user in a virtual reality environment. The process includes applying a plurality of physiological sensors to a user, wherein the plurality of physiological sensors includes one or more brain sensors (see 1-2 in FIG. 1a). The process further includes receiving physiological sensor signals from the physiological sensors and preparing the physiological sensor signals for further processing. This may be by removing at least some of the noise and artifacts. The step might further include or alternatively include addressing fault tolerance with respect to sensor placement. The process also includes producing an emotion-predictive signal by utilizing an emotion database, wherein the emotion database has been developed based on empirical data from physiological sensors with known emotional states using deep learning; and delivering the emotion-predictive signal to a virtual-reality system or other computer-implemented system.

Figure 2A:
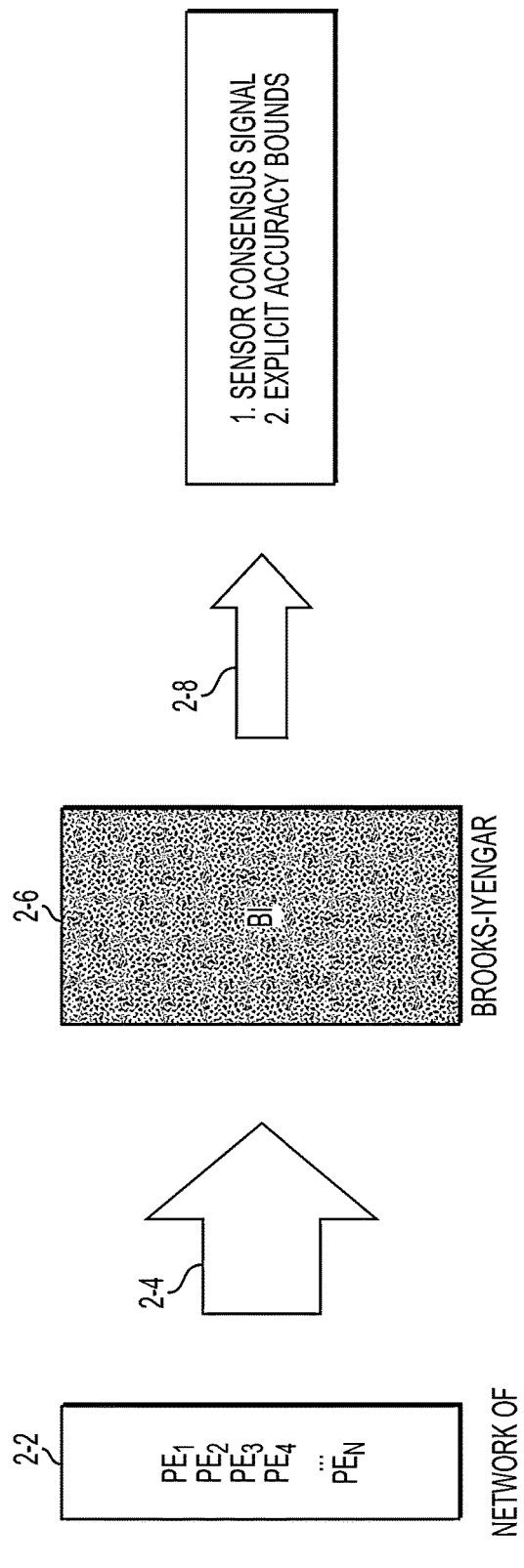
FIG. 2a is schematic diagram representing a Brooks-Iyengar algorithm used with a plurality of sensors for a general application.

Referring now primarily to FIG. 2a, an illustrative embodiment of a solution to signals from a plurality of physiological sensors is presented. See the discussion further below on the Byzantine Fault Problem and the issues related to aggregating multiple sensor inputs. Any of a number of techniques might be used to aggregate the multiple sensors. For example, without limitation, the Kalman filter (widely used in signal processing), Bayesian networks (used in Neural networks), Dempster-Shafer (probability calculus), or Brooks-Iyengar algorithm might be used. While a number of these may be used, the Brooks-Iyengar algorithm is used as an example. The Brooks-Iyengar algorithm dates back to the 1990s and is well documented in other applications.

Sensor inputs 2-2 may come from the physiological sensors 1-2 in FIG. 1a. In particular the focus here is on the sensors where multiple inputs are coming in for a particular aspect. For instance if one certain device is involved like an EEG device, the device will have multiple sensors and it may be desirable to process signals from an integrated signal. And so the signals should be integrated. In some embodiments, there also may be a situation where three different inputs are used that have only one sensor; so then integration of different sensors from individual sources is desired and in which case the integration approaches herein would also be applicable.

In integrating signals from multiple sensors for the same measure, the integration approach featured in FIG. 2a may be used, namely, the Brooks-Iyengar algorithm. If one has multiple sensors of the same type, it could detect that a subset of them are faulty. In the figure, the input from those different sensors are represented by 2-4, and then the Brooks-Iyengar algorithm represented at 2-6 is used. The signals may be digital signals or analog. The Brooks-Iyengar 2-6 is a module within the system or platform 1-4 (FIGS. 1a, 1b). The output 2-8 from the Brooks-Iyengar 2-6 module is a consensus of integrated signals. As shown, there may be two aspects: what it believes to be the true signal and accuracy bounds (a range of signals).

Figure 2B:
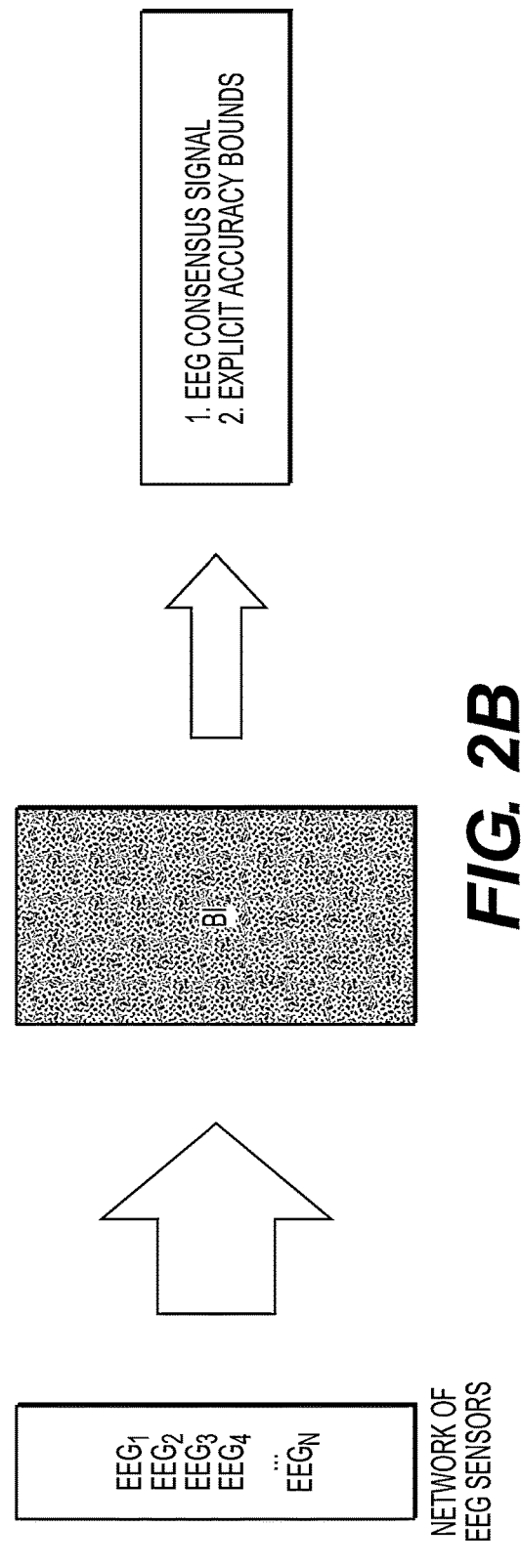
FIG. 2b is schematic diagram representing the Brooks-Iyengar algorithm used with a plurality of sensors for an EEG application.

Referring now primarily to FIG. 2b, a Brooks-Iyengar approach that is the same as FIG. 2a is presented, except this illustrative embodiment is for a network of EEG signals.

Referring now primarily to FIGS. 3.1 to 3.29, an illustrative embodiment of various signal patterns is presented for an EEG system on a user for a 20-lead or 20-sensor arrangement. The figure is a schematic plan view on to the top of a user's head or scalp 3-2 with the face being at 3-10 and the back of the head at 3-12. All of the circles, e.g., 3-4, are sensors or electrodes distributed on the user's scalp 3-2 or nearby. Sensors 3-6 and 3-8 are near the user's ears. The letters on the sensors are commonly accepted names or labels which have been assigned by neurologists or neuro scientists.

A number of approaches may be used to address the signals from the sensors. While not being bound by a particular theory, the Brooks-Iyengar works on redundancy and the sensors that are in vicinity of each other will pick up signals that are close by; the consensus of which represents the signal of an area. When a user has brain activity, for example in the area of F7, F3, Fz, Fp1, all four of those sensors should pick the activity up. And then the Brooks-Iyengar algorithm would find a consensus between those four signals and figure out what the true signal is. The other figures, FIGS. 3.2-3.29, are showing other signal groupings that may occur and reflect the complexity of combinations that may be involved in different embodiments. Sensor signals may be considered in different groupings. Different areas reflect or react differently to different emotions or mental states. The signals may be used to analyze and to get at the underlying emotion or mental state of the user.

In one illustrative embodiment, the sensors that are highlighted in each of FIGS. 3.1 to 3.29 are as follows: FIG. 3.1: Fp1, F7, F3, Fz; FIG. 3.2: Fz, Fp2, F4, F8; FIG. 3.3: Fp1, F3, Fz, Fp2, F4; FIG. 3.4: A1, T3, C3, F7; FIG. 3.5: F7, F3, T3, C3; FIG. 3.6 F3, Fz, C3, Cz; FIG. 3.7: Fz, F4, Cz, C4; FIG. 3.8: F4, F8, C4, T4; FIG. 3.9: F8, C4, T4, A2; FIG. 3.10: C4, T4, T6, F8; FIG. 3.11: F4, C4, T4, P4; FIG. 3.12: F4, Cz, C4, P4; FIG. 3.13: Fz, C3, Cz, C4, Pz; FIG. 3.14: Fz, C3, Cz, Pz; FIG. 3.15: F3, C3, Cz, P3; FIG. 3.16: F3, T3, C3, P3; FIG. 3.17: F7, T3, C3, T5; FIG. 3.18: F7, A1, T3, T5; FIG. 3.19: A1, T3, C3, T5; FIG. 3.20: T3, C3, T5, P3; FIG. 3.21: C3, Cz, P3, Pz; FIG. 3.22: Cz, C4, Pz, P4; FIG. 3.23: C4, T4, P4, T6; FIG. 3.24: C4, T4, A2, T6; FIG. 3.25: T5, P3, Pz, O1; FIG. 3.26: Pz, P4, T6, O2; FIG. 3.27: P3, Pz, P4, O1, O2; FIG. 3.28: A1, T3, C3, Cz; and FIG. 3.29: Cz, C4, T4, A2.

Referring now primarily to FIGS. 4.1 to 4.73, a user's 4-1 scalp 4-2 is again presented from the top, oriented with a face or nose portion at 4-4 and a back of the head portion at 4-6. Analogous to FIG. 3, an array of sensors 4-8 is attached to the user 4-1, except this time a 32-lead or 32-sensor arrangement is used. The sensor array 4-8 is used to develop physiological sensor signals and ultimately to determine the user's emotion or mental state. The groupings of sensors, represented by darkened sensors, are processed with an integrated function, and in some embodiments, the Brooks-Iyengar algorithm.

In one embodiment, the sensors that are highlighted in each of FIGS. 4.1-4.73 are as follows: FIG. 4.1: Fp1, F7, F3, FC5; FIG. 4.2: Fp1, F7, F3, Fz; FIG. 4.3: Fp1, F3, Fz, FC1; FIG. 4.4: Fp1, Fp2, F3, Fz F4; FIG. 4.5: Fz, Fp2, F4, FC2; FIG. 4.6: Fz, Fp2, F4, F8; FIG. 4.7: Fp2, F4, F8, FC6; FIG. 4.8: FT9, F7, FC5, T7; FIG. 4.9: FT9, F7, F3, FC5; FIG. 4.10: F7, F3, FC5, FC1; FIG. 4.11: F3, FC5, FC1, C3; FIG. 4.12: FC5, F3, Fz, FC1; FIG. 4.13: F3, Fz, FC1, FC2; FIG. 4.14: FC1, Fz, FC2, Cz; FIG. 4.15: FC1, Fz, F4, FC2; FIG. 4.16: Fz, FC2, F4, FC6; FIG. 4.17: FC2, F4, FC6, C4; FIG.

4.18: FC2, F4, F8, FC6; FIG. 4.19: F4, F8, FC6, FT10; FIG. 4.20: FC6, F8, T8, FT10; FIG. 4.21: C4, FC6, T8, FT10; FIG. 4.22: C4, FC6, T8, CP6; FIG. 4.23: FC2, FC6, C4, T8; FIG. 4.24: Cz, FC2, FC6, C4; FIG. 4.25: Cz, FC2, C4, CP2; FIG. 4.26: FC1, FC2, Cz, C4; FIG. 4.27: C3, FC1, FC2, Cz; FIG. 4.28: C3, FC 1, Cz, CP1; FIG. 4.29: FC5, FC1, C3, Cz; FIG. 4.30: T7, FC5, FC1, C3; FIG. 4.31: T7, FC5, C3, CP5; FIG. 4.32: FT9, FC5, T7, C3; FIG. 4.33: FT9, TP9, T7, FC5; FIG. 4.34: TP9, T7, FC5, CP5; FIG. 4.35: TP9, T7, CP5, P7; FIG. 4.36: TP9, T7, C3, CP5; FIG. 4.37: T7, C3, CP5, CP1; FIG. 4.38: CP5, C3, CP1, P3; FIG. 4.39: CP5, C3, Cz, CP1; FIG. 4.40: C3, CP1, Cz, CP2; FIG. 4.41: CP1, Cz, Pz, CP2; FIG. 4.42: CP1, Cz, CP2, C4; FIG. 4.43: Cz, CP2, C4, CP6; FIG. 4.44: CP2, C4, P4, CP6; FIG. 4.45: CP2, C4, CP6, T8; FIG. 4.46: C4, CP6, T8, TP10; FIG. 4.47: CP6, P8, T8, TP10; FIG. 4.48: P4, CP6, P8, TP10; FIG. 4.49: CP2, P4, CP6, P8; FIG. 4.50: Pz, CP2, P4, CP6; FIG. 4.51: Pz, CP2, P4, O2; FIG. 4.52: CP1, CP2, Pz, P4; FIG. 4.53: P3, CP1, CP2, Pz; FIG. 4.54: CP1, P3, Pz, O1; FIG. 4.55: CP5, CP1, P3, Pz; FIG. 4.56: CP5, CP1, P7, P3; FIG. 4.57: TP9, CP5, P7, P3; FIG. 4.58: CP5, P7, P3, O1; FIG. 4.59: P7, P3, Pz, O1; FIG. 4.60: P3, Pz, O1, Oz; FIG. 4.61: O1, Pz, Oz, O2; FIG. 4.62: Pz, Oz, O2, P4; FIG. 4.63: Pz, P4, P8, O2; FIG. 4.64: O2, P4, CP6, P8; FIG. 4.65: Fz, Cz, Pz, Oz; FIG. 4.66: C3, Cz, C4, T8; FIG. 4.67: T7, C3, Cz, C4; FIG. 4.68: FC1, FC2, Cz, CP1, CP2; FIG. 4.69: FT9, Fp1, F7, F3, Fz, FC5, T7, C3; FIG. 4.70: Fz, Fp2, F4, F8, FC6, FT10, C4, T8; FIG. 4.71: C4, T8, CP6, P4, P8, TP10, Pz, Oz, O2; FIG. 4.72: TP9, T7, C3, CP5, P7, P3, Pz, O1, Oz; and FIG. 4.73: P3, Pz, P4, O1, Oz, O2.

Figure 5:
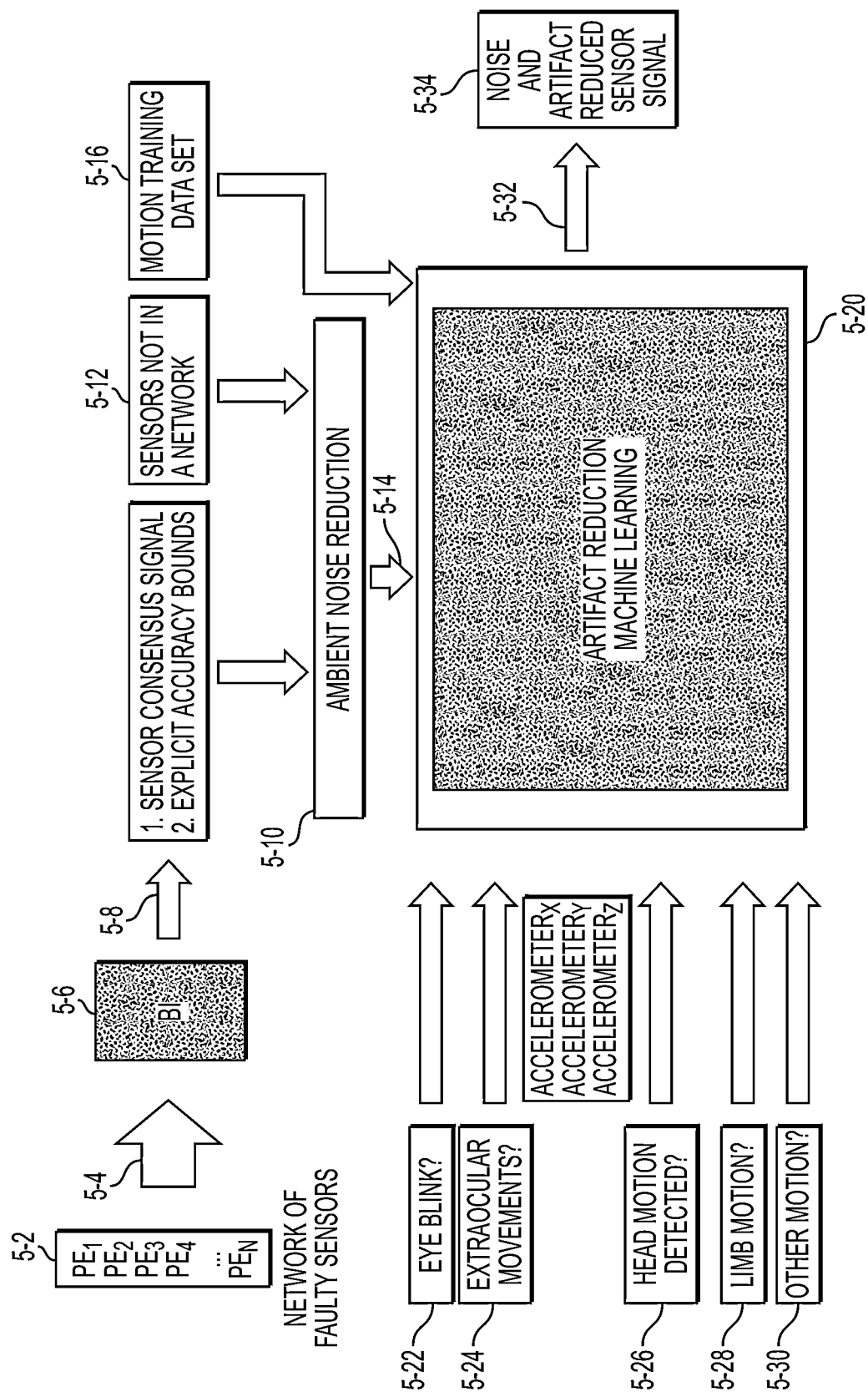
FIG. 5 is a schematic diagram representing artifact reduction machine learning according to one illustrative embodiment.

Referring now primarily to FIG. 5, a system is shown for determining the emotional or mental state of a user. A plurality of physiological sensor signals 5-2 are the input 5-4 to the Brooks-Iyengar module 5-6, which runs on a processor (see FIG. 1). The Brooks-Iyengar module 5-6 output 5-8 (sensor consensus signal among the sensors and accuracy bounds) is delivered to an ambient noise reduction module 5-10. Other signals from individual sensors 5-12 may also be delivered to the ambient noise reduction module 5-10. The ambient noise reduction module 5-10 electronically or digitally removes things that basically are caused by the environment, e.g., 60 hertz noise in U.S.; the noise is filtered out. The filtered signals 5-14 continue for further processing and are introduced into an artifact reduction machine learning module 5-20.

A motion training data set 516 is also provided to the artifact reduction machine learning module 5-20. The training data set 516 allows the system to know what the prototypical example is. In some embodiments, the system will try to emulate the training data set. The system will see a number of cases and then the system will try to mathematically emulate that anytime it gets another input. The data set may be generated from a number of calibrations with patients or users doing certain motions or movements to introduce the artifacts.

Other aspects may be factored in to increase the accuracy of the system. The system may process signals such that certain known and recorded events, e.g., blinking of eyes 5-22, can be monitored and accommodated in real time or near real time. A system-wide clock signal may be used as a reference. Other inputs may be considered as well, e.g., extraocular movements 5-24, head motion 5-26 (three accelerometers), limb motion 5-28, other motion 5-30.

The artifact reduction machine learning module 5-20 outputs 5-32 a noise and artifact reduced sensor signal 5-34. That signal 5-34 may be correlated with the user's emotion at the time or mental state. The system may thus be used to detect the emotional state or mental state of a user. The learning aspect allows for improving accuracy with time.

Figure 6:
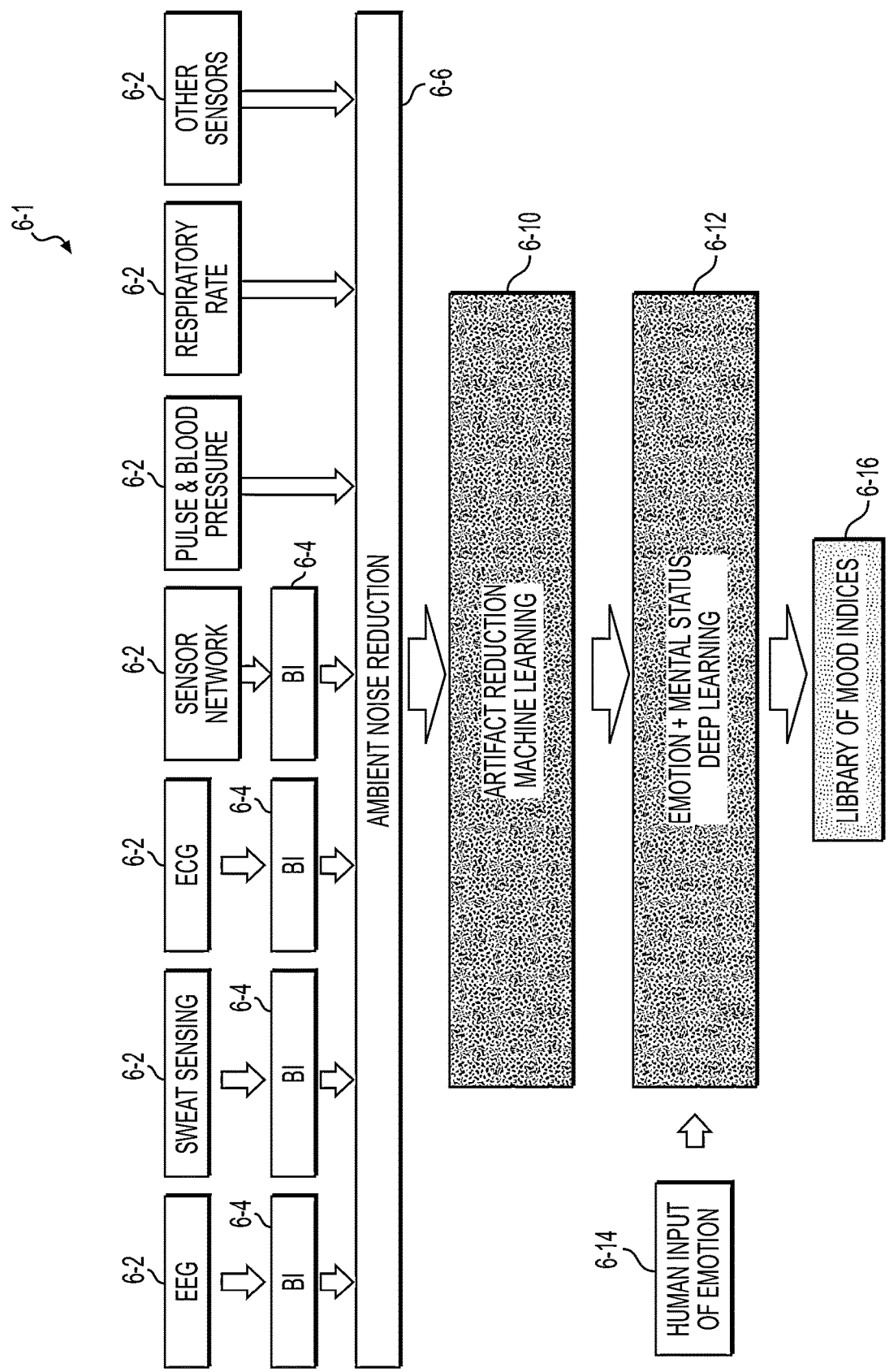
FIG. 6 is a schematic diagram representing emotion deep learning according to one illustrative embodiment.

Referring now primarily to FIG. 6, an embodiment of a system 6-1 is presented. The system 6-1 includes a plurality of sensors 6-2 receiving signals from a user (not shown; see 1-1 in FIG. 1*a*). The plurality of sensors 6-2 may take many different forms, e.g., EEG, sweat sensor, ECG, sensor network, pulse, blood pressure, respiratory rate, or others. For those involving redundant or multiple signals (see the discussion with FIG. 2-4), an integrator module, e.g., Brooks-Iyengar algorithm module 6-4, is used to arrive at the signals to be used for further processing. The signals from the Brooks-Iyengar algorithm module 6-4 and the singular sensors are delivered to an ambient noise reduction module 6-6 and then to the artifact reduction machine learning module 6-10. That produces a signal that may be used to correlate with the user's emotion for learning or may be used to predict the current emotion or mental state of the user.

The signal is delivered to the deep learning module 6-12. The deep learning module 6-12 considers temporal things and, with reference to a clock signal, knows exactly when these things are happening.

Input 6-14 is like a survey. A user or another person may input the user's emotions at various times. The system takes all the inputs and associates them with the indicated emotion. That approach can be used to make a library to prepare a mood library or database 6-16. The empirical data is correlated with known emotional states.

Figure 7:
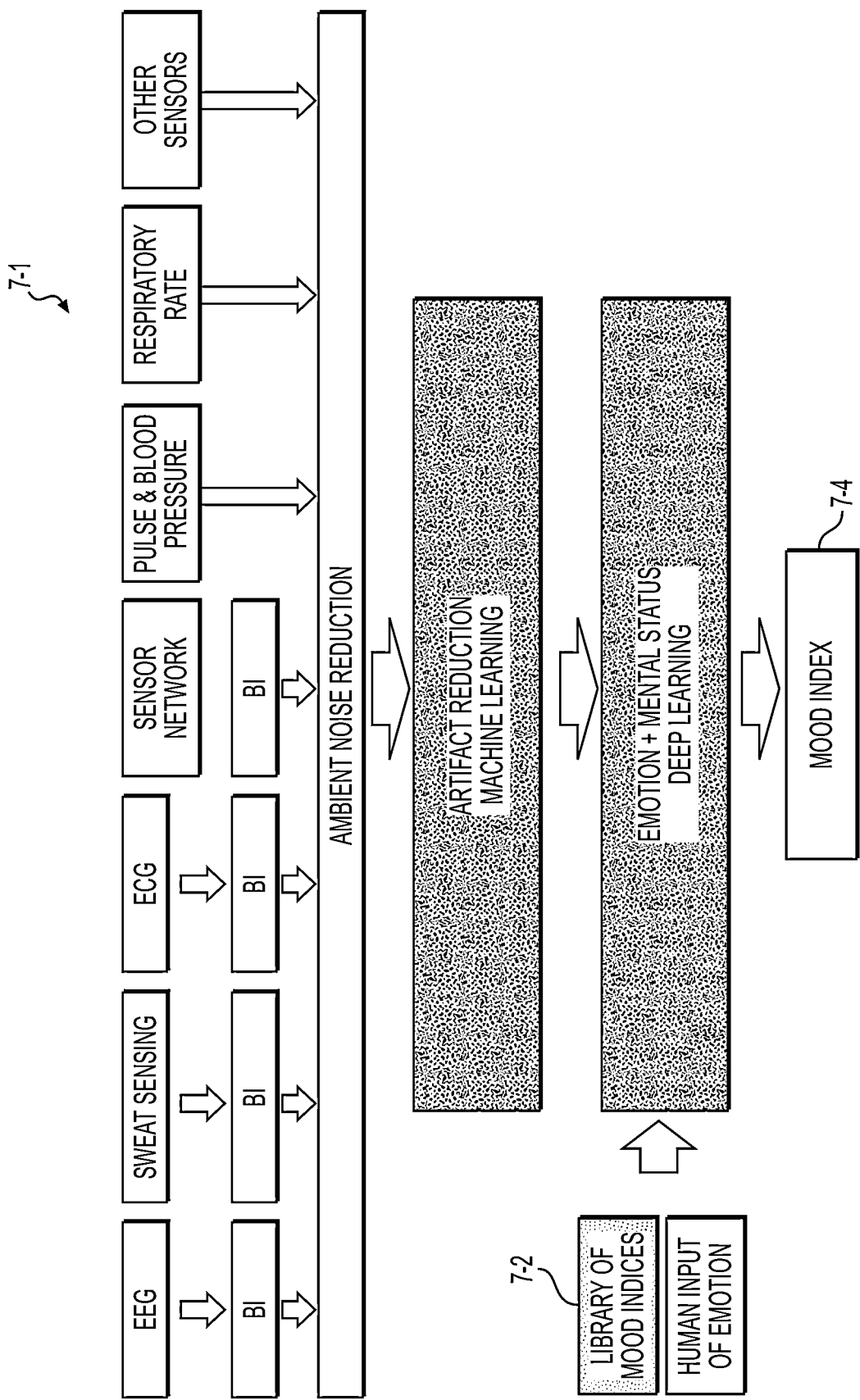
FIG. 7 is a schematic diagram representing emotion deep learning according to one illustrative embodiment.

Referring now primarily to FIG. 7, the system 7-1 is analogous in most respects to that of FIG. 6. This one includes a mood index 7-4 or signal. The mood index is a collection of emotional or mental states that the system has adjudicated after the summation of all the sensors. And then it filters back to those outputs whatever they are, e.g., the devices (see, e.g., 1-12, 1-14, 1-16, 1-18, 1-20 in FIG. 1B) or another person 1-22. The mood index may then lead the device or another person to do something in response.

The output from system 7-1 may be use for many purposes. For example, if one is an advertising firm, the firm is immediately getting this feedback of what emotion is being created by the ad or presentation being shown. And, it is doing this in real time. In another example, the output could tell a system on a car that the user is about to fall asleep or a gaming system that the user is very stressed.

Figure 8:
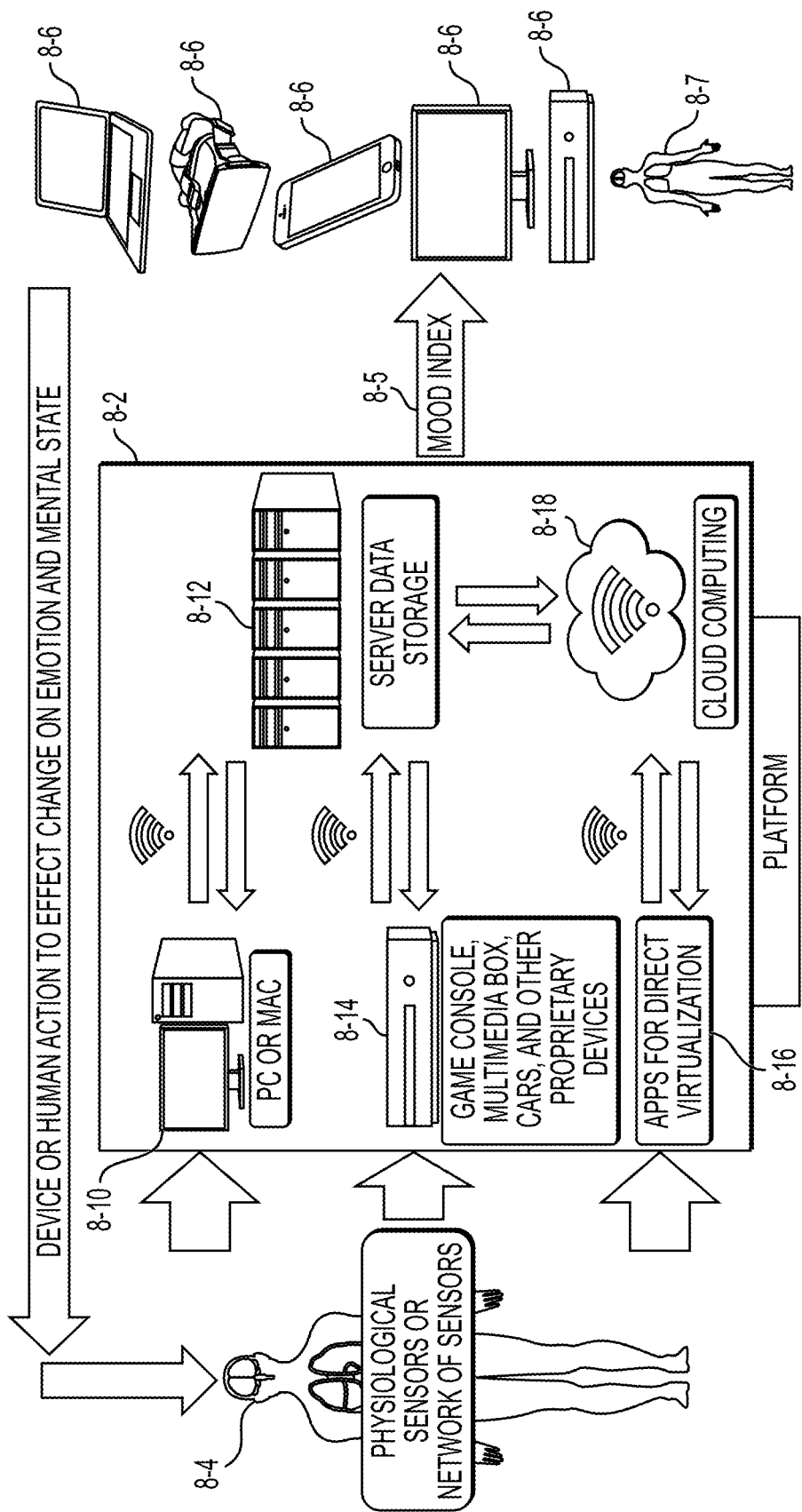
FIG. 8 is a schematic diagram representing operation and data storage for a system for human-computer interface according to one illustrative embodiment.

Referring now primarily to FIG. 8, another system 8-2 is presented. The system 8-2 analyzes the user 8-4 and puts out a signal indicative of the mood 8-5 to one or more devices 8-6 or to another user/person 8-7.

There are many options or embodiments for the arrangement. One may have a pc or mac or other processor-based system doing a lot of the processing locally and only using the server to get an updated training set or any other updates. The local computing power 8-10 may be used and the servers 8-12 used for acquiring and updating the learning set and also acquiring other updates. For example, data locally can be uploaded to the server; the learning set on the server is updated; once updated, the server can send the entire learning set back to a local environment in some embodiments. A console at 8-14, e.g., an XBOX, may receive the data and serve as the local interface. It may or may not perform the same level of processing that a pc or mac would do; the console has a specific tailored software for it but performs the same function—it provides local processing, it may update portions of the training set into the server, and then it acquires the updated form back from the server.

When a mobile phone or iPad or other tablet is being used, the computation portion may also occur in the cloud as referenced at 8-18. The cloud-based processor would interface with the servers 8-12 as shown.

Aspects of the emotion prediction module, according to some embodiments, are further discussed below.

Input and Output

The emotion-predictive module is the software implementation by which data from various physiological sensors or sensor networks are synchronously extracted, consensualized, noise reduced, and analyzed via deep learning. While referenced herein as a single system for convenience, it should be understood that the system may take various forms and embodiments.

The system includes deep learning that adapts, memorizes, and recognizes patterns learned from current and all prior interactions with users. There are multiple applications for the emotion-predictive module in which an overall mood may be elicited by sensor data acquisition and processing. In some applications, it is important to derive the person's emotional or mental state in real-time as the person may be subjected to changes in environment, perception, and personal experience. One purpose of the software platform is to modify or optimize for a particular mood index or emotional state through the deep learning feedback loop depending on the application desired. Therefore, based on its integrated components and processing properties, the platform defines an emotional state or mood from the modulation of data acquired from a variety of sensors; in particular, in some embodiments, the platform works with electroencephalogram (EEG), electrocardiogram (ECG) and pulse rate monitors, blood pressure monitoring, sweat detectors, respiratory monitors, or other sensors.

In some embodiments, the software platform, however, is both input (FIG. 1a) and output (FIG. 1b) agnostic, and it is brand insensitive. It may be compatible with any single sensor or network of sensors measuring physiological parameters which serve as the input to the system and has the ability to expand its repertoire based on necessity and application. The platform includes the ability to process large amounts of physiological data from a multitude of sensor or sensor network efficiently, despite faults and mishaps in sensor integration and process it through a deep learning algorithm to extract relevant emotional data. The platform may be output agnostic and can work with any entity—both living and nonliving—which can appreciate the software's analysis and recommendations on emotions in order to serve a specific application or function. Examples include virtual reality headsets or projectors that can modulate a human's perceived reality, multimedia devices like streaming media players which can change videos or songs based on the human's enjoyment, next generation gaming consoles which can provide new dimension to gaming experience by utilizing emotions, machines such as automobile or airplane that benefit from knowing if the operator is physically or emotionally unfit to operate, and other humans who are presenting, advertising, or performing and desire to know what the audience thinks in real-time.

The emotion prediction software is a software platform or software-based system that leverages sensor network integration and artificial intelligence or deep learning to figure out how a human feels. It serves as an enabler for deeper interactions with the human and can therefore be integrated into any day-to-day applications. The platform considers a fundamental aspect of humanity when interacting with the human: a person's feelings and emotions.

Byzantine Fault Problem

Determining human emotions and feelings is a complex problem that benefits from an efficient integration of multiple sensors or sensor networks each measuring a different physiological parameter. Information regarding emotion is transmitted from the hardware-human interface along with noise from a variety of sources. Some of the noise is related to a faulty sensor contributing to an inaccurate read, which may ultimately affect how decisions are made further downstream in the processing.

The Byzantine fault problem depicts a mythical situation whereby the Byzantine army lay siege to a city. The commander-in-chief has a number of troops under him which are stationed at key locations around the city under different generals. The leadership consists of the commander-in-chief and the generals who can discuss military strategy at will through messengers. If the entire army strikes in a coordinated effort, the likelihood of success is high. If some part of the army strikes and some part of the army retreats, then the entire army may be destroyed and the conquest may be doomed to fail. The question is, how can the leadership exchange information in such a way that information from traitors be detected as false and information from the loyal members be reconciled as true in the consensus?

The described situation can be generalized to a network of sensors with N independent processing elements (PE), where up to $\tau$ elements are faulty. The algorithm that solves this problem must guarantee the following: 1) the nonfaulty elements must be in consensus with each other regarding the information received from any other processor X; 2) if X is not faulty, the consensus should equal the information sent from X. The number of faulty elements $\tau$ must be less than one third of the total PEs. In other words, to tolerate $\tau$ faults, the system is required to have at least 3 $\tau$+1 PEs. Each individual PE is should be connected with at least 2 $\tau$+1 other PEs.

Detecting emotions typically requires a multitude of sensors that are working together, each measuring a specific physiological parameter. Some of these sensors may be elements of a larger sensor network. For example, EEG leads are strategically positioned throughout a person's scalp to form a network of detectors that map the electrical activity of the brain. EEG leads nearby to each other register redundancies in brain waves; a consensus between these sensors could then be determined both spatially with regards to location of the scalp and temporally with regards to timing of particular events.

Redundancy in sensors enables robust data acquisition: one that is less susceptible to sensor malfunction, incorrectly aligned or positioned sensor, weak signal, or interference. However, sensor redundancy introduces an aggregate of inherent errors and erroneous readings. In the fusion of sensors, the problem that needs to be addressed is: given N sensors, each with a limited accuracy, and no more than $\tau$ sensors being faulty at any one time, what is the smallest dynamic range needed to detect the correct signal?

The Brooks-Iyengar algorithm (FIG. 2a) combines sensor fusion capabilities with an efficient algorithm that solves the Byzantine Fault Problem. In processing noisy EEG signals (FIG. 2b), the Brooks-Iyengar algorithm can be tailored to determine the smallest dynamic range of the sensors as well as to reconcile an approximate true signal amongst a subset of sensors in the network. The Brooks-Iyengar algorithm is formalized as:

Input: a set of sensor data; Output: a real number giving the precise answer and a range giving explicit accuracy bounds; Step 1: each physical element receives values from all other physical elements and forms a set designated as V; Step 2: Perform the optimal region algorithm on V and return a set designated as A containing the ranges of values where at least N minus τ physical elements intersect; Step 3: Output the accuracy bounds which is the range defined by the lowest bound and the largest upper bound in A; Step 4: Sum the midpoints of each range in A multiplied by the number of sensors whose readings intersect in that range and divide by the number of factors.

For the EEG system, subgroups of 4 to 6 nearby sensors are analyzed and processed through the Brooks-Iyengar algorithm to detect the true signal in each region of the scalp. These groupings are illustrated for 20-lead (FIGS. 3.1 to 3.29) and 32-lead (FIGS. 4.1 to 4.73) EEG systems.

The Brooks-Iyengar algorithm can enable a robust infrastructure for sensor processing efficiently in O nlog(n) time. Due to the platform's allowance for variability in sensor inputs across one setup to another, the Brooks-Iyengar algorithm is implemented not only for EEG readouts, but for any and all physiological sensors that potentially could have redundancies in the system.

Motion Reduction

Motion artifact is a single identifiable and significant contributor of noise that needs to be adequately addressed for any effective determination of a mood index. Motion can affect the signal in a number of ways. The following are examples of mechanisms that can disrupt the signal: 1) any change or alteration in the contact between human and sensor resulting in electrostatic interference; 2) inherent sensitivities of the sensor to spatial accelerations; and 3) involuntary, automatic, or partially involuntary human movements that are superimposed on top of the relevant signal.

Periodic or repetitive motions such as blinking, resting tremors, and respiration generate a specific signature that can be recognized and then subtracted out. Certain movements such as head or limb motion can be corroborated by evidence of acceleration and deceleration from strategically placed accelerometers, which thereby allow the unwanted change in signal to be filtered out. Nevertheless, there are motions that are either not repetitive or periodic in nature such as extraocular movements. In addition, these motions are more subtle and cannot be reliably registered by another type of sensor.

To address the problem of motion, in some embodiments, the emotion-prediction software platform has a predetermined list of motions that can alter the signal for a particular type of sensor. For each type of motion, specific calibration measurements are taken for the human user. For example, the software platform may require the person to perform head motions such as pitch, yaw, and roll. Comprehensive measurements are also done for all other motions such as eye blinking, limb movement, inspiration and expiration, and extraocular movements. Finally, activity of the person at rest is recorded to detect any baseline movements such as resting tremors or twitches. The data from the calibration measurements is combined with a motion database containing all prior experiences that the software has had with human movements (training set). A machine learning algorithm utilizes the motion database to recognize key features of each motion as detected by the sensors and then makes appropriate adjustments to remove the artifact from the signal. Although the machine learning takes into consideration experiences that it has had with prior human movements, the entire process is individualized for the current user. FIG. 5 presents an illustrative block diagram for artifact reduction. Sensors in a network, such as EEG leads, are processed through the Brooks-Iyengar algorithm. Individual sensors can be processed directly through the artifact reduction.

Emotion Learning

The culmination of integrating sensors and sensor networks to take physiological measurements, implementing Byzantine fault tolerance, and reducing noise and motion artifacts, is the ability to extract useful data that can be appropriately processed by deep learning to determine a mood index, or emotion predictive signal, which is a surrogate for a person's emotional or mental status. The deep learning algorithm generates a library of mood indices (see, e.g., FIG. 6) based on a large number of users and their inputs. This library is constantly growing, evolving, and updating as more and more users utilize devices and applications that incorporate the platform. Regarding emotions, users for the training set are required to provide baseline information: a standardized set of images, sounds, and videos that are known to evoke specific feelings are played to the user to elicit a response. In addition, the users are asked to rate their feelings and the intensity of their feelings for correlation purposes. The training set also contains data that ranges an entire spectrum of wakefulness for mental status analysis; for example, users are monitored from when they are wide awake, to when they are somnolent, and eventually to when they are in light or in deep sleep.

The deep learning works with available sensor data and tries to extract a mood index from pattern recognition (see, e.g., FIG. 7). It draws upon a library of mood indices, which includes its previous experiences with human emotions and mental status, to assign in real time a mood index to the user. Although the EEG sensor network forms the backbone for detecting mood, emotions, and how awake a person is, synchronous data from any other sensors such as ECG, pulse rate, blood pressure, respiratory rate, and sweat production rate can corroborate, cross check, or augment the accuracy of detection. The system continues to function even if there is missing data from a subset of sensor types. In other words, the deep learning continues to work on an EEG only system even without synchronous data from any of the other physiological sensors or sensor networks. In some applications, e.g. detection of acute stress, fear, pain, or panic, it is possible to omit EEG information instead for data on heart rate, blood pressure change, and sweat production rate to correctly attribute an appropriate mood index.

The emotion-prediction module can compare not only the physiological sensor data of an individual with that of other individuals in an entire population but also with that of the individual's own internal control. In applications that seek precision analysis of a person's feelings and emotions, objective data can be generated from an individual's experience with a standardized set of images, sounds, and videos. The individual can provide subjective data by rating the experience and the intensity of the response. The objective and subjective data can be reconciled to form the individual's own internal control. The combined mood index from all individuals form the population data. Any differences, whether subtle or significant, that is present in the individual but is not universal in the population is accounted for by the deep learning. In focusing on single human analysis, the platform recognizes that each human will inevitably experience a feeling or an emotion differently. The platform can identify human emotions and mental states based on its prior interactions with a large number of individuals and the library of mood indices that was generated from such interactions but the platform can also personalize and fine-tune its analyses based on its interactions with a single individual.

Illustrative Software Operation and Data Storage

In one embodiment, the platform is developed and hosted on a linux-based server. Operation of the emotion-prediction system is hardware and operating system agnostic. The platform is an enabler of a specific function; therefore, versatility to allow different methods of utility are developed for its ease of integration into existing hardware, devices, and software.

FIG. 8 presents an illustrative software operation and data storage arrangement. According to some embodiments, three methods for accessing the platform may be used:

a. PC and MAC—The emotion-prediction platform is able to run natively on any operating system. APIs may allow ease of integration into other software. An internet connection may be used for access to the platform server for library updates and additional support. In one illustrative embodiment, the hardware includes one or more of the following: Intel Core i7 or better; Graphics card: Radeon or NVIDIA GTX with 2 GB or more; Hard drive: 128 GB or more (preferably solid-state drive); Memory: 16 GB or more.

b. System hardware—The system is able to run natively on available hardware such as gaming consoles or multimedia devices. These devices may only require a highly specialized function within platform; therefore, a customized version could be implemented to curtail unnecessary use of computing power. However, to appreciate the full capabilities of some embodiments of the platform, these devices may require additional, dedicated hardware. An internet connection may be required for accessing the system server for library updates and additional support.

c. Virtualization—The system can be accessed through a virtual environment. Software on PC/MAC or App on mobile device can connect to a server and access the system software. The technology that enables real-time virtualization of software is employed to deliver system to any computing device including mobile phones and tablet computers. This allows mobile Apps to incorporate the functionalities of the platform through cloud computing. An internet connection may be required to connect to the platform server.

Illustrative Applications

The following are illustrative applications of the systems and methods.

1. Video game console—The seventh-generation video game consoles, including the NINTENDO WII, THE SONY PLAYSTATION 3, AND THE MICROSOFT XBOX 360, implemented technologies that enable the tracking of human movements in the spatial dimension which opened the avenue for physically interactive games. Simultaneously the gaming industry has for years been pushing for improvements in graphic rendering for more realistic gameplay. In the eighth generation of video game consoles, the technology has finally achieved, for the first time, the rendering of realistic facial expression demonstrating emotions in characters. With an embodiment of the platform, these gaming consoles can track player emotions and thereby allow game developers to explore new interactions between characters and player. For example, in historical role-playing games (RPG), the player assumes the role of the character and experiences the fantasy of going on adventures. At every juncture, the player is given the ability to select from a multiple choice of decisions which is then played out. With the ability to detect human feelings, RPGs of the future can have characters that interact with humans on the emotional level. Characters in the games can become more human-like and annoy, sadden, anger, please, disgust, or excite the player. The platform can provide the game with the knowledge of the player's emotions which can then be used to alter the course of actions or the outcome of the gameplay.

2. Multimedia—Streaming devices, such as APPLE TV, AMAZON FIRE, ROKU, and CHROME CAST, have taken home entertainment to the next level. On demand shows or movies on Netflix, Hulu, or Amazon prime are just a few push buttons away. Music and other videos can be played at any time on an YouTube app. Music apps such as Pandora or iHeartRadio provides continuous shuffling and playback of music from a person's favorite genre. An embodiment of the platform, or system, can enable these streaming devices to interact with the human in more ways than just through user input on a push button. For example, by incorporating the platform, apps that play movie or stream videos can gauge the viewer's interest from a preview or a short blurb. Instead of the viewer taking extra time and initiative to rate a movie, the device or app using the platform can already determine how entertaining the movie is for the viewer. If a viewer chooses to view a scary or a funny movie, for example, the platform can figure out if the movie achieved its goal of being scary or funny. Specific advertisements to the viewer's liking can now be discovered without invading into the viewer's search history on Google and thereby increasing the likelihood of the viewer pursuing more information regarding the product. Music apps can figure out if the person likes or dislikes the music being played; therefore, the app can change songs or alter the genre altogether.

3. Every advertising campaign has several goals: 1) to catch the attention of the viewer through visuals and audio so that an image is imprinted in the viewer's mind; and 2) to suggest in a convincing fashion such that viewers feel like they ought to purchase a product, go to the movie, or buy a lifestyle. In many ways, advertising efforts are all centered on predicting what people feel, what people desire, what people expect, and what people are concerned about. Commercials, billboards, radio ads, computer ads are all aimed at catching the attention of an audience. As a result, advertising agencies spend a large part of their budgets to test subjects as to their likes or dislikes of specific advertising approaches. This usually works by showing an ad (advertisement) to a tester and asking him or her to rate the ad in real time with a hand-held device. The platform changes how advertising agencies can elicit this information. If the testers are fitted with an EEG along with other physiological sensors and are asked to view a commercial, the platform automatically detects the opinions of the tester even before any voluntary input is made. The platform can provide real-time feedback to the advertiser and indicate whether the tester is, for example, "happy" or "not happy", excited or not excited, neutral or disgusted with the product. The creators of the commercial can alter the strategy based on both involuntary and voluntary input from the tester. This utility of the platform can be generalized to other settings such as a business presentation, a car show, a performance, or even stand-up comedies.

4. Driving a car serves multiple purposes, primarily delivering a person from point A to point B. But, humans, as a whole, do end up spending a significant proportion of their time in cars. Therefore, enhancing of these experiences becomes important to automobile manufacturers. Like in all modes of transportation, the priority is to allow a person to reach their destination safely. Priority two is the reaching of the destination in a timely fashion. But an evolving third priority is to provide an appropriate experience for the passenger that is connected to his/her mental and physical well-being. An embodiment of the platform provides a tool that integrates disparate physiological sensor data in learning about the emotional or physical state of the driver. In doing so, The platform can determine the emotional state of a driver or passenger and adjust the car's functioning and environment to enhance the three priorities outlined above in transportation—safety, efficacy, and comfort. The following vignettes provide examples of ways the platform can be implemented: 1) Driver safety—The platform can detect somnolence versus wakefulness from fatigue or from inebriation. The platform can enable the car to arouse the driver but if the driver continues to be somnolent, the car can pull over to the side. 2) Efficiency—The platform can detect whether a driver is concentrated or distracted while on the road. If the platform senses a distracted driver, the car can employ ways to redirect the driver to the task. One method is to modulate the frequency or the display in the which the speed of the vehicle, speed limit, and fuel consumption is conveyed to the driver. Another method is to verbally cue the driver to the road ahead. If the car has exhausted all means to refocus the driver, the system can recommend a break from driving; 3) Comfort—The platform can detect whether a person is uncomfortable in the car. The platform can determine the music, lighting level, and the temperature that defines a driver's or a passenger's most "comfortable" state. The car acts as the output to the platform and the cars features are adaptable to sensor acquired data.

5. Virtual reality (VR) devices combine visual, auditory, and sensory experiences to synergistically immerse a human in an entirely new sensorium, one that is completely different from his or her primary reality. Modern day VR devices are able to convey detailed visual and auditory information with high definition images and realistic sounds. Three hundred sixty degree viewing capability enabled by head position tracking technologies and tactile illusions created by haptic feedback further empower a person's suspension of disbelief. The platform can be adapted into different VR software applications that require focus on a particular emotion. For example, the platform can focus on happiness in order to discover the user's happy place; the platform could focus on fear in an app for haunted house; the platform could focus on excitement in an app that provides virtual roller coaster ride. Rather than waiting for an ultimate, summary response of an experience, the apps could leverage the platform's deep learning capabilities to permit real time feedback to both the controller of the input or the virtual reality machine. The platform can be the driver for virtual reality environment change based on the emotion that it is focusing on.

EEG Data Augmentation

The operation of a conventional EEG system requires the strategic positioning of electrodes spaced throughout a person's scalp. International standards for electrode positioning include the 10-20, 10-10, and 10-5 systems. The number of electrodes utilized may vary depending on the purpose of the study. Increasing the number of electrodes will increase the density of data acquisition, providing more information per unit area of the scalp, but will also increase the setup time of the study and the complexity of data analysis. For practical reasons, many studies utilize between 20 to 32 electrodes (as opposed to 64 or more) without a significant reduction in the level of detail. Nevertheless, the discrete positioning of each electrode poses a nontrivial spatial geometric concern.

Whereas Brooks-Iyengar (BI) algorithm presented above is concerned primarily with fault tolerance and teasing out the true signal from sensors, the use of a data augmentation algorithm, e.g., the Weng-Roya data augmentation algorithm, addresses the problem of imprecise positioning of sensors on a user's head as well as any anatomical variation in head sizes across different users. For example, imagine having a television screen playing some repetitive patterns. Now, imagine having 10 sensors that can read a small square area on the TV. If those sensors are placed slightly at different positions every time data acquisition is done, even with repetitive patterns, the deep learning will lose accuracy because each sensor is seeing something different with different runs. So the data augmentation addresses this situation.

For applications where the exact positioning of the electrodes relative to the brain is important, the accuracy for detecting an event, e.g., based on correlations with prior recorded events, would be noticeably reduced. Regardless of how carefully the electrodes are mounted, there will always be an uncertainty in terms of where the electrodes are mounted on the person's scalp as well as their positions relative to that of one another. For example, even on the same person, there will be variations each time the electrodes are placed on the person's scalp. Furthermore, from person to person where the head sizes and shapes are not uniform, the precise location of a certain electrode relative to the brain may not be the same even if the electrodes are placed based on international standards.

In one illustrative embodiment, a WR data augmentation method is used by which imprecisions in electrode positioning can be mitigated. First, the part of the skull where the EEG leads are placed is assumed to be in the shape of a partial sphere which can be represented in spherical coordinates as shown in FIG. 9A. In the model presented, the stereographic projection is from the lower pole. The precise locations of all electrodes are defined based on the exact positions of where the electrodes are mounted on an unstretched EEG cap. Knowing the size of the cap and the length of the arc in theta and rho direction enables the projection of the electrode locations onto a Cartesian representation.

$$R = \frac{\text{full arc}}{\pi}$$

$$\phi = \frac{m_{arc}}{R}$$

$$r' = \sin(\varphi) \cdot R$$

$$\theta = \frac{P_{arc}}{r'}$$

Figure 9B:
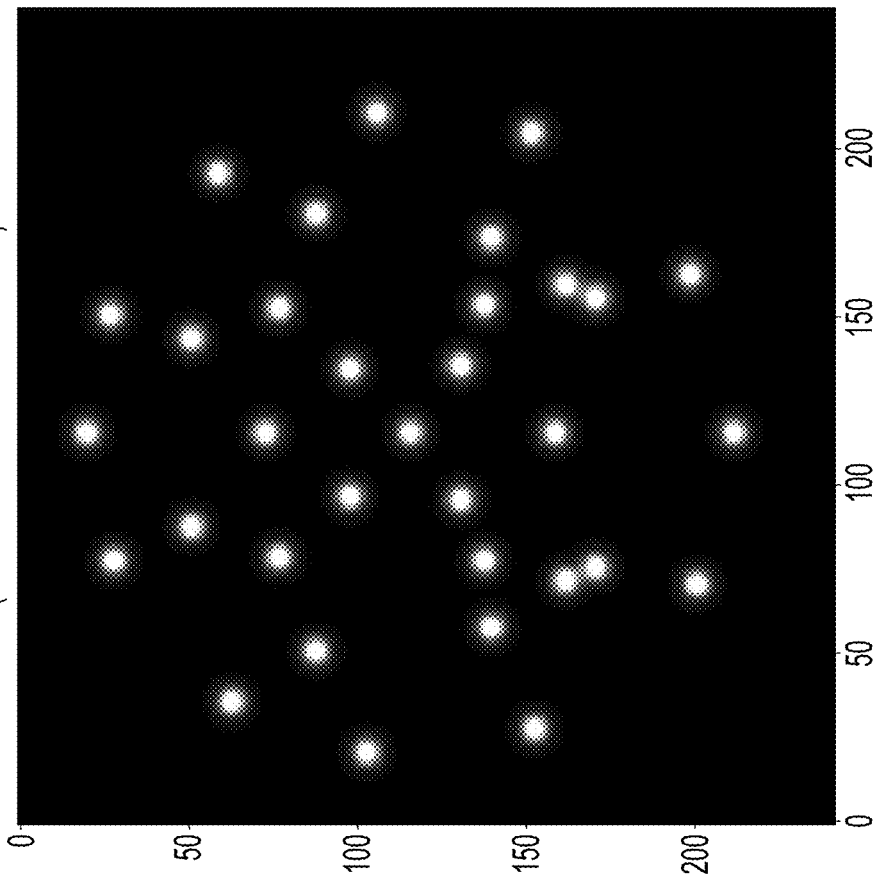
FIG. 9B is a schematic presentation of a 32-electrode system mapped onto a person's scalp in a Cartesian representation.
Figure 9A:
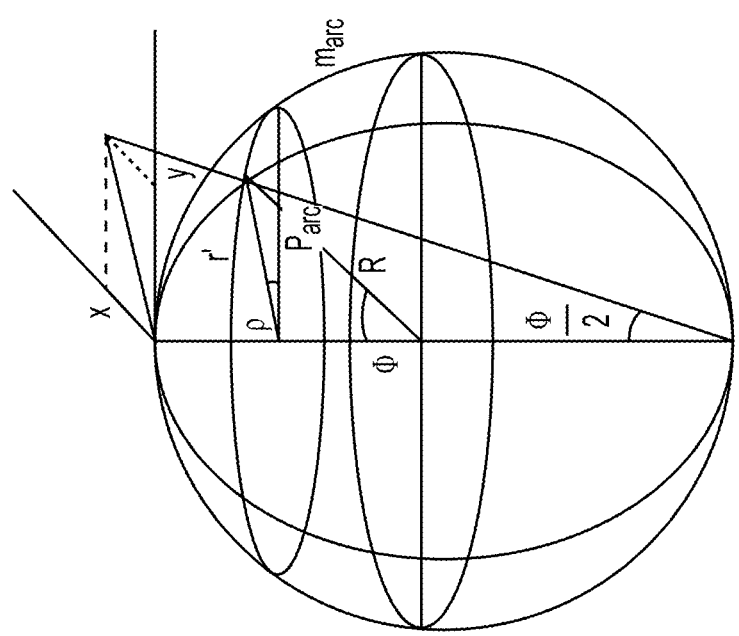
FIG. 9A is a schematic presentation of how leads on a human skull may be represented in spherical coordinates.

FIG. 9B illustrates the Cartesian representation of a 32-electrode system mapped onto a person's scalp where the top of the figure is the nasion (towards the person's nose) and the bottom of the figure is the inion (towards the base of the skull). Although a 32-electrode system is illustrated here, this algorithm can be used for any number of electrodes.

Next, one may construct a frame-by-frame map of brain electrical activity based on the measurements taken from each available electrode. The signal within a particular time window from each electrode may be embed in a 2-D normal probability distribution with an average ($\mu$) at the center of the electrode location and a standard deviation ($\sigma$) based on the intensity of the brain wave at that location.

$$a_{x,y} = \frac{1}{2\pi\sigma^2} \exp\left[\left(\frac{\left[\frac{x-\mu}{\sigma}\right]^2 + \left[\frac{y-\mu}{\sigma}\right]^2}{-2}\right)\right]$$

Figure 9C:
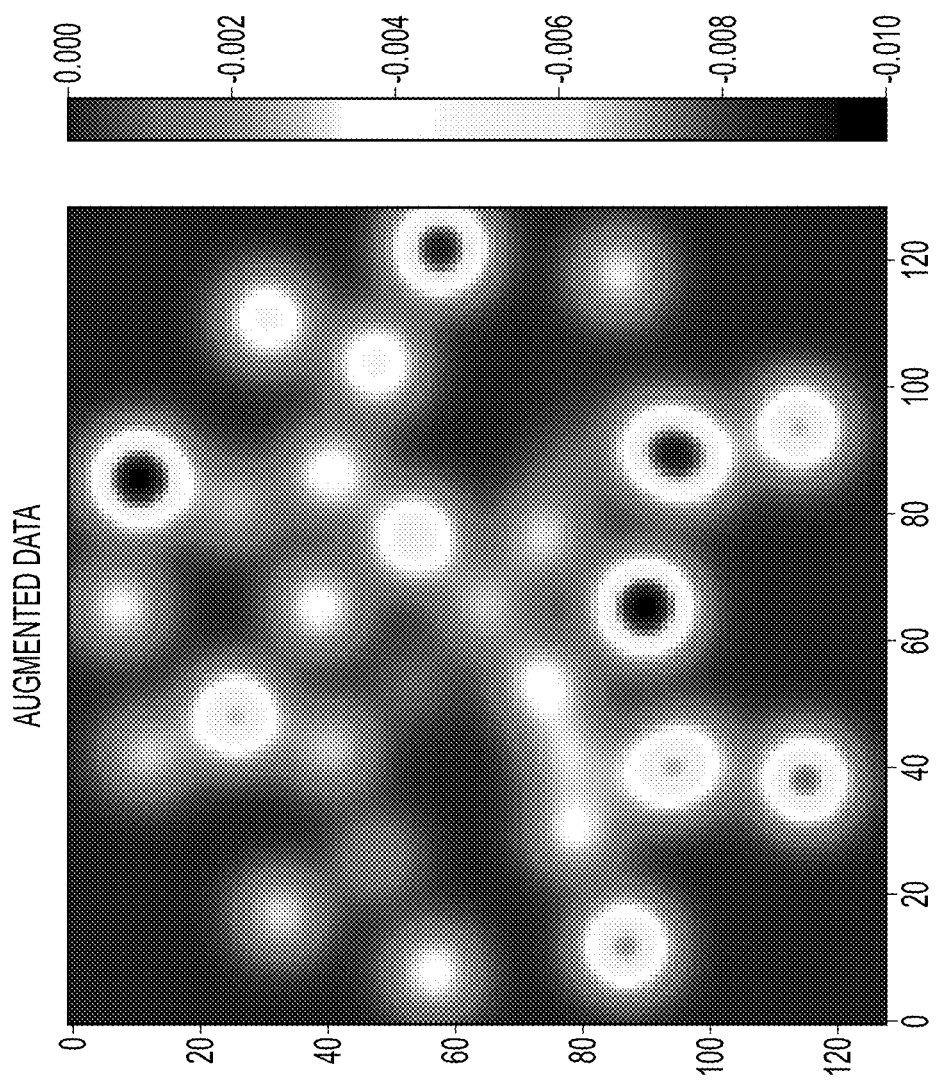
FIG. 9C is a schematic presentation of a 32-electrode system mapped onto a person's scalp with respective probabilities of signs mapped thereon.

In one implementation, a dummy grid is created and populated with the appropriate 2-D normal distributions centered at each projected electrode position. The intensity of the brainwaves as conveyed by the signals from each electrode is then multiplied by their respective probabilities. An example of this representation is shown in FIG. 9C. The size of the dummy grid is approximately determined by the size of the electrode projection onto a Cartesian representation as well as the trade-off between the level of detail required and the computational costs associated with deep learning on large datasets. One may perform this process frame-by-frame at each time interval; and when the frames are stitched together, the result is a 3-D block which represents a probability distribution of fluctuations in brain signals throughout time. Lastly, the entire block may be orientated to the correct location on the scalp based on the projection of the electrodes onto the Cartesian representation.

In FIG. 9B, starting at the lower left corner, the abscissa axis goes 0, 50, 100, 150, 200, and from the same corner the ordinate axis goes 200, 150, 100, 50, 0. In FIG. 9C, starting at the lower left corner, the abscissa axis goes 0, 20, 40, 60, 80, 100, 120, and from the same corner the ordinate axis goes 120, 100, 80, 60, 40, 20, 0. The scale to the right of the main imaging in FIG. 9C goes from the bottom −0.010, −0.008, −0.006, −0.004, −0.002, and 0.000.

The data augmentation enables tolerance to the imprecisions of EEG sensor positioning and therefore improves the accuracy of detection and classification of a brain event where sensitivity to sensor location is significant. The WR data augmentation method does the following: 1) accounts for different head sizes as the relative positions of the electrodes mounted on an EEG sensor cap would remain approximately the same when projected onto the Cartesian system; 2) accounts for slight variations in sensor positioning by considering a probabilistic distribution of brain wave intensities rather than an absolute intensity at the exact location of the sensor; and 3) allows for some fault tolerance since electrodes located nearby will pick up some of the same electrical activities from the brain and therefore effectively reconstructing a true signal via redundancy.

Deep Learning for Emotion and Mental State Classification

Figure 10:
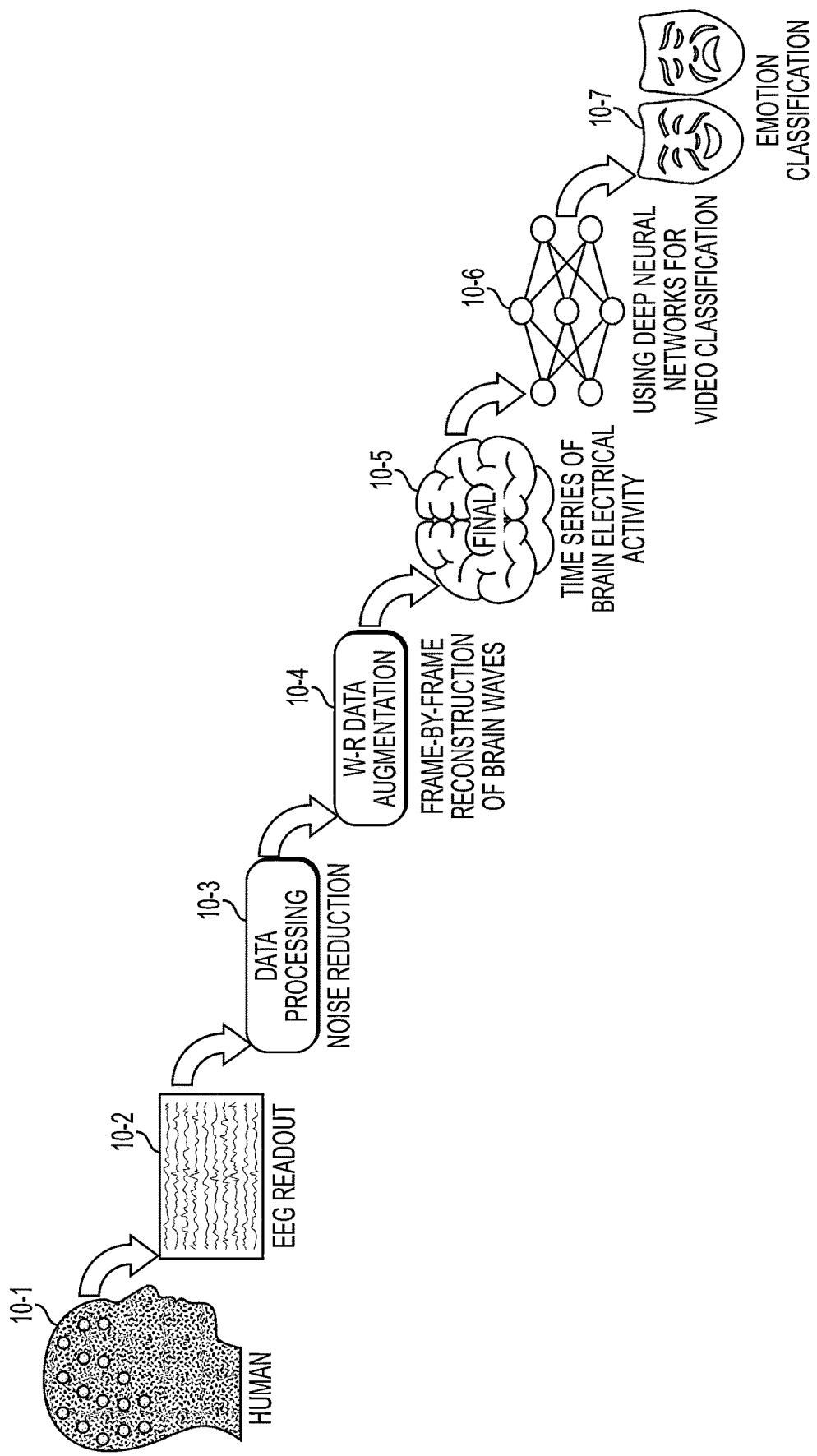
FIG. 10 is a schematic process flow for emotion and mental state classification according on one illustrative embodiment.

FIG. 10 presents a workflow of an entire algorithm in one illustrative embodiment. First data is acquired from the human 10-1 via the EEG system. Brain waves containing useful information are often embedded within the noisy EEG readout 10-2. Preprocessing the data increases the likelihood of discovering the useful signal. To minimize noise, the NePy preprocessing module or other noise reduction is employed at 10-3. The NEPy is a python package that is available under the open source MIT License. It facilitates the processing of raw EEG data taken directly from a readout. This module detrends the data to remove low frequency noise and baseline drifts in the data. It also removes the power line frequency established at 50 or 60 Hz. Finally, it uses a bandpass filter to limit the data between 2-45 Hz. Other like packages or approaches may be used as one skilled in the art would appreciate.

The preprocessed data is then augmented at 10-4, such as via the WR data augmentation method as previously described. The output is a 3-D block which represents a probability distribution of fluctuations in brain signals throughout time 10-5. Deep learning is employed for emotion and mental state classification at 10-6. A frame-by-frame analysis of the augmented data is performed employing time series techniques such as Long Short Term Memory (LSTM) and Recurrent Neural Network (RNN) as well as 2-D and 3-D convolution neural networks (CNN). The combination of time series techniques and CNN allows one to leverage video classification methods to extract the information hidden in 2D frames with respect to time. Deep neural network (DNN) is then employed to classify the mental state, the emotion, and the intensity of the emotion of the human at 10-7.

A multithreaded, highly parallel approach has been implemented for deep learning. MirroredStrategy, a tool in TensorFlow, may be employed to efficiently distribute and enable training synchronously on multiple graphic processing units (GPU). In other words, in one example, the power of four or more GPUs may be harnessed simultaneously to process large arrays of data in several batches. The deep learning architecture may use Tensorflow 2.0 and Keras. The training, validation, and testing of the architecture may all be done in Ubuntu Linux; it should be understood, however, that the practical operation of the deep learning software is not limited by an operating system and can be packaged for any platform.

Emotion-Intelligent VR System

State-of-the-art virtual reality (VR) systems create a secondary reality via a synergy that results from visual, auditory, and sensory feedback. A headset projecting high definition images and realistic sounds conveys visual and auditory information. Head position tracking allows a person to view the virtual world from a first-person point of view while haptic feedback generates tactile sensations.

An illustrative method is presented by which involuntary inputs from a person could be taken into consideration when interacting with a VR system. Standard interactions with VR systems or other gaming consoles in general require voluntary inputs via a Human Interface Device (HID). Voluntary inputs involve the user making a conscious decision and telling the virtual reality system what his or her preference or volition is. This requires the user to perform a willful gesture, motion, or push buttons on a handheld remote control. Involuntary input involves collecting and processing data from the user for information without the user having volunteered that information.

In one illustrative embodiment, brainwaves are collected via EEG and the platform or method utilizes deep machine learning to analyze them for emotion and mental state content. Although the user is aware that an EEG monitoring is taking place, he or she may not be continuously aware of the EEG monitoring while experiencing the VR. Positive and negative emotions are classified from the brain waves and are then provided to the VR system as input. The feedback loop between the VR system and the human through the EEG allows the enhancement of the human experience in virtual reality.

Figure 11:
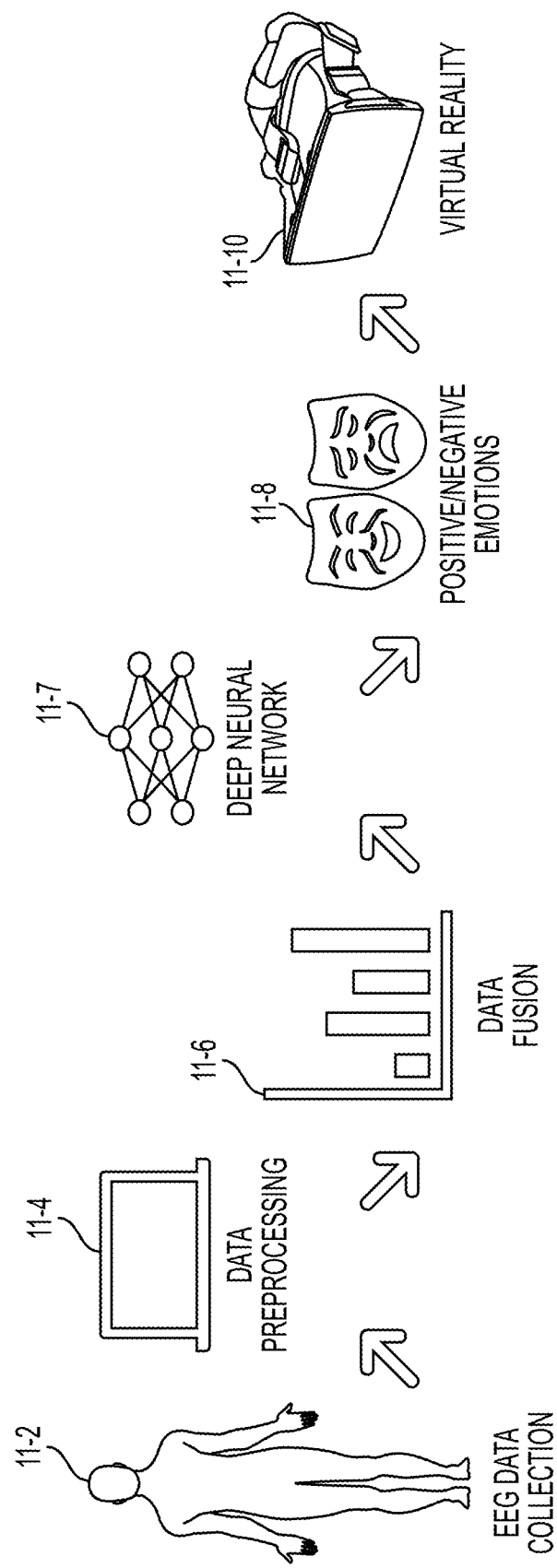
FIG. 11 is a schematic process flow of an illustrative deep-learning algorithm for involuntary input.

Referring now primarily to FIG. 11, the workflow of an illustrative deep learning algorithm for involuntary input is presented as an aspect of using the platform. First, data is acquired from the human via the EEG system at 11-2. During preprocessing at 11-4, the data is detrended to remove baseline drift in the EEG readout. Electrical noise such as 50 or 60 Hz is filtered out. A bandpass filter limits the brain waves between 2 and 45 Hz. Next, data is normalized, and data fusion is performed at 11-6. A deep learning 1-D approach 11-7 has been employed in this embodiment to classify emotion and mental state from the preprocessed EEG data a 11-8, which may be used by the VR system at 11-10. The architecture performs feature extraction on 32 1-D time series. Conversion of data for analyses in the frequency domain via FFT enables a more efficient use of memory. Training, validation, and testing may be done on a graphic processing unit (GPU) in Ubuntu Linux. However, for practical applications, this deep learning software may be compiled and packaged to run on a CPU. For VR system integration in this illustrative embodiment, the deep learning software can run independently on any platform; it calls on labstreaminglayer (LSL) to obtain data from the EEG system, and it communicates emotion and mental state predictions in real time with the VR system.

In one illustrative embodiment, a test virtual reality software to demonstrate the integration including different levels utilizes Unity and is powered by the Unity 3D game engine. Each level contains several different attributes; examples include but are not limited to mountains, trees, snow, houses, lakes, cars, city, hiking trails, airplanes, beach, ocean, and space exploration. At the start screen, users can select attributes that they prefer by grabbing a miniature of each attribute and placing it in the desirable bin. The system has a stored database of usernames and the attributes that the user prefers. The user may then proceed to levels with attributes that he or she prefers. While in this environment, the user can manually tell the system to either omit (dislike) or skip (neither like or dislike) a level if it is not to his or her liking.

Figure 12:
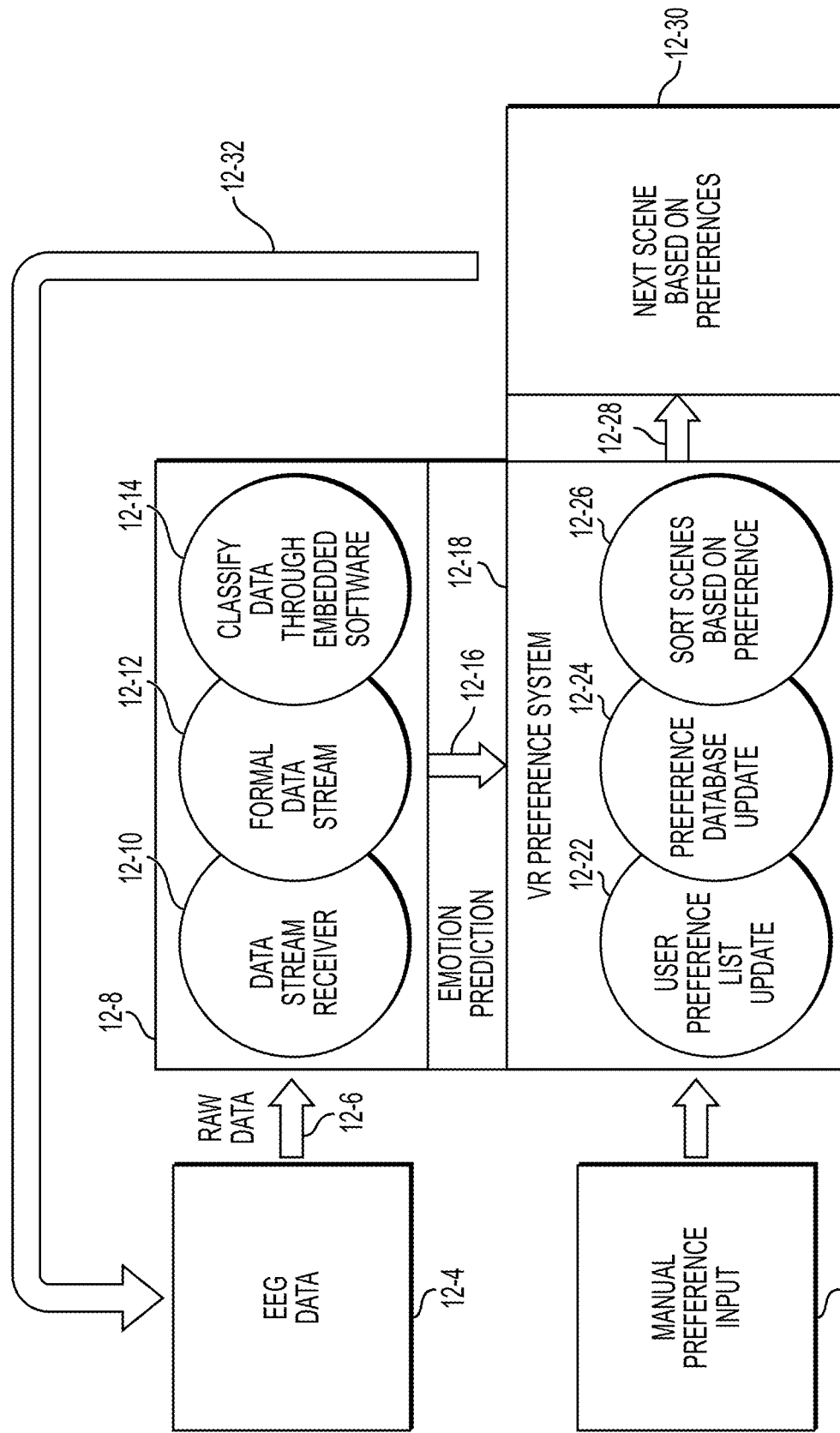
FIG. 12 is a schematic process flow of an illustrative system for integrating involuntary input with a virtual reality software system.

Referring now primarily to FIG. 12, an illustrative embodiment of a system 12-2 that integrates the involuntary input with the virtual reality software is presented. The EEG readout (involuntary input) can communicate to the test VR environment whether the user has a positive or negative emotional response to a level. If the user has a positive response, the test VR environment will take note of the level as a "like" for future use and continue to project the current level. If the user has a negative response, the test VR environment will take note of the environment as a "dislike" for future use and skip to the next level. The deep learning code that is used to process the EEG data is designed for processing and training on the graphic processing unit (GPU). However, for use with the VR system, the software may be converted for execution on the central processing unit (CPU) and embedded into the VR software as an executable. This process allows the software to be used with any number of VR environments and for any other purpose that may leverage emotion information as an input.

With reference still to FIG. 12, an illustrative embodiment of the AI/VR system 12-2 is shown. The data from the EEG 12-4 goes in as raw data 12-6 into the platform 12-8 and manual preference input, which may be entered with a controller by the user at 12-20, is entered to the VR preference system 12-18. Those two inputs 12-4 and 12-20 are integrated to come up with the output, which is the next scene 12-30 experienced by the user 12-32, e.g., a human user.

The EEG machine is attached to human being 12-32, and the EEG produces the data 12-4 from which the raw data 12-6 is delivered to the next module 12-8. That module 12-8 produces an emotion prediction signal 12-16, which is fed into the virtual reality preference system 12-18.

The module 12-8 is a version of the platform. The data stream receiver is at 12-10. The associated process analyzes the data and then, having done a preliminary analysis, the module 12-8 is able to take that cleaned up data from 12-12 and use what was generated from machine learning described earlier in the application—the information from GPU computing or other systems. That information is used here to classify what emotion the user 12-32 is experiencing. That is the emotion prediction signal delivered at 12-16.

The data stream receiver 12-10 receives the raw data 12-6 and that is put in a usable form at 12-12. In 12-12, noise is removed and other preparations may be made as previously referenced. At 12-14, the emotion classification is done using the techniques described earlier in this disclosure to predict an emotional response of the user 12-32.

Elsewhere, the use of the GPU to do machine learning was referenced. One should understand with reference to FIG. 12, that once the machine learning is done, the learning can be hardcoded somewhere and when new data comes in, the device can just use that data to process and do the analysis. It does not require using the server or the GPU but can do everything locally in this kind of illustrative embodiment.

Then the emotion prediction information or signal 12-16 is fed into the VR preference system 12-18. That emotion prediction information 12-16 can be used in many ways in other aspects of a system or device. In this illustrative embodiment, the input 12-20, preference system 12-18, and output 12-30 are used in a virtual reality system. The virtual reality is augmented or enhanced with emotion prediction 12-16 from what it would otherwise be. This module 12-18, 12-30 can be thought of as a test virtual reality environment. A challenging piece is getting the emotion prediction 12-16 ready for use, but that input may then be used by many different types of applications. The virtual reality environment represented by 12-20, 12-18, and 12-30 is only one example.

12-20 is a manual input. It is like the controller that users would have when inputting things into the virtual reality system. 12-30 is the response or output. In this case, system 12-20, 12-18, 12-30 changes the level based on how a person feels about what they are experiencing and as communicated by the emotion prediction signal 12-16. The user could explicitly say using 12-20 that they do not like what they are experiencing or the emotions can may be detected and utilized to change levels through 12-8, 12-16. The level is just a change of environment. The system can remember the user's preferences. For example, if the user does not like a particular thing, the system will remember that and avoid that. In a general example, if mountains were shown to a user and a beach was shown to the user, the system may tell that the user loves the mountains and hates the beach; thereafter the system would avoid beaches and try to use mountains. Many other possibilities exist for the preferences.

Based on the preferences, the system takes into account both the emotion prediction 12-16 and the person's input from 12-20. If a person's explicitly provides an input at 12-20, that input will change the scene or level at 12-30 right away. The emotion prediction 12-16 will do a probabilistic input concerning what the user 12-32 experiences. It may not be immediate but if the system gets enough data it will change the scene. The user preference list 12-22 allows the user not only to choose but allows them to tell the virtual reality system their priority of preferences.

In one illustrative embodiment, a system is provided that uses an algorithm to address inconsistences or faults with the physical sensors. For example, the algorithm may be the BI or the WR data augmentation discussed above. After using that to get better data, deep learning may be used to determine a likely emotion associated therewith.

In one illustrative embodiment, the WR data augmentation algorithm and technique described above is used to address the imprecisions of EEG sensor positioning. This alone can bring improvements in performance to address a technical issue.

In one illustrative embodiment, the illustrative system uses a remote computing system to do difficult computation work and then loads the resultant data into a local processor for real-time processing proximate the point of data capture. In other words, the capabilities that resulted from a process extremely heavy in computation is made available to a local processor and thus forms the brain-computer interface.

Although the present invention and its advantages have been disclosed in the context of certain illustrative, non-limiting embodiments, it should be understood that various changes, substitutions, permutations, and alterations can be made without departing from the scope of the invention as defined by the claims. It will be appreciated that any feature that is described in a connection to any one embodiment may also be applicable to any other embodiment.

What is claimed:

1. A method of predicting and using emotions of a user in a virtual reality environment, the method comprising:
  applying a plurality of physiological sensors to a user, wherein the plurality of physiological sensors includes one or more brain sensors on a user's scalp;
  receiving physiological sensor signals from the physiological sensors;
  preparing the physiological sensor signals for further processing by removing at least some of the noise and artifacts;
  processing the data to address fault tolerance and compensating for imprecisions in sensor positioning on the user's scalp;
  producing an emotion-predictive signal by utilizing an emotion database, wherein the emotion database has been developed based on empirical data from physiological sensors with known emotional states using deep learning;
  delivering the emotion-predictive signal to a virtual-reality system; and
  wherein the plurality of physiological sensors comprise a plurality of EEG sensors, and wherein the step of processing the data to address fault tolerance and compensating for imprecisions in sensor positioning on the user's scalp comprises:
    projecting positions of the EEG sensors in spherical coordinates onto a cartesian system to eliminate dependency on anatomical head size,
    assigning a two-dimensional spatial probability to the EEG sensors on the user's scalp based on each sensor's signal intensity,
    embedding an EEG signal at each time interval into a two-dimensional spatial probability for each EEG sensor to form frames and a frame-by-frame map of brain electrical activities,
    stitching the frames together in time to form a three-dimensional block, wherein time is the third dimension, and which represents a probability distribution of fluctuations in brain signals throughout time,
    aligning the three dimensional block to the correct anatomical position of the head, and
    outputting the three-dimensional block to the emotion database for emotion prediction.

2. The method of claim 1, wherein the step of producing an emotion-predictive signal is performed on a local processor, and wherein the emotion database is developed using deep learning on a server and subsequently delivered to the local processor.

3. The method of claim 1, wherein the step of processing the data to address fault tolerance and compensating for imprecisions in sensor positioning on the user's scalp comprises:
  iteratively establishing a subnetwork of sensors comprising at least four nearby electrodes on a scalp of the user;
  finding a consensus of redundant signals amongst the subnetwork of sensors; and
  outputting a consensus signal to a deep learning module for emotion prediction.

* * * * *